United States Patent
Milne et al.

(10) Patent No.: US 9,272,984 B2
(45) Date of Patent: *Mar. 1, 2016

(54) FATTY ACID ACETYLATED SALICYLATES AND THEIR USES

(71) Applicant: Catabasis Pharmaceuticals, Inc., Cambridge, MA (US)

(72) Inventors: Jill C. Milne, Brookline, MA (US); Michael R. Jirousek, Cambridge, MA (US); Jean E. Bemis, Arlington, MA (US); Jesse J. Smith, Waltham, MA (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/251,257

(22) Filed: Apr. 11, 2014

(65) Prior Publication Data

US 2014/0221323 A1    Aug. 7, 2014

Related U.S. Application Data

(60) Continuation of application No. 13/427,639, filed on Mar. 22, 2012, now Pat. No. 8,735,378, which is a division of application No. 12/499,779, filed on Jul. 8, 2009, now Pat. No. 8,173,831.

(60) Provisional application No. 61/148,658, filed on Jan. 30, 2009, provisional application No. 61/104,363, filed on Oct. 10, 2008, provisional application No. 61/104,364, filed on Oct. 10, 2008, provisional application No. 61/104,366, filed on Oct. 10, 2008, provisional application No. 61/078,983, filed on Jul. 8, 2008.

(51) Int. Cl.
| | |
|---|---|
| *C07C 233/55* | (2006.01) |
| *C07C 69/86* | (2006.01) |
| *C07C 69/94* | (2006.01) |

(Continued)

(52) U.S. Cl.
CPC ............... *C07C 233/55* (2013.01); *C07C 69/86* (2013.01); *C07C 69/94* (2013.01); *C07C 233/18* (2013.01); *C07C 233/49* (2013.01); *C07C 235/52* (2013.01); *C07C 235/60* (2013.01); *C07C 237/22* (2013.01); *C07C 271/28* (2013.01); *C07C 275/42* (2013.01); *C07D 295/182* (2013.01); *C07D 295/192* (2013.01); *A61K 31/60* (2013.01)

(58) Field of Classification Search
None
See application file for complete search history.

(56) References Cited

U.S. PATENT DOCUMENTS

| | | | |
|---|---|---|---|
| 4,036,951 | A | 7/1977 | Halpern et al. |
| 4,199,576 | A | 4/1980 | Reller et al. |
| 4,264,517 | A | 4/1981 | Liang |
| 4,276,430 | A | 6/1981 | Reller et al. |
| 4,551,279 | A | 11/1985 | Mueller et al. |

(Continued)

FOREIGN PATENT DOCUMENTS

| | | |
|---|---|---|
| EP | 0675103 A2 | 10/1995 |
| ES | 428254 A1 | 8/1976 |

(Continued)

OTHER PUBLICATIONS

Harris, W.S., et al., Omeg-3 fatty acids and coronary heart disease risk: Clinical and mechanistic perspectives, 2008, Atherosclerosis, vol. 197 pp. 12-24.*

(Continued)

*Primary Examiner* — Yate K Cutliff
(74) *Attorney, Agent, or Firm* — Goodwin Procter LLP

(57) ABSTRACT

The invention relates to Fatty Acid Acetylated Salicylate Derivatives; compositions comprising an effective amount of a Fatty Acid Acetylated Salicylate Derivative; and methods for treating or preventing an inflammatory disorder comprising the administration of an effective amount of a Fatty Acid Acetylated Salicylate Derivative.

16 Claims, 3 Drawing Sheets

(51) Int. Cl.

| | |
|---|---|
| C07C 233/18 | (2006.01) |
| C07C 233/49 | (2006.01) |
| C07C 235/60 | (2006.01) |
| C07C 237/22 | (2006.01) |
| C07C 271/28 | (2006.01) |
| C07C 275/42 | (2006.01) |
| C07D 295/182 | (2006.01) |
| C07D 295/192 | (2006.01) |
| C07C 235/52 | (2006.01) |
| A61K 31/60 | (2006.01) |

(56) References Cited

U.S. PATENT DOCUMENTS

| | | | |
|---|---|---|---|
| 4,670,465 | A | 6/1987 | Guzman et al. |
| 5,603,959 | A | 2/1997 | Horrobin et al. |
| 5,728,732 | A | 3/1998 | Corey et al. |
| 5,760,261 | A | 6/1998 | Guttag |
| 5,792,786 | A | 8/1998 | Whittaker et al. |
| 6,245,811 | B1 | 6/2001 | Horrobin et al. |
| 6,353,124 | B1 | 3/2002 | Whittaker et al. |
| 6,387,945 | B2 | 5/2002 | Packer et al. |
| 6,602,902 | B2 | 8/2003 | Shashoua et al. |
| 6,956,077 | B1 | 10/2005 | Akiyama et al. |
| RE40,546 | E | 10/2008 | Clarkson et al. |
| 7,560,473 | B2 | 7/2009 | Wang et al. |
| 8,173,831 | B2 | 5/2012 | Milne et al. |
| 8,729,293 | B2 | 5/2014 | Milne et al. |
| 8,735,378 | B2 | 5/2014 | Milne et al. |
| 8,735,379 | B2 | 5/2014 | Milne et al. |
| 8,946,451 | B2 | 2/2015 | Milne et al. |
| 9,085,527 | B2 | 7/2015 | Vu et al. |
| 2001/0002404 | A1 | 5/2001 | Webb et al. |
| 2003/0059865 | A1 | 3/2003 | Nelson |
| 2004/0254357 | A1 | 12/2004 | Zaloga et al. |
| 2007/0155747 | A1 | 7/2007 | Dasse et al. |
| 2010/0041748 | A1 | 2/2010 | Milne et al. |
| 2010/0184730 | A1 | 7/2010 | Vu et al. |
| 2011/0082120 | A1 | 4/2011 | Milne et al. |
| 2011/0082192 | A1 | 4/2011 | Milne et al. |
| 2012/0238530 | A1 | 9/2012 | Milne et al. |
| 2012/0238585 | A1 | 9/2012 | Milne et al. |
| 2012/0238586 | A1 | 9/2012 | Milne et al. |
| 2012/0238756 | A1 | 9/2012 | Milne et al. |
| 2012/0277305 | A1 | 11/2012 | Milne et al. |
| 2013/0059801 | A1 | 3/2013 | Milne et al. |
| 2014/0221323 | A1 | 8/2014 | Milne et al. |
| 2014/0315786 | A1 | 10/2014 | Jirousek et al. |
| 2015/0099723 | A1 | 4/2015 | Milne et al. |

FOREIGN PATENT DOCUMENTS

| | | | |
|---|---|---|---|
| GB | 1581443 | A | 12/1980 |
| JP | S62223159 | A | 10/1987 |
| JP | 2004168024 | A | 6/2004 |
| WO | WO-86/03199 | A1 | 6/1986 |
| WO | WO-96/33155 | A1 | 10/1996 |
| WO | WO-96/34846 | A1 | 11/1996 |
| WO | WO-96/34855 | A1 | 11/1996 |
| WO | WO-96/34858 | A1 | 11/1996 |
| WO | WO-98/18751 | A1 | 5/1998 |
| WO | WO-01/45744 | A2 | 6/2001 |
| WO | WO-2006/066894 | A1 | 6/2006 |
| WO | WO-2007/116027 | A1 | 10/2007 |
| WO | WO-2009/138437 | A1 | 11/2009 |
| WO | WO-2011/089529 | A1 | 7/2011 |
| WO | WO-2012/003563 | A1 | 1/2012 |
| WO | WO-2013/175357 | A2 | 11/2013 |

OTHER PUBLICATIONS

Ferrari, R., The role of TNF in cardiovascular disease, 1999, Pharmacological Research, vol. 40, No. 2, pp. 97-105.*

Bays et al., "Eicosapentaenoic acid ethyl ester (AMR101) therapy in patients with very high triglyceride levels (from the multi-center, placebo-controlled, randomized, double-blind, 12-week study with an open label extension [MARINE] trial)" Am. J. Cardiol., 2011, 108(5):682-690.

Jacobson, "A new pure ω-3 eicosapentaenoic acid ethyl ester (AMR101) for the management of hypertriglyceridemia: the MARINE trial," Expert Rev.Cardiovasc.Ther., 2012, 10(6):687-695.

Mehta and deGoma, "Pharmacologic Interactions of Multidrug Therapy for Dyslipidemia," Curr. Atheroscler. Rep., 2013, 15(3):303.

Harris et al., "Omega-3 Fatty Acids and Coronary Heart Disease Risk: Clinical and Mechanistic Perspectives," Atherosclerosis, 2008, 197(1):12-24.

Gao et al., "Redox Regulation, NF-kB, and Atrial Fibrillation," Antioxid Redox Signal., 2009, 11(9) 2265-2277.

Ferrari, "The Role of TNF in Cardiovascular Disease," Pharmacol. Res., 1999, 40(2):97-105.

Beers et al., "Wild-Type Microglia Extend Survival in PU.1 Knockout Mice with Familial Amyotrophic Lateral Sclerosis," Proc. Natl. Acad. Sci. USA, 2006, 103(43): 16021-16026.

Marcora and Kennedy, "The Huntington's Disease Mutation Impairs Huntingtin's Role in the Transport of NF-•Bfrom the Synapse to the Nucleus," Hum. Mol. Genet., 2010, 19(22):4373-4384.

Ellrichmann et al., "Efficacy of Fumaric Acid Esters in the R6/2 and YAC128 Models of Huntington's Disease," PLoS One, 2011, 6(1):e16172.

Mattson and Meffert, "Roles for NF-•Bin Nerve Cell Survival, Plasticity and Disease," Cell Death Differ., 2006, 13(5):852-860.

Wahner et al., "Non-Steroidal Anti-Inflammatory Drugs may Protect against Parkinson's Disease," Neurology, 2007, 69(19): 1836-1842.

Irazurta et al., "Modulation of Nuclear Factor Kappa B Activation and Decreased Markers of Neurological Injury Associated with Hypothermic Therapy in Experimental Bacterial Meningitis," Crit. Care Med., 2002, 30(11): 2553-2559.

Pahan and Schmid, "Activation of Nuclear Factor Kappa B in the Spinal Cord of Experimental Allergic Encephalomyelitis," Neurosci. Lett., 2000, 287(1):17-20.

Dollard et al., "Activation of Nuclear Factor Kappa B in Brains from Children with HIV-I Encephalitis," Neuropathol. Appl. Neurobiol., 1995, 21(6): 518-528.

Rayavarapu et al., "Idiopathic Inflammatory Myopathies: Pathogenic Mechanisms of Muscle Weakness," Skelet. Muscle, 2013, 3:13.

Wyke and Tisdale et al., "NF-•BMediates Proteolysis-Inducing Factor Induced Protein Degradation and Expression of the Ubiquitin-Proteasome System in Skeletal Muscle" Br J Cancer, 2005, 92(4):711-21.

Jackman et al., "Nuclear Factor-κB Signaling and Transcriptional Regulation in Skeletal Muscle Atrophy" Exp. Physiol., 2013, 98(1):19-24.

"L-DOPA," Retrieved from: http://en.wikipedia.org/siki/levodopa (2008) (5 pages).

"Prodrug," Retrieved from: http://en.wikipedia.org/siki/prodrug (2008) (2 pages).

European Search Report for European Patent Application No. 14176625.3 dated Nov. 13, 2014 (5 pages).

Ferrucci, L. et al., "Relationship of plasma polyunsaturated fatty acids to circulating inflammatory markers," J. Clin. Endocrin. Metab., 2006, 91(2):439-446.

Han, H.-K. et al., "Targeted Prodrug Design to Optimize Drug Delivery," AAPS Pharm Sci, 2000, 2(1), Article 6, DOI 10.1208/ps020106 (11 pages).

Higdon, J. et al., "Essential Fatty acids", Linus Pauling Inst, Oregon State Univ., pp. 1-48 (2005).

International Search Report and Written Opinion for International Application No. PCT/US2009/049982, mailed Oct. 14, 2009.

Opposition filed by Chilean Pharmaceutical Labs Industrial Association in Chilean Patent Application No. 24-2011 dated Aug. 11, 2011 (English translation; 4 pages).

Zhu, D.-H. et al. "Synthesis of One N-Methylaminocarbamate Containing Disulfide Linkage," Huaxue Shiji, vol. 29, pp. 389-393, 2007.

Gerwick et al. "Phenolic Lipids From Related marine Algae of the Order Dictyotales" *Phytochemistry*, vol. 21, No. 3, pp. 633-637, 1982.

* cited by examiner

FATTY ACID ACETYLATED SALICYLATES AND THEIR USES

1. PRIORITY

This application is a continuation of U.S. patent application Ser. No. 13/427,639 filed Mar. 22, 2012, which claims the benefit of U.S. patent application Ser. No. 12/499,779 filed Jul. 8, 2009, which claims the benefit of U.S. Provisional Application No. 61/148,658, filed Jan. 30, 2009, U.S. Provisional Application No. 61/104,363, filed Oct. 10, 2008, U.S. Provisional Application No. 61/104,364, filed Oct. 10, 2008, U.S. Provisional Application No. 61/104,366, filed Oct. 10, 2008, and U.S. Provisional Application No. 61/078,983, filed Jul. 8, 2008. The entire disclosures of those applications are relied on and incorporated into this application by reference.

2. FIELD OF THE INVENTION

The invention relates to Fatty Acid Acetylated Salicylate Derivatives, Fatty Acid Acetylated Diflunisal Derivatives, and Fatty Acid Acetylated Triflusal Derivatives ("Compounds of the Invention"); compositions comprising an effective amount of a Fatty Acid Acetylated Salicylate Derivative, a Fatty Acid Acetylated Diflunisal Derivative, and/or a Fatty Acid Acetylated Triflusal Derivative ("Compound of the Invention"); and methods for treating or preventing an inflammatory disease comprising the administration of an effective amount of a Compound of the invention. All patents, patent applications and publications cited herein are hereby incorporated by reference in their entireties.

3. BACKGROUND OF THE INVENTION

Inflammatory pathways underlie the key pathophysiology of many chronic and acute diseases. Unresolved inflammation is important in many chronic disorders, including, but not limited to, heart disease, atherosclerosis, type 1 and type 2 diabetes, dyslipidemia, asthma, arthritis (including rheumatoid arthritis (RA)), osteoarthritis, cystic fibrosis, muscle wasting disease (including muscular dystrophy), pain, insulin resistance, oxidative stress, inflammatory bowel disease (IBD) (including colitis and Crohn's disease), and neurodegenerative disease (including Alzheimer's disease).

In more recent years, the study of inflammation has gone deeper into the cell. Cell-signaling molecules have been identified that modulate the expression of genes that control the inflammatory response, including the pro-inflammatory response and the anti-inflammatory response. One of the central regulators that balance the genes encoding anti- and proinflammation factors is Nuclear Factor Kappa Beta (NFκB). NFκB is a family of transcriptions factors that include p50 (NFκB1), p52 (NFκB2), p65 (RelA), c-Rel and RelB. These nuclear factors are held as complexes or dimeric pairs in an inactive state in the cytoplasm as a complex by a NFκB inhibitory factor IκB. The IκB proteins include IκBα, IκBβ, and IκBε, but others also exist. The inactive NFκB complex is released from the cytoplasm by phosphorylation of the IκB protein through kinases such as IKKβ. The kinases regulating NFκB activity are activated by immune responses or cellular stresses. Thus, in the cytoplasmic NFκB complex such as IkB/p65/p50, IkB becomes phosphorylated through kinases such as IKKβ and releases dimeric pairs of NFκB to the nucleus such as p65/p50. In the nucleus, NFκB regulates genetic expression of proinflammatory factors such as cytokines like TNFα, IL-6, and IL-1β in addition to enzymes such as cyclooxygenase-2 (COX-2) one of the enzymes that converts arachidonic acid to prostaglandin H2 (PGH2). These factors induce inflammation in various tissues. In addition, depending upon the cellular context and the NFκB nuclear factors released NFκB can cause the expression of anti-inflammatory genes.

Salicylates and other non-steroidal anti-inflammatory drugs (NSAIDs) can influence the NFκB pathway, allowing people to derive relief and reduced inflammation from these drugs. Aspirin and COX inhibitors act to reduce inflammation by reversibly or irreversibly blocking access to the hydrophobic channel via acetylation of serine 530 (COX-1) or Serine 516 (COX-2). For some selective NSAIDs with a carboxylate group, there is significant charge-charge interaction with Arginine 120. This binding or interaction blocks the cyclooxygenase enzyme that forms $PGH_2$. Salicylate does not irreversibly inhibit cyclooxygenase because it lacks the ability to acylate the COX enzyme and has little, if any, direct inhibitory action on the COX enzyme at concentrations that are relevant in vivo. Salicylate has been shown to inhibit the activity of IKKβ and thereby inhibit NFκB leading to reduced expression of COX-2 in an inflammatory state where COX-2 expression has been induced.

Another example of an NSAID is diflunisal:

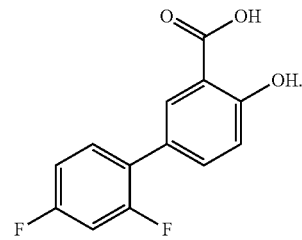 [SMILES: O=C(O)c1cc(-c2ccc(F)cc2F)ccc1O]

Yet another example of an NSAID is triflusal:

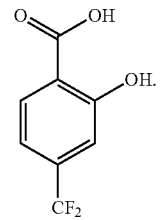

Diflunisal and Triflusal are commonly used to relieve pain, tenderness, swelling and stiffness caused by osteoarthritis and rheumatoid arthritis, and to relieve mild to moderate ain generally.

Problems arise in salicylate therapy due to side effects, which means alternative ways need to be developed and pursued to reduce NFκB activity. Some salicylates, when given orally, have a key disadvantage of causing gastric ulcers over the long term in chronic administration. In addition, salicylates can be strong irritants, thought to be caused by the high local concentration of these COX inhibitors. Many of the unwanted effects of aspirin are caused by the inappropriate inhibition of COX or the NFκB pathway. Although NSAIDs inhibit COX and are efficacious anti-inflammatory agents, adverse effects limit their use.

Other anti-inflammatory agents that modulate NFκB activity are omega-3 polyunsaturated fatty acids (PUFA). Omega-3 fatty acids also reduce IL-1, which is an activator of NFκB, and increase anti-inflammatory cytokines, such as IL-10, and adipokines, such as adiponectin. Oily cold water fish, such as salmon, trout, herring, and tuna are the source of dietary marine omega-3 fatty acids with eicosapentaenoic acid (EPA) and docosahexaenoic acid (DHA) being the key marine derived omega-3 fatty acids. Leafy green vegetables, and certain beans, nuts or oils, such as soybeans, walnuts, flaxseed, and canola oil, are also rich dietary sources of omega-3 fatty acids.

The anti-inflammatory effects of omega-3 fatty acids have been widely studied with positive results for several chronic inflammatory diseases. TNFα and IL-6 are cytokines that increase dramatically during inflammatory processes and are commonly measured as markers of inflammation. Greater intake of omega-3 PUFA has been shown to associate strongly with lower levels of circulating TNFα and IL-6 (Ferrucci et al., 2006). Furthermore, higher intake of omega-3 PUFA has also been associated with increased levels of markers of anttinflammation, including the well-characterized anti-inflammatory cytokine IL-10 (Ferruccci et al, 2006). Animal models of colitis indicate that fish oil decreases colonic damage and inflammation, weight loss, and mortality. Fish oil supplements in patients with IBD have shown to modulate levels of inflammatory mediators and may be beneficial for the induction and maintenance of remission in ulcerative colitis.

In the management of RA and other inflammatory conditions, side effects limit the use of NSAIDs. A clinical trial showed that 39 percent of patients with RA supplemented with cod liver oil were able to reduce their daily NSAID requirement by greater than 30 percent. Omega-3 fatty acids have been used to reduce the risk for sudden death caused by cardiac arrhythmias, have been taken as dietary supplements and the ethyl ester of omega-3 fatty acids as a combination therapy is used to treat dyslipidemia.

Furthermore, omega-3 fatty acids have been shown to improve insulin sensitivity and glucose tolerance in normoglycemic men and in obese individuals. Omega-3 fatty acids have also been shown to improve insulin resistance in obese and non-obese patients with an inflammatory phenotype. Lipid, glucose and insulin metabolism have been show to be improved in overweight hypertensive subjects through treatment with omega-3 fatty acids.

DHA or EPA, C22 and C20 omega-3 fatty acids, are metabolized to active anti-inflammatory metabolites, some of which include resolvins and protectins, and activate various anti-inflammatory pathways.

The ability to simultaneously blunt proinflammatory pathways, for example those that affect levels of C-reactive protein (CRP), TNFα and IL-6 cytokines, while stimulating anti-inflammatory pathways by shunting omega-3 fatty acids, such as DHA and EPA, into metabolic pathways that ultimately produce resolvins, protectins and other metabolites that resolve inflammation would be a great benefit in treating the aforementioned diseases. Inflammation could be particularly vulnerable to a two-pronged attack, inhibiting pro-inflammatory pathways and upregulating anti-inflammatory pathways.

4. SUMMARY OF THE INVENTION

The invention is based in part on the discovery of Fatty Acid Acetylated Salicylate Derivatives and their demonstrated effects in the simultaneous upregulation of anti-inflammatory pathways and down regulation of proinflammatory pathways. The invention is also based in part on the discovery of Fatty Acid Acetylated Diflunisal Derivatives and their upregulation of anti-inflammatory pathways and down regulation of proinflammatory pathways. Additionally, the invention is based in part on the discovery of Fatty Acid Acetylated Triflusal Derivatives and their upregulation of anti-inflammatory pathways and down regulation of proinflammatory pathways. These novel compounds are useful in the treatment or prevention of diseases associated with inflammation.

Accordingly, in one aspect, compounds of the Formula I are described:

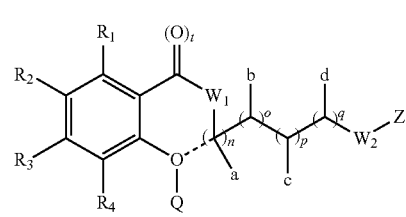

Formula I and pharmaceutically acceptable salts, hydrates, solvates, prodrugs, enantiomers, and stereoisomers thereof;

wherein $R_1, R_2, R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2C_1$-$C_3$ alkyl;

$W_1$ and $W_2$ are each independently null, O, or NH, or when $W_1$ and $W_2$ are both NH, then both $W_1$ and $W_2$ can be taken together to form a piperidine moiety;

- - - - - represents an optional bond that when present requires that Q is null;

a and c are each independently H, $CH_3$, —$OCH_3$, —$OCH_2CH_3$, or C(O)OH;

b is H, $CH_3$, C(O)OH, or O—Z;

d is H or C(O)OH;

each n, o, p, and q is independently 0 or 1;

each Z is H or

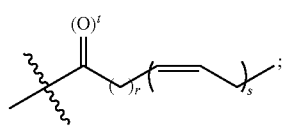

with the proviso that there is at least one

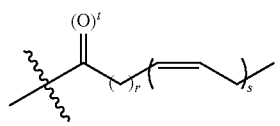

in the compound;

each r is independently 2 or 3;

each s is independently 5 or 6;

each t is independently 0 or 1;

Q is null, C(O)CH₃, Z,

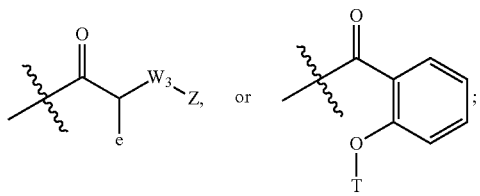

e is H or any one of the side chains of the naturally occurring amino acids;
W₃ is null, —O—, or —N(R)—;
R is H or C₁-C₃ alkyl; and
T is H, C(O)CH₃, or Z.

In another aspect, compounds of the Formula Ia are described:

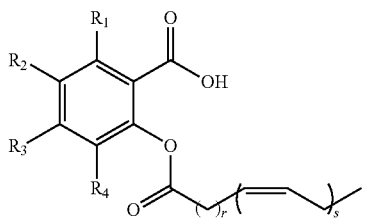

Formula Ia and pharmaceutically acceptable salts, hydrates, solvates, prodrugs, enantiomers, and stereoisomers thereof;
wherein
R₁, R₂, R₃, and R₄ are each independently selected from the group consisting of H, Cl, F, CN, NH₂, —NH(C₁-C₃ alkyl), —N(C₁-C₃ alkyl)₂, —NH(C(O)C₁-C₃ alkyl), —N(C(O)C₁-C₃ alkyl)₂, —C(O)H, —C(O)C₁-C₃ alkyl, —C(O)OC₁-C₃ alkyl, —C(O)NH₂, —C(O)NH(C₁-C₃ alkyl), —C(O)N(C₁-C₃ alkyl)₂, —C₁-C₃ alkyl, —O—C₁-C₃ alkyl, —S(O)C₁-C₃ alkyl, and —S(O)₂C₁-C₃ alkyl;
r is 2 or 3; and
s is 5 or 6.

In another aspect compounds of the Formula Ib are described:

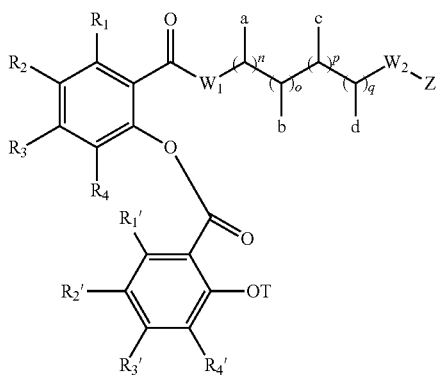

Formula Ib and pharmaceutically acceptable salts, hydrates, solvates, prodrugs, enantiomers, and stereoisomers thereof;

wherein
R₁, R₂, R₃, R₄, R₁', R₂', R₃', and R₄' are each independently selected from the group consisting of H, Cl, F, CN, NH₂, —NH(C₁-C₃ alkyl), —N(C₁-C₃ alkyl)₂, —NH(C(O)C₁-C₃ alkyl), —N(C(O)C₁-C₃ alkyl)₂, —C(O)H, —C(O)C₁-C₃ alkyl, —C(O)OC₁-C₃ alkyl, —C(O)NH₂, —C(O)NH(C₁-C₃ alkyl), —C(O)N(C₁-C₃ alkyl)₂, —C₁-C₃ alkyl, —O—C₁-C₃ alkyl, —S(O)C₁-C₃ alkyl, and —S(O)₂C₁-C₃ alkyl;
W₁ and W₂ are each independently null, O, or NH, or when W₁ and W₂ are both NH, then both W₁ and W₂ can be taken together to form a piperidine moiety;
a and c are each independently H, CH₃, —OCH₃, —OCH₂CH₃, or C(O)OH;
b is H, CH₃, C(O)OH, or O—Z;
d is H or C(O)OH;
each of n, o, p, and q is independently 0 or 1;
each Z is H or

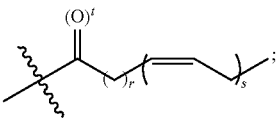

with the proviso that there is at least one

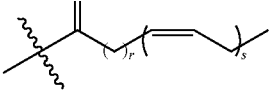

in the compound;
each r is independently 2 or 3;
each s is independently 5 or 6;
each t is 0 or 1; and
T is H, C(O)CH₃, or Z.

In another aspect compounds of the Formula Ic are described:

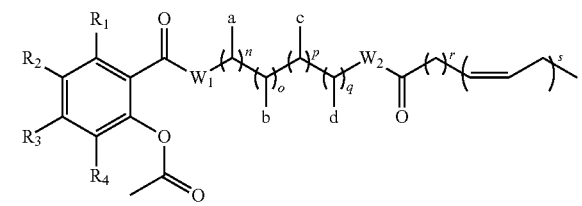

Formula Ic and pharmaceutically acceptable salts, hydrates, solvates, enantiomers, and stereoisomers thereof,
wherein
R₁, R₂, R₃, and R₄ are each independently selected from the group consisting of H, Cl, F, CN, NH₂, —NH(C₁-C₃ alkyl), —N(C₁-C₃ alkyl)₂, —NH(C(O)C₁-C₃ alkyl), —N(C(O)C₁-C₃ alkyl)₂, —C(O)H, —C(O)C₁-C₃ alkyl, —C(O)OC₁-C₃ alkyl, —C(O)NH₂, —C(O)NH(C₁-C₃ alkyl), —C(O)N(C₁-C₃ alkyl)₂, —C₁-C₃ alkyl, —O—C₁-C₃ alkyl, —S(O)C₁-C₃ alkyl, and —S(O)₂C₁-C₃ alkyl;
W₁ and W₂ are each independently null, O, or NH, or when W₁ and W₂ are both NH, then both W₁ and W₂ can be taken together to form a piperidine moiety;

a and c are each independently H, CH$_3$, —OCH$_3$, —OCH$_2$CH$_3$, or C(O)OH;

b is H, CH$_3$, C(O)OH, or O—Z;

d is H or C(O)OH;

n, o, p, and q are each independently 0 or 1;

Z is H, or

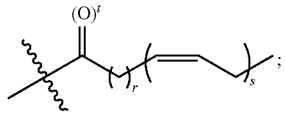

each r is independently 2 or 3;

each s is independently 5 or 6; and t is 0 or 1.

In another aspect, compounds of the Formula Id are described:

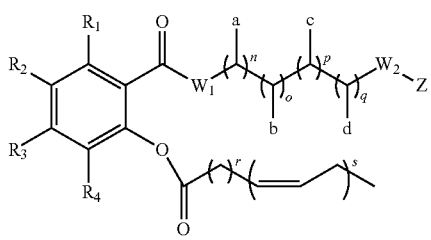

Formula Id and pharmaceutically acceptable salts, hydrates, solvates, prodrugs, enantiomers, and stereoisomers thereof;

wherein

R$_1$, R$_2$, R$_3$, and R$_4$ are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, and —S(O)$_2$C$_1$-C$_3$ alkyl;

W$_1$ and W$_2$ are each independently null, O, or NH, or when W$_1$ and W$_2$ are both NH, then both W$_1$ and W$_2$ can be taken together to form a piperidine moiety;

a and c are each independently H, CH$_3$, —OCH$_3$, —OCH$_2$CH$_3$, or C(O)OH;

b is H, CH$_3$, C(O)OH, or O—Z;

d is H or C(O)OH;

n, o, p, and q are each independently 0 or 1;

Z is H, or

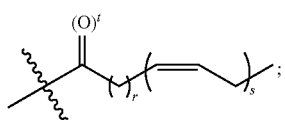

each r is independently 2 or 3;

each s is independently 5 or 6; and each t is independently 0 or 1.

In another aspect, compounds of the Formula Ie are described:

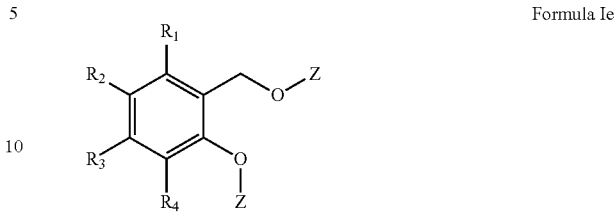

Formula Ie and pharmaceutically acceptable salts, hydrates, solvates, prodrugs, enantiomers, and stereoisomers thereof;

wherein

R$_1$, R$_2$, R$_3$, and R$_4$ are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, and —S(O)$_2$C$_1$-C$_3$ alkyl;

each Z is independently H, —C(O)CH$_3$ or

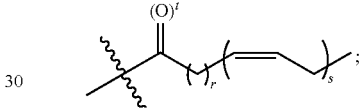

with the proviso that there is at least one

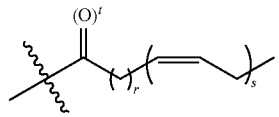

in the compound;

each r is independently 2 or 3;

each s is independently s is 5 or 6; and each t is independently 0 or 1.

In another aspect, compounds of the Formula If are described:

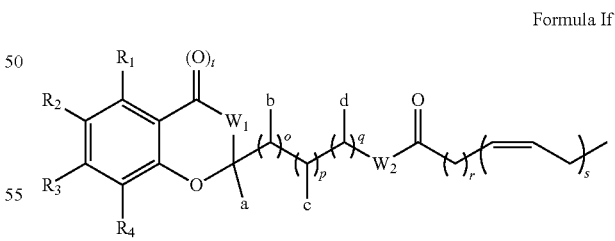

Formula If and pharmaceutically acceptable salts, hydrates, solvates, prodrugs, enantiomers, and stereoisomers thereof;

wherein

R$_1$, R$_2$, R$_3$, and R$_4$ are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, and —S(O)$_2$C$_1$-C$_3$ alkyl;

$W_1$ is O, or NH;
$W_2$ is null, O, or NH;
a and c are each independently H, $CH_3$, —$OCH_3$, —$OCH_2CH_3$, or C(O)OH;
b is H, $CH_3$, C(O)OH, or O—Z;
d is H or C(O)OH;
Z is H, or

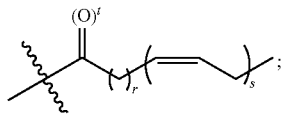

each o, p, and q is independently 0 or 1;
each r is independently 2 or 3;
each s is independently 5 or 6; and
each t is independently 0 or 1.

In another aspect, compounds of the Formula Ig are described:

Formula Ig

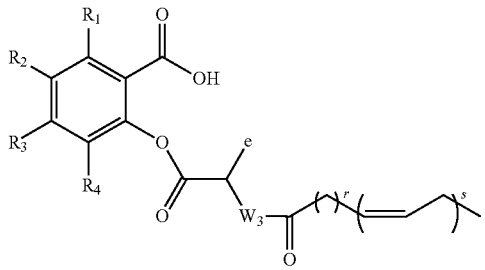

and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;
$W_3$ is null, O, or NR;
R is H or $C_1$-$C_3$ alkyl;
e is H or any one of the side chains of the naturally occurring amino acids;
r is 2 or 3; and
s is 5 or 6.

In another aspect, compounds of the Formula II are described:

Formula II

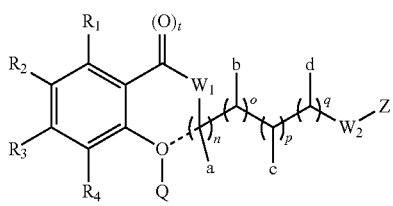

and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;

$W_1$ and $W_2$ are each independently null, O, or NH, or when $W_1$ and $W_2$ are both NH, then both $W_1$ and $W_2$ can be taken together to form a piperidine moiety;

- - - - - represents an optional bond that when present requires that Q is then null;

a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
each Z is H or

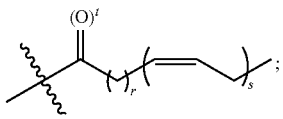

with the proviso that there is at least one

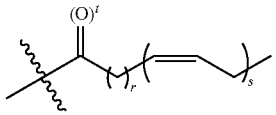

in the compound;
each r is independently 7;
each s is independently 3;
each t is independently 0 or 1;
Q is null, H, C(O)$CH_3$, Z,

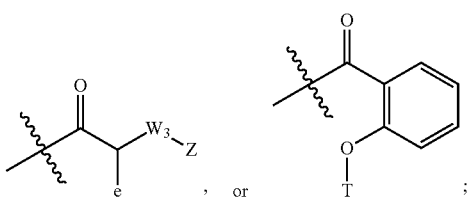

e is H or any one of the side chains of the naturally occurring amino acids;
$W_3$ is null, —O—, or —N(R)—;
R is H or $C_1$-$C_3$ alkyl; and
T is H, C(O)$CH_3$, or Z.

In another aspect, compounds of the Formula III are described:

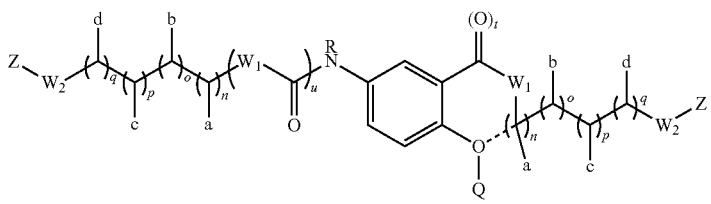 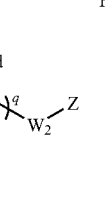

Formula III and pharmaceutically acceptable salts, hydrates, solvates, prodrugs, enantiomers, and stereoisomers thereof;
wherein
each $W_1$ and $W_2$ are independently null, O, or NH, or when $W_1$ and $W_2$ are both NH, then both $W_1$ and $W_2$ can be taken together to form a piperidine moiety;
- - - - - represents an optional bond that when present requires that Q is null;
each a and c are independently H, $CH_3$, —$OCH_3$, —$OCH_2CH_3$, or C(O)OH;
each b is H, $CH_3$, C(O)OH, or O—Z;
each d is H or C(O)OH;
each n, o, p, and q is independently 0 or 1;
each Z is H or

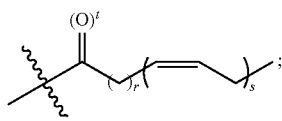

with the proviso that there is at least one

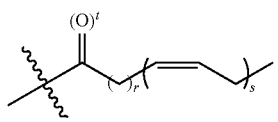

in the compound;
each r is independently 2, 3, or 7;
each s is independently 3, 5, or 6;
each t is independently 0 or 1;
u is 0 or 1;
with the proviso that when r is 7, s is 3;
Q is null, C(O)$CH_3$, Z,

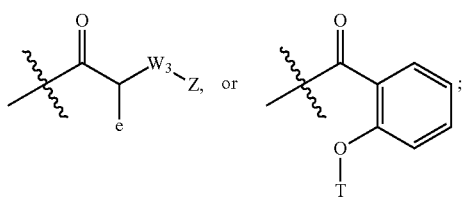

e is H or any one of the side chains of the naturally occurring amino acids;
$W_3$ is null, —O—, or —N(R)—;
R is H or $C_1$-$C_3$ alkyl; and
T is H, C(O)$CH_3$, or Z.

In yet another aspect, compounds of the Formula IIIa are described:

Formula IIIa

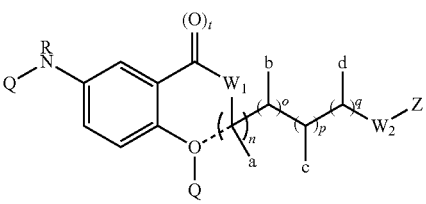

and pharmaceutically acceptable salts, hydrates, solvates, prodrugs, enantiomers, and stereoisomers thereof;
wherein
each $W_1$ and $W_2$ are independently null, O, or NH, or when $W_1$ and $W_2$ are both NH, then both $W_1$ and $W_2$ can be taken together to form a piperidine moiety;
- - - - - represents an optional bond that when present requires that Q is null;
each a and c are independently H, $CH_3$, —$OCH_3$, —$OCH_2CH_3$, or C(O)OH;
each b is H, $CH_3$, C(O)OH, or O—Z;
each d is H or C(O)OH;
each n, o, p, and q is independently 0 or 1;
each Z is H or

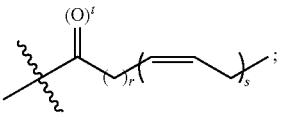

with the proviso that there is at least one

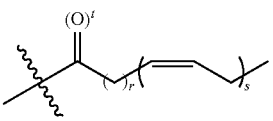

in the compound;
each r is independently 2, 3, or 7;
each s is independently 3, 5, or 6;
each t is independently 0 or 1;
with the proviso that when r is 7, s is 3;

each Q is null, H, C(O)CH$_3$, Z,

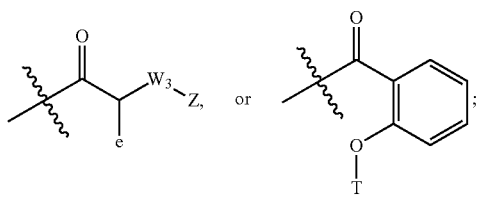

each e is H or any one of the side chains of the naturally occurring amino acids;
W$_3$ is null, —O—, or —N(R)—;
R is H or C$_1$-C$_3$ alkyl; and
T is H, C(O)CH$_3$, or Z.
In another aspect, compounds of Formula IV are described herein:

Formula IV

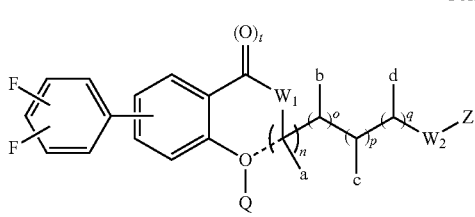

and pharmaceutically acceptable salts, hydrates, solvates, prodrugs, enantiomers, and stereoisomers thereof;
wherein
W$_1$ and W$_2$ are each independently null, O, or NH;
- - - - - represents an optional bond that when present requires that Q is null;
a and c are each independently H, CH$_3$, —OCH$_3$, —OCH$_2$CH$_3$, or C(O)OH;
b is H, CH$_3$, C(O)OH, or O—Z;
d is H or C(O)OH;
each n, o, p, and q is independently 0 or 1;
each Z is H or

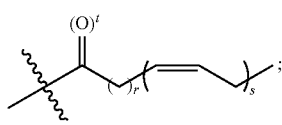

with the proviso that there is at least one

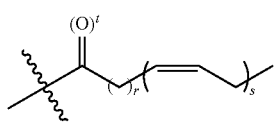

in the compound;
each r is independently 2 or 3;
each s is independently 5 or 6;
each t is independently 0 or 1;

Q is null, C(O)CH$_3$, Z, or

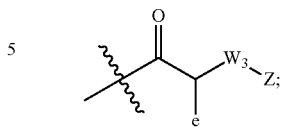

e is H, —C(O)OH, or any one of the side chains of the naturally occurring amino acids;
W$_3$ is null, —O—, —N(R)—; and
R is H or C$_1$-C$_3$ alkyl.
In another aspect, compounds of the Formula IVa are described:

Formula IVa

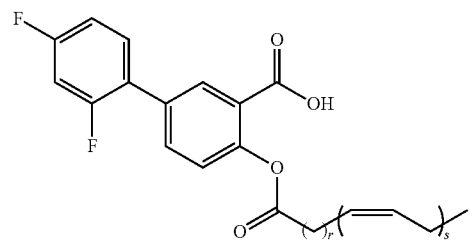

and pharmaceutically acceptable salts, hydrates, solvates, prodrugs, enantiomers, and stereoisomers thereof;
wherein
r is 2 or 3; and
s is 5 or 6.
In another aspect, compounds of the Formula IVb are described:

Formula IVb

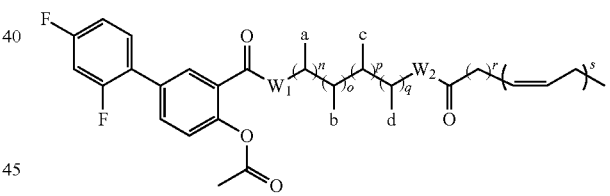

and pharmaceutically acceptable salts, hydrates, solvates, enantiomers, and stereoisomers thereof,
wherein
W$_1$ and W$_2$ are each independently null, O, or NH;
a and c are each independently H, CH$_3$, —OCH$_3$, —OCH$_2$CH$_3$, or C(O)OH;
b is H, CH$_3$, C(O)OH, or O—Z;
d is H or C(O)OH;
each n, o, p, and q is independently 0 or 1;
Z is H or

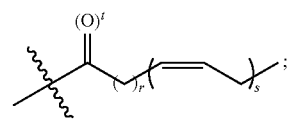

each r is independently 2 or 3;
each s is independently 5 or 6; and
t is 0 or 1.

In another aspect, compounds of the Formula IVc are described:

Formula IVc and pharmaceutically acceptable salts, hydrates, solvates, prodrugs, enantiomers, and stereoisomers thereof;

wherein $W_1$ and $W_2$ are each independently null, O, or NH;

a and c are each independently H, $CH_3$, —$OCH_3$, —$OCH_2CH_3$, or C(O)OH;

b is H, $CH_3$, C(O)OH, or O—Z;

d is H or C(O)OH;

each of n, o, p, and q is independently 0 or 1;

each Z is independently null, H, or with the proviso that there is at least one in the compound;

each r is independently 2 or 3;

each s is independently 5 or 6; and each t is independently 0 or 1.

In another aspect, compounds of the Formula IVd are described:

Formula IVd and pharmaceutically acceptable salts, hydrates, solvates, prodrugs, enantiomers, and stereoisomers thereof;

wherein each Z is independently null, H, or with the proviso that there is at least one in the compound;

each r is independently 2 or 3;

each s is independently s is 5 or 6; and each t is independently 0 or 1.

In another aspect, compounds of the Formula IVe are described:

Formula IVe and pharmaceutically acceptable salts, hydrates, solvates, prodrugs, enantiomers, and stereoisomers thereof;

wherein $W_1$ is O, or NH;

$W_2$ is null, O, or NH;

a and c are each independently H, $CH_3$, —$OCH_3$, —$OCH_2CH_3$, or C(O)OH;

b is H, $CH_3$, C(O)OH, or O—Z;

d is H or C(O)OH;

each o, p, and q is independently 0 or 1;

Z is H or each r is independently 2 or 3;

each s is independently 5 or 6; and each t is independently 0 or 1.

In another aspect, compounds of the Formula IVf are described:

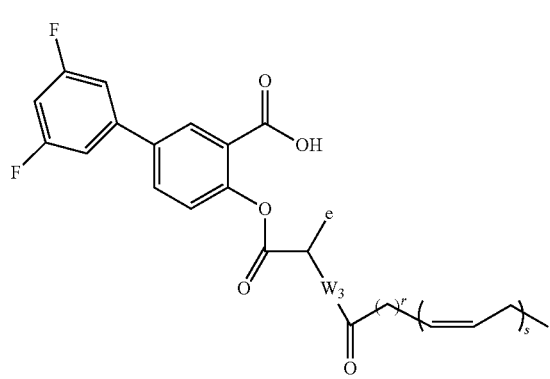

Formula IVf and pharmaceutically acceptable salts, hydrates, solvates, prodrugs, enantiomers, and stereoisomers thereof;
wherein
e is H, —C(O)OH or any one of the side chains of the naturally occurring amino acids;
$W_3$ is null, —O—, —N(R)—; and
R is H or $C_1$-$C_3$ alkyl,
r is 2 or 3; and
s is 5 or 6.

In another aspect, compounds of the Formula IVg are described:

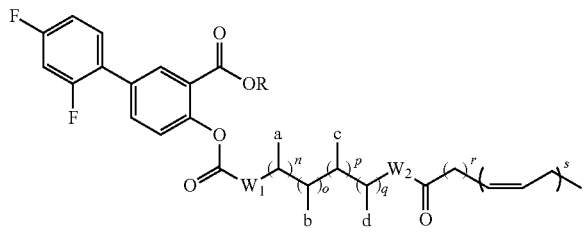

Formula IVg and pharmaceutically acceptable salts, hydrates, solvates, prodrugs, enantiomers, and stereoisomers thereof;
wherein
R is H or $C_1$-$C_3$ alkyl;
$W_1$ and $W_2$ are each independently null, O, or NH;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
Z is H or

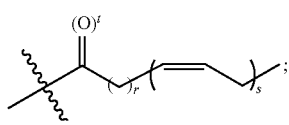

each r is independently 2 or 3;
each s is independently 5 or 6; and
each t is independently 0 or 1.

In still another aspect, compounds of the Formula V are described:

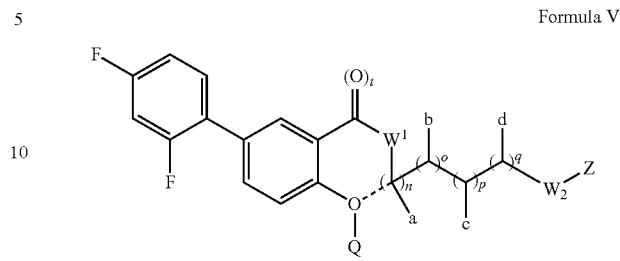

Formula V and pharmaceutically acceptable salts, hydrates, solvates, prodrugs, enantiomers, and stereoisomers thereof;
wherein
$W_1$ and $W_2$ are each independently null, O, or NH;
- - - - - represents an optional bond that when present requires that Q is then null;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
each Z is independently null, H, or

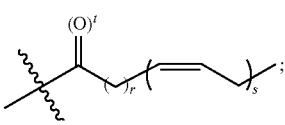

with the proviso that there is at least one

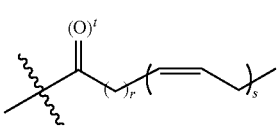

in the compound;
each r is independently 7;
each s is independently 3;
each t is independently 0 or 1;
Q is null, C(O)$CH_3$, Z, or

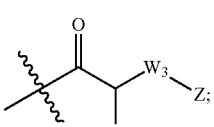

and
$W_3$ is null, —O—, —N(R)—;
R is H or $C_1$-$C_3$ alkyl and
e is H, —C(O)OH or any one of the side chains of the naturally occurring amino acids.

In yet another aspect, compounds of the Formula VI are described:

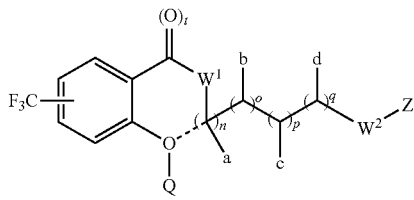

Formula VI and pharmaceutically acceptable salts, hydrates, solvates, prodrugs, enantiomers, and stereoisomers thereof;
wherein
$W_1$ and $W_2$ are each independently null, O, or NH;
- - - - - represents an optional bond that when present requires that Q is null;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
each Z is H or

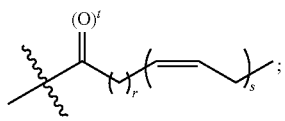

with the proviso that there is at least one

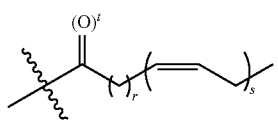

in the compound;
each r is independently 0, 1, 2 or 3;
each s is independently an integer from 1 to 10;
each t is independently 0 or 1;
Q is null, $C(O)CH_3$, Z, or

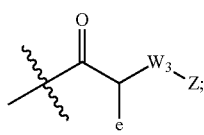

e is H, —C(O)OH, or any one of the side chains of the naturally occurring amino acids;
$W_3$ is null, —O—, —N(R)—; and
R is H or $C_1$-$C_3$ alkyl.

In another aspect, compounds of the Formula VIa are described:

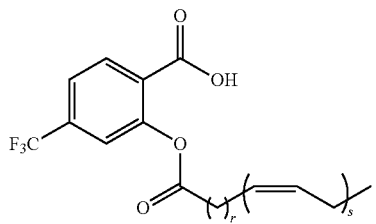

Formula VIa and pharmaceutically acceptable salts, hydrates, solvates, prodrugs, enantiomers, and stereoisomers thereof;
wherein
r is 2 or 3; and
s is independently 5 or 6.

In another aspect, compounds of the Formula VIb are described:

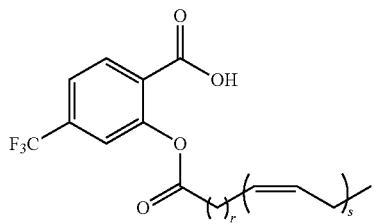

Formula VIb and pharmaceutically acceptable salts, hydrates, solvates, enantiomers, and stereoisomers thereof,
wherein
$W_1$ and $W_2$ are each independently null, O, or NH;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
Z is H or

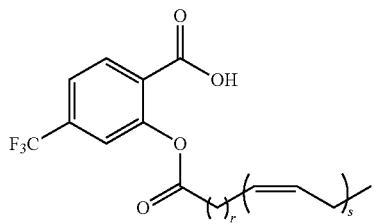

each r is independently 2 or 3;
each s is independently 5 or 6; and
each t is independently 0 or 1.

In another aspect, compounds of the Formula VIc are described:

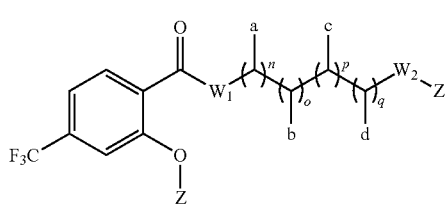

Formula VIc and pharmaceutically acceptable salts, hydrates, solvates, prodrugs, enantiomers, and stereoisomers thereof;

wherein
W₁ and W₂ are each independently null, O, or NH;
a and c are each independently H, CH₃, —OCH₃, —OCH₂CH₃, or C(O)OH;
b is H, CH₃, C(O)OH, or O—Z;
d is H or C(O)OH;
each of n, o, p, and q is independently 0 or 1;
each Z is independently null, H, or

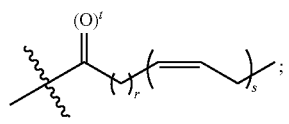

with the proviso that at least one Z is

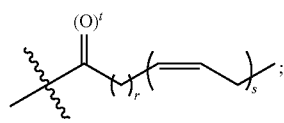

each r is independently 2 or 3;
each s is independently 5 or 6; and
each t is independently 0 or 1.

In another aspect, compounds of the Formula VId are described:

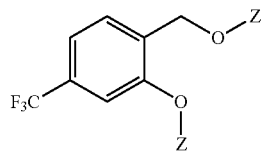

Formula VId and pharmaceutically acceptable salts, hydrates, solvates, prodrugs, enantiomers, and stereoisomers thereof;
wherein
each Z is independently H, —C(O)CH₃ or

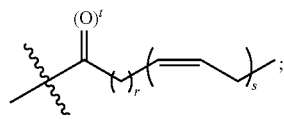

with the proviso that at least one Z is

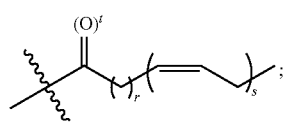

each r is independently 2 or 3;
each s is independently 5 or 6; and
each t is independently 0 or 1.

In another aspect, compounds of the Formula VIe are described:

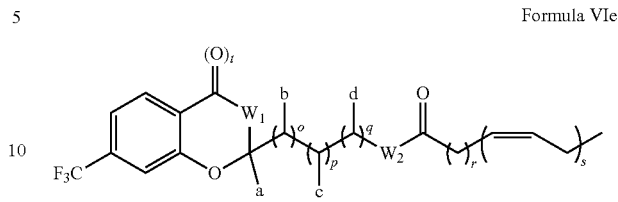

Formula VIe and pharmaceutically acceptable salts, hydrates, solvates, prodrugs, enantiomers, and stereoisomers thereof;
wherein
W₁ is O, or NH;
W₂ is null, O, or NH;
a and c are each independently H, CH₃, —OCH₃, —OCH₂CH₃, or C(O)OH;
b is H, CH₃, C(O)OH, or O—Z;
d is H or C(O)OH;
each o, p, and q is independently 0 or 1;
Z is H or

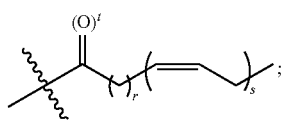

each r is independently 2 or 3;
each s is independently 5 or 6; and
t is independently 0 or 1.

In another aspect, compounds of the Formula VIf are described:

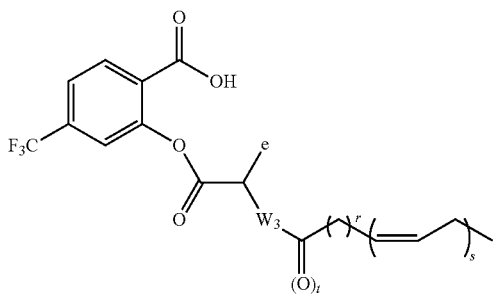

Formula VIf and pharmaceutically acceptable salts, hydrates, solvates, prodrugs, enantiomers, and stereoisomers thereof;
wherein
e is H, —C(O)OH or any one of the side chains of the naturally occurring amino acids;
W₃ is null, —O—, —N(R)—; and
R is H or C₁-C₃ alkyl,
r is 2 or 3;
s is 5 or 6; and
t is 0 or 1.

In another aspect, compounds of the Formula VIg are described:

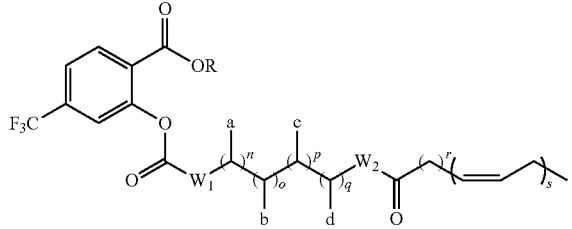

Formula VIg and pharmaceutically acceptable salts, hydrates, solvates, prodrugs, enantiomers, and stereoisomers thereof;
wherein
R is H or $C_1$-$C_3$ alkyl;
$W_1$ and $W_2$ are each independently null, O, or NH;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
Z is H or

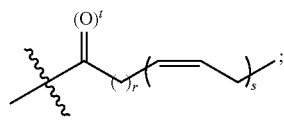

each r is independently 2 or 3;
each s is independently 5 or 6; and
each t is independently 0 or 1.

In another aspect, compounds of the Formula VII are described:

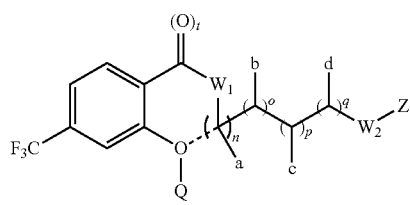

Formula VII and pharmaceutically acceptable salts, hydrates, solvates, prodrugs, enantiomers, and stereoisomers thereof;
wherein
$W_1$ and $W_2$ are each independently null, O, or NH;
- - - - - represents an optional bond that when present requires that Q is then null;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;

each Z is H or

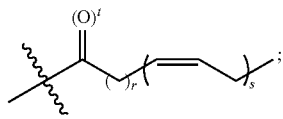

with the proviso that there is at least one

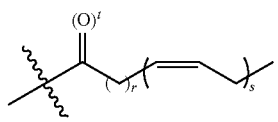

in the compound;
each r is independently 7;
each s is independently 3;
each t is independently 0 or 1;
Q is null, C(O)$CH_3$, Z, or

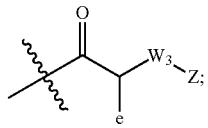

and
$W_3$ is null, —O—, —N(R)—;
R is H or $C_1$-$C_3$ alkyl; and
e is H, —C(O)OH or any one of the side chains of the naturally occurring amino acids.

In a further aspect, compounds of the Formula I' are described:

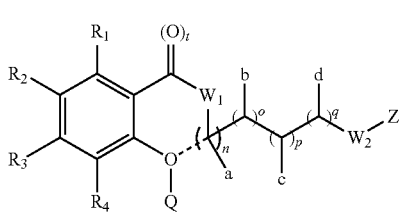

Formula I' and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;
$W_1$ and $W_2$ are each independently null, O, or NH, or when $W_1$ and $W_2$ are both NH, then both $W_1$ and $W_2$ can be taken together to form a piperidine moiety;
- - - - - represents an optional bond that when present requires that Q is null;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;

each Z is H,

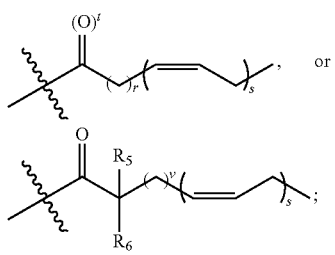, or

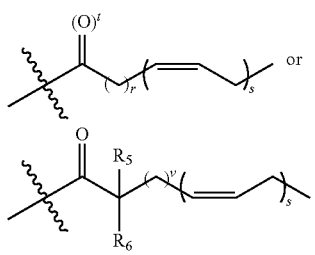;

with the proviso that there is at least one

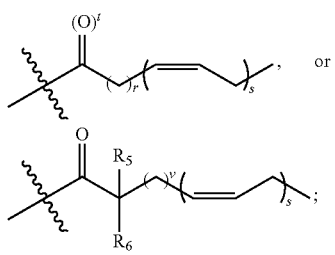, or

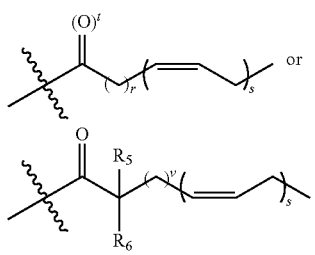

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;
Q is null, C(O)CH$_3$, Z,

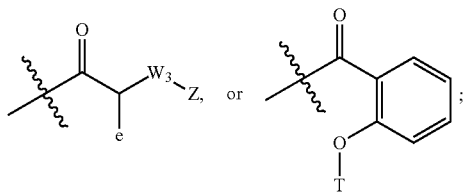

e is H or any one of the side chains of the naturally occurring amino acids;
$W_3$ is null, —O—, or —N(R)—;
R is H or $C_1$-$C_3$ alkyl; and
T is H, C(O)CH$_3$, or Z.

In another aspect, compounds of the Formula Ia' are described:

Formula Ia'

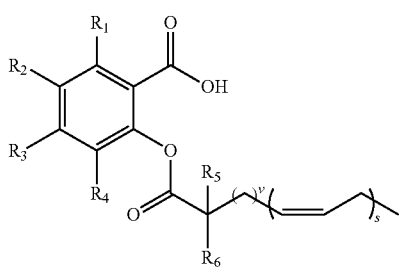

and pharmaceutically acceptable salts, hydrates, solvates, prodrugs, enantiomers, and stereoisomers thereof;

wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;
s is 5 or 6;
v is 1 or 2; and
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In another aspect compounds of the Formula Ib' are described:

Formula Ib'

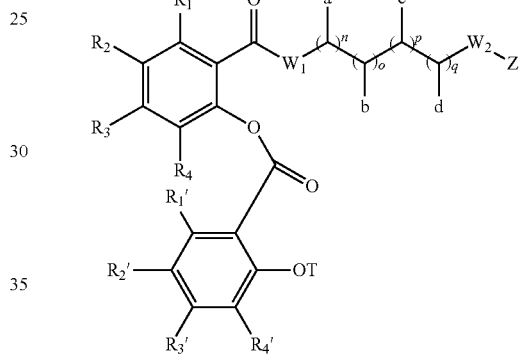

and pharmaceutically acceptable salts, hydrates, solvates, prodrugs, enantiomers, and stereoisomers thereof;
wherein
$R_1$, $R_2$, $R_3$, $R_4$, $R_1'$, $R_2'$, $R_3'$, and $R_4'$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;
$W_1$ and $W_2$ are each independently null, O, or NH, or when $W_1$ and $W_2$ are both NH, then both $W_1$ and $W_2$ can be taken together to form a piperidine moiety;
a and c are each independently H, $CH_3$, —OCH$_3$, —OCH$_2$CH$_3$, or C(O)OH;
b is H, $CH_3$, C(O)OH, or O—Z;
d is H or C(O)OH;
each of n, o, p, and q is independently 0 or 1;
each Z is H,

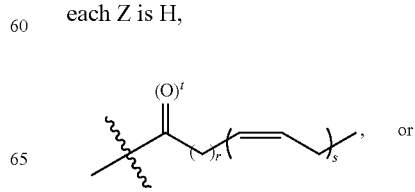, or

-continued

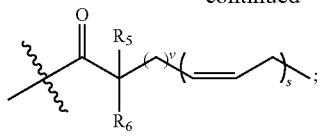

with the proviso that there is at least one

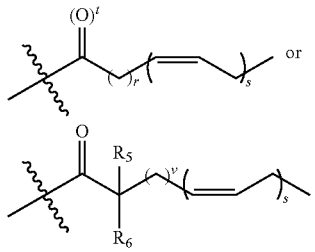

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and
T is H, C(O)CH$_3$, or Z.

In another aspect compounds of the Formula Ic' are described:

Formula Ic'

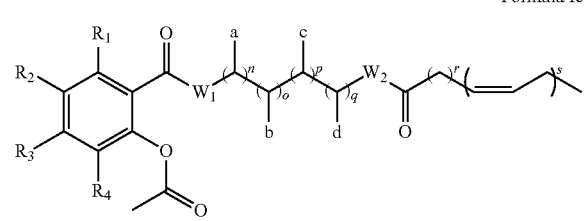

and pharmaceutically acceptable salts, hydrates, solvates, enantiomers, and stereoisomers thereof,
wherein
$R_1$, $R_2$, $R_3$, and $R_4$ are each independently selected from the group consisting of H, Cl, F, CN, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)NH$_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;
$W_1$ and $W_2$ are each independently null, O, or NH, or when $W_1$ and $W_2$ are both NH, then both $W_1$ and $W_2$ can be taken together to form a piperidine moiety;
a and c are each independently H, CH$_3$, —OCH$_3$, —OCH$_2$CH$_3$, or C(O)OH;
b is H, CH$_3$, C(O)OH, or O—Z;
d is H or C(O)OH;
n, o, p, and q are each independently 0 or 1;

each Z is H,

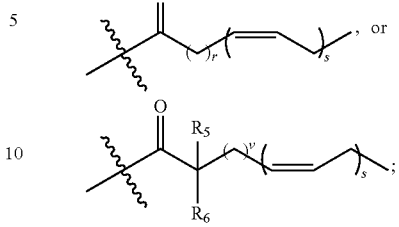

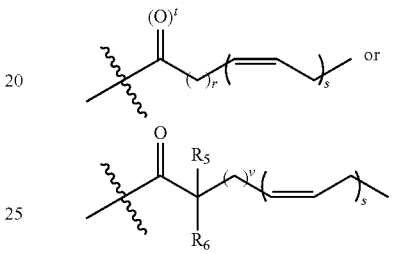

with the proviso that there is at least one

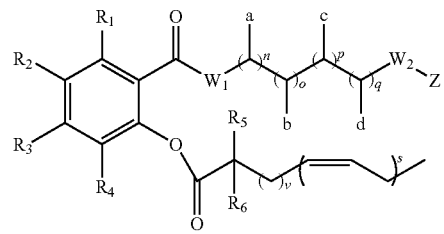

in the compound;
each r is independently 2 or 3;
each s is independently 5 or 6;
each t is independently 0 or 1;
each v is 1 or 2; and
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In another aspect, compounds of the Formula Id' are described:

Formula Id'

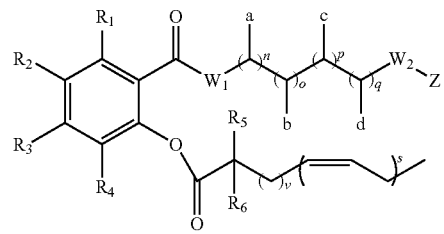

and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)NH$_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;
$W_1$ and $W_2$ are each independently null, O, or NH, or when $W_1$ and $W_2$ are both NH, then both $W_1$ and $W_2$ can be taken together to form a piperidine moiety;

a and c are each independently H, CH$_3$, —OCH$_3$, —OCH$_2$CH$_3$, or C(O)OH;
b is H, CH$_3$, C(O)OH, or O—Z;
d is H or C(O)OH;
n, o, p, and q are each independently 0 or 1;
each Z is H,

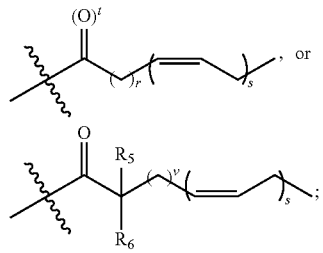, or

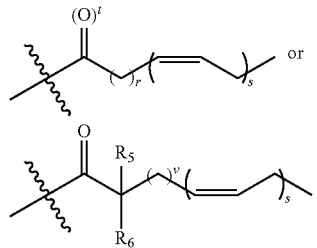;

with the proviso that there is at least one

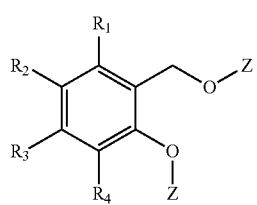

in the compound;
each r is independently 2 or 3;
each s is independently 5 or 6;
each t is independently 0 or 1;
each v is 1 or 2; and
R$_5$ and R$_6$ are each independently hydrogen, deuterium, C$_1$-C$_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl.

In another aspect, compounds of the Formula Ie' are described:

Formula Ie'

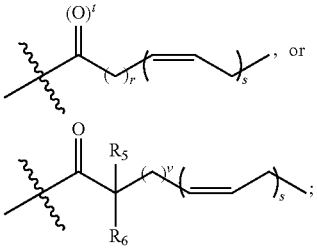

and pharmaceutically acceptable salts, hydrates, solvates, prodrugs, enantiomers, and stereoisomers thereof;
wherein
R$_1$, R$_2$, R$_3$, and R$_4$ are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, and —S(O)$_2$C$_1$-C$_3$ alkyl;
each Z is independently H, —C(O)CH$_3$,

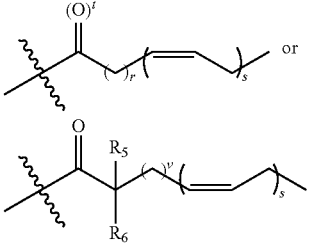, or with the proviso that there is at least one in the compound;
each r is independently 2 or 3;
each s is independently s is 5 or 6; and
each t is independently 0 or 1
each v is 1 or 2; and
R$_5$ and R$_6$ are each independently hydrogen, deuterium, C$_1$-C$_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl.

In another aspect, compounds of the Formula If' are described:

Formula If' and pharmaceutically acceptable salts, hydrates, solvates, prodrugs, enantiomers, and stereoisomers thereof;
wherein
R$_1$, R$_2$, R$_3$, and R$_4$ are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, and —S(O)$_2$C$_1$-C$_3$ alkyl;

$W_1$ is O, or NH;

$W_2$ is null, O, or NH;

a and c are each independently H, $CH_3$, —$OCH_3$, —$OCH_2CH_3$, or C(O)OH;

b is H, $CH_3$, C(O)OH, or O—Z;

d is H or C(O)OH;

each o, p, and q is independently 0 or 1;

each Z is H,

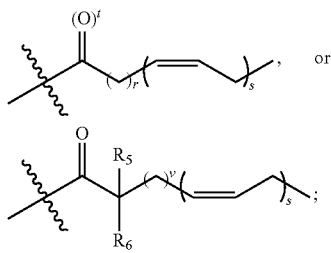

with the proviso that there is at least one

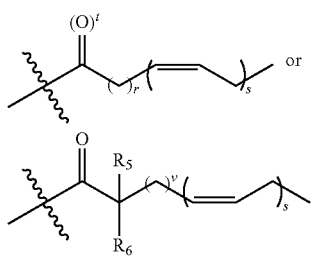

in the compound;

each r is independently 2 or 3;

each s is independently 5 or 6;

each t is independently 0 or 1;

each v is 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In another aspect, compounds of the Formula Ig' are described:

Formula Ig'

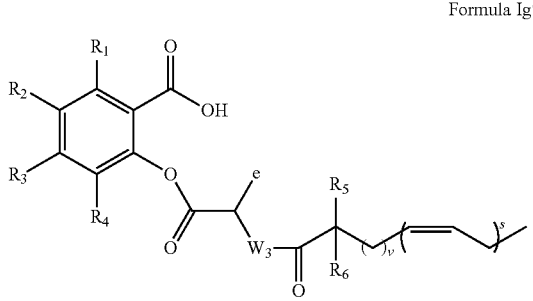

and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;

$W_3$ is null, O, or NH;

e is H or any one of the side chains of the naturally occurring amino acids;

v is 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and s is 5 or 6.

In another aspect, compounds of the Formula II' are described:

Formula II'

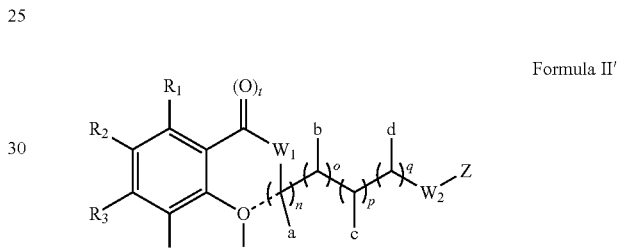

and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;

$W_1$ and $W_2$ are each independently null, O, or NH, or when $W_1$ and $W_2$ are both NH, then both $W_1$ and $W_2$ can be taken together to form a piperidine moiety;

- - - - - represents an optional bond that when present requires that Q is then null;

a and c are each independently H, $CH_3$, —$OCH_3$, —$OCH_2CH_3$, or C(O)OH;

b is H, $CH_3$, C(O)OH, or O—Z;

d is H or C(O)OH;

each n, o, p, and q is independently 0 or 1;

each Z is H,

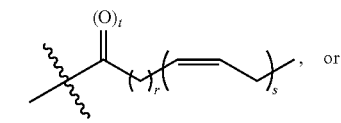

-continued

[structure with R5, R6, v, s]

with the proviso that there is at least one

[structure with (O)t, r, s]  or

[structure with R5, R6, v, s]

in the compound;
each r is 7;
each s is 3;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;
Q is null, C(O)CH$_3$, Z,

[structure with W3-Z, e]  ,  or  [structure with phenyl, O-T] , e is H or any one of the side chains of the naturally occurring amino acids;
$W_3$ is null, —O—, or —N(R)—;
R is H or $C_1$-$C_3$ alkyl; and
T is H, C(O)CH$_3$, or Z.

In another aspect, compounds of the Formula III' are described:

and pharmaceutically acceptable salts, hydrates, solvates, prodrugs, enantiomers, and stereoisomers thereof;
wherein
each $W_1$ and $W_2$ are independently null, O, or NH, or when $W_1$ and $W_2$ are both NH, then both $W_1$ and $W_2$ can be taken together to form a piperidine moiety;
- - - - - represents an optional bond that when present requires that Q is null;
each a and c are independently H, CH$_3$, —OCH$_3$, —OCH$_2$CH$_3$, or C(O)OH;
each b is H, CH$_3$, C(O)OH, or O—Z;
each d is H or C(O)OH;
each n, o, p, and q is independently 0 or 1;
each Z is H,

[structure with (O)t, r, s]  , or

[structure with R5, R6, v, s]  ;

with the proviso that there is at least one

[structure with (O)t, r, s]  or

[structure with R5, R6, v, s]

in the compound;
each r is independently 2, 3, or 7;
each s is independently 3, 5, or 6;
each t is independently 0 or 1;
each v is 1 or 2;
each $R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;
u is 0 or 1;
with the proviso that when r is 7, s is 3;

Formula III'

[large structure of Formula III' showing Z-W2, d, b, q, p, o, n, W1, c, a, O, N(R), u, phenyl with (O)t, W1, b, d, o, q, W2-Z, n, p, a, c, O, Q]

Q is null, C(O)CH$_3$, Z,

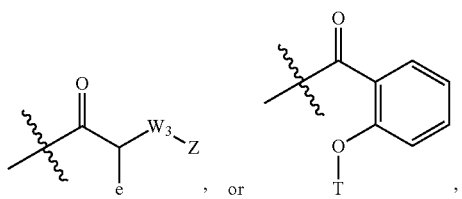, or 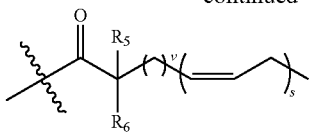, e is H or any one of the side chains of the naturally occurring amino acids;
W$_3$ is null, —O—, or —N(R)—;
R is H or C$_1$-C$_3$ alkyl; and
T is H, C(O)CH$_3$, or Z.

In yet another aspect, compounds of the Formula IIIa' are described:

Formula IIIa'

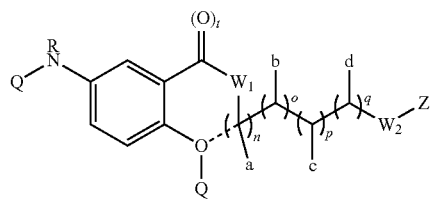

and pharmaceutically acceptable salts, hydrates, solvates, prodrugs, enantiomers, and stereoisomers thereof;
wherein
each W$_1$ and W$_2$ are independently null, O, or NH, or when W$_1$ and W$_2$ are both NH, then both W$_1$ and W$_2$ can be taken together to form a piperidine moiety;
- - - - - represents an optional bond that when present requires that Q is null;
each a and c are independently H, CH$_3$, —OCH$_3$, —OCH$_2$CH$_3$, or C(O)OH;
each b is H, CH$_3$, C(O)OH, or O—Z;
each d is H or C(O)OH;
each n, o, p, and q is independently 0 or 1;
each Z is H,

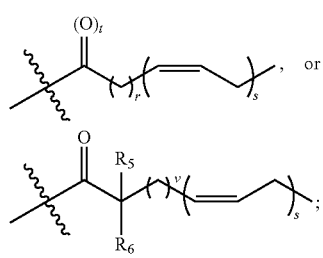, or with the proviso that there is at least one

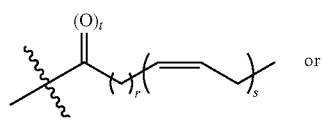 or

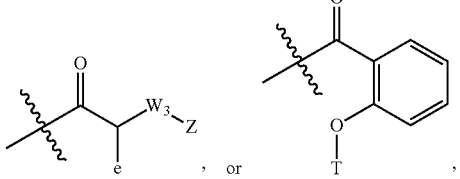

in the compound;
each r is independently 2, 3, or 7;
each s is independently 3, 5, or 6;
each t is independently 0 or 1;
each v is 1 or 2;
each R$_5$ and R$_6$ are independently hydrogen, deuterium, C$_1$-C$_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl;
with the proviso that when r is 7, s is 3;
each Q is null, C(O)CH$_3$, Z,

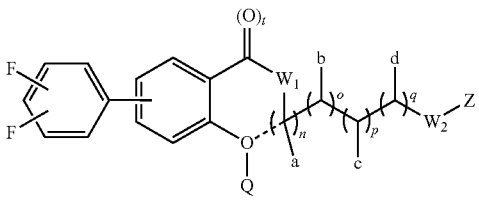

each e is H or any one of the side chains of the naturally occurring amino acids;
W$_3$ is null, —O—, or —N(R)—;
R is H or C$_1$-C$_3$ alkyl; and
T is H, C(O)CH$_3$, or Z.

In another aspect, compounds of Formula IV' are described herein:

Formula IV' and pharmaceutically acceptable salts, hydrates, solvates, prodrugs, enantiomers, and stereoisomers thereof;
wherein
W$_1$ and W$_2$ are each independently null, O, or NH;
- - - - - represents an optional bond that when present requires that Q is null;
a and c are each independently H, CH$_3$, —OCH$_3$, —OCH$_2$CH$_3$, or C(O)OH;
b is H, CH$_3$, C(O)OH, or O—Z;
d is H or C(O)OH;
each n, o, p, and q is independently 0 or 1;

each Z is H,

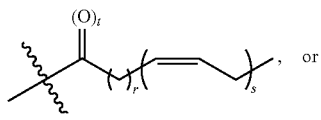, or

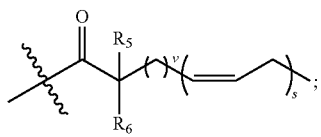

with the proviso that there is at least one

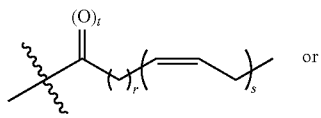, or

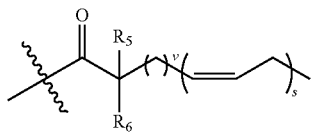

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

Q is null, C(O)CH$_3$, Z, or

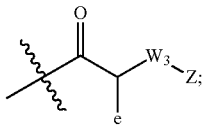

e is H, —C(O)OH, or any one of the side chains of the naturally occurring amino acids;
$W_3$ is null, —O—, —N(R)—; and
R is H or $C_1$-$C_3$ alkyl.

In another aspect, compounds of the Formula IVa' are described:

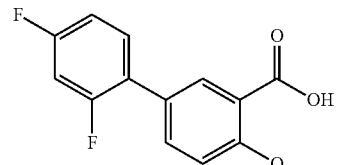

Formula IVa' and pharmaceutically acceptable salts, hydrates, solvates, prodrugs, enantiomers, and stereoisomers thereof;
wherein
v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and
s is 5 or 6.

In another aspect, compounds of the Formula IVb' are described:

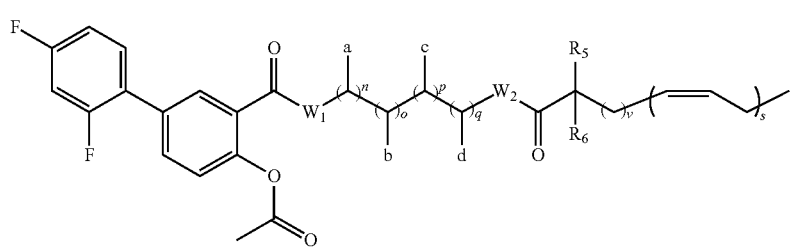

Formula IVb' and pharmaceutically acceptable salts, hydrates, solvates, enantiomers, and stereoisomers thereof, wherein $W_1$ and $W_2$ are each independently null, O, or NH;

a and c are each independently H, $CH_3$, —$OCH_3$, —$OCH_2CH_3$, or C(O)OH;

b is H, $CH_3$, C(O)OH, or O—Z;

d is H or C(O)OH;

each n, o, p, and q is independently 0 or 1;

each Z is H,

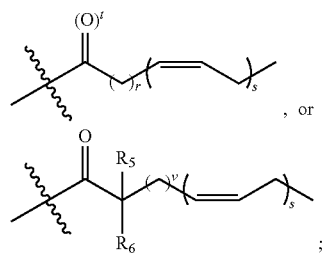

, or

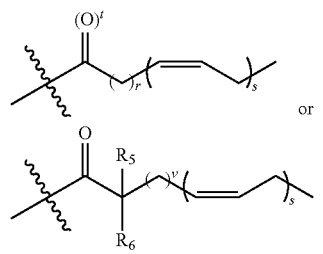

;

with the proviso that there is at least one

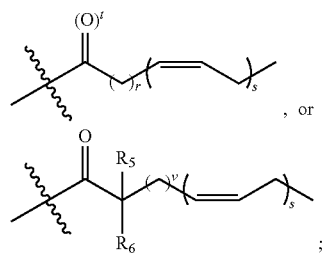

or

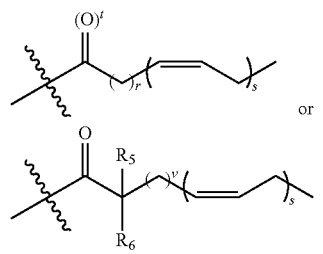

in the compound;

each r is independently 2 or 3;

each s is independently 5 or 6;

each t is independently 0 or 1;

each v is 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl.

In another aspect, compounds of the Formula IVc' are described:

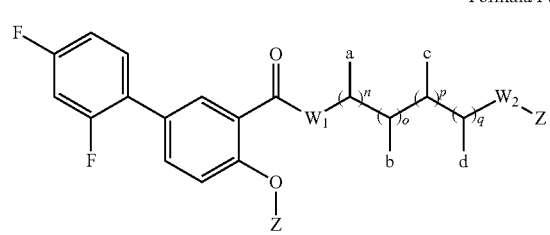

Formula IVc' and pharmaceutically acceptable salts, hydrates, solvates, prodrugs, enantiomers, and stereoisomers thereof;

wherein $W_1$ and $W_2$ are each independently null, O, or NH;

a and c are each independently H, $CH_3$, —$OCH_3$, —$OCH_2CH_3$, or C(O)OH;

b is H, $CH_3$, C(O)OH, or O—Z;

d is H or C(O)OH;

each of n, o, p, and q is independently 0 or 1;

each Z is null, H,

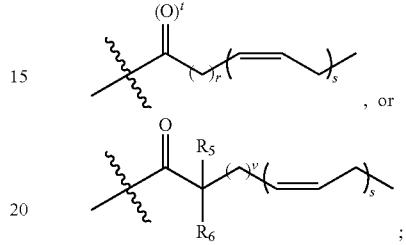

, or

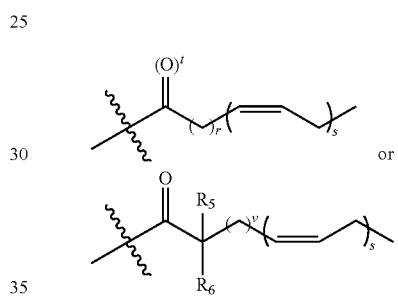

;

with the proviso that there is at least one

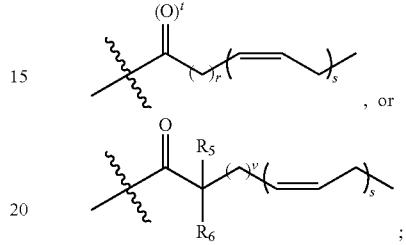

or

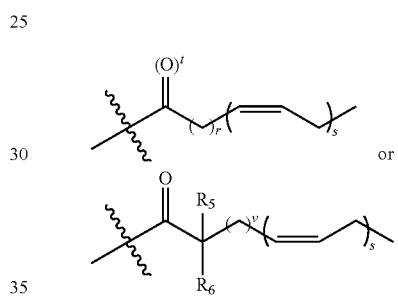

in the compound;

each r is independently 2 or 3;

each s is independently 5 or 6;

each t is independently 0 or 1;

each v is 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl.

In another aspect, compounds of the Formula IVd' are described:

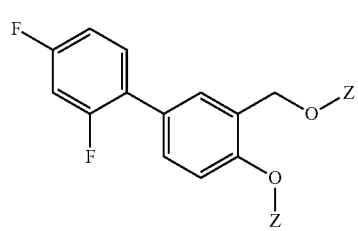

Formula IVd' and pharmaceutically acceptable salts, hydrates, solvates, prodrugs, enantiomers, and stereoisomers thereof;

wherein
each Z is null, H,

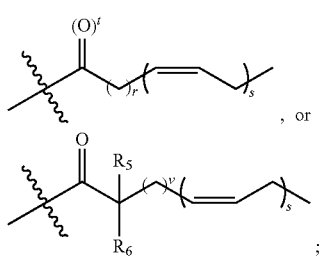

, or

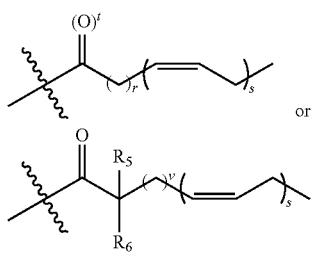

;

with the proviso that there is at least one

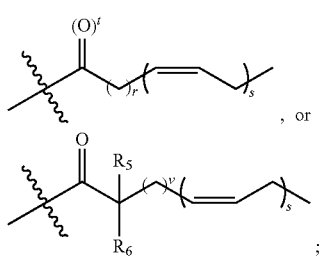

or

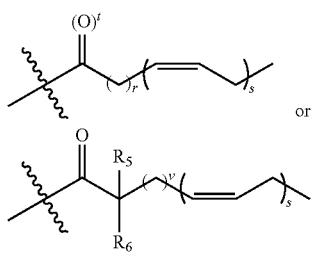

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In another aspect, compounds of the Formula IVe' are described:

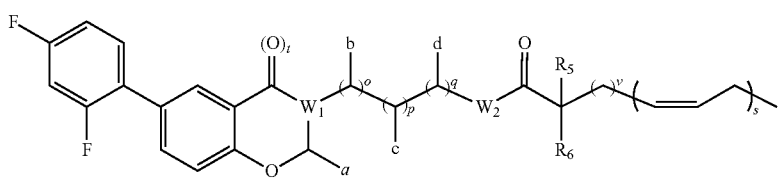

Formula IVe' and pharmaceutically acceptable salts, hydrates, solvates, prodrugs, enantiomers, and stereoisomers thereof;
wherein $W_1$ is O, or NH;

$W_2$ is null, O, or NH;

a and c are each independently H, $CH_3$, —$OCH_3$, —$OCH_2CH_3$, or C(O)OH;

b is H, $CH_3$, C(O)OH, or O—Z;

d is H or C(O)OH;

each o, p, and q is independently 0 or 1;

each Z is H,

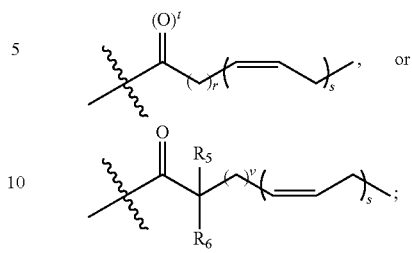

, or

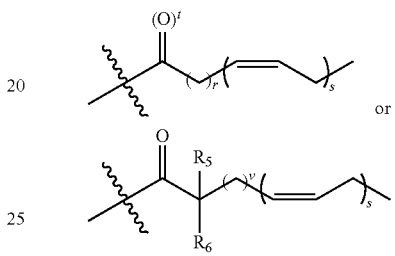

;

with the proviso that there is at least one

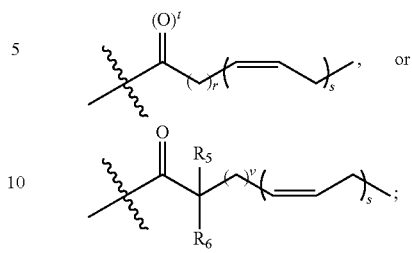

or

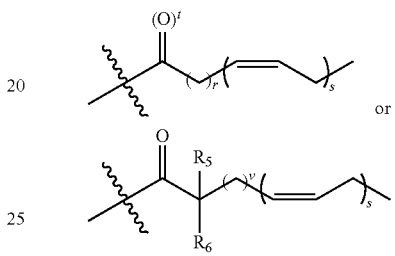

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In another aspect, compounds of the Formula IVf' are described:

Formula IVf'

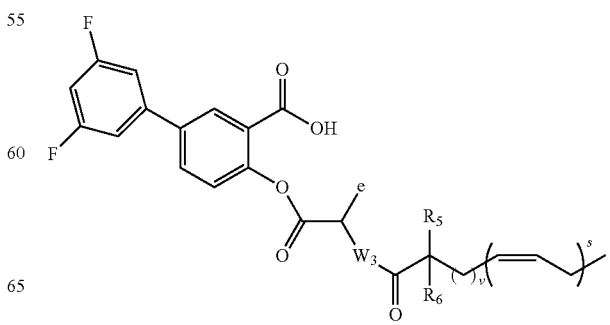

and pharmaceutically acceptable salts, hydrates, solvates, prodrugs, enantiomers, and stereoisomers thereof;
wherein
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

e is H, —C(O)OH or any one of the side chains of the naturally occurring amino acids;

$W_3$ is null, —O—, —N(R)—; and

R is H or $C_1$-$C_3$ alkyl, v is 1 or 2;

s is 5 or 6.

In another aspect, compounds of the Formula IVg' are described:

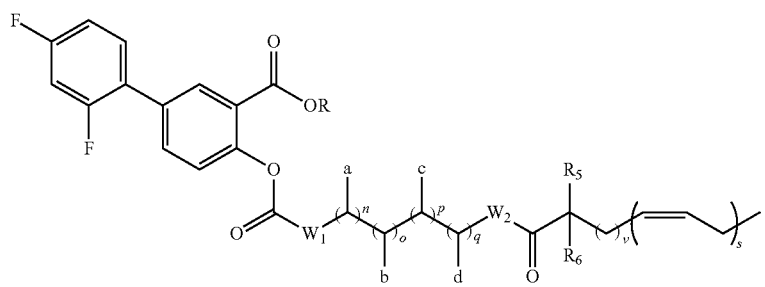

Formula IVg' and pharmaceutically acceptable salts, hydrates, solvates, prodrugs, enantiomers, and stereoisomers thereof;
wherein
R is H or $C_1$-$C_3$ alkyl;

$W_1$ and $W_2$ are each independently null, O, or NH;

a and c are each independently H, CH$_3$, —OCH$_3$, —OCH$_2$CH$_3$, or C(O)OH;

b is H, CH$_3$, C(O)OH, or O—Z;

d is H or C(O)OH;

each n, o, p, and q is independently 0 or 1;

each Z is H,

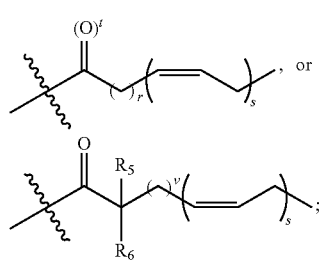, or

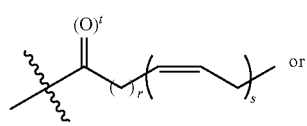

with the proviso that there is at least one

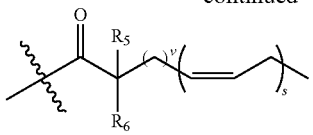

in the compound;

each r is independently 2 or 3;

each s is independently 5 or 6;

each t is independently 0 or 1;

each v is 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In still another aspect, compounds of the Formula V' are described:

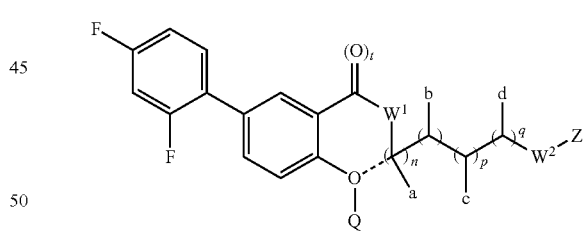

Formula V' and pharmaceutically acceptable salts, hydrates, solvates, prodrugs, enantiomers, and stereoisomers thereof;
wherein
$W_1$ and $W_2$ are each independently null, O, or NH;

- - - - - represents an optional bond that when present requires that Q is then null;

a and c are each independently H, CH$_3$, —OCH$_3$, —OCH$_2$CH$_3$, or C(O)OH;

b is H, CH$_3$, C(O)OH, or O—Z;

d is H or C(O)OH;

each n, o, p, and q is independently 0 or 1;

each Z is independently null, H,

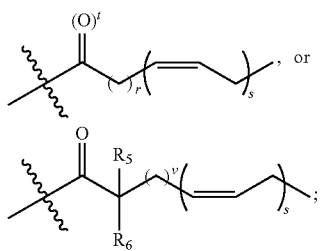

with the proviso that there is at least one

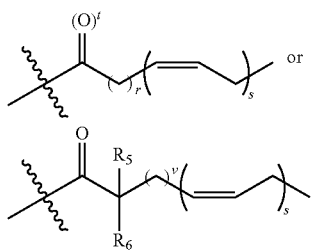

in the compound;
each r is independently 7;
each s is independently 3;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;
Q is null, C(O)CH$_3$, Z, or

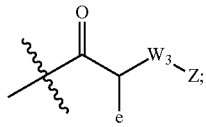

$W_3$ is null, —O—, —N(R)—;
R is H or $C_1$-$C_3$ alkyl; and
e is H, —C(O)OH or any one of the side chains of the naturally occurring amino acids.

In yet another aspect, compounds of the Formula VI' are described:

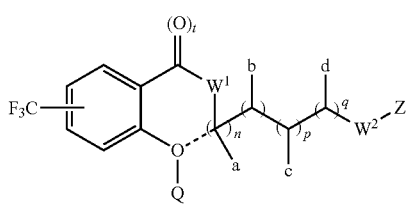

Formula VI' and pharmaceutically acceptable salts, hydrates, solvates, prodrugs, enantiomers, and stereoisomers thereof;

wherein
$W_1$ and $W_2$ are each independently null, O, or NH;
- - - - - represents an optional bond that when present requires that Q is null;
a and c are each independently H, CH$_3$, —OCH$_3$, —OCH$_2$CH$_3$, or C(O)OH;
b is H, CH$_3$, C(O)OH, or O—Z;
d is H or C(O)OH;
each n, o, p, and q is independently 0 or 1;
each Z is H,

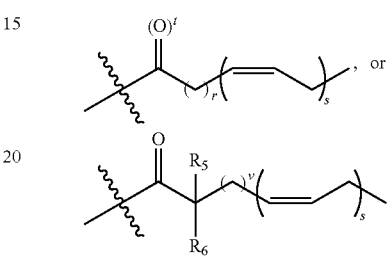

with the proviso that there is at least one

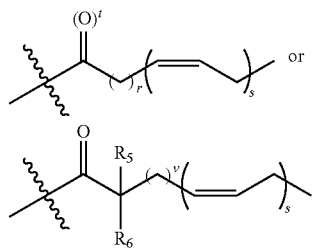

in the compound;
each r is independently 0, 1, 2, or 3;
each s is independently an integer from 1 to 10;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;
Q is null, C(O)CH$_3$, Z, or

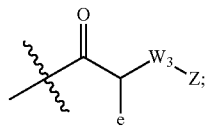

e is H, —C(O)OH, or any one of the side chains of the naturally occurring amino acids;
$W_3$ is null, —O—, —N(R)—; and
R is H or $C_1$-$C_3$ alkyl.

In another aspect, compounds of the Formula VIa' are described:

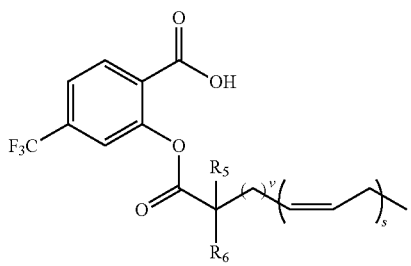

Formula VIa' and pharmaceutically acceptable salts, hydrates, solvates, prodrugs, enantiomers, and stereoisomers thereof;
wherein
v is 1 or 2; $R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and
s is independently 5 or 6.

In another aspect, compounds of the Formula VIb' are described:

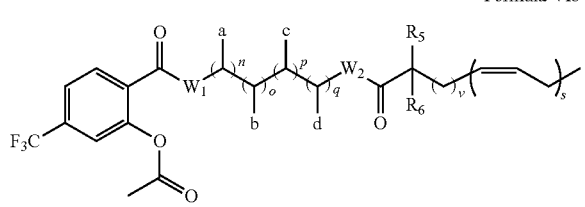

Formula VIb' and pharmaceutically acceptable salts, hydrates, solvates, enantiomers, and stereoisomers thereof,
wherein
$W_1$ and $W_2$ are each independently null, O, or NH;
a and c are each independently H, $CH_3$, —OCH$_3$, —OCH$_2$CH$_3$, or C(O)OH;
b is H, $CH_3$, C(O)OH, or O—Z;
d is H or C(O)OH;
each n, o, p, and q is independently 0 or 1;
each Z is H,

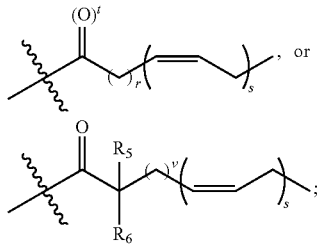

, or

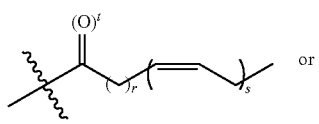

with the proviso that there is at least one

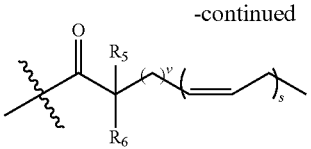

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In another aspect, compounds of the Formula VIc' are described:

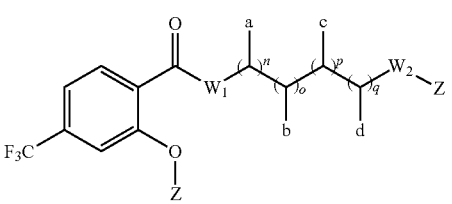

Formula VIc' and pharmaceutically acceptable salts, hydrates, solvates, prodrugs, enantiomers, and stereoisomers thereof;
wherein
$W_1$ and $W_2$ are each independently null, O, or NH;
a and c are each independently H, $CH_3$, —OCH$_3$, —OCH$_2$CH$_3$, or C(O)OH;
b is H, $CH_3$, C(O)OH, or O—Z;
d is H or C(O)OH;
each of n, o, p, and q is independently 0 or 1;
each Z is independently null, H,

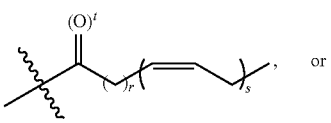

, or

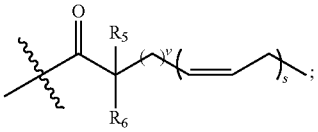

;

with the proviso that there is at least one

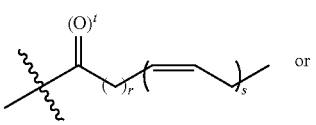

or

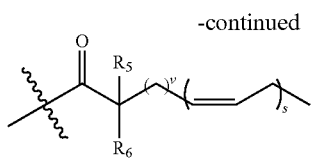

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In another aspect, compounds of the Formula VId' are described:

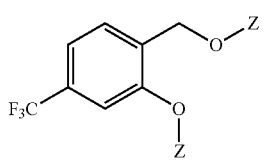

Formula VId' and pharmaceutically acceptable salts, hydrates, solvates, prodrugs, enantiomers, and stereoisomers thereof;
wherein
each Z is independently H,

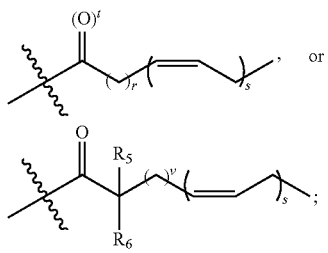

with the proviso that there is at least one

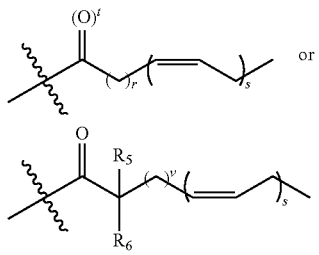

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In another aspect, compounds of the Formula VIe' are described:

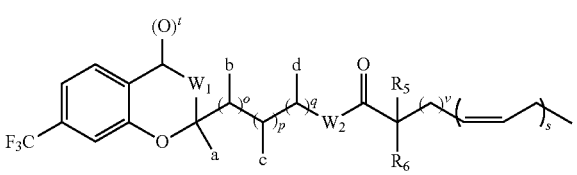

Formula VIe' and pharmaceutically acceptable salts, hydrates, solvates, prodrugs, enantiomers, and stereoisomers thereof;
wherein
$W_1$ is O, or NH;
$W_2$ is null, O, or NH;
a and c are each independently H, CH$_3$, —OCH$_3$, —OCH$_2$CH$_3$, or C(O)OH;
b is H, CH$_3$, C(O)OH, or O—Z;
d is H or C(O)OH;
each o, p, and q is independently 0 or 1;
each Z is H,

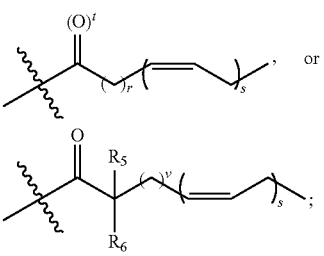

with the proviso that there is at least one

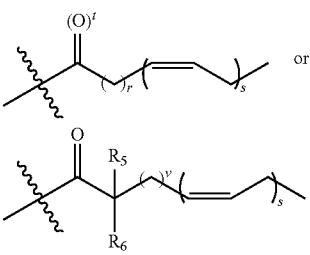

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl.

In another aspect, compounds of the Formula VIf' are described:

Formula VIf'

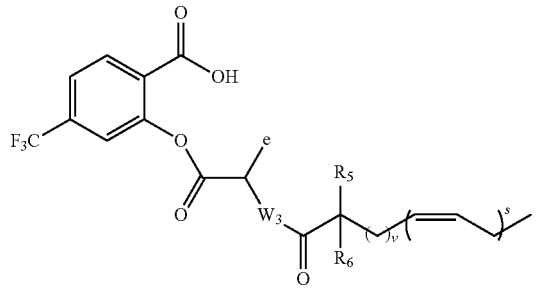

and pharmaceutically acceptable salts, hydrates, solvates, prodrugs, enantiomers, and stereoisomers thereof;
wherein
e is H, —C(O)OH or any one of the side chains of the naturally occurring amino acids;
W$_3$ is null, —O—, —N(R)—; and
R is H or C$_1$-C$_3$ alkyl,
each v is 1 or 2;
R$_5$ and R$_6$ are each independently hydrogen, deuterium, C$_1$-C$_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl;
s is 5 or 6.

In another aspect, compounds of the Formula VIg' are described:

Formula VIg'

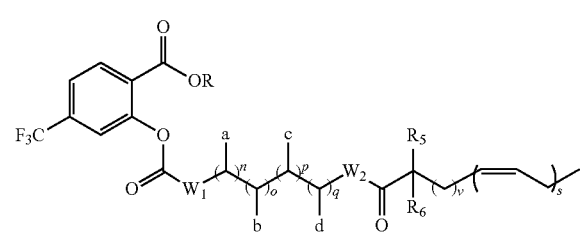

and pharmaceutically acceptable salts, hydrates, solvates, prodrugs, enantiomers, and stereoisomers thereof;
wherein
R is H or C$_1$-C$_3$ alkyl;
W$_1$ and W$_2$ are each independently null, O, or NH;
a and c are each independently H, CH$_3$, —OCH$_3$, —OCH$_2$CH$_3$, or C(O)OH;
b is H, CH$_3$, C(O)OH, or O—Z;
d is H or C(O)OH;
each n, o, p, and q is independently 0 or 1;

each Z is H,

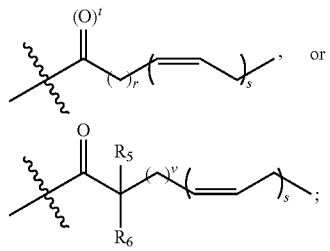

, or

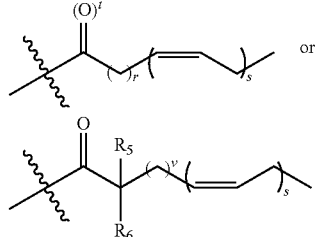

;

with the proviso that there is at least one

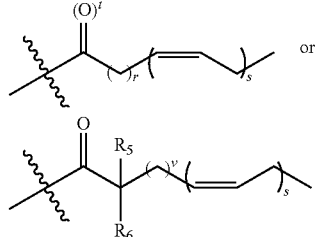

or

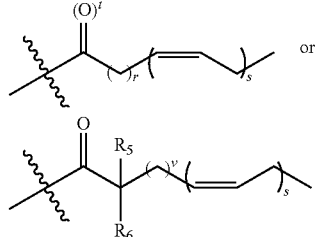

in the compound;
each r is independently 2 or 3;
each s is independently 5 or 6;
each t is independently 0 or 1;
each v is 1 or 2;
R$_5$ and R$_6$ are each independently hydrogen, deuterium, C$_1$-C$_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl.

In another aspect, compounds of the Formula VII' are described:

Formula VII'

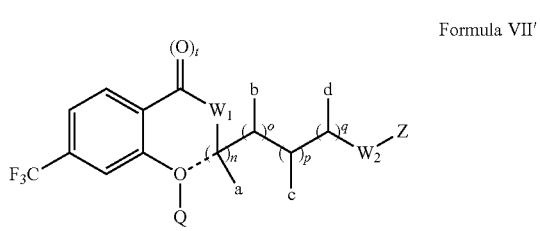

and pharmaceutically acceptable salts, hydrates, solvates, prodrugs, enantiomers, and stereoisomers thereof;
wherein
W$_1$ and W$_2$ are each independently null, O, or NH;
- - - - - represents an optional bond that when present requires that Q is then null;
a and c are each independently H, CH$_3$, —OCH$_3$, —OCH$_2$CH$_3$, or C(O)OH;
b is H, CH$_3$, C(O)OH, or O—Z;
d is H or C(O)OH;
each n, o, p, and q is independently 0 or 1;

each Z is H,

, or with the proviso that there is at least one

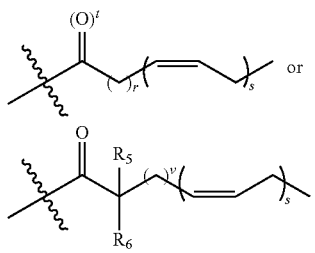

or in the compound;
each r is independently 7;
each s is independently 3;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;
Q is null, C(O)CH$_3$, Z, or

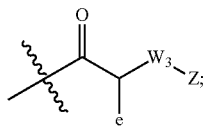

and
$W_3$ is null, —O—, —N(R)—;
R is H or $C_1$-$C_3$ alkyl; and
e is H, —C(O)OH or any one of the side chains of the naturally occurring amino acids.

In any of the above Formulae, any one or more of H may be substituted with a deuterium. It is also understood in any of the above Formulae that a methyl subtituent can be substituted with a $C_1$-$C_6$ alkyl.

Also described are pharmaceutical formulations comprising at least one Compound of the Invention.

Also described herein are methods of simultaneously up regulating antiinflammation pathways and down regulating proinflammation pathways in a cell by administering to the cell a Compound of the Invention.

Also described herein are methods of simultaneously up regulating antiinflammation pathways and down regulating proinflammation pathways in a patient in need thereof, by administering to the patient an effective amount of a Compound of the Invention.

Also described herein are methods of treating a disease susceptible to treatment with a Compound of the Invention in a patient in need thereof by administering to the patient an effective amount of a Compound of the Invention.

Also described herein are methods of treating diseases associated with inflammation by administering to a patient in need thereof an effective amount of a Compound of the Invention.

The invention also includes pharmaceutical compositions that comprise an effective amount of a Compound of the Invention and a pharmaceutically acceptable carrier. The compositions are useful for treating or preventing an inflammatory disease. The invention includes a Compound of the Invention when provided as a pharmaceutically acceptable prodrug, a hydrate, a salt, such as a pharmaceutically acceptable salt, enantiomer, stereoisomer, or mixtures thereof.

The details of the invention are set forth in the accompanying description below. Although any methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

5. BRIEF DESCRIPTION OF THE FIGURES

6. DETAILED DESCRIPTION OF THE INVENTION

Figure 1:
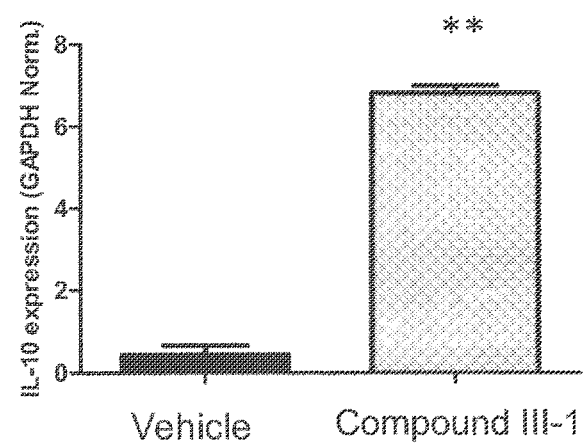
FIG. 1 is a graphic representation of the data showing the effects of a Compound of the Invention on IL-10 levels in 3T3-L1 adipocytes.

Inflammation is the underlying cause of and pathological contributor to many chronic diseases including type 2 diabetes, rheumatoid arthritis, psoriasis, inflammatory bowel disease, Parkinson's disease, Alzheimer's disease, multiple sclerosis, epilepsy, and cancer, etc. Inflammation is the body's natural protective response to insult, injury and infection. The normal inflammatory process is highly regulated. The process is initiated by a stimulus which leads to the induction of pro-inflammatory pathways. The response persists while the stimulus is present and is turned off during the resolving phase of inflammation. During each of these phases of the inflammatory response different enzymes, receptors, and effectors, are activated and inactivated. If the stimulus persists, chronic inflammation ensues and results in an imbalance in the pro- and anti-inflammatory pathways. Current therapies that target inflammation have been directed in general at single molecular targets or effectors in single pathways. For example, TNFα antibodies, TNFα soluble receptors, COX-2 inhibitors, CCR2 antagonists, p38 inhibitors, etc. target just the pro-inflammatory arm of inflammation. In general these approaches are not disease modifying and are associated with side effects that result from an imbalanced inflammatory response. The simultaneous targeting of both the pro- and anti-inflammatory pathways in the normal inflammatory response provides superior activity in targeting inflammation, disease modifying activity, and a reduced side effect profile. The Compounds of the Invention possess the ability to inhibit pro-inflammatory pathways, while simultaneously activating anti-inflammatory pathways. The simultaneous targeting of these pathways leads to synergistic efficacy and thus the two activities must be delivered to the target cell and/or tissue together.

The Compounds of the Invention have been designed to bring together salicylate analogs and omega 3 fatty acids into a single molecular conjugate. Salicylate analogs inhibit the pro-inflammatory pathway through inhibition of NFκB. The omega 3 fatty acids including DHA, EPA, and ALA activate the anti-inflammatory pathway. The Compounds of the Invention thus possess two activities—the ability to blunt pro-inflammatory activity and the ability to activate anti-inflammatory activity. Compounds of the Invention exhibit potent NFκB and TNFα inhibitory activity in a mouse macrophage cell line, RAW264.7, while the individual components, a salicylate analog and a EFA, alone or in combination together, do not. The activity of the Compounds of the Invention is substantially greater than the sum of the components suggesting that the activity induced by the Compounds of the Invention is synergistic.

Definitions

The following definitions are used in connection with the Fatty Acid Acetylated Salicylate Derivatives, the Fatty Acid Acetylated Diflunisal Derivatives, and Fatty Acid Acetylated Triflusal Derivatives:

The term "Compound of the Invention" refers to a Fatty Acid Acetylated Salicylate Derivative described herein, wherein Salicylate Derivative includes, without limitation, salicylic acid and substituted salicylates such as aminosalicylic acid, a Fatty Acid Acetylated Diflunisal Derivative described herein, or a Fatty Acid Acetylated Triflusal Derivative described herein. The term "Compounds of the Invention" refers to more than one Compound of the Invention and may be Fatty Acid Acetylated Salicylate Derivatives, Fatty Acid Acetylated Diflunisal Derivatives, Fatty Acid Acetylated Triflusal Derivatives, or some combination thereof. The Compounds of the Invention include any and all possible isomers, stereoisomers, enantiomers, diastereomers, tautomers, pharmaceutically acceptable salts, hydrates, solvates, and prodrugs thereof.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "any one of the side chains of the naturally occurring amino acids" as used herein means a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine, and Tyrosine.

The term "fatty acid" as used herein means an omega-3 fatty acid and fatty acids that are metabolized in vivo to omega-3 fatty acids. Non-limiting examples of fatty acids are all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA or all-cis-5,8,11,14,17-eicosapentaenoic acid), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), or tetracosahexaenoic acid (nisinic acid or all-cis-6,9,12,15,18,21-tetracosenoic acid).

A "subject" is a mammal, e.g., a human, mouse, rat, guinea pig, dog, cat, horse, cow, pig, or non-human primate, such as a monkey, chimpanzee, baboon or rhesus.

The invention also includes pharmaceutical compositions comprising an effective amount of a Compound of the Invention and a pharmaceutically acceptable carrier. The invention includes a Compound of the Invention when provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

An "effective amount" when used in connection with a Compound of the Invention is an amount effective for treating or preventing an inflammatory disease.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating" with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwised indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a Compound of the Invention.

The following abbreviations are used herein and have the indicated definitions: DCC is dicyclohexylcarbodiimide, CDI is 1,1'-carbonyldiimidazole, EDC is 1-Ethyl-3-[3-dimethylaminopropyl]carbodiimide hydrochloride, HEPES is 4-(2-hydroxyethyl)-1-piperazineethanesulfonic acid, SA is salicylic acid, 5-ASA is 5-aminosalicylic acid, SDS is dodecyl sulfate (sodium salt), TNF is tumor necrosis factor, TRIS is Tris(hydroxymethyl)aminomethane, Ts is tosyl (p-toluenesulfonyl), RT is room temperature, and h is hour.

Compounds

The present invention provides Fatty Acid Acetylated Salicylate Derivatives according to Formula I, Formula Ia, Formula Ib, Formula Ic, Formula Id, Formula Ie, Formula If, Formula Ig, Formula II, and Formula III as set forth below. The present invention also provides, a Fatty Acid Acetylated Diflunisal Derivatives according to Formula IV, Formula IVa, Formula IVb, Formula IVc, Formula IVd, Formula IVe, Formula IVf, Formula IVg, and Formula V, as set forth below. The present invention additionally provides Fatty Acid Acetylated Triflusal Derivatives according to Formula VI, Formula VIa, Formula VIb, Formula VIc, Formula VId, Formula VIe, Formula VIf, Formula VIg, and Formula VII, as set forth below.

Described herein are compounds of the Formula I:

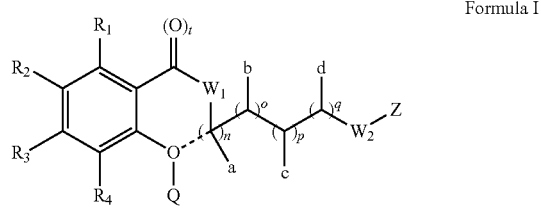

Formula I and pharmaceutically acceptable salts, hydrates, solvates, prodrugs, enantiomers, and stereoisomers thereof;

wherein $R_1$, $R_2$, $R_3$, $R_4$, $W_1$, $W_2$, a, b, c, d, e, the symbol - - - - -, Z, n, o, p, q, r, s, t, Q, and T are as defined above for compounds of Formula I.

In some embodiments, $R_2$ is Cl or F.

In other embodiments, $R_3$ is Cl or F.

In some embodiments, $W_1$ is O.

In some embodiments, $W_2$ is O.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond.

In some embodiments, a and c are each independently H, $CH_3$, —$OCH_3$, $OCH_2CH_3$, or $C(O)OH$;

In some embodiments, b is O—Z, Z is

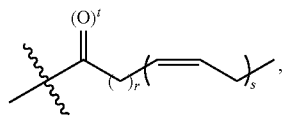

and t is 1.

In some embodiments, d is C(O)OH.

In some embodiments n, o, p, and q are each 1.

In some embodiments, n is 0.

In some embodiments, Z is

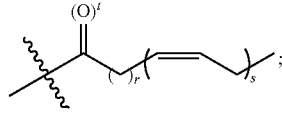

and r is 2.

In some embodiments, Z is

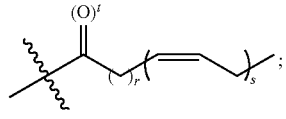

and r is 3.

In some embodiments, Z is

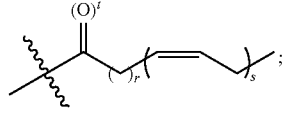

and s is 5.

In some embodiments, Z is

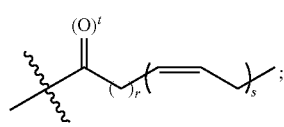

and s is 6.

In some embodiments, t is 1.

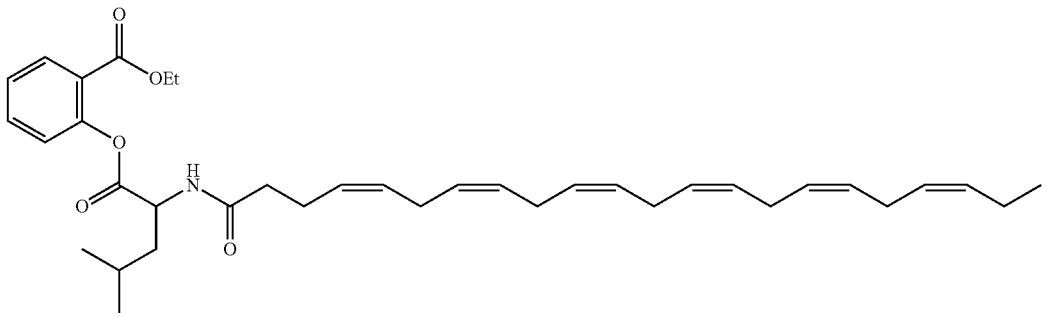

In some embodiments, Q is C(O)CH$_3$.

In some embodiments, Q is Z.

In some embodiments, Q is

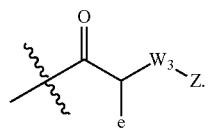

In some embodiments, Q is

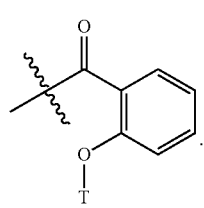

In some embodiments, T is H.

In some embodiments, T is C(O)CH$_3$.

In some embodiments, T is Z.

In some embodiments, e is any one of the side chains of the naturally occurring amino acids.

In some embodiments, e is H.

In other illustrative embodiments, compounds of the Formula I are as set forth below:

Described herein are compounds of the Formula Ia:

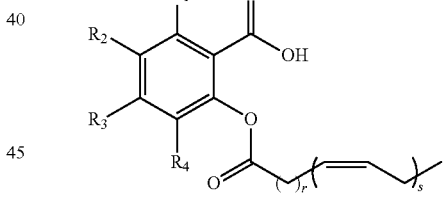

Formula Ia and pharmaceutically acceptable salts, hydrates, solvates, prodrugs, enantiomers, and stereoisomers thereof;
wherein
R$_1$, R$_2$, R$_3$, R$_4$, r, and s are as defined above for compounds of Formula Ia.

In some embodiments, R$_2$ is Cl or F.
In other embodiments, R$_3$ is Cl or F.
In some embodiments, r is 2.
In some embodiments, r is 3.
In some embodiments, s is 5.
In some embodiments, s is 6.
In some embodiments, t is 1.
In other illustrative embodiments, compounds of Formula Ia are as set forth below:

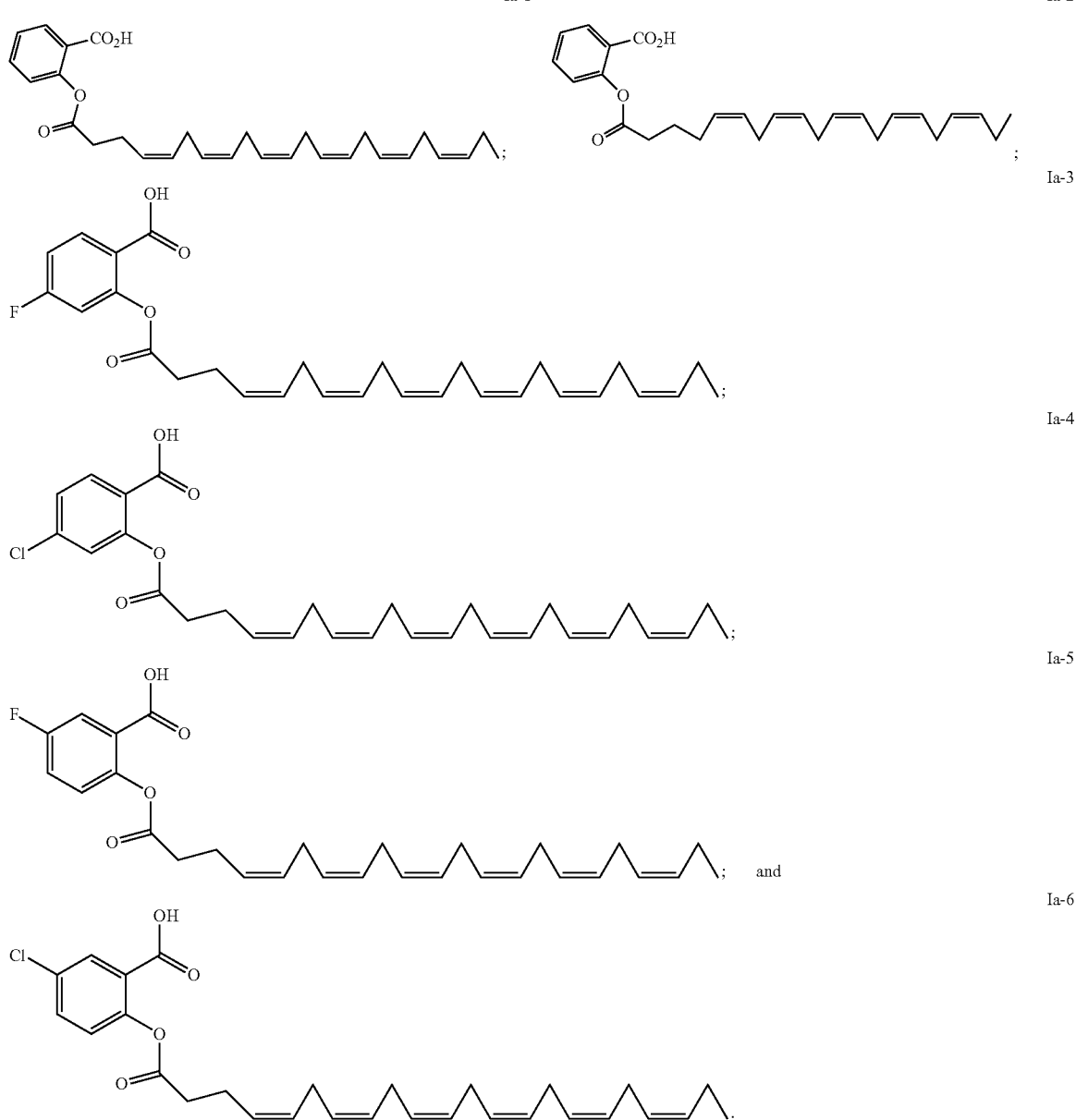

Described herein are compounds of the Formula Ib:

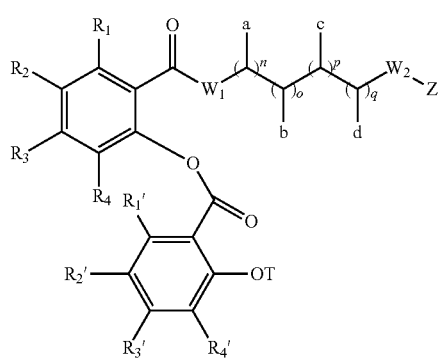

Formula Ib and pharmaceutically acceptable salts, hydrates, solvates, prodrugs, enantiomers, and stereoisomers thereof;

wherein $R_1$, $R_2$, $R_3$, $R_4$, $R_1'$, $R_2'$, $R_3'$, $R_4'$ and $W_1$, $W_2$, a, c, b, d, n, o, p, q, Z, r, s, t, and T are as defined above for the compounds of Formula Ib.

In some embodiments, $R_2$ is Cl or F.

In other embodiments, $R_3$ is Cl or F.

In some embodiments, $W_1$ is O.

In some embodiments, $W_2$ is O.

In some embodiments, a and c are each independently H, $CH_3$, —$OCH_3$, —$OCH_2CH_3$, or C(O)OH;

In some embodiments, b is O—Z, Z is

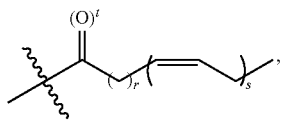

and t is 1.

In some embodiments, d is C(O)OH.
In some embodiments n, o, p, and q are each 1.
In some embodiments, n is 0.
In some embodiments, Z is

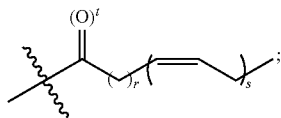

and r is 2.
In some embodiments, Z is

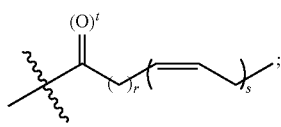

and r is 3.

In some embodiments, Z is

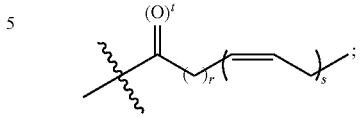

and s is 5.

In some embodiments, Z is

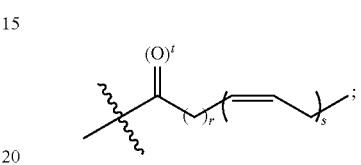

and s is 6.

In some embodiments, t is 1.
In some embodiments, T is H.
In some embodiments, T is C(O)CH$_3$.
In some embodiments, T is Z.

In other illustrative embodiments, compounds of Formula Ib are as set forth below:

Ib-1

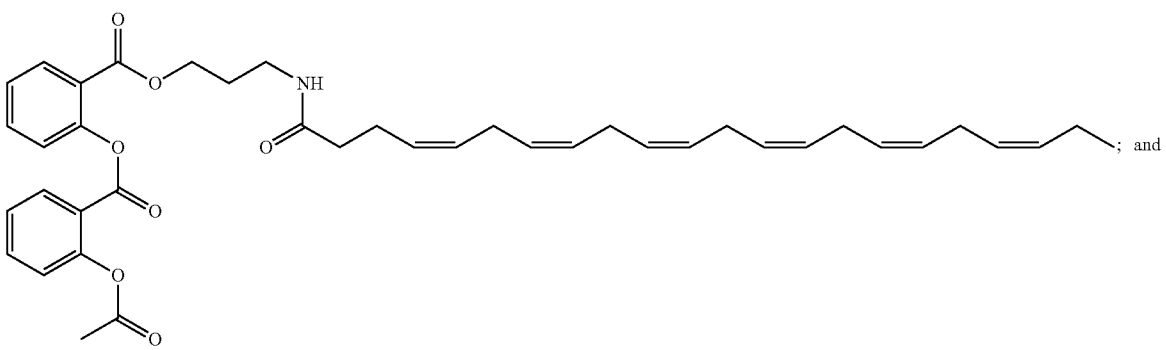

; and

Ib-2

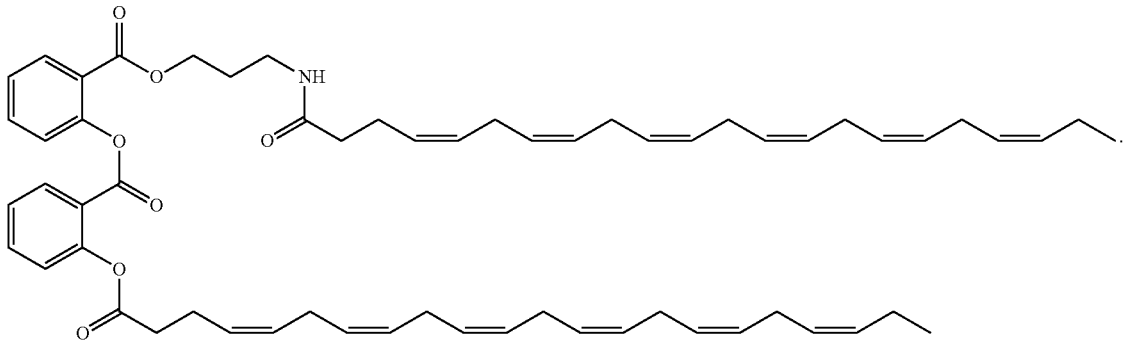

.

In another aspect, compounds of the Formula Ic are described:

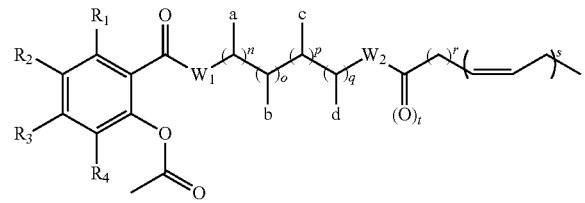

Formula Ic and pharmaceutically acceptable salts, hydrates, solvates, prodrugs, enantiomers, and stereoisomers thereof;
wherein
$R_1$, $R_2$, $R_3$, $R_4$, $W_1$, $W_2$, a, c, b, d, n, o, p, q, Z, r, s, and t are as defined above for the compounds of the Formula Ic.

In some embodiments, $R_2$ is Cl or F.
In other embodiments, $R_3$ is Cl or F.
In some embodiments, $W_1$ is O.
In some embodiments, $W_2$ is O.
In some embodiments, a and c are each independently H, $CH_3$, —$OCH_3$, —$OCH_2CH_3$, or C(O)OH.
In some embodiments, b is O—Z, Z is

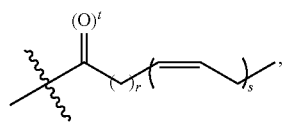

and t is 1.
In some embodiments, d is C(O)OH.
In some embodiments n, o, p, and q are each 1.
In some embodiments, n is 0.

In some embodiments, Z is

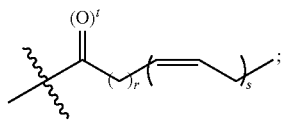

and r is 2.
In some embodiments, Z is

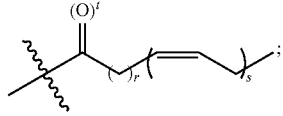

and r is 3.
In some embodiments, Z is

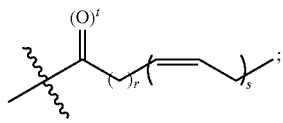

and s is 5.
In some embodiments, Z is

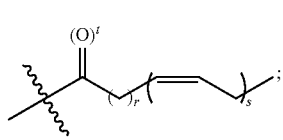

and s is 6.
In some embodiments, t is 1.
In some embodiments, T is H.
In some embodiments, T is C(O)$CH_3$.
In some embodiments, T is Z.
In other illustrative embodiments, compounds of Formula Ic are as set forth below:

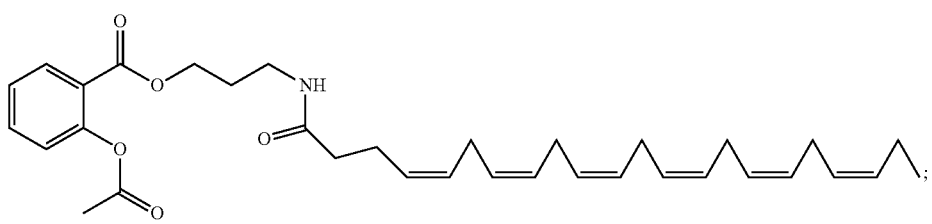

Ic-1

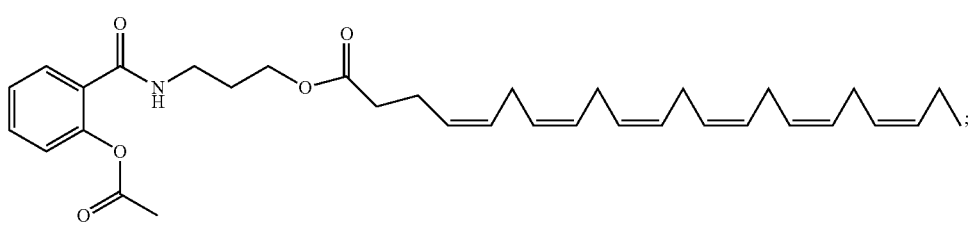

Ic-2

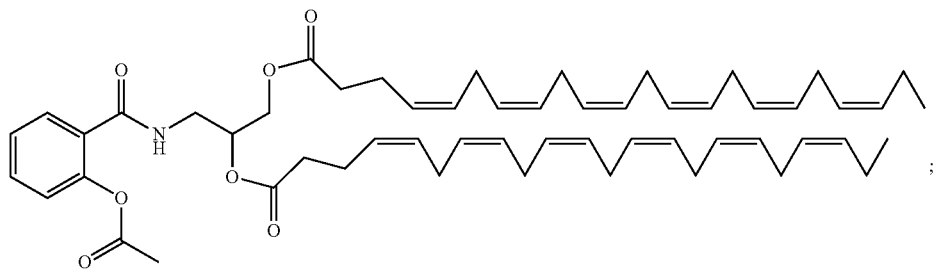
Ic-3
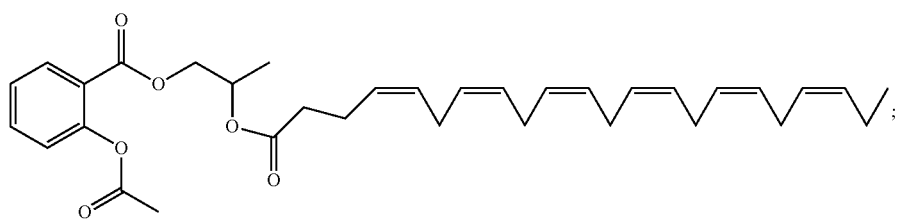
Ic-4
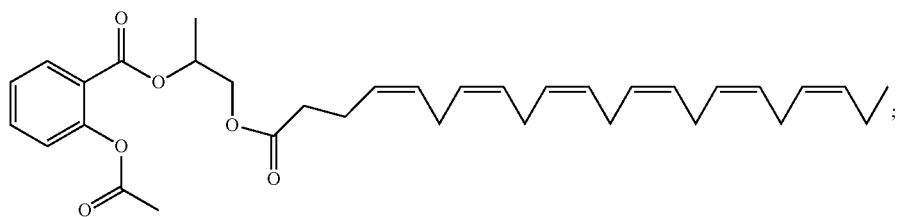
Ic-5
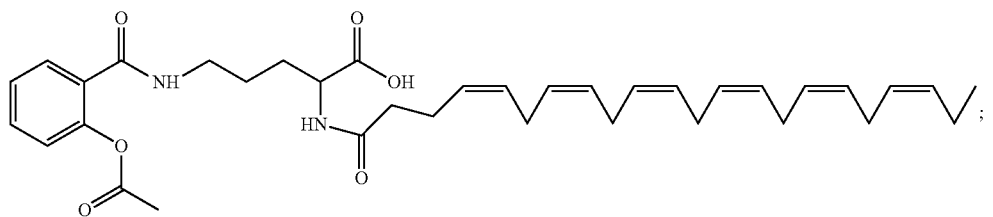
Ic-6
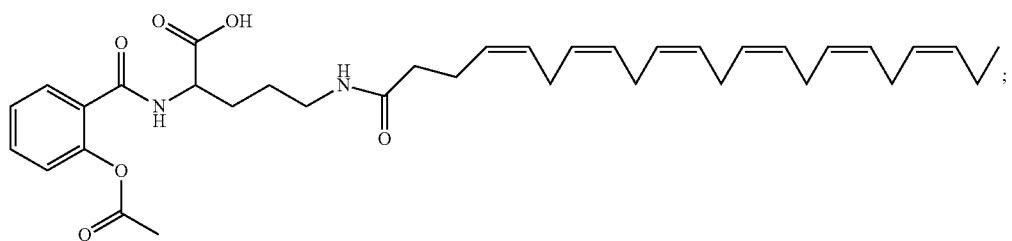
Ic-7

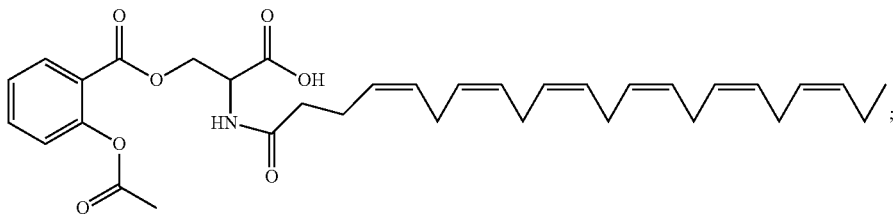

Ic-8

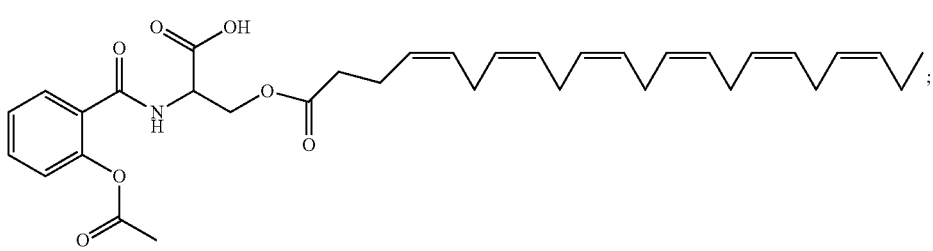

Ic-9

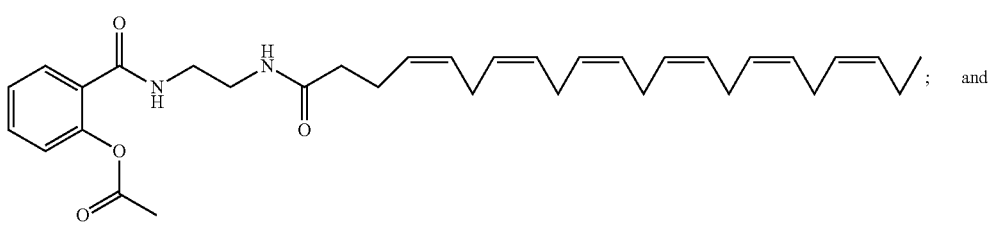

Ic-10

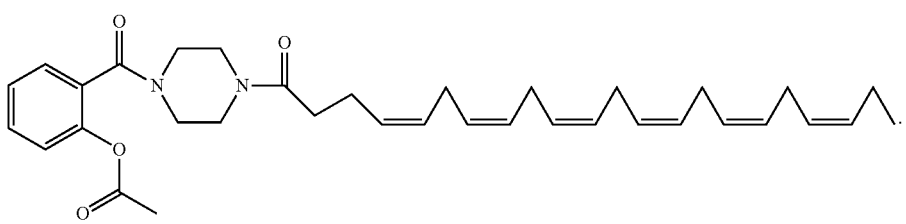

Ic-11

In another aspect, compounds of the Formula Id are described:

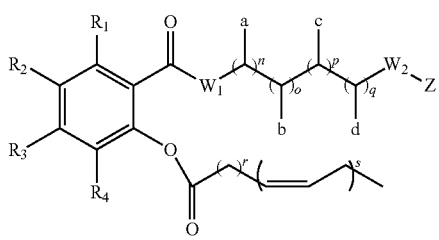

Formula Id and pharmaceutically acceptable salts, hydrates, solvates, prodrugs, enantiomers, and stereoisomers thereof; wherein $R_1$, $R_2$, $R_3$, $R_4$ $W_1$, $W_2$, a, b, c, d, n, o, p, q, Z, r, s, and t are as defined above for the compounds of the Formula Id.

In some embodiments, $R_2$ is Cl or F.
In other embodiments, $R_3$ is Cl or F.
In some embodiments, $W_1$ is O.
In some embodiments, $W_2$ is O.
In some embodiments, a and c are each independently H, $CH_3$, —$OCH_3$, —$OCH_2CH_3$, or C(O)OH;
In some embodiments, b is O—Z, Z is

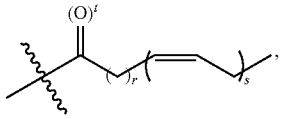

and t is 1.
In some embodiments, d is C(O)OH.
In some embodiments n, o, p, and q are each 1.
In some embodiments, n is 0.
In some embodiments, Z is

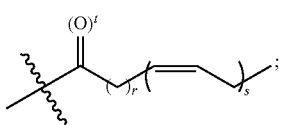

and r is 2.

In some embodiments, Z is
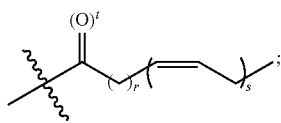
and r is 3.
In some embodiments, Z is
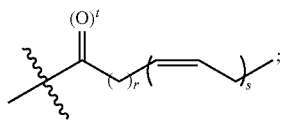
and s is 5.
In some embodiments, Z is
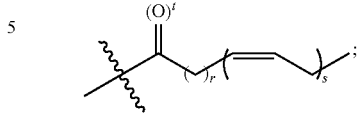
and s is 6.
In some embodiments, t is 1.
In some embodiments, T is H.
In some embodiments, T is C(O)CH$_3$.
In some embodiments, T is Z.
In other illustrative embodiments, compounds of Formula Id are as set forth below:
Id-1
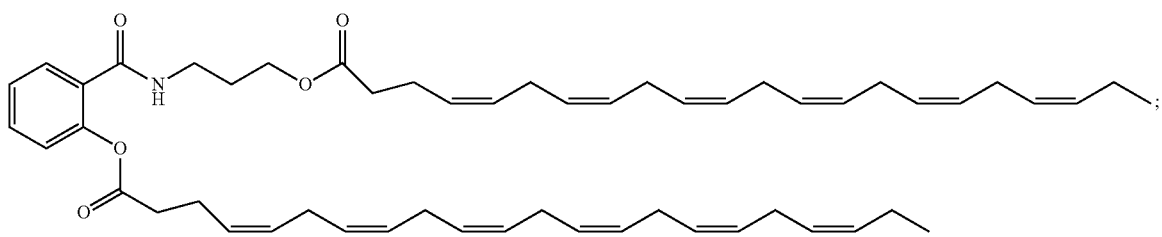
Id-2
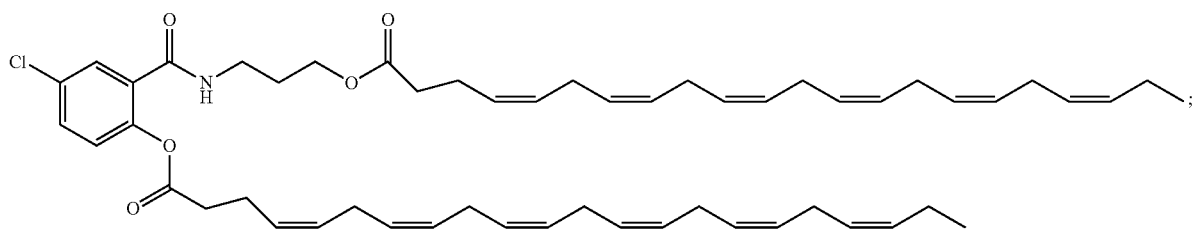
Id-3
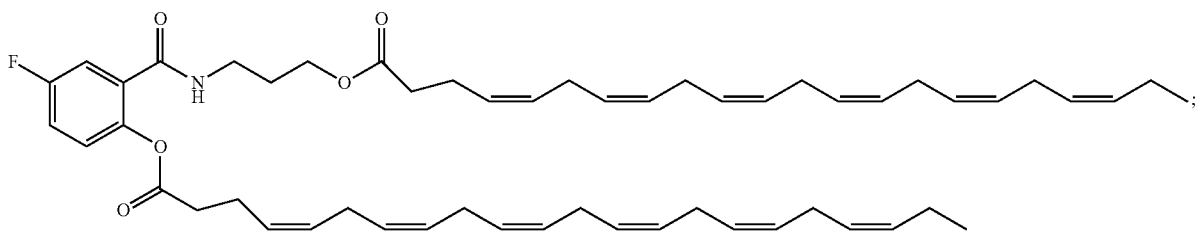
Id-4
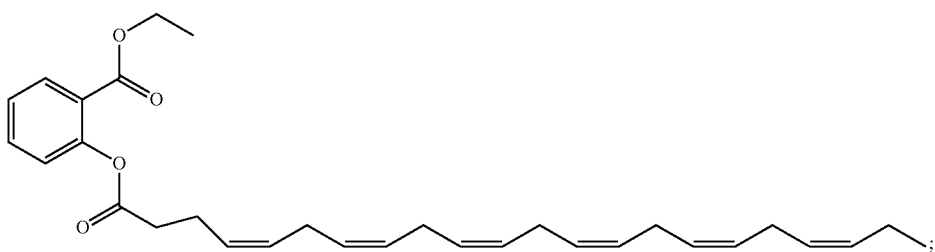

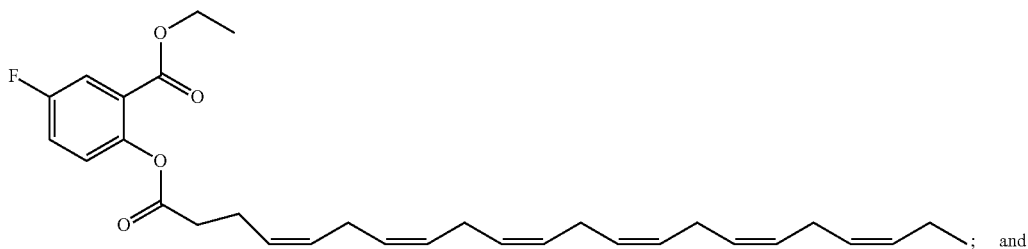

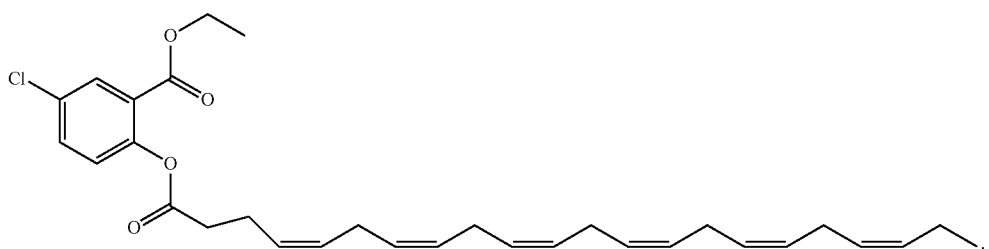

In another aspect, compounds of the Formula Ie are described:

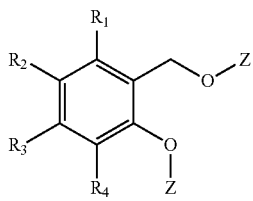

Formula Ie and pharmaceutically acceptable salts, hydrates, solvates, prodrugs, enantiomers, and stereoisomers thereof;
wherein
$R_1$, $R_2$, $R_3$, $R_4$, Z, r, s, and t are as defined above for the compounds of Formula Ie.

In some embodiments, $R_2$ is Cl or F.
In other embodiments, $R_3$ is Cl or F.
In some embodiments, Z is

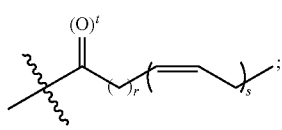

and r is 2.

In some embodiments, Z is

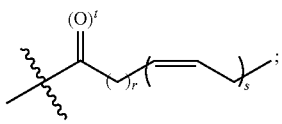

and r is 3.
In some embodiments, Z is

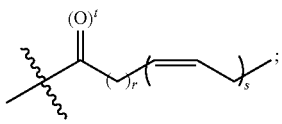

and s is 5.
In some embodiments, Z is

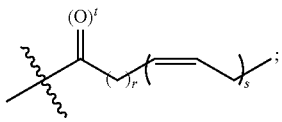

and s is 6.
In some embodiments, t is 1.
In other illustrative embodiments, compounds of Formula Ie are as set forth below:

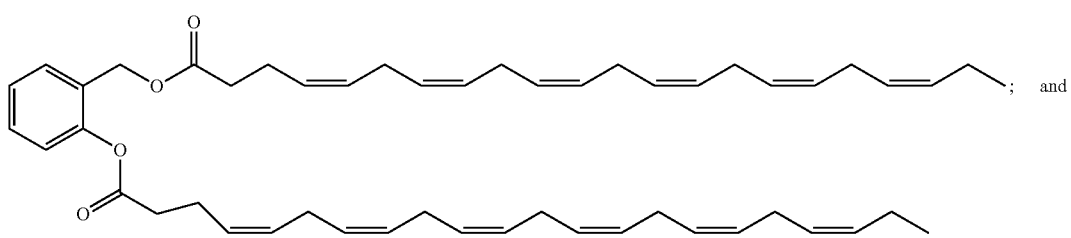

Ie-2

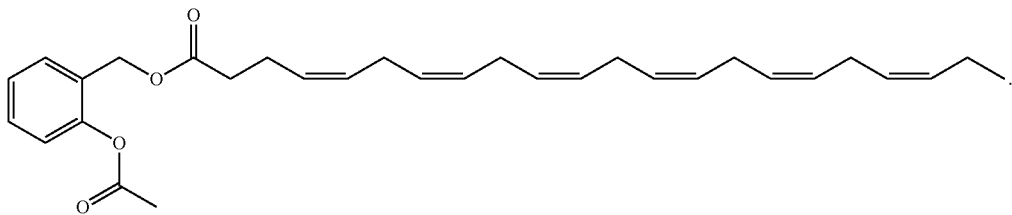

In another aspect, compounds of the Formula If are described:

Formula If

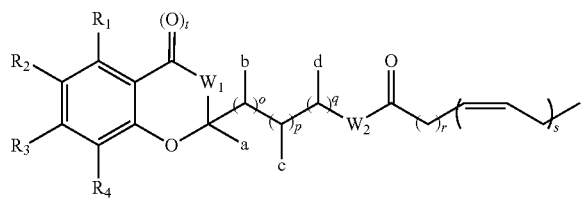

and pharmaceutically acceptable salts, hydrates, solvates, prodrugs, enantiomers, and stereoisomers thereof;
wherein $R_1$, $R_2$, $R_3$, $R_4$ $W_1$, $W_2$, a, b, c, d, Z, o, p, q, r, s, and t are as defined above for the compounds of the Formula If.

In some embodiments, $R_2$ is Cl or F.
In other embodiments, $R_3$ is Cl or F.
In some embodiments, $W_1$ is O.
In some embodiments, $W_2$ is O.
In some embodiments, a and c are each independently H, $CH_3$, —$OCH_3$, —$OCH_2CH_3$, or C(O)OH;
In some embodiments, b is O—Z, Z is

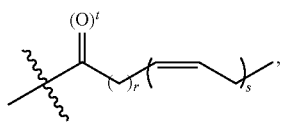

and t is 1.
In some embodiments, d is C(O)OH.
In some embodiments n, o, p, and q are each 1.
In some embodiments, n is 0.

In some embodiments, Z is

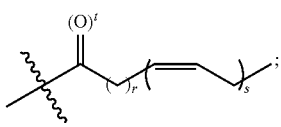

and r is 2.
In some embodiments, Z is

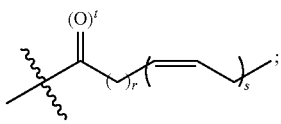

and r is 3.
In some embodiments, Z is

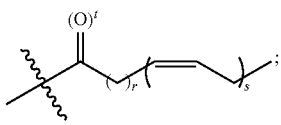

and s is 5.
In some embodiments, Z is

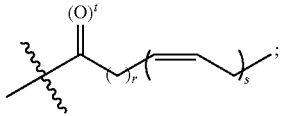

and s is 6.
In some embodiments, t is 1.
In other illustrative embodiments, compounds of Formula If are as set forth below:

If-1

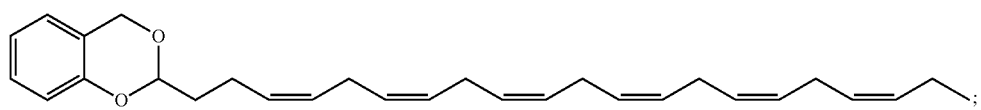

If-2

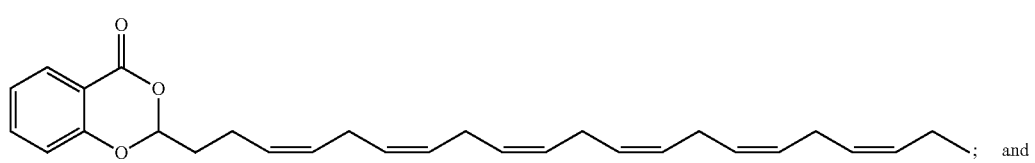

; and

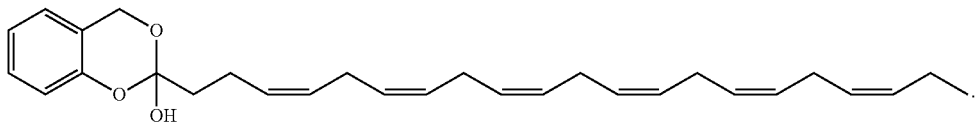

In another aspect, compounds of the Formula Ig are described.

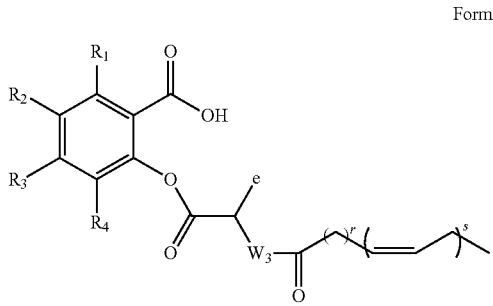

and pharmaceutically acceptable salts, hydrates, solvates, prodrugs, enantiomers, and stereoisomers thereof;
wherein
$R_1, R_2, R_3, R_4, W_3, R, e, r,$ and s are as described above for the compounds of Formula Ig.

In some embodiments, $W_3$ is O.
In some embodiments, e is sec-butyl.
In some embodiments, e is any one of the side chains of the naturally occurring amino acids.
In some embodiments, r is 2.
In some embodiments, r is 3.
In some embodiments, s is 5.
In some embodiments, s is 6.
In some embodiments, t is 1.
In other illustrative embodiments, compounds of Formula Ig are as set forth below:

In another aspect, compounds of the Formula II are described

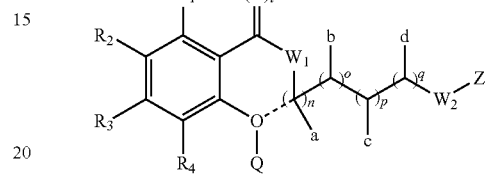

and pharmaceutically acceptable salts, hydrates, solvates, prodrugs, enantiomers, and stereoisomers thereof;
wherein
$R_1, R_2, R_3, R_4, W_1, W_2,$ a, b, c, d, e, the symbol -----, Z, n, o, p, q, r, s, t, Q, and T are as defined above for compounds of Formula II.

In some embodiments, $R_2$ is Cl or F. In other embodiments, $R_3$ is Cl or F. In some embodiments, $W_1$ is O. In some embodiments, $W_2$ is O.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, ----- represents a bond. In some embodiments, a and c are each independently H, $CH_3$,

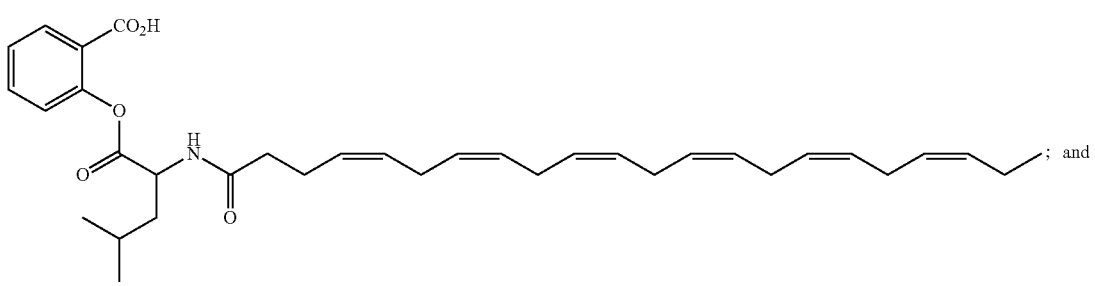

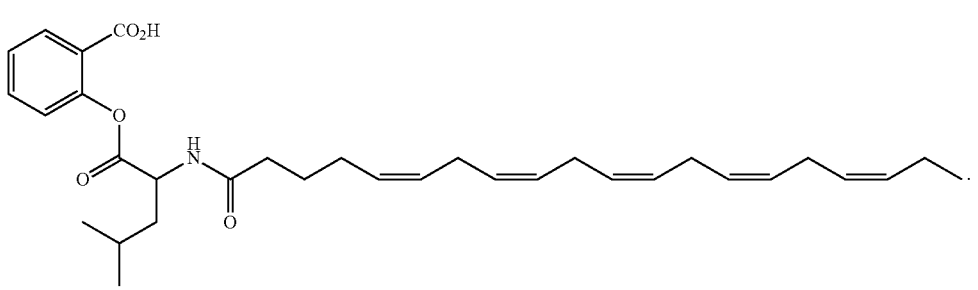

—OCH$_3$, —OCH$_2$CH$_3$, or C(O)OH. In some embodiments, b is O—Z and Z is

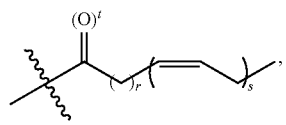

and t is 1. In some embodiments, d is C(O)OH. In some embodiments n, o, p, and q are each 1. In some embodiments, n is 0. In some embodiments, Z is

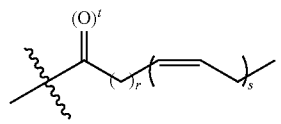

and R is 7. In other embodiments, Z is

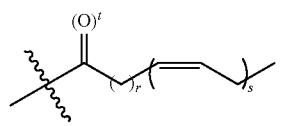

and S is 3. In some embodiments, t is 1. In some embodiments, Q is C(O)CH$_3$. In some embodiments, Q is Z. In some embodiments, Q is

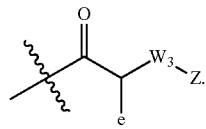

In some embodiments, Q is

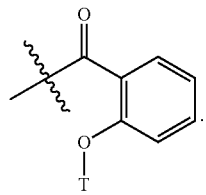

In some embodiments, T is H. In some embodiments, T is C(O)CH$_3$. In some embodiments, T is Z. In some embodiments, e is any one of the side chains of the naturally occurring amino acids. In some embodiments, e is H.

In another aspect, compounds of Formula III are described:

and pharmaceutically acceptable salts, hydrates, solvates, prodrugs, enantiomers, and stereoisomers thereof;

wherein $W_1$, $W_2$, - - - - -, a, b, c, d, n, o, p, q, Z, r, s, t, u, Q, T, e, $W_3$, R are as defined above for compounds of Formula III.

In some embodiments, $R_2$ is Cl or F. In other embodiments, $R_3$ is Cl or F. In some embodiments, $W_1$ is O. In some embodiments, $W_2$ is O.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, CH$_3$, —OCH$_3$, —OCH$_2$CH$_3$, or C(O)OH. In some embodiments, b is O—Z and Z is

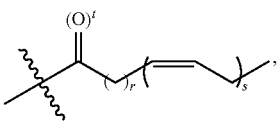

and t is 1. In some embodiments, d is C(O)OH. In some embodiments n, o, p, and q are each 1. In some embodiments, n is 0. In some embodiments, Z is

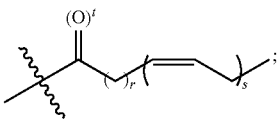

and r is 2. In some embodiments, Z is

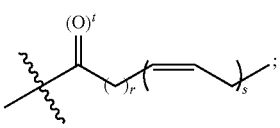

and r is 3. In some embodiments, Z is

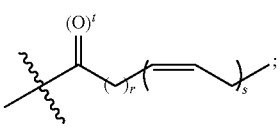

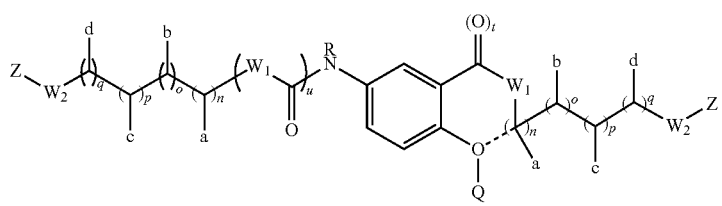

Formula III and s is 5. In some embodiments, Z is

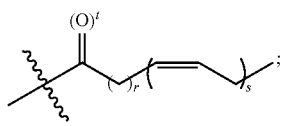

and s is 6. In some embodiments, t is 1. In some embodiments, Q is C(O)CH$_3$. In some embodiments, Q is Z. In some embodiments, Q is

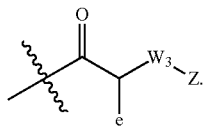

In some embodiments, Q is

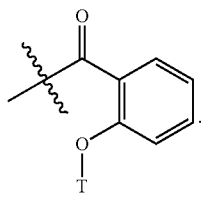

In some embodiments, T is H. In some embodiments, T is C(O)CH$_3$. In some embodiments, T is Z. In some embodiments, e is any one of the side chains of the naturally occurring amino acids. In some embodiments, e is H.

In yet another aspect, compounds of the Formula IIIa are described:

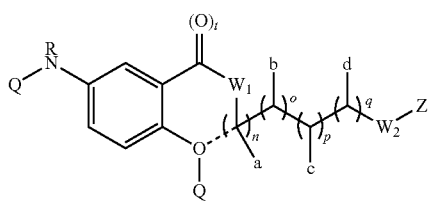

Formula IIIa and pharmaceutically acceptable salts, hydrates, solvates, prodrugs, enantiomers, and stereoisomers thereof;

wherein $W_1$, $W_2$, -----, a, b, c, d, n, o, p, q, Z, r, s, t, Q, T, e, $W_3$, R are as defined above for compounds of Formula IIIa.

In some embodiments, $W_1$ is O. In some embodiments, $W_2$ is O.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, CH$_3$, —OCH$_3$, —OCH$_2$CH$_3$, or C(O)OH. In some embodiments, b is O—Z, Z is

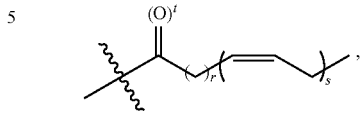

and t is 1. In some embodiments, d is C(O)OH. In some embodiments n, o, p, and q are each 1. In some embodiments, n is 0. In some embodiments, Z is

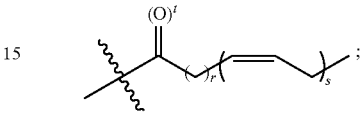

and r is 2. In some embodiments, Z is

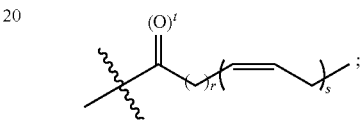

and r is 3. In some embodiments, Z is

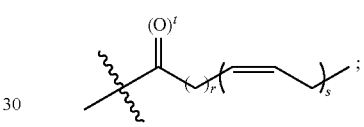

and s is 5. In some embodiments, Z is

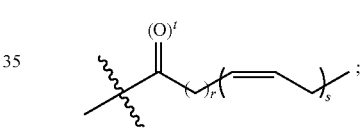

and s is 6. In some embodiments, t is 1. In some embodiments, Q is C(O)CH$_3$. In some embodiments, Q is Z. In some embodiments, Q is

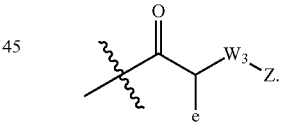

In some embodiments, $W_3$ is O. In other embodiments, $W_3$ is N(R). In further embodiments, $W_3$ is NH. In some embodiments, e is any one of the side chains of the naturally occurring amino acids. In some embodiments, e is H.

In some embodiments, Q is

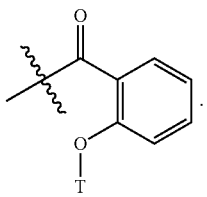

In some embodiments, T is H. In some embodiments, T is C(O)CH$_3$. In some embodiments, T is Z. In some embodiments, e is any one of the side chains of the naturally occurring amino acids. In some embodiments, e is H.

In other illustrative embodiments, compounds of Formula III and IIIa are as set forth below:
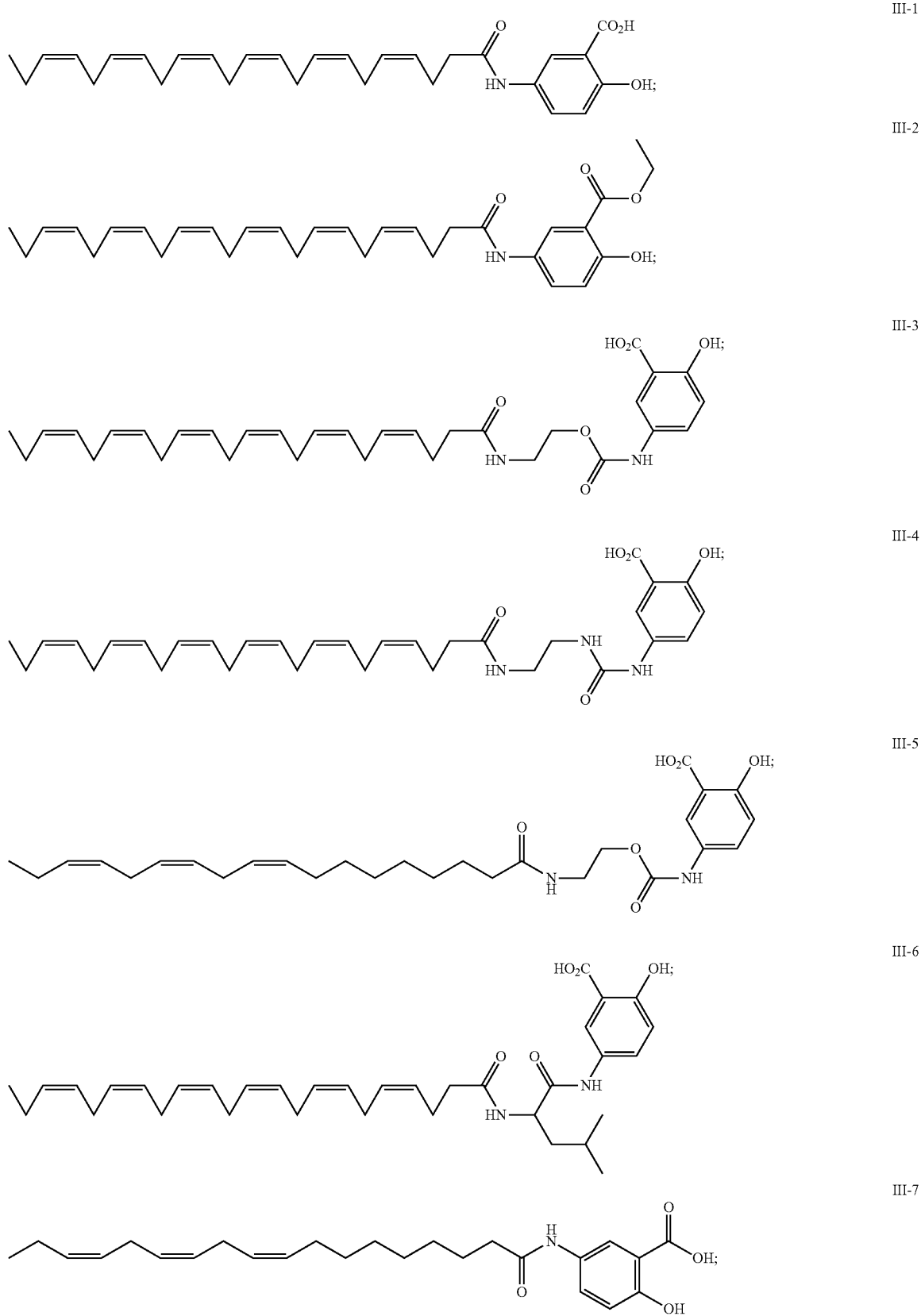

III-8

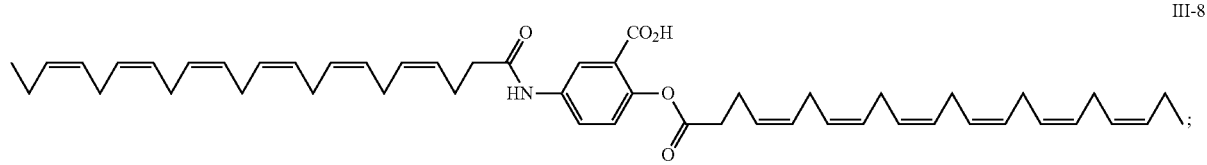

III-9

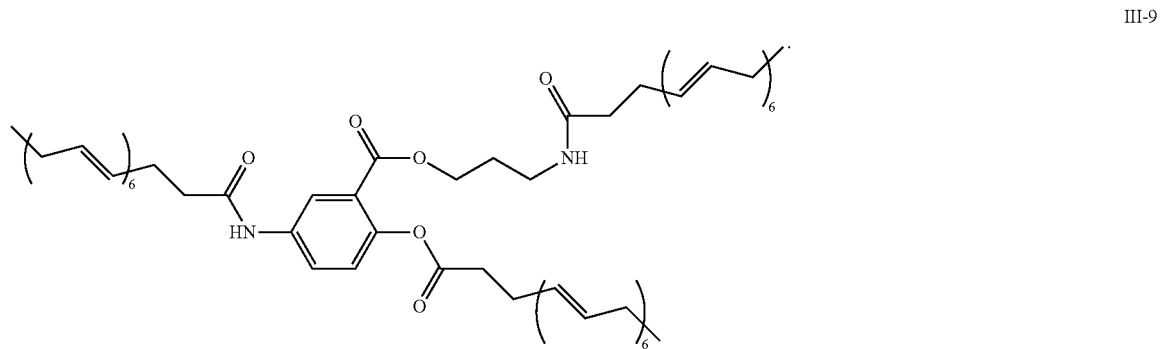

Compounds of the Formula IV are also described herein:

Formula IV

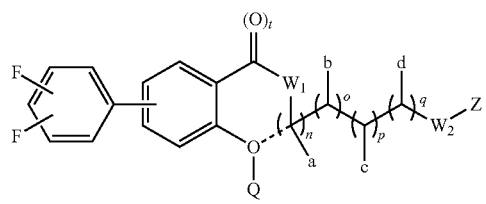

and pharmaceutically acceptable salts, hydrates, solvates, prodrugs, enantiomers, and stereoisomers thereof;

wherein $W_1$, $W_2$, - - - - -, a, b, c, d n, o, p, q, Z, r, s, t, u, Q, e, $W_3$, and R are as defined as above for Formula IV.

In some embodiments, $W_1$ is O. In other embodiments, $W_1$ is NH. In some embodiments, $W_2$ is O. In other embodiments, $W_2$ is NH.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, $CH_3$, —$OCH_3$, —$OCH_2CH_3$, or C(O)OH. In some embodiments, b is O—Z, Z is

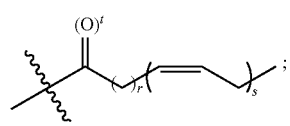

and t is 1. In some embodiments, d is C(O)OH. In some embodiments n, o, p, and q are each 1. In some embodiments, n is 0. In some embodiments, Z is

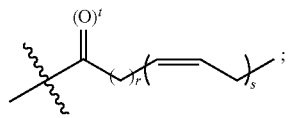

and r is 2. In some embodiments, Z is

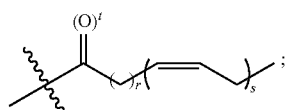

and r is 3. In some embodiments, Z is

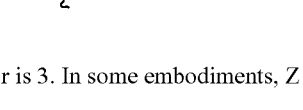

and s is 5. In some embodiments, Z is

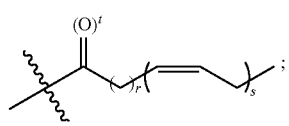

and s is 6. In some embodiments, t is 1. In some embodiments, Q is H. In other embodiments, Q is C(O)CH$_3$. In some embodiments, Q is Z. In some embodiments, Q is

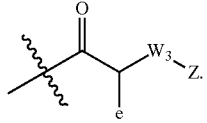

In some embodiments, e is any one of the side chains of the naturally occurring amino acids. In some embodiments, e is H. In other embodiments, e is —C(O)OH. In some embodiments, W$_3$ is —NR—. In some embodiments, W$_3$ is O.

In another aspect, compounds of the Formula IVa are described:

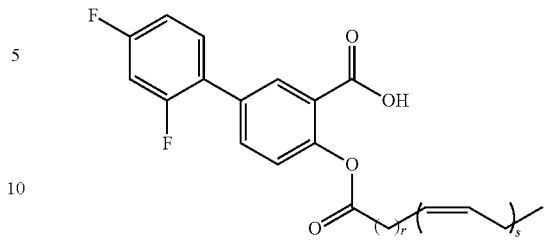

Formula IVa and pharmaceutically acceptable salts, hydrates, solvates, prodrugs, enantiomers, and stereoisomers thereof;
wherein r and are as defined above for Formula IVa.
In some embodiments, r is 2. In some embodiments, r is 3. In some embodiments, s is 5. In some embodiments, s is 6.
Illustrative compounds of Formula IVa include:

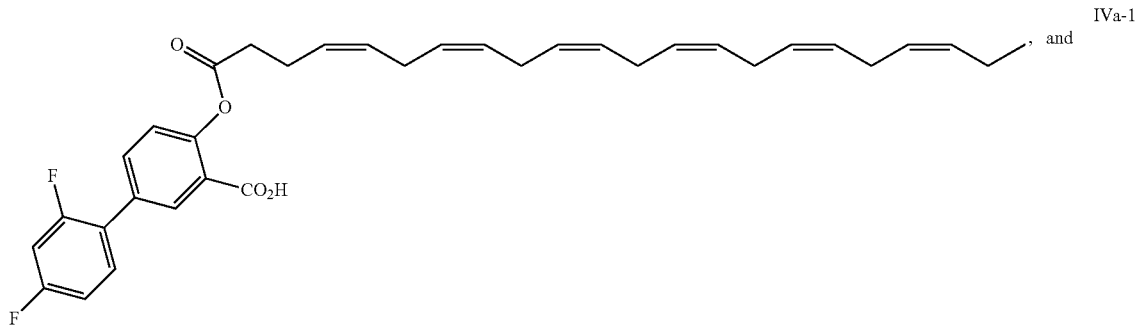

IVa-1, and

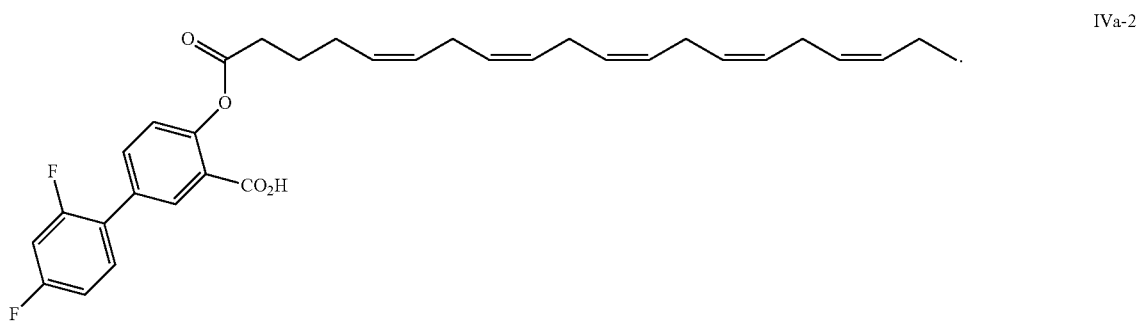

IVa-2.

In another aspect, compounds of the Formula IVb are described:

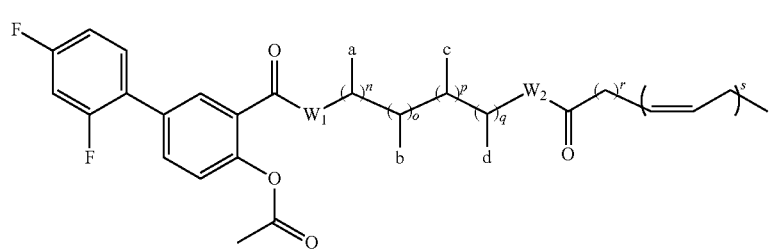

Formula IVb and pharmaceutically acceptable salts, hydrates, solvates, enantiomers, and stereoisomers thereof, wherein $W_1$, $W_2$, a, b, c, d n, o, p, q, Z r, s, and t are as defined above for Formula IVb.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is

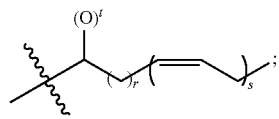

and t is 1. In some embodiments, d is C(O)OH. In some embodiments n, o, p, and q are each 1. In some embodiments, n is 0.

In some embodiments, Z is

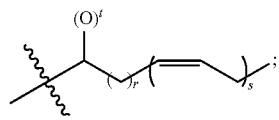

and r is 2. In some embodiments, Z is

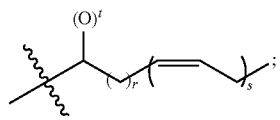

and r is 3. In some embodiments, Z is

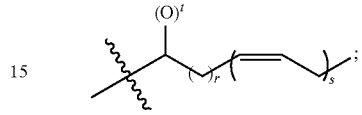

and s is 5. In some embodiments, Z is

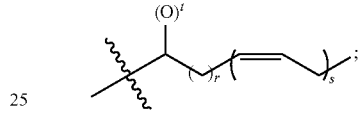

and s is 6. In other embodiments, Z is not H. In some embodiments, t is 1.

Illustrative compounds of Formula IVb include:

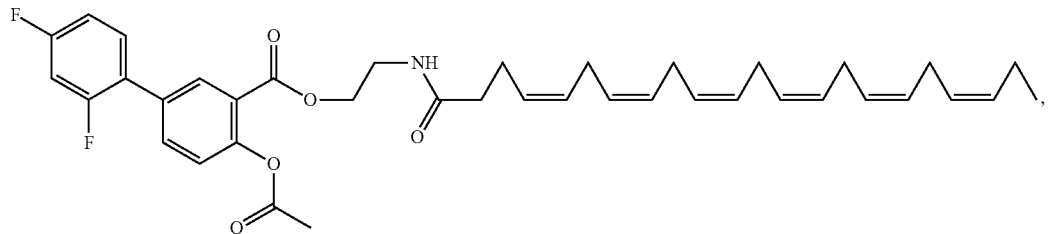

IVb-1

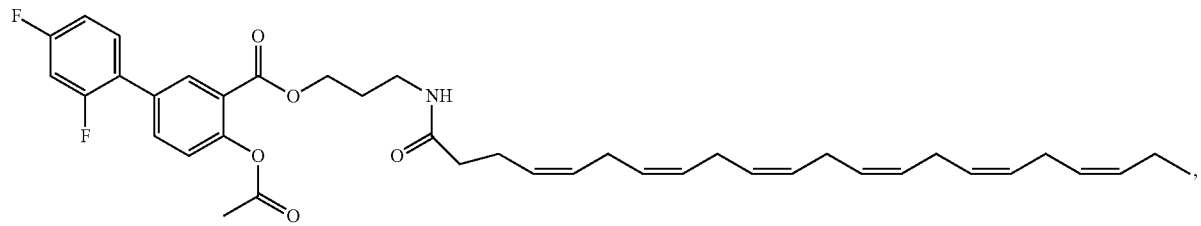

IVb-2

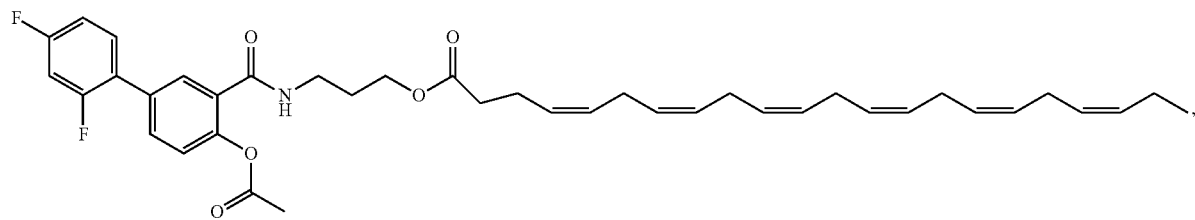

IVb-3

-continued
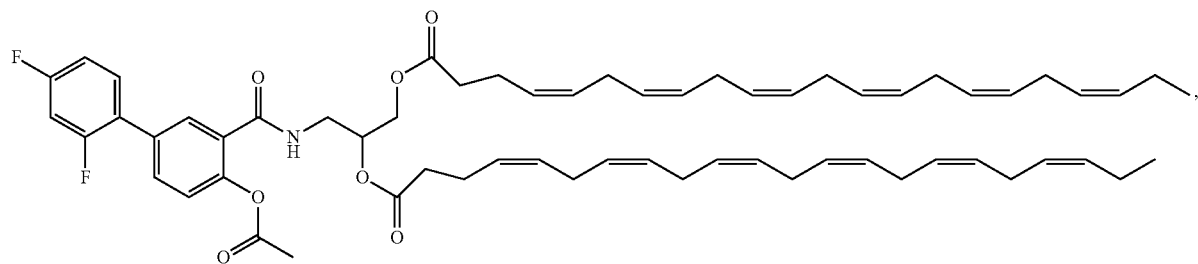
IVb-4
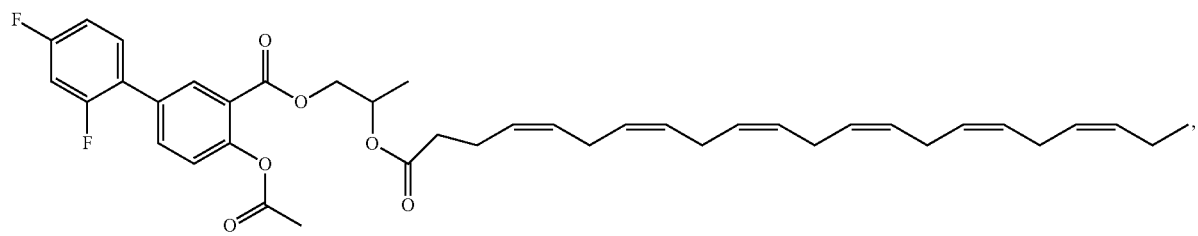
IVb-5
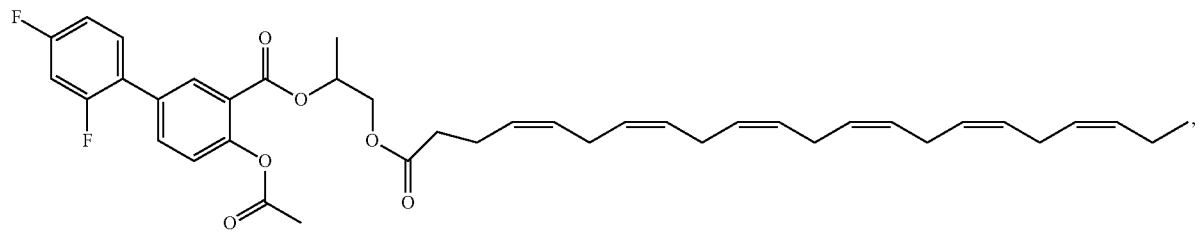
IVb-6
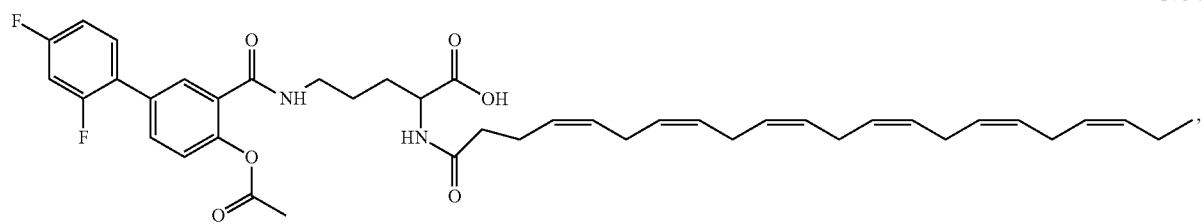
IVb-7
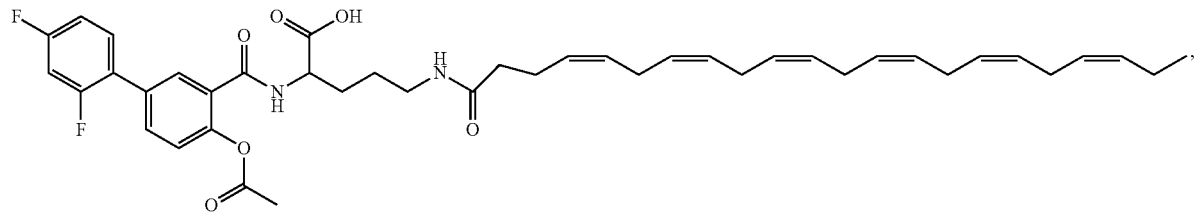
IVb-8
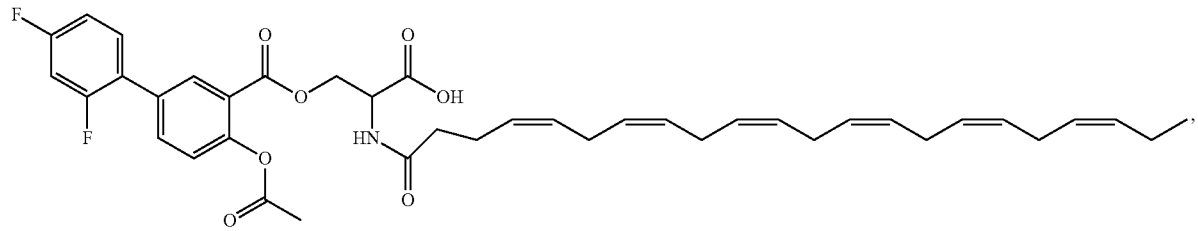
IVb-9

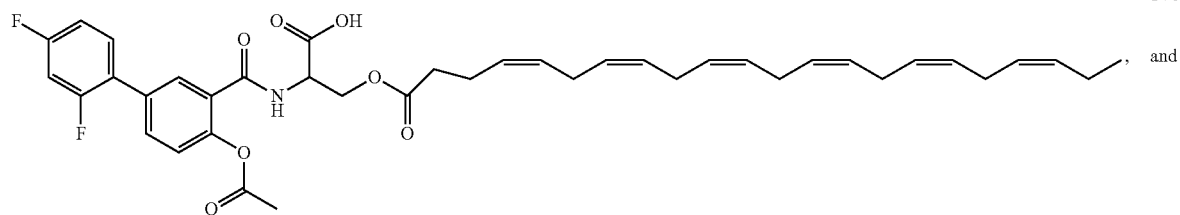

In another aspect, compounds of the Formula IVc are described:

Formula IVc and pharmaceutically acceptable salts, hydrates, solvates, prodrugs, enantiomers, and stereoisomers thereof;

wherein $W_1$, $W_2$, a, b, c, d, n, o, p, q, Z, r, s, and t are as defined above for Formula IVc.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is and t is 1. In some embodiments, d is C(O)OH. In some embodiments n, o, p, and q are each 1. In some embodiments, n is 0. In some embodiments, Z is and r is 2. In some embodiments, Z is and r is 3. In some embodiments, Z is and s is 5. In some embodiments, Z is and s is 6. In some embodiments, at most one Z is H. In some embodiments, Z is not H. In other embodiments, Z is not —C(O)$CH_3$. In some embodiments, t is 1.

Illustrative compounds of Formula IVc are:
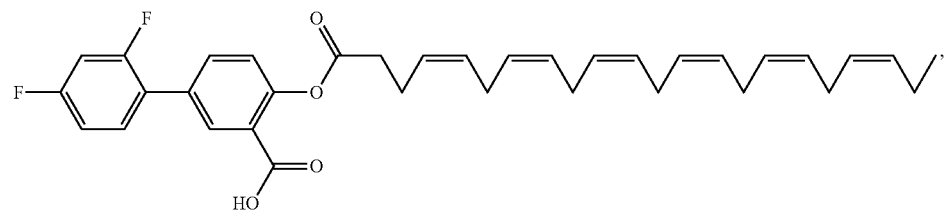
IVc-1
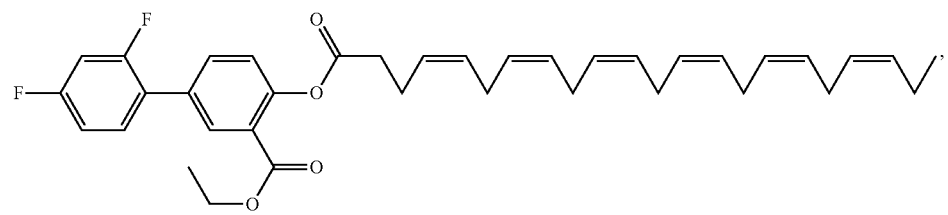
IVc-2
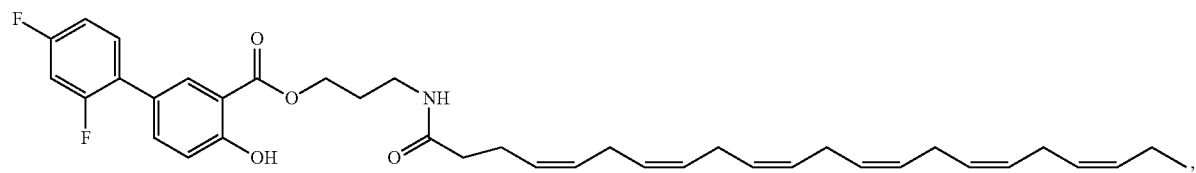
IVc-3
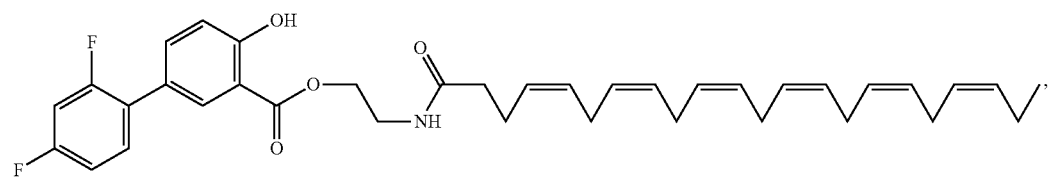
IVc-4

-continued

IVc-5
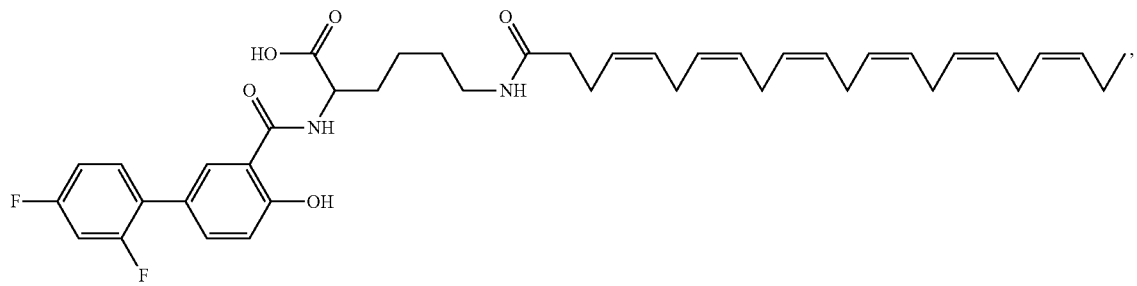,

IVc-6
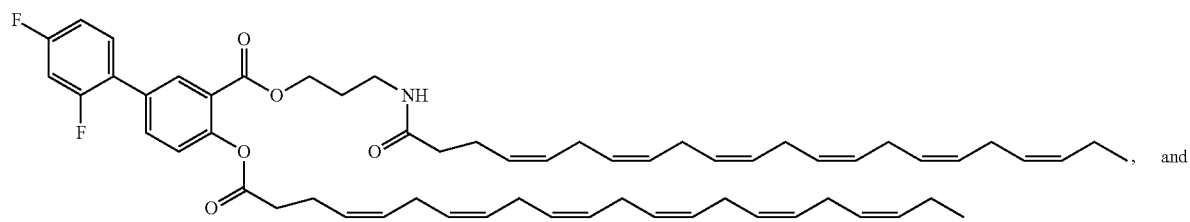, and

IVc-7
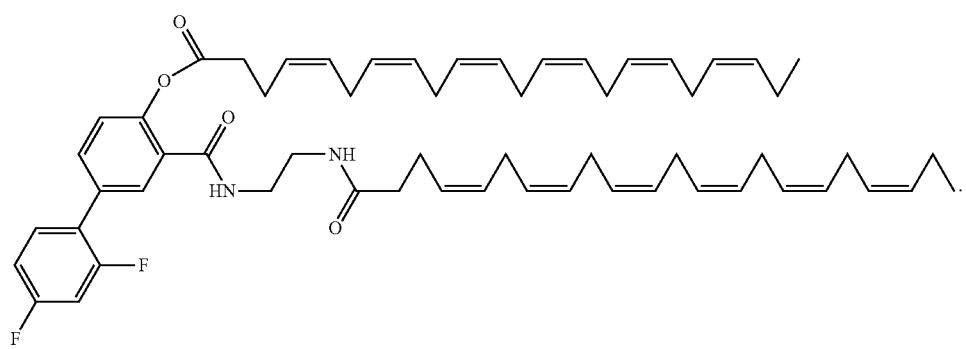.

In another aspect, compounds of the Formula IVd are described:

Formula IVd
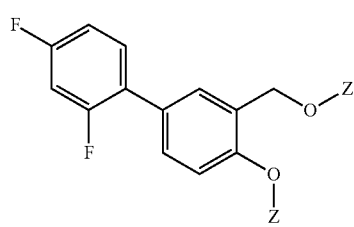

and pharmaceutically acceptable salts, hydrates, solvates, prodrugs, enantiomers, and stereoisomers thereof; wherein Z, r, s, and t are as defined above for Formula IVd.

In some embodiments, Z is

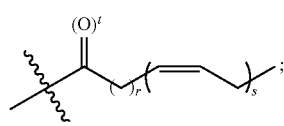

and r is 2. In some embodiments, Z is

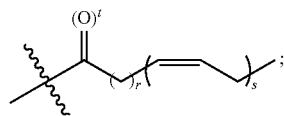

and r is 3. In some embodiments, Z is

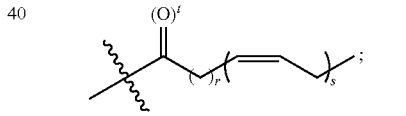

and s is 5. In some embodiments, Z is

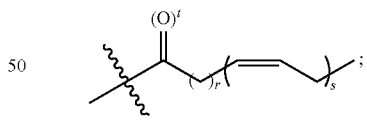

and s is 6. In some embodiments, t is 1.

In another aspect, compounds of the Formula IVe are described:

Formula IVe
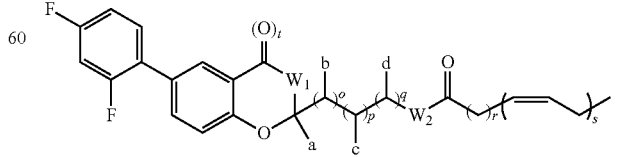

and pharmaceutically acceptable salts, hydrates, solvates, prodrugs, enantiomers, and stereoisomers thereof;

wherein $W_1$, $W_2$ a, b, c, d, o, p, q, Z, r, s, t, and u are as defined above for Formula IVe.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH. In some embodiments, b is O—Z, Z is

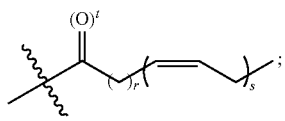

and t is 1. In some embodiments, d is C(O)OH. In some embodiments n, o, p, and q are each 1. In some embodiments, n is 0. In some embodiments, Z is

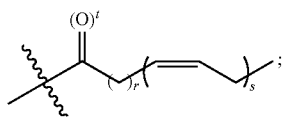

and r is 2. In some embodiments, Z is

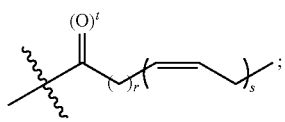

and r is 3. In some embodiments, Z is

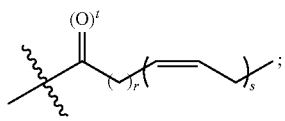

and s is 5. In some embodiments, Z is

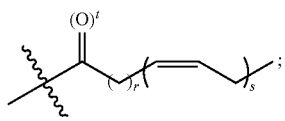

and s is 6. In some embodiments, t is 1.

An illustrative compound of Formula IVe is:

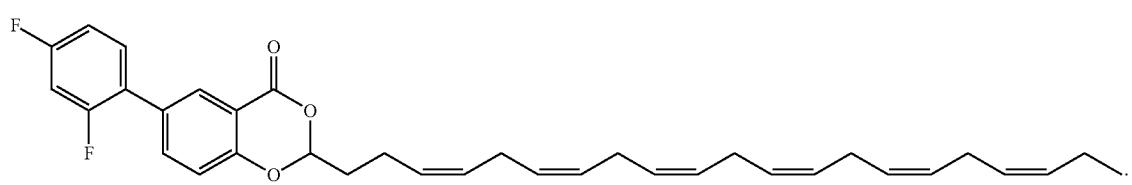 [SMILES: CC/C=C\C/C=C\C/C=C\C/C=C\C/C=C\C/C=C\CCC1OC(=O)c2cc(-c3ccc(F)cc3F)ccc2O1]

In another aspect, compounds of the Formula IVf are described:

Formula IVf

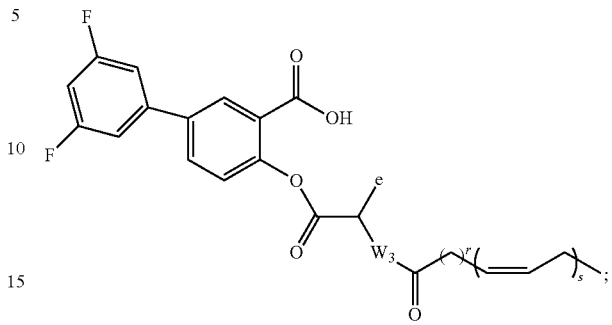

and pharmaceutically acceptable salts, hydrates, solvates, prodrugs, enantiomers, and stereoisomers thereof;

wherein e, $W_3$, R, r, and s are as defined above for Formula IVf.

In some embodiments, $W_3$ is O. In some embodiments, e is sec-butyl. In other embodiments, e is —C(O)OH. In still other embodiments, e is H. In some embodiments, $W_3$ is —NR—. In some embodiments, $W_3$ is O. In some embodiments, Z is

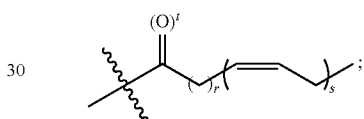

and r is 2. In some embodiments, Z is

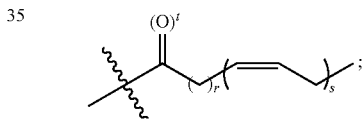

and r is 3. In some embodiments, Z is

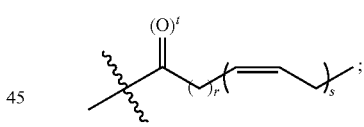

and s is 5. In some embodiments, Z is

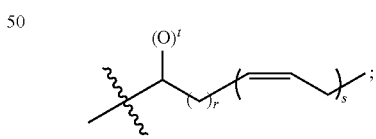

and s is 6. In some embodiments, t is 1.

Illustrative compounds of Formula IVf include:
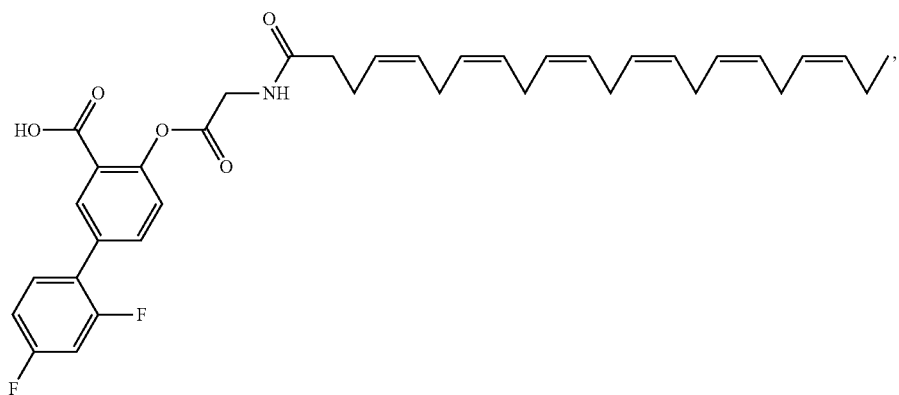
IVf-1
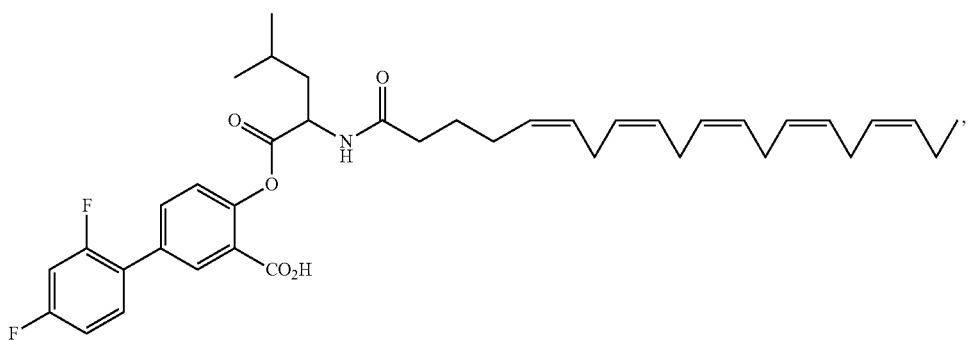
IVf-2
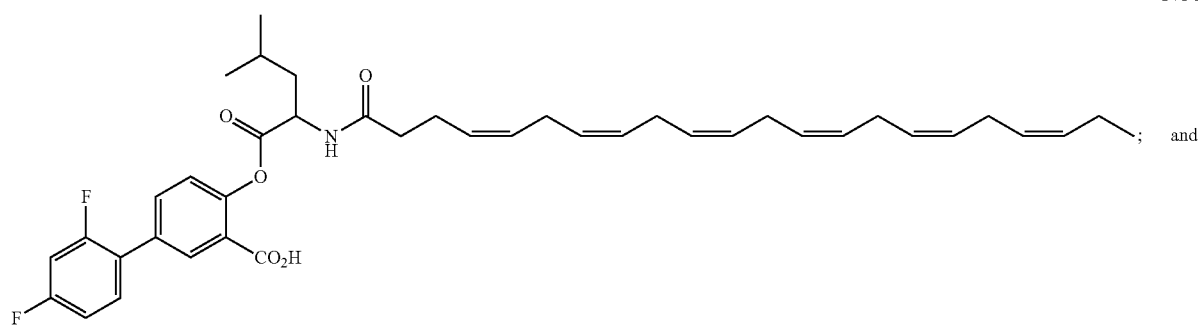
IVf-3; and
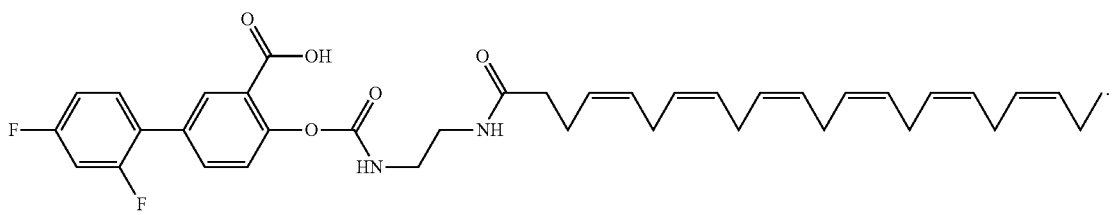
IVf-4

In another aspect, compounds of the Formula IVg are described:

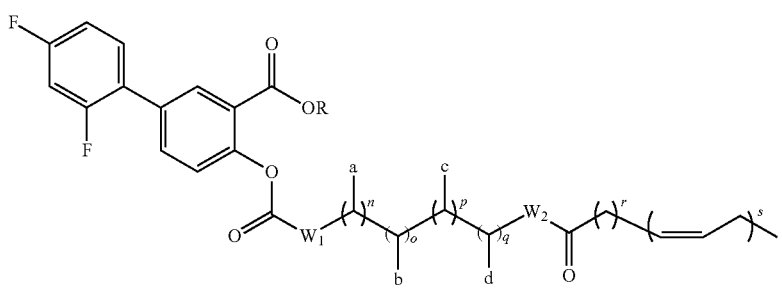

Formula IVg and pharmaceutically acceptable salts, hydrates, solvates, prodrugs, enantiomers, and stereoisomers thereof;

wherein R, $W_1$, $W_2$, a, b, c, d, n, o, p, q, Z, r, s, and t are as defined above for Formula IVg.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, $-OCH_3$, $-OCH_2CH_3$, or C(O)OH; In some embodiments, b is O—Z, Z is

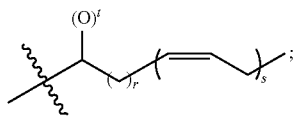

and t is 1. In some embodiments, d is C(O)OH. In some embodiments n, o, p, and q are each 1. In some embodiments, n is 0. In some embodiments, Z is

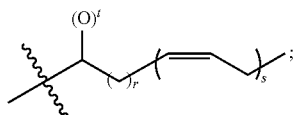

and r is 2. In some embodiments, Z is

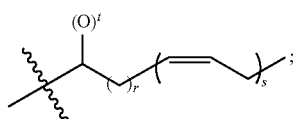

and r is 3. In some embodiments, Z is

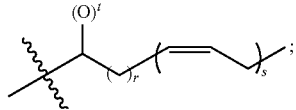

and s is 5. In some embodiments, Z is

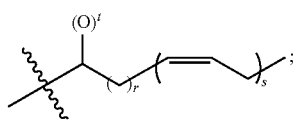

and s is 6. In some embodiments, at most one Z is H. In some embodiments, Z is not H. In other embodiments, Z is not —C(O)$CH_3$. In some embodiments, t is 1.

Illustrative compounds of Formula IVg include:

IVg-1

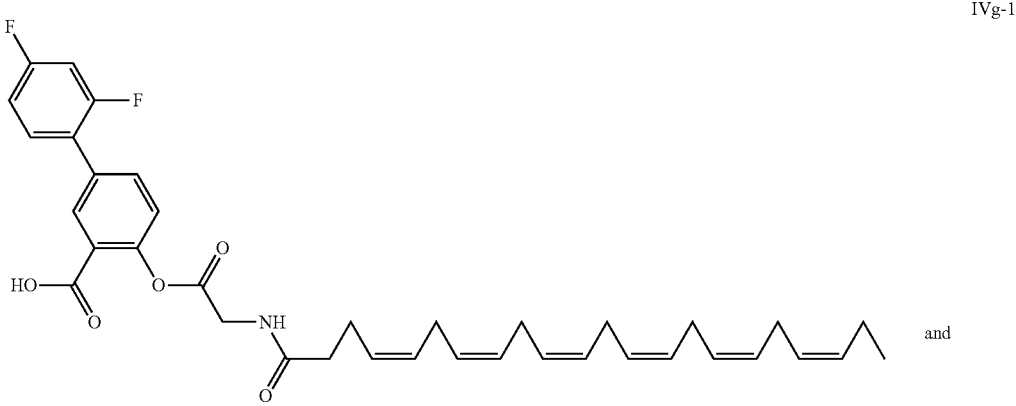

and

-continued

IVg-2

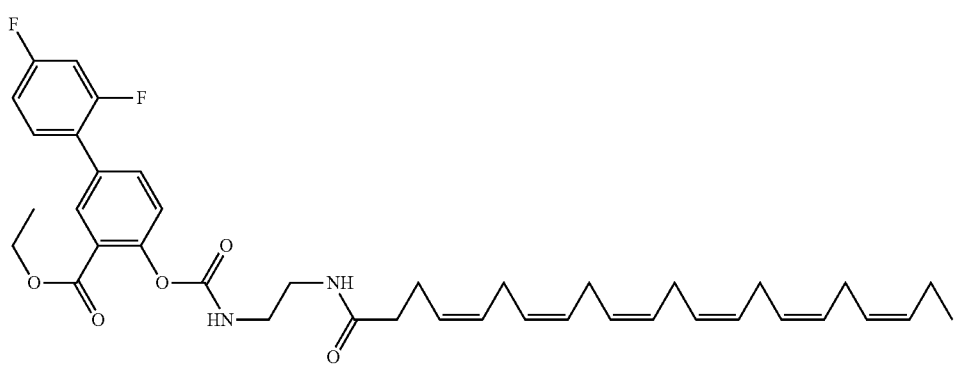

In another aspect, compounds of the Formula V are described:

Formula V

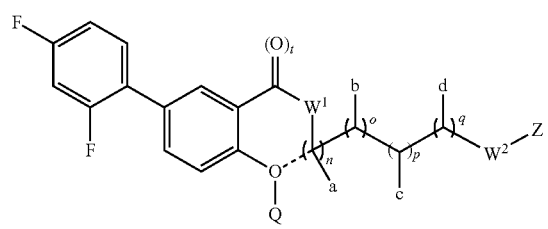

and pharmaceutically acceptable salts, hydrates, solvates, prodrugs, enantiomers, and stereoisomers thereof;

wherein $W_1$, $W_2$, -----, Q, a, b, c, d, e, $W_3$, n, o, p, q, Z, r, s, and t are as defined above for Formula V.

In some embodiments, $W_1$ is O. In some embodiments, $W_1$ is NH. In some embodiments, $W_2$ is O. In some embodiments, $W_2$ is NH.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, $CH_3$, —$OCH_3$, —$OCH_2CH_3$, or C(O)OH. In some embodiments, b is O—Z, Z is

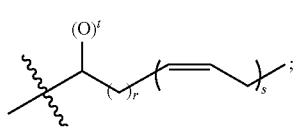

and t is 1. In some embodiments, d is C(O)OH. In some embodiments n, o, p, and q are each 1. In some embodiments, n is 0. In some embodiments, Z is

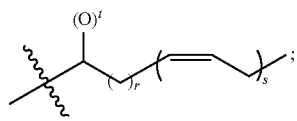

and r is 7. In some embodiments, Z is

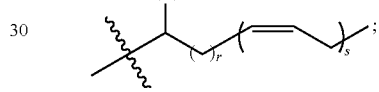

and s is 3. In some embodiments, t is 1. In some embodiments, Q is C(O)$CH_3$, In some embodiments, Q is Z. In some embodiments, Q is

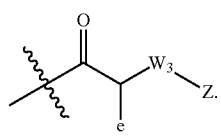

In some embodiments, e is any one of the side chains of the naturally occurring amino acids. In some embodiments, e is H. In other embodiments, e is —C(O)OH. In some embodiments, $W_3$ is —NR—. In some embodiments, $W_3$ is O.

Also described herein are compounds of the Formula VI:

Formula VI

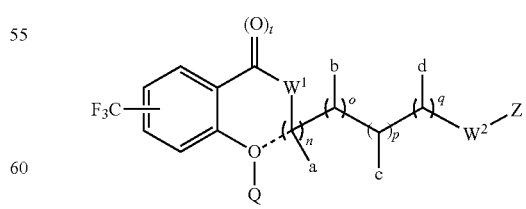

and pharmaceutically acceptable salts, hydrates, solvates, prodrugs, enantiomers, and stereoisomers thereof;

wherein $W_1$, $W_2$, - - - - -, a, b, c, d n, o, p, q, Z, r, s, t, u, Q, e, $W_3$, and R are as defined above for Formula VI.

In some embodiments, $W_1$ is O. In other embodiments, $W_1$ is NH. In some embodiments, $W_2$ is O. In other embodiments, $W_2$ is NH.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, $CH_3$, —$OCH_3$, —$OCH_2CH_3$, or C(O)OH. In some embodiments, b is O—Z, Z is

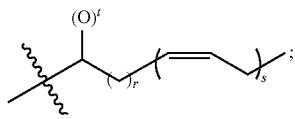

and t is 1. In some embodiments, d is C(O)OH. In some embodiments n, o, p, and q are each 1. In some embodiments, n is 0. In some embodiments, Z is

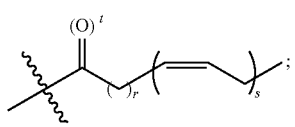

and r is 2. In some embodiments, Z is

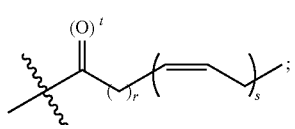

and r is 3. In some embodiments, Z is

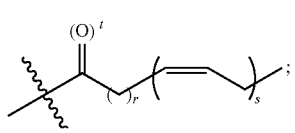

and s is 5. In some embodiments, Z is

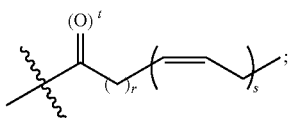

and s is 6. In some embodiments, t is 1. In some embodiments, Q is H. In other embodiments, Q is $C(O)CH_3$. In some embodiments, Q is Z. In some embodiments, Q is

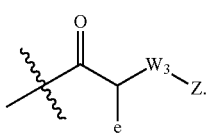

In some embodiments, e is any one of the side chains of the naturally occurring amino acids. In some embodiments, e is H. In other embodiments, e is —C(O)OH. In some embodiments, $W_3$ is —NH—. In some embodiments, $W_3$ is O.

In another aspect, compounds of the Formula VIa are described:

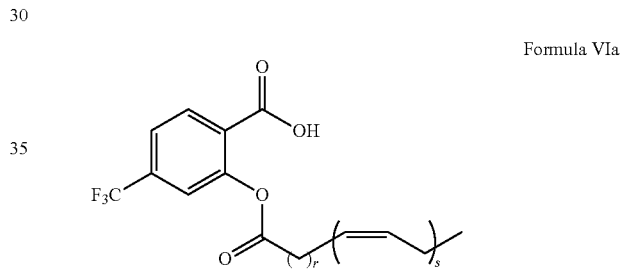

Formula VIa and pharmaceutically acceptable salts, hydrates, solvates, prodrugs, enantiomers, and stereoisomers thereof;

wherein r and s are as defined above for Formula VIa.

In some embodiments, r is 2. In some embodiments, r is 3. In some embodiments, s is 5. In some embodiments, s is 6.

Illustrative compounds of Formula VIa include:

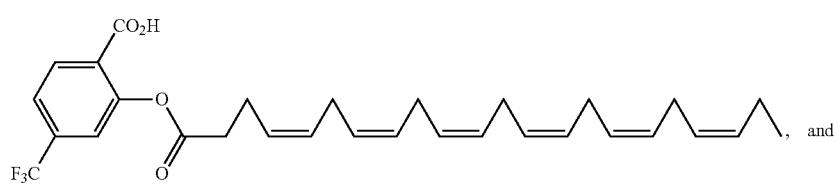

VIa-1

, and

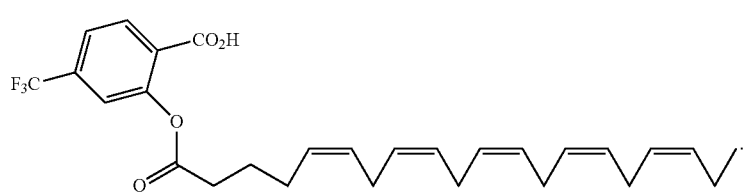

VIa-2

In another aspect, compounds of the Formula VIb are described:

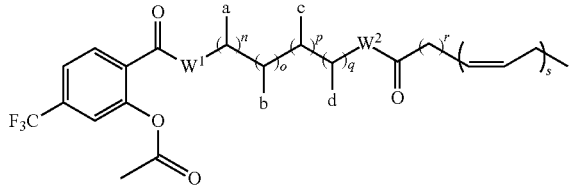

Formula VIb and pharmaceutically acceptable salts, hydrates, solvates, enantiomers, and stereoisomers thereof, wherein $W_1$, $W_2$, a, b, c, d n, o, p, q, Z r, s, and t are as defined above for Formula VIb.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, $-OCH_3$, $-OCH_2CH_3$, or C(O)OH; In some embodiments, b is O—Z, Z is

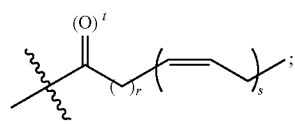

and t is 1. In some embodiments, d is C(O)OH. In some embodiments n, o, p, and q are each 1. In some embodiments, n is 0.

In some embodiments, Z is

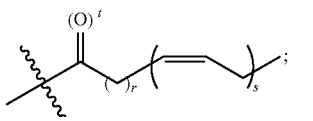

and r is 2. In some embodiments, Z is

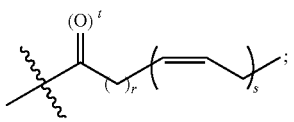

and r is 3. In some embodiments, Z is

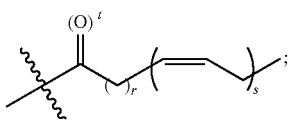

and s is 5. In some embodiments, Z is

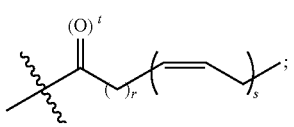

and s is 6. In some embodiments, t is 1.

Illustrative compounds of Formula VIb include:

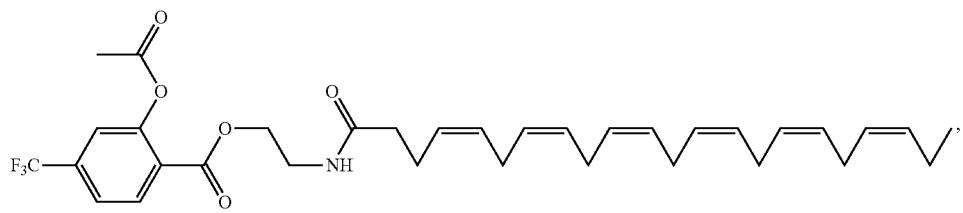

VIb-1

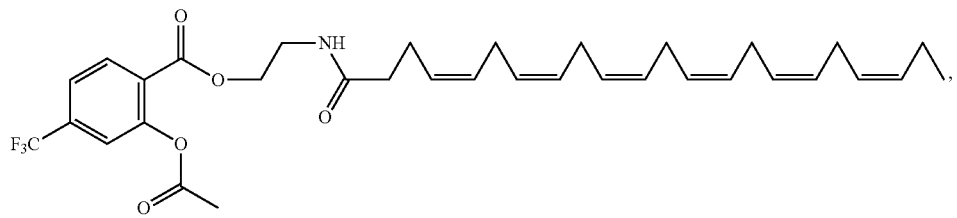

VIb-2

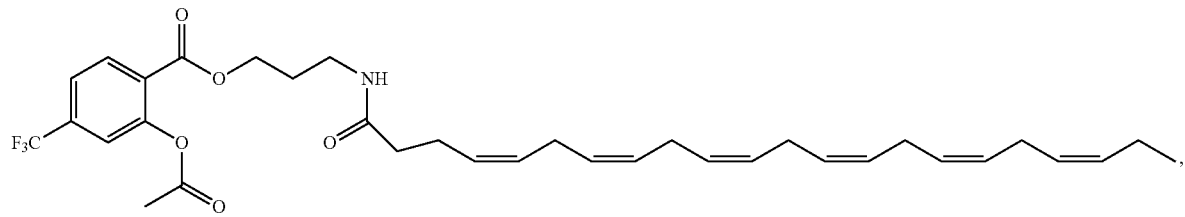

VIb-3

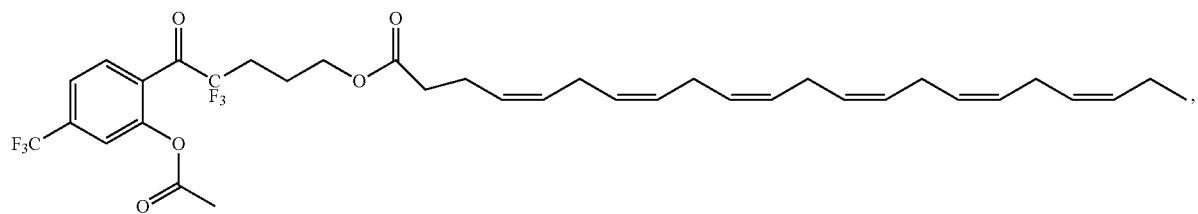
VIb-4
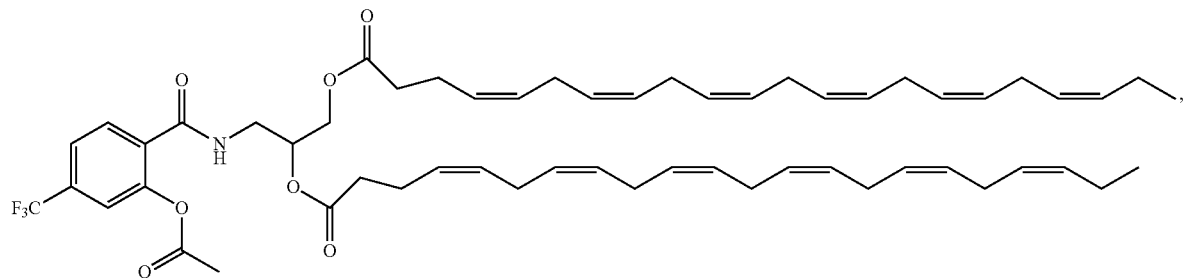
VIb-5
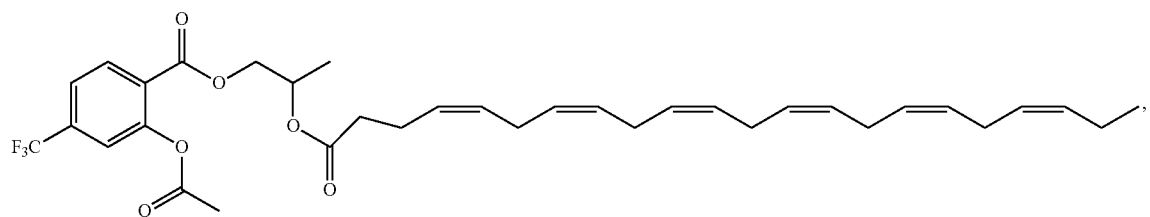
VIb-6
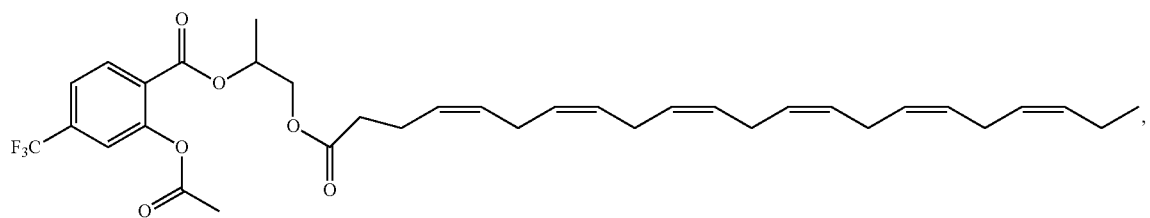
VIb-7
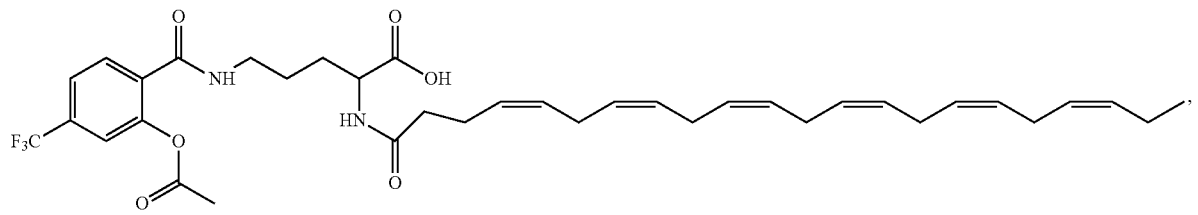
VIb-8
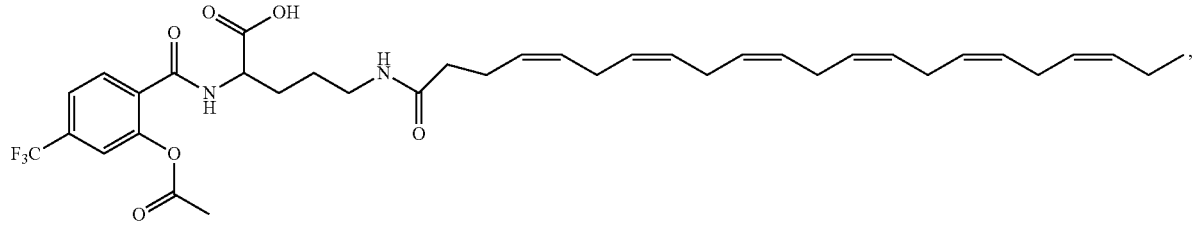
VIb-9

-continued

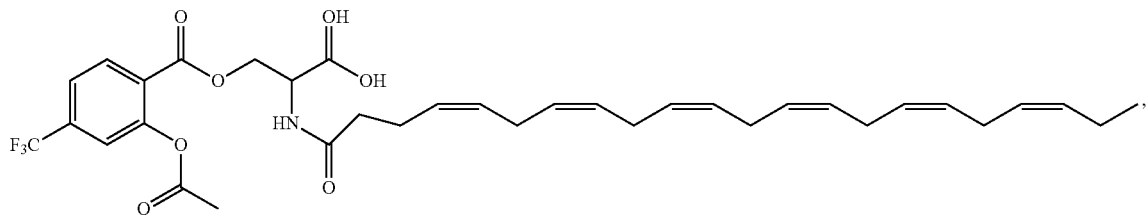
VIb-10

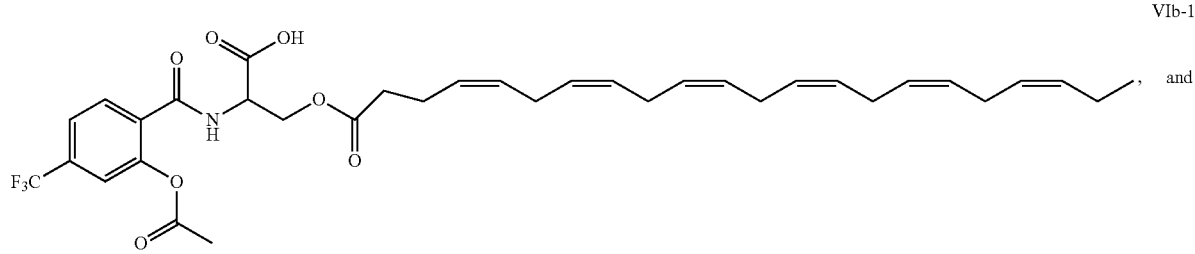
VIb-11, and

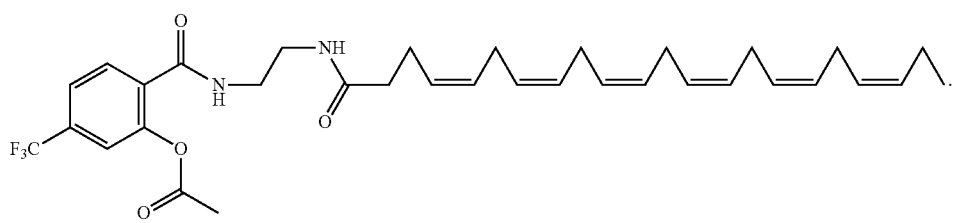
VIb-12

In another aspect, compounds of the Formula VIc are described:

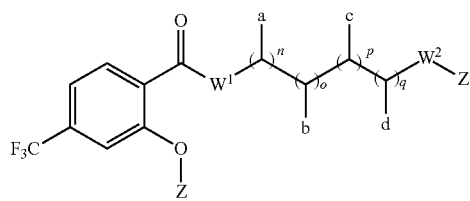
Formula VIc and pharmaceutically acceptable salts, hydrates, solvates, prodrugs, enantiomers, and stereoisomers thereof;

wherein $W_1$, $W_2$, a, b, c, d, n, o, p, q, Z, r, s, and t are as defined above for Formula VIc.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is

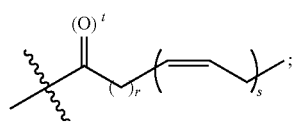

and t is 1. In some embodiments, d is C(O)OH. In some embodiments n, o, p, and q are each 1.

In some embodiments, n is 0. In some embodiments, Z is

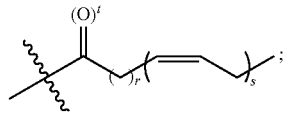

and r is 2. In some embodiments, Z is

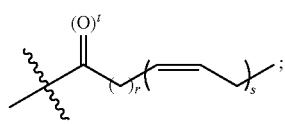

and r is 3. In some embodiments, Z is

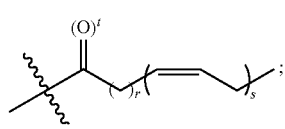

and s is 5. In some embodiments, Z is

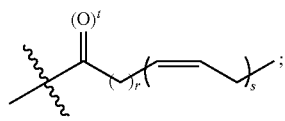

and s is 6. In some embodiments, at most one Z is H. In some embodiments, Z is not H. In other embodiments, Z is not —C(O)$CH_3$. In some embodiments, t is 1.

Illustrative compounds of Formula VIc are:
VIc-1
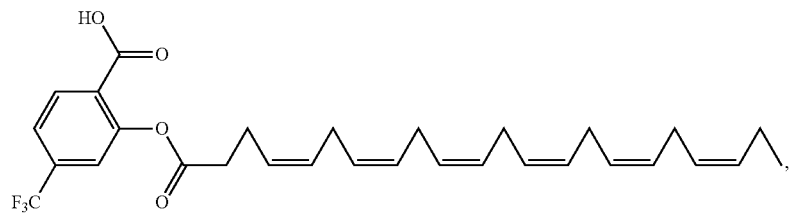
VIc-2
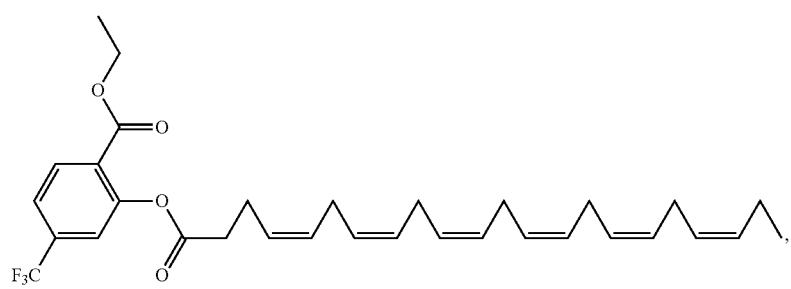
VIc-3
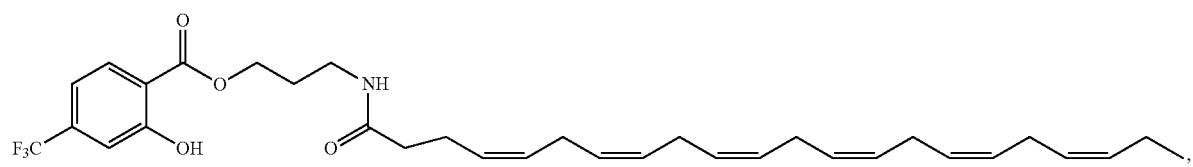
VIc-4
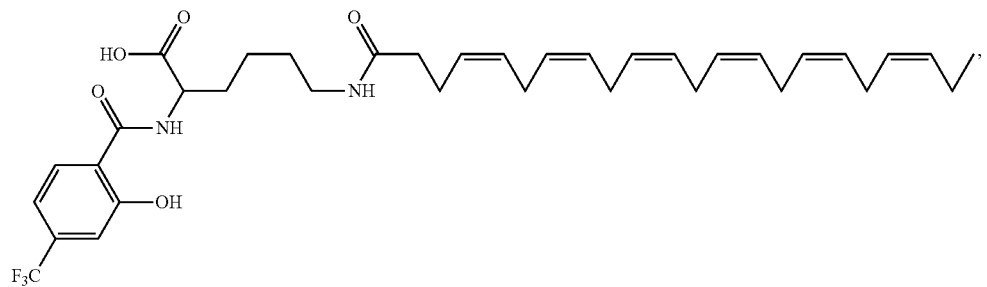
VIc-5

-continued

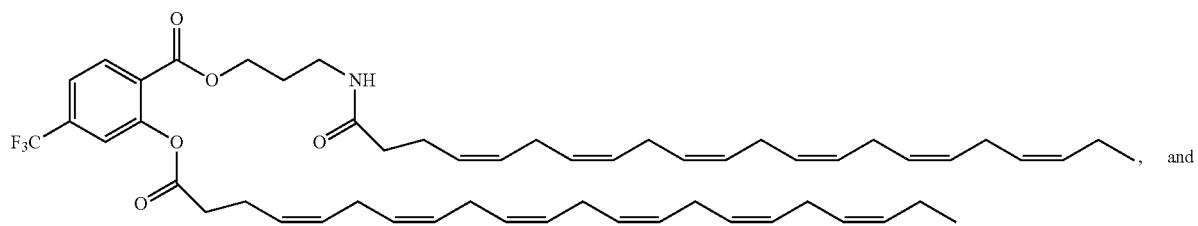

VIc-6

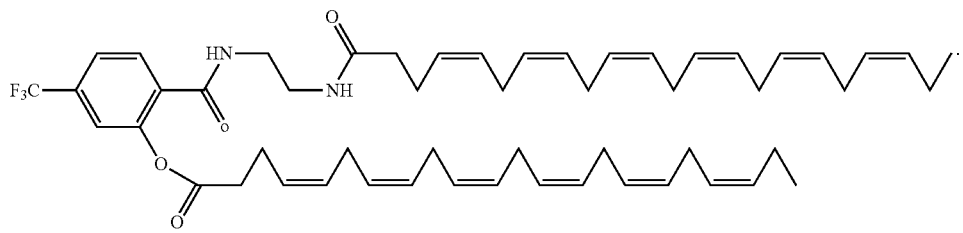

VIc-7

In another aspect, compounds of the Formula VId are described:

Formula VId

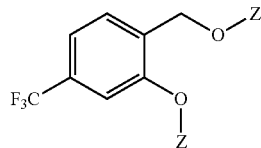

and pharmaceutically acceptable salts, hydrates, solvates, prodrugs, enantiomers, and stereoisomers thereof;

wherein Z, r, s, and t are as defined above for Formula VId.

In some embodiments, Z is

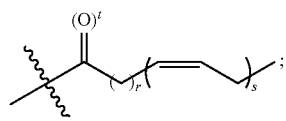

and r is 2. In some embodiments, Z is

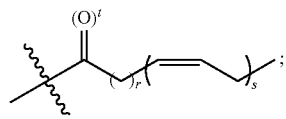

and r is 3. In some embodiments, Z is

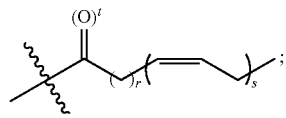

and s is 5. In some embodiments, Z is

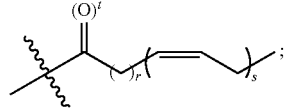

and s is 6. In some embodiments, t is 1.

In another aspect, compounds of the Formula VIe are described:

Formula VIe

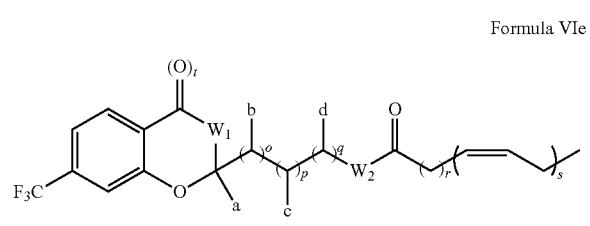

and pharmaceutically acceptable salts, hydrates, solvates, prodrugs, enantiomers, and stereoisomers thereof;

wherein $W_1$, $W_2$, a, b, c, d, o, p, q, Z, r, s, and t, are as defined above for Formula VIe.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH. In some embodiments, b is O—Z, Z is

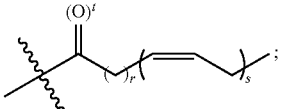

and t is 1. In some embodiments, d is C(O)OH. In some embodiments n, o, p, and q are each 1.

In some embodiments, n is 0. In some embodiments, Z is

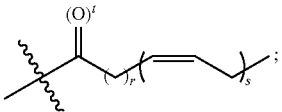

and r is 2. In some embodiments, Z is

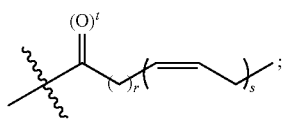

and r is 3. In some embodiments, Z is

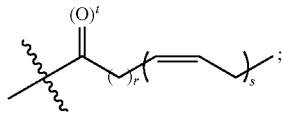

and s is 5. In some embodiments, Z is

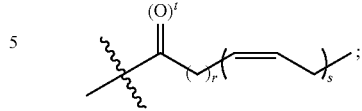

and s is 6. In some embodiments, t is 1.

An illustrative compound of Formula VIe is:

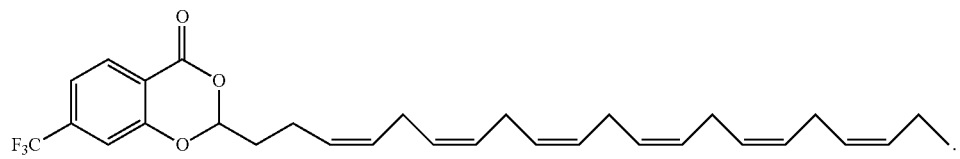 [SMILES: CC/C=C\C/C=C\C/C=C\C/C=C\C/C=C\C/C=C\CCC1OC(=O)c2ccc(C(F)(F)F)cc2O1]

In another aspect, compounds of the Formula VIf are described:

Formula VIf

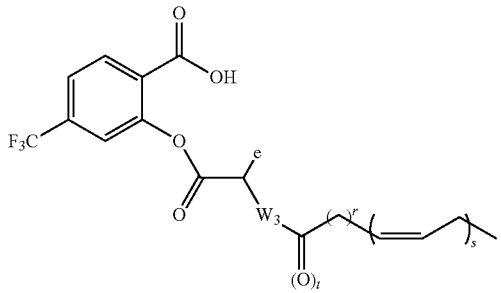

and pharmaceutically acceptable salts, hydrates, solvates, prodrugs, enantiomers, and stereoisomers thereof;

wherein e, $W_3$, R, r, s, and t are as defined above for Formula VIf.

In some embodiments, $W_3$ is O. In some embodiments, e is sec-butyl. In other embodiments, e is —C(O)OH. In still other embodiments, e is H. In some embodiments, $W_3$ is —NR—. In some embodiments, $W_3$ is O. In some embodiments, r is 2. In some embodiments, r is 3. In some embodiments, s is 5. In some embodiments, s is 6. In some embodiments, t is 1.

Illustrative compounds of Formula VIf include:

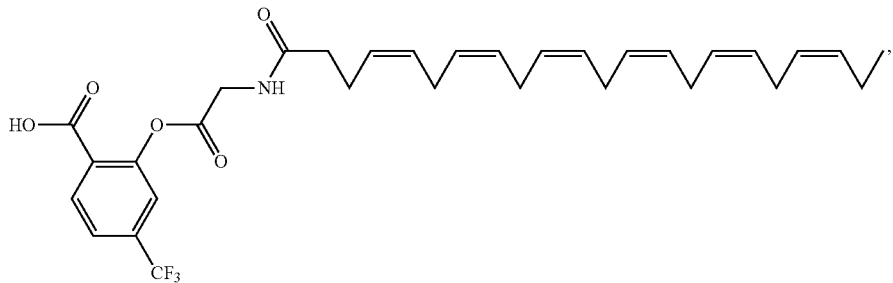

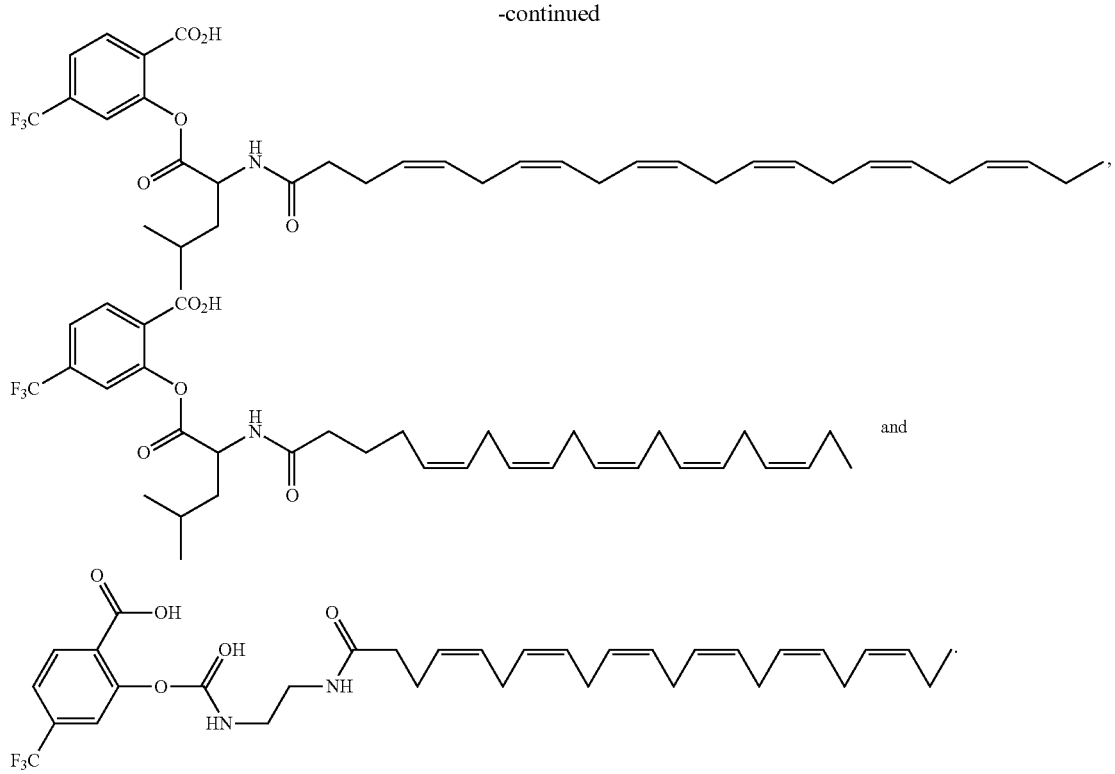

In another aspect, compounds of the Formula VIg are described:

Formula VIg

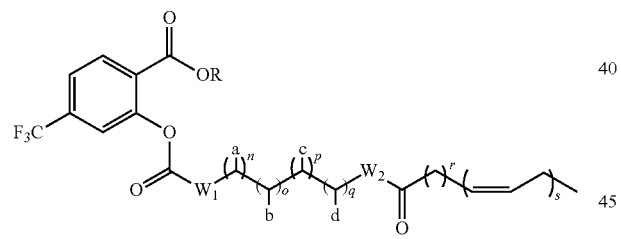

and pharmaceutically acceptable salts, hydrates, solvates, prodrugs, enantiomers, and stereoisomers thereof;

wherein R, $W^1$, $W^2$, a, b, c, d, n, o, p, q, Z, r, s, and t are as defined above for Formula VIg.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is

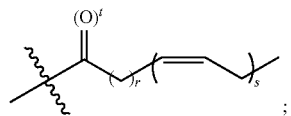

and t is 1. In some embodiments, d is C(O)OH. In some embodiments n, o, p, and q are each 1. In some embodiments, n is 0. In some embodiments, Z is

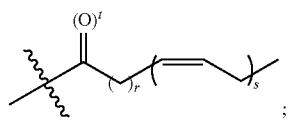

and r is 2. In some embodiments, Z is

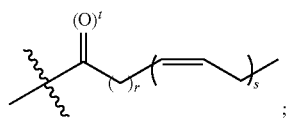

and r is 3. In some embodiments, Z is

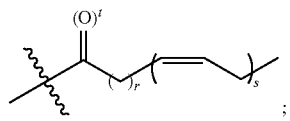

and s is 5. In some embodiments, Z is

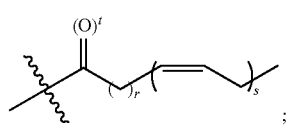

and s is 6. In some embodiments, at most one Z is H. In some embodiments, Z is not H. In other embodiments, Z is not —C(O)$CH_3$. In some embodiments, t is 1.

Illustrative compounds of Formula VIg include:

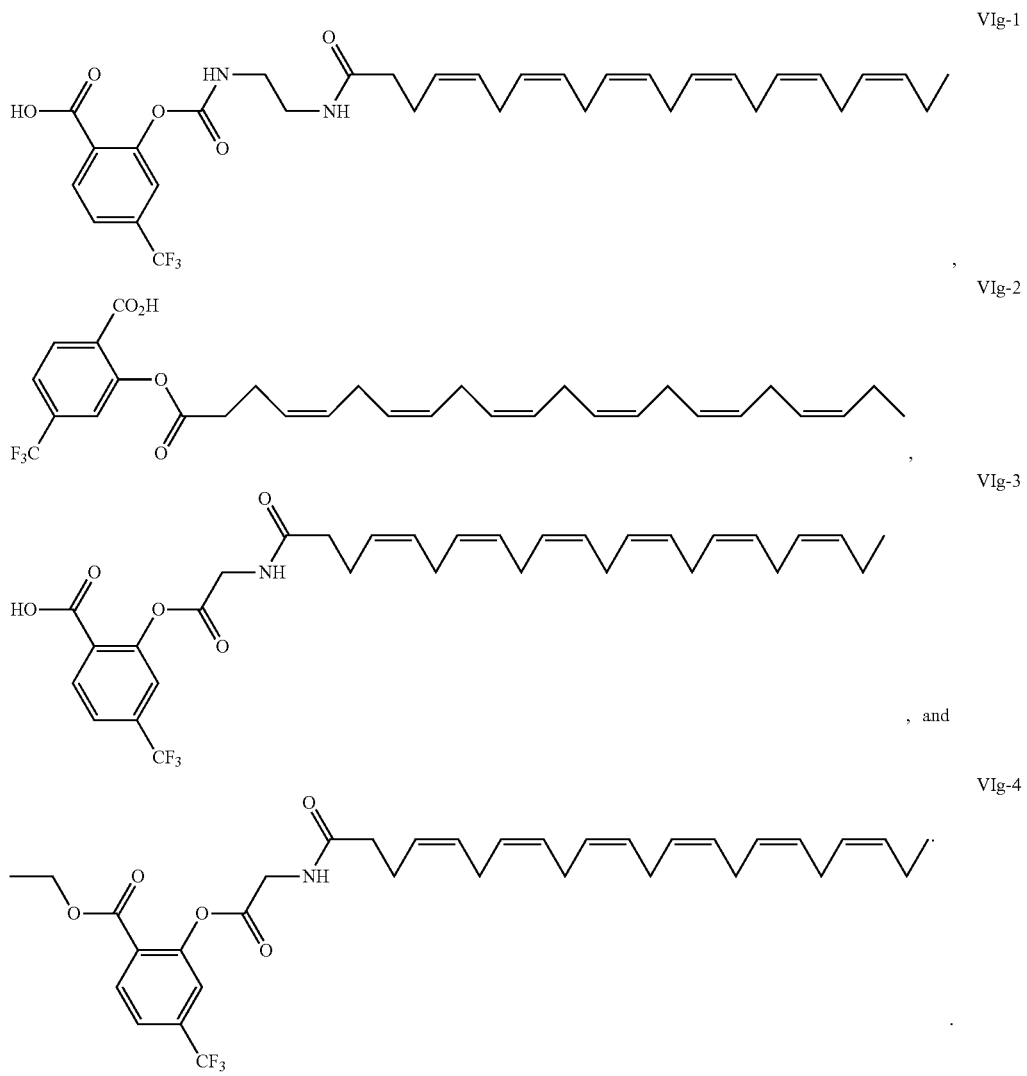

In another aspect, compounds of the Formula VII are described:

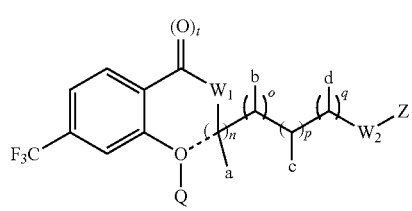

Formula VII and pharmaceutically acceptable salts, hydrates, solvates, prodrugs, enantiomers, and stereoisomers thereof;

wherein $W_1$, $W_2$, - - - - -, Q, a, b, c, d, e, $W_3$, n, o, p, q, Z, r, s, and t are as defined above for Formula VII.

In some embodiments, $W_1$ is O. In some embodiments, $W_1$ is NH. In some embodiments, $W_2$ is O. In some embodiments, $W_2$ is NH.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, $CH_3$, —$OCH_3$, —$OCH_2CH_3$, or C(O)OH. In some embodiments, b is O—Z, Z is

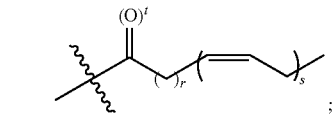

and t is 1. In some embodiments, d is C(O)OH. In some embodiments n, o, p, and q are each 1. In some embodiments, n is 0. In some embodiments, Z is

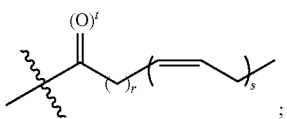

and r is 7. In some embodiments, Z is

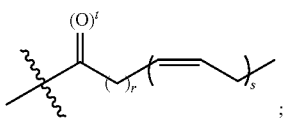

and s is 3. In some embodiments, t is 1. In some embodiments, Q is C(O)CH$_3$. In some embodiments, Q is Z. In some embodiments, Q is

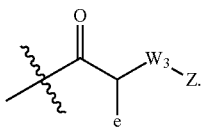

In some embodiments, e is any one of the side chains of the naturally occurring amino acids. In some embodiments, e is H. In other embodiments, e is —C(O)OH. In some embodiments, W$_3$ is —NR—. In some embodiments, W$_3$ is O.

In a further aspect, compounds of the Formula I' are described:

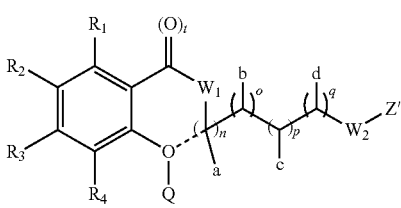

Formula I' and pharmaceutically acceptable salts, hydrates, solvates, prodrugs, enantiomers, and stereoisomers thereof;

wherein

R$_1$, R$_2$, R$_3$, and R$_4$ are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, and —S(O)$_2$C$_1$-C$_3$ alkyl;

W$_1$ and W$_2$ are each independently null, O, or NH, or when W$_1$ and W$_2$ are both NH, then both W$_1$ and W$_2$ can be taken together to form a piperidine moiety;

- - - - - represents an optional bond that when present requires that Q is null;

a and c are each independently H, CH$_3$, —OCH$_3$, —OCH$_2$CH$_3$, or C(O)OH;

b is H, CH$_3$, C(O)OH, or O—Z;

d is H or C(O)OH;

each n, o, p, and q is independently 0 or 1;

each Z is H,

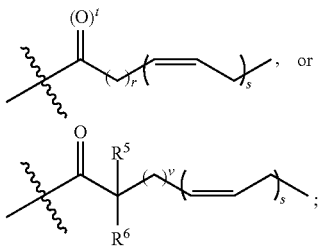

with the proviso that there is at least one

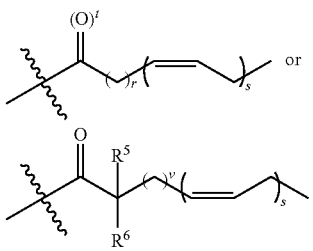

in the compound;

each r is independently 2 or 3;
each s is independently 5 or 6;
each t is independently 0 or 1;
each v is 1 or 2;

R$_5$ and R$_6$ are each independently hydrogen, deuterium, C$_1$-C$_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl;

Q is null, C(O)CH$_3$, Z,

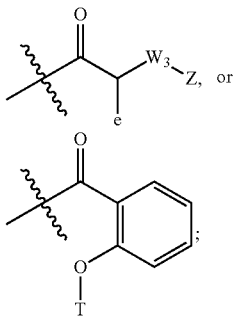

e is H or any one of the side chains of the naturally occurring amino acids;

W$_3$ is null, —O—, or —N(R)—;
R is H or C$_1$-C$_3$ alkyl; and
T is H, C(O)CH$_3$, or Z.

In some embodiments, R$_2$ is Cl or F. In other embodiments, R$_3$ is Cl or F. In some embodiments, W$_1$ is O. In some embodiments, W$_2$ is O.

In some embodiments, W$_1$ is N. In other embodiments W$_1$ is N substituted with a C$_1$-C$_6$ alkyl. In other embodiments, W$_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, $CH_3$, —$OCH_3$, —$OCH_2CH_3$, or C(O)OH. In some embodiments, b is O—Z, Z is

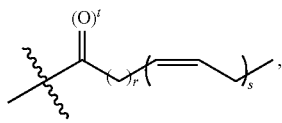

and t is 1. In some embodiments, d is C(O)OH. In some embodiments n, o, p, and q are each 1. In some embodiments, n is 0. In some embodiments, Z is

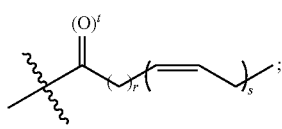

and r is 2. In some embodiments, Z is

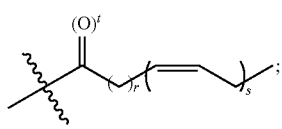

and r is 3. In some embodiments, Z is

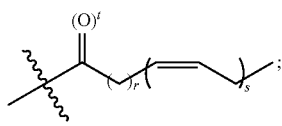

and s is 5. In some embodiments, Z is

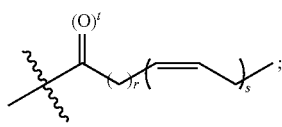

and s is 6. In some embodiments, t is 1. In some embodiments, Z is

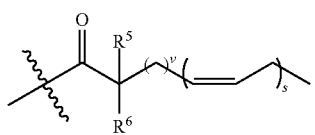

and r is 2. In other embodiments, Z is

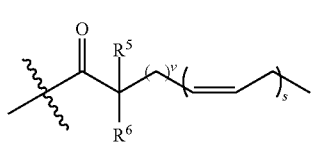

and s is 3. In some embodiments, Z is

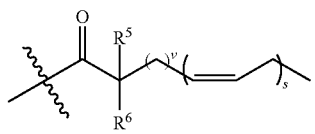

and s is 5. In other embodiments, Z is

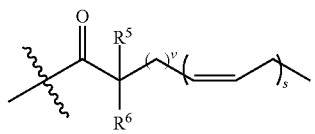

and s is 6. In some embodiments, Q is $C(O)CH_3$. In some embodiments, Q is Z. In some embodiments, Q is

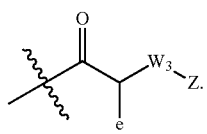

In some embodiments, Q is

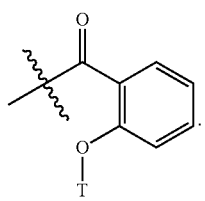

In some embodiments, T is H. In some embodiments, T is $C(O)CH_3$. In some embodiments, T is Z. In some embodiments, e is any one of the side chains of the naturally occurring amino acids. In some embodiments, e is H.

In another aspect, compounds of the Formula Ia' are described:

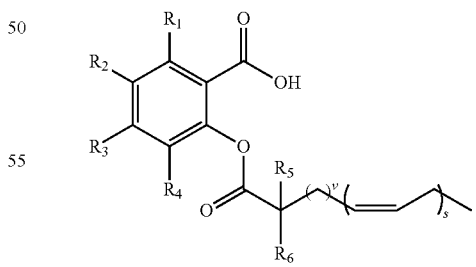

Formula Ia' and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, and —S(O)$_2$C$_1$-C$_3$ alkyl;

r is 2 or 3;
s is 5 or 6;
each v is 1 or 2; and

R$_5$ and R$_6$ are each independently hydrogen, deuterium, C$_1$-C$_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl.

In some embodiments, R$_2$ is Cl or F. In other embodiments, R$_3$ is Cl or F. In some embodiments, r is 2. In some embodiments, r is 3. In some embodiments, s is 5. In some embodiments, s is 6. In some embodiments, t is 1. In some embodiments v is 2.

In another aspect compounds of the Formula Ib' are described:

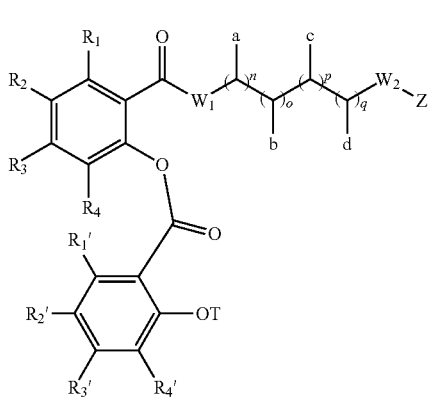

Formula Ib' and pharmaceutically acceptable salts, hydrates, solvates, prodrugs, enantiomers, and stereoisomers thereof;
wherein R$_1$, R$_2$, R$_3$, R$_4$, R$_1$', R$_2$', R$_3$', and R$_4$' are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, and —S(O)$_2$C$_1$-C$_3$ alkyl;

W$_1$ and W$_2$ are each independently null, O, or NH, or when W$_1$ and W$_2$ are both NH, then both W$_1$ and W$_2$ can be taken together to form a piperidine moiety;

a and c are each independently H, CH$_3$, —OCH$_3$, —OCH$_2$CH$_3$, or C(O)OH;
b is H, CH$_3$, C(O)OH, or O—Z;
d is H or C(O)OH;
each of n, o, p, and q is independently 0 or 1;
each Z is H,

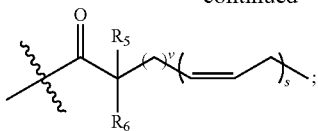

, or

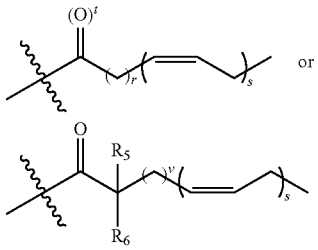

with the proviso that there is at least one

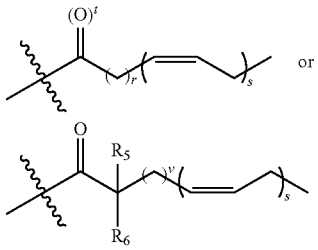

or in the compound;
each r is independently 2 or 3;
each s is independently 5 or 6;
each t is independently 0 or 1;
each v is 1 or 2;

R$_5$ and R$_6$ are each independently hydrogen, deuterium, C$_1$-C$_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl; and T is H, C(O)CH$_3$, or Z.

In some embodiments, R$_2$ is Cl or F. In other embodiments, R$_3$ is Cl or F. In some embodiments, W$_1$ is O. In some embodiments, W$_2$ is O. In some embodiments, a and c are each independently H, CH$_3$, —OCH$_3$, —OCH$_2$CH$_3$, or C(O)OH; In some embodiments, b is O—Z, Z is

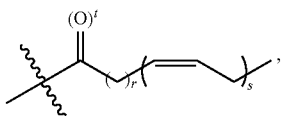

and t is 1. In some embodiments, d is C(O)OH. In some embodiments n, o, p, and q are each 1. In some embodiments, n is 0. In some embodiments, Z is

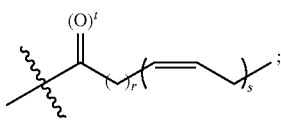

and r is 2. In some embodiments, Z is

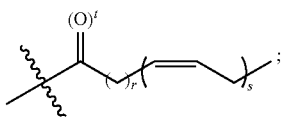

and r is 3. In some embodiments, Z is

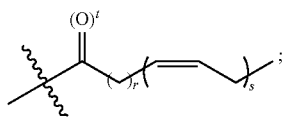

and s is 5. In some embodiments, Z is

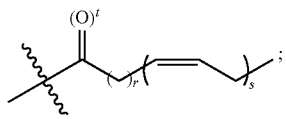

and s is 6. In some embodiments, t is 1. In some embodiments, Z is

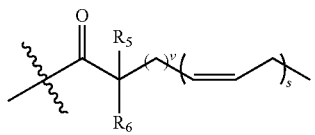

and r is 2. In other embodiments, Z is

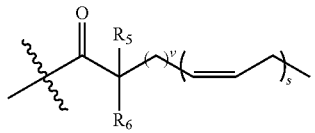

and s is 3. In some embodiments, Z is

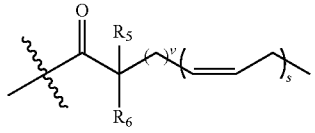

and s is 5. In other embodiments, Z is

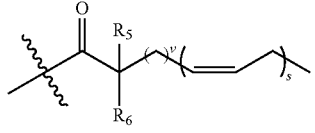

and s is 6. In some embodiments, T is H. In some embodiments, T is C(O)CH$_3$. In some embodiments, T is Z.

In another aspect compounds of the Formula Ic' are described:

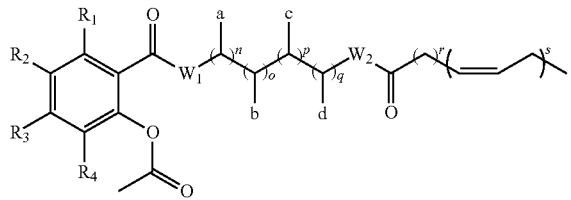

Formula Ic' and pharmaceutically acceptable salts, hydrates, solvates, enantiomers, and stereoisomers thereof,
wherein
R$_1$, R$_2$, R$_3$, and R$_4$ are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, and —S(O)$_2$C$_1$-C$_3$ alkyl; W$_1$ and W$_2$ are each independently null, O, or NH, or when W$_1$ and W$_2$ are both NH, then both W$_1$ and W$_2$ can be taken together to form a piperidine moiety;
a and c are each independently H, CH$_3$, —OCH$_3$, —OCH$_2$CH$_3$, or C(O)OH;
b is H, CH$_3$, C(O)OH, or O—Z;
d is H or C(O)OH;
n, o, p, and q are each independently 0 or 1;
each Z is H,

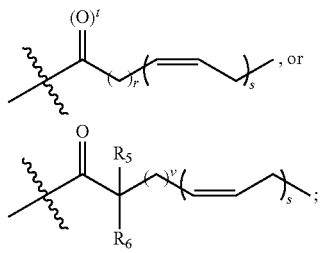

, or with the proviso that there is at least one

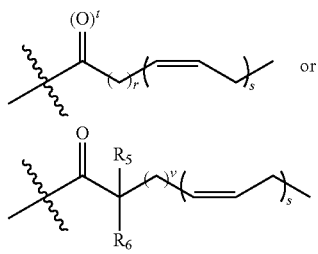

in the compound;
each r is independently 2 or 3;
each s is independently 5 or 6;
each t is independently 0 or 1;
each v is 1 or 2; and
R$_5$ and R$_6$ are each independently hydrogen, deuterium, C$_1$-C$_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl.

In some embodiments, R$_2$ is Cl or F. In other embodiments, R$_3$ is Cl or F.
In some embodiments, W$_1$ is O. In some embodiments, W$_2$ is O. In some embodiments, a and c are each independently H, CH$_3$, —OCH$_3$, —OCH$_2$CH$_3$, or C(O)OH; In some embodiments, b is O—Z, Z is

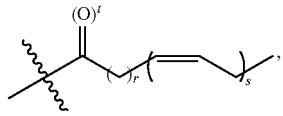

and t is 1. In some embodiments, d is C(O)OH. In some embodiments n, o, p, and q are each 1. In some embodiments, n is 0. In some embodiments, Z is

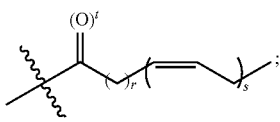

and r is 2. In some embodiments, Z is

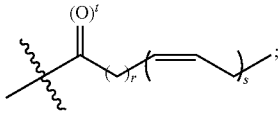

and r is 3. In some embodiments, Z is

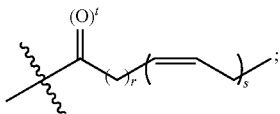

and s is 5. In some embodiments, Z is

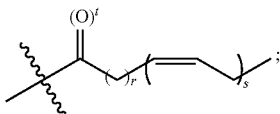

and s is 6. In some embodiments, t is 1. In some embodiments, Z is

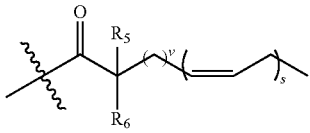

and r is 2. In other embodiments, Z is

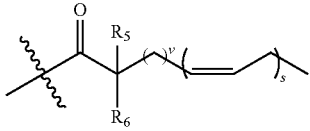

and s is 3. In some embodiments, Z is

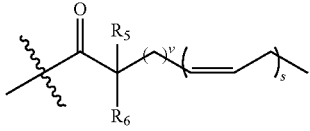

and s is 5. In other embodiments, Z is

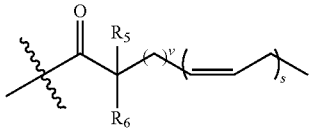

and s is 6.

In another aspect, compounds of the Formula Id' are described:

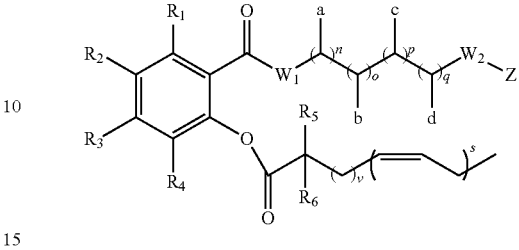

Formula Id' and pharmaceutically acceptable salts, hydrates, solvates, prodrugs, enantiomers, and stereoisomers thereof; wherein $R_1, R_2, R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —$C(O)C_1$-$C_3$ alkyl, —$C(O)OC_1$-$C_3$ alkyl, —$C(O)NH_2$, —$C(O)NH(C_1$-$C_3$ alkyl), —$C(O)N(C_1$-$C_3$ alkyl)$_2$, —$C_1$-$C_3$ alkyl, —O—$C_1$-$C_3$ alkyl, —$S(O)C_1$-$C_3$ alkyl, and —$S(O)_2C_1$-$C_3$ alkyl;

$W_1$ and $W_2$ are each independently null, O, or NH, or when $W_1$ and $W_2$ are both NH, then both $W_1$ and $W_2$ can be taken together to form a piperidine moiety;

a and c are each independently H, $CH_3$, —$OCH_3$, —$OCH_2CH_3$, or C(O)OH;

b is H, $CH_3$, C(O)OH, or O—Z;

d is H or C(O)OH;

n, o, p, and q are each independently 0 or 1;

each Z is H,

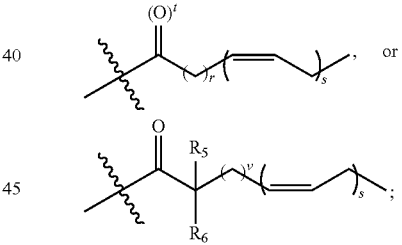, or

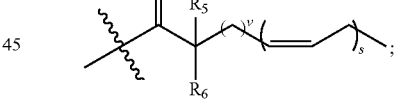;

with the proviso that there is at least one

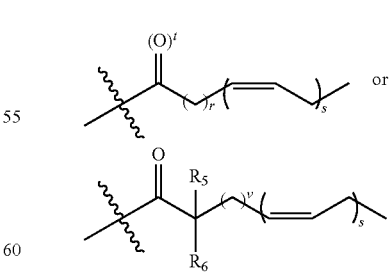, or

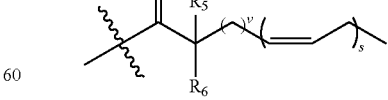

in the compound;

each r is independently 2 or 3;
each s is independently 5 or 6;
each t is independently 0 or 1;
each v is 1 or 2; and $R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In some embodiments, $R_2$ is Cl or F. In other embodiments, $R_3$ is Cl or F. In some embodiments, $W_1$ is O. In some embodiments, $W_2$ is O. In some embodiments, a and c are each independently H, $CH_3$, —$OCH_3$, —$OCH_2CH_3$, or C(O)OH; In some embodiments, b is O—Z, Z is

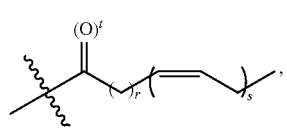

and t is 1. In some embodiments, d is C(O)OH. In some embodiments n, o, p, and q are each 1. In some embodiments, n is 0. In some embodiments, Z is

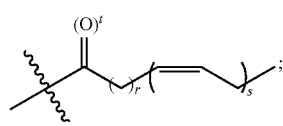

and r is 2. In some embodiments, Z is

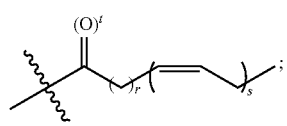

and r is 3. In some embodiments, Z is

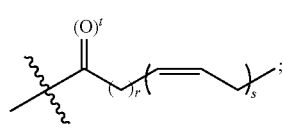

and s is 5. In some embodiments, Z is

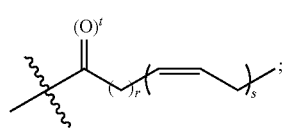

and s is 6. In some embodiments, Z is

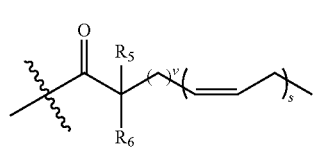

and r is 2. In other embodiments, Z is

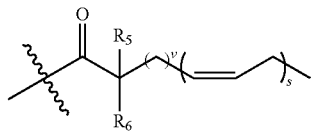

and s is 3. In some embodiments, Z is

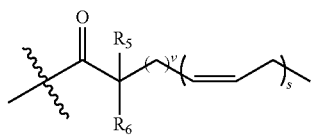

and s is 5. In other embodiments, Z is

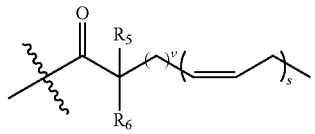

and s is 6. In some embodiments, t is 1. In some embodiments, T is H. In some embodiments, T is C(O)$CH_3$. In some embodiments, T is Z.

In another aspect, compounds of the Formula Ie' are described:

Formula Ie'

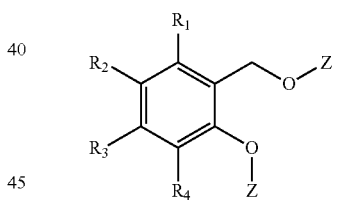

and pharmaceutically acceptable salts, hydrates, solvates, prodrugs, enantiomers, and stereoisomers thereof;
wherein $R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;

each Z is independently H, —C(O)$CH_3$,

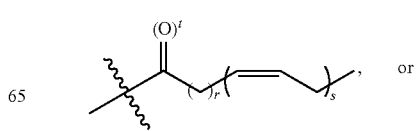

-continued

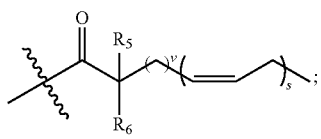

with the proviso that there is at least one

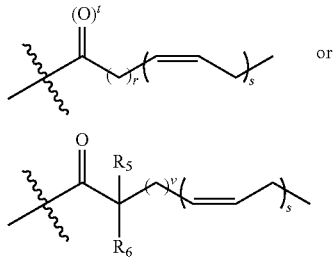

in the compound;

each r is independently 2 or 3;
each s is independently s is 5 or 6; and
each t is independently 0 or 1
each v is 1 or 2; and $R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In some embodiments, $R_2$ is Cl or F. In other embodiments, $R_3$ is Cl or F. In some embodiments, Z is

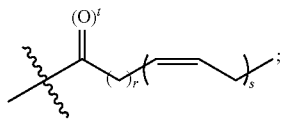

and r is 2. In some embodiments, Z is

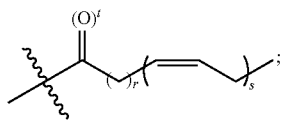

and r is 3. In some embodiments, Z is

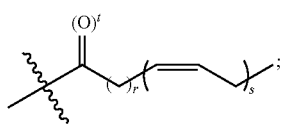

and s is 5. In some embodiments, Z is

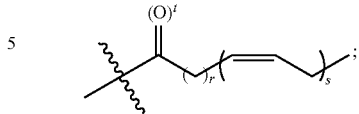

and s is 6. In some embodiments, Z is

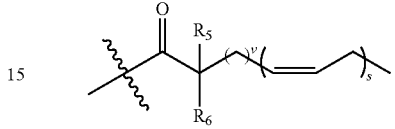

and r is 2. In other embodiments, Z is

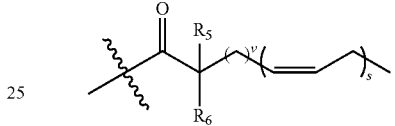

and s is 3. In some embodiments, Z is

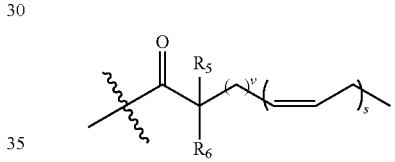

and s is 5. In other embodiments, Z is

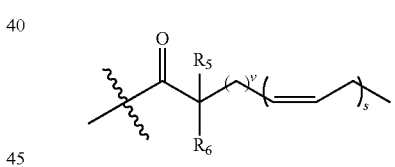

and s is 6. In some embodiments, t is 1.

In another aspect, compounds of the Formula If' are described:

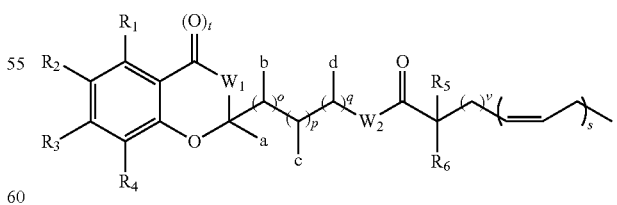

Formula If' and pharmaceutically acceptable salts, hydrates, solvates, prodrugs, enantiomers, and stereoisomers thereof; wherein $R_1$, $R_2$, $R_3$, and $R_4$ are each independently selected from the group consisting of H, Cl, F, CN, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-

C₃ alkyl)₂, —C(O)H, —C(O)C₁-C₃ alkyl, —C(O)OC₁-C₃ alkyl, —C(O)NH₂, —C(O)NH(C₁-C₃ alkyl), —C(O)N(C₁-C₃ alkyl)₂, —C₁-C₃ alkyl, —O—C₁-C₃ alkyl, —S(O)C₁-C₃ alkyl, and —S(O)₂C₁-C₃ alkyl;

W₁ is O, or NH;
W₂ is null, O, or NH;
a and c are each independently H, CH₃, —OCH₃, —OCH₂CH₃, or C(O)OH;
b is H, CH₃, C(O)OH, or O—Z;
d is H or C(O)OH;
each o, p, and q is independently 0 or 1;
each Z is H,

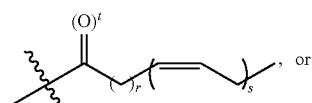, or

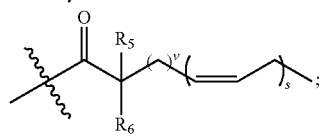;

with the proviso that there is at least one

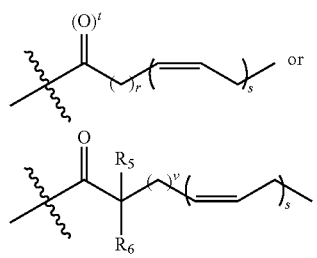

in the compound;
each r is independently 2 or 3;
each s is independently 5 or 6;
each t is independently 0 or 1;
each v is 1 or 2;
R₅ and R₆ are each independently hydrogen, deuterium, C₁-C₄ alkyl, halogen, —OH, —C(O)C₁-C₄ alkyl, —O-aryl, —O-benzyl, —OC(O)C₁-C₄ alkyl, —C₁-C₃ alkene, —C₁-C₃ alkyne, —C(O)C₁-C₄ alkyl, NH₂, —NH(C₁-C₃ alkyl), —N(C₁-C₃ alkyl)₂, —NH(C(O)C₁-C₃ alkyl), —N(C(O)C₁-C₃ alkyl)₂, —SH, —S(C₁-C₃ alkyl), —S(O)C₁-C₃ alkyl, —S(O)₂C₁-C₃ alkyl.

In some embodiments, R₂ is Cl or F. In other embodiments, R₃ is Cl or F. In some embodiments, W₁ is O. In some embodiments, W₂ is O. In some embodiments, a and c are each independently H, CH₃, —OCH₃, —OCH₂CH₃, or C(O)OH. In some embodiments, b is O—Z, Z is

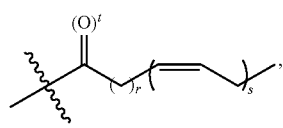

and t is 1. In some embodiments, d is C(O)OH. In some embodiments n, o, p, and q are each 1. In some embodiments, n is 0. In some embodiments, Z is

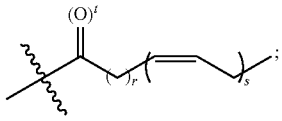

and r is 2. In some embodiments, Z is

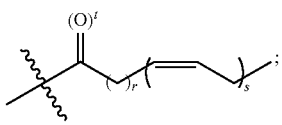

and r is 3. In some embodiments, Z is

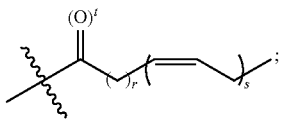

and s is 5. In some embodiments, Z is

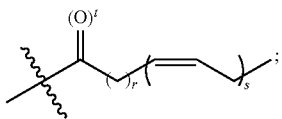

and s is 6. In some embodiments, Z is

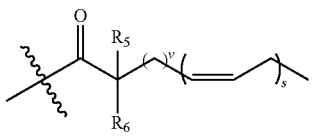

and r is 2. In other embodiments, Z is

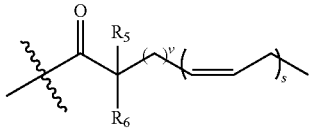

and r is 3. In some embodiments, Z is

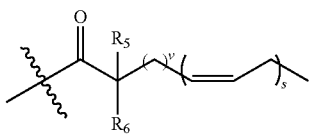

and s is 5. In other embodiments, Z is

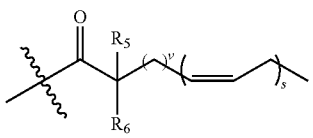

and s is 6. In some embodiments, t is 1.

In another aspect, compounds of the Formula Ig' are described:

Formula Ig'

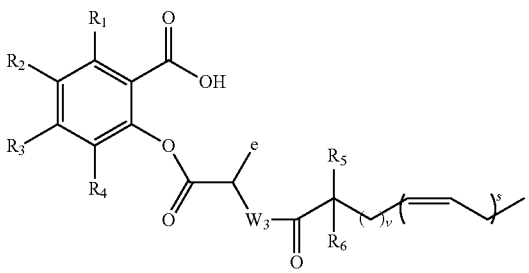

and pharmaceutically acceptable salts, hydrates, solvates, prodrugs, enantiomers, and stereoisomers thereof;
wherein $R_1$, $R_2$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —$C(O)C_1$-$C_3$ alkyl, —$C(O)OC_1$-$C_3$ alkyl, —$C(O)NH_2$, —$C(O)NH(C_1$-$C_3$ alkyl), —$C(O)N(C_1$-$C_3$ alkyl)$_2$, —$C_1$-$C_3$ alkyl, —O—$C_1$-$C_3$ alkyl, —$S(O)C_1$-$C_3$ alkyl, and —$S(O)_2C_1$-$C_3$ alkyl;

$W_3$ is null, O, or NH;

e is H or any one of the side chains of the naturally occurring amino acids;

each v is 1 or 2;

$R_5$ and $R_6$ are each independently hydrogen, deuterium, $C_1$-$C_4$ alkyl, halogen, —OH, —$C(O)C_1$-$C_4$ alkyl, —O-aryl, —O-benzyl, —$OC(O)C_1$-$C_4$ alkyl, —$C_1$-$C_3$ alkene, —$C_1$-$C_3$ alkyne, —$C(O)C_1$-$C_4$ alkyl, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —SH, —$S(C_1$-$C_3$ alkyl), —$S(O)C_1$-$C_3$ alkyl, —$S(O)_2C_1$-$C_3$ alkyl; and s is 5 or 6.

In some embodiments, $W_3$ is O. In some embodiments, e is sec-butyl. In some embodiments, r is 2. In some embodiments, r is 3. In some embodiments, s is 5. In some embodiments, s is 6. In some embodiments, t is 1.

In another aspect, compounds of the Formula II' are described:

Formula II'

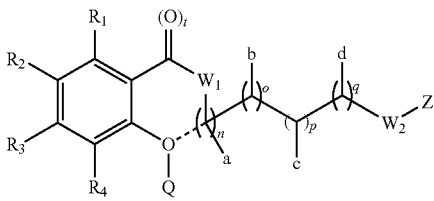

and pharmaceutically acceptable salts, hydrates, solvates, prodrugs, enantiomers, and stereoisomers thereof;
wherein $R_1$, $R_2$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —$C(O)C_1$-$C_3$ alkyl, —$C(O)OC_1$-$C_3$ alkyl, —$C(O)NH_2$, —$C(O)NH(C_1$-$C_3$ alkyl), —$C(O)N(C_1$-$C_3$ alkyl)$_2$, —$C_1$-$C_3$ alkyl, —O—$C_1$-$C_3$ alkyl, —$S(O)C_1$-$C_3$ alkyl, and —$S(O)_2C_1$-$C_3$ alkyl;

$W_1$ and $W_2$ are each independently null, O, or NH, or when $W_1$ and $W_2$ are both NH, then both $W_1$ and $W_2$ can be taken together to form a piperidine moiety;

- - - - - represents an optional bond that when present requires that Q is then null;

a and c are each independently H, $CH_3$, —$OCH_3$, —$OCH_2CH_3$, or C(O)OH;

b is H, $CH_3$, C(O)OH, or O—Z;

d is H or C(O)OH;

each n, o, p, and q is independently 0 or 1;

each Z is H,

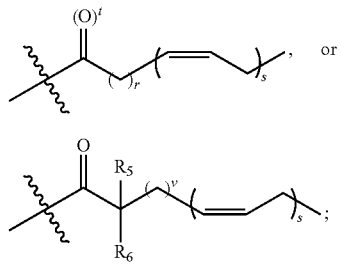, or with the proviso that there is at least one

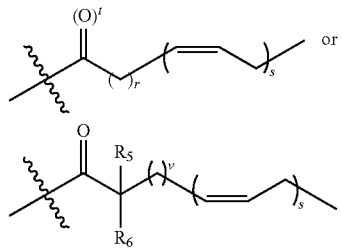, or in the compound;

each r is 7;

each s is 3;

each t is independently 0 or 1;

each v is 1 or 2;

$R_5$ and $R_6$ are each independently hydrogen, deuterium, $C_1$-$C_4$ alkyl, halogen, —OH, —$C(O)C_1$-$C_4$ alkyl, —O-aryl, —O-benzyl, —$OC(O)C_1$-$C_4$ alkyl, —$C_1$-$C_3$ alkene, —$C_1$-$C_3$ alkyne, —$C(O)C_1$-$C_4$ alkyl, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —SH, —$S(C_1$-$C_3$ alkyl), —$S(O)C_1$-$C_3$ alkyl, —$S(O)_2C_1$-$C_3$ alkyl;

Q is null, H, C(O)CH$_3$, Z,

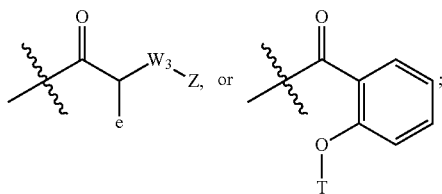

e is H or any one of the side chains of the naturally occurring amino acids;

W$_3$ is null, —O—, or —N(R)—;

R is H or C$_1$-C$_3$ alkyl; and

T is H, C(O)CH$_3$, or Z.

In some embodiments, R$_2$ is Cl or F. In other embodiments, R$_3$ is Cl or F. In some embodiments, W$_1$ is O. In some embodiments, W$_2$ is O.

In some embodiments, W$_1$ is N. In other embodiments W$_1$ is N substituted with a C$_1$-C$_6$ alkyl. In other embodiments, W$_1$ is an oxidized N.

In some embodiments, W$_2$ is N. In other embodiments W$_2$ is N substituted with a C$_1$-C$_6$ alkyl. In other embodiments, W$_2$ is an oxidized N.

In some embodiments, - - - - - represents a bond. In some embodiments, a and c are each independently H, CH$_3$, —OCH$_3$, —OCH$_2$CH$_3$, or C(O)OH. In some embodiments, b is O—Z, Z is

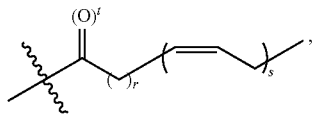

and t is 1. In some embodiments, d is C(O)OH. In some embodiments n, o, p, and q are each 1. In some embodiments, n is 0. In some embodiments, Z is

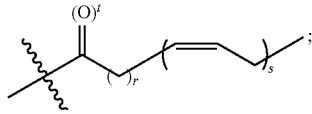

and r is 7. In some embodiments, Z is

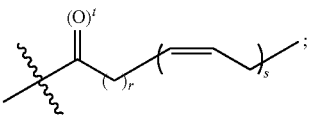

and s is 3. In some embodiments, Z is

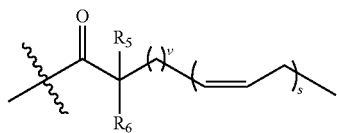

and r is 7. In some embodiments, Z is

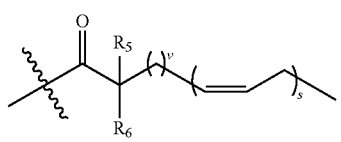

and s is 3. In some embodiments, t is 1. In some embodiments, Q is C(O)CH$_3$. In some embodiments, Q is Z. In some embodiments, Q is

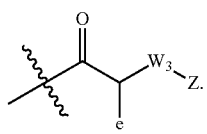

In some embodiments, Q is

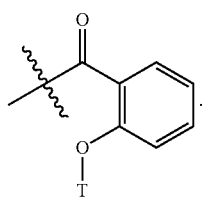

In some embodiments, T is H. In some embodiments, T is C(O)CH$_3$. In some embodiments, T is Z. In some embodiments, e is any one of the side chains of the naturally occurring amino acids. In some embodiments, e is H.

In another aspect, compounds of the Formula III' are described:

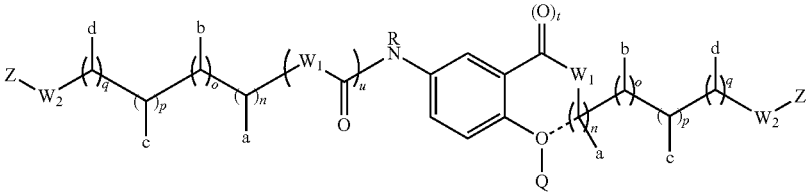

Formula III' and pharmaceutically acceptable salts, hydrates, solvates, prodrugs, enantiomers, and stereoisomers thereof;

wherein each $W_1$ and $W_2$ are independently null, O, or NH, or when $W_1$ and $W_2$ are both NH, then both $W_1$ and $W_2$ can be taken together to form a piperidine moiety;

- - - - - represents an optional bond that when present requires that Q is null; each a and c are independently H, $CH_3$, —$OCH_3$, —$OCH_2CH_3$, or C(O)OH;

each b is H, $CH_3$, C(O)OH, or O—Z;

each d is H or C(O)OH;

each n, o, p, and q is independently 0 or 1;

each Z is H,

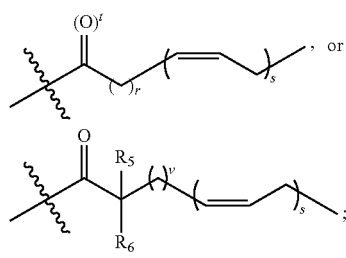, or

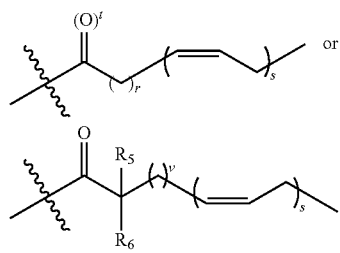;

with the proviso that there is at least one

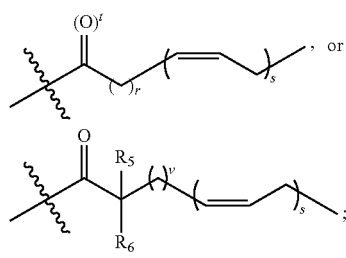 or

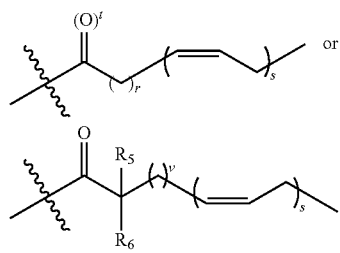

in the compound;

each r is independently 2, 3, or 7;
each s is independently 3, 5, or 6;
each t is independently 0 or 1;
each v is 1 or 2;
each $R_5$ and $R_6$ are independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl;

u is 0 or 1;
with the proviso that when r is 7, s is 3;
Q is null, C(O)$CH_3$, Z,

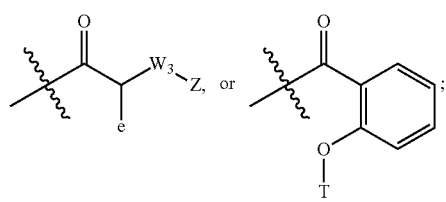

e is H or any one of the side chains of the naturally occurring amino acids;

$W_3$ is null, —O—, or —N(R)—;

R is H or $C_1$-$C_3$ alkyl; and

T is H, C(O)$CH_3$, or Z.

In some embodiments, $W_1$ is O. In some embodiments, $W_2$ is O.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, $CH_3$, —$OCH_3$, —$OCH_2CH_3$, or C(O)OH. In some embodiments, b is O—Z, Z is

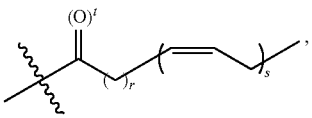, and t is 1. In some embodiments, d is C(O)OH. In some embodiments n, o, p, and q are each 1. In some embodiments, n is 0. In some embodiments, Z is

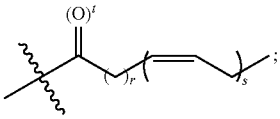;

and r is 2. In some embodiments, Z is

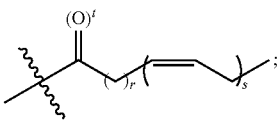;

and r is 3. In some embodiments, Z is

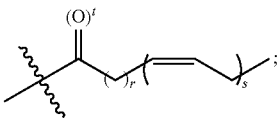;

and s is 5. In some embodiments, Z is

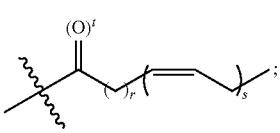;

and s is 6. In some embodiments, Z is

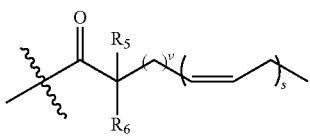

and r is 2. In other embodiments, Z is

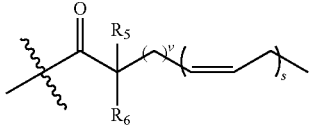

and r is 3. In some embodiments, Z is

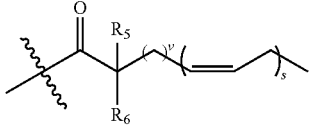

and s is 5. In other embodiments, Z is

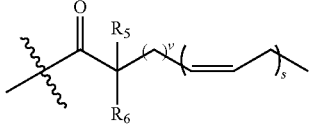

and s is 6. In some embodiments, t is 1. In some embodiments, Q is C(O)CH$_3$. In some embodiments, Q is Z. In some embodiments, Q is

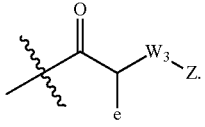

In some embodiments, Q is

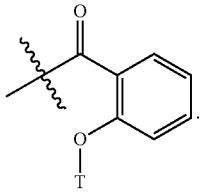

In some embodiments, T is H. In some embodiments, T is C(O)CH$_3$. In some embodiments, T is Z. In some embodiments, e is any one of the side chains of the naturally occurring amino acids. In some embodiments, e is H.

In yet another aspect, compounds of the Formula IIIa' are described:

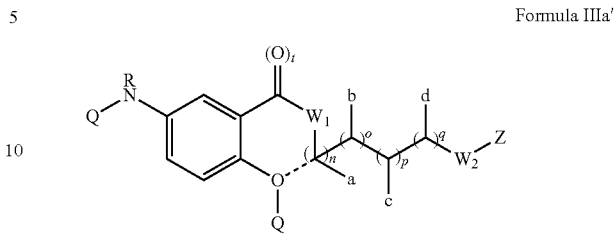

Formula IIIa' and pharmaceutically acceptable salts, hydrates, solvates, prodrugs, enantiomers, and stereoisomers thereof;
wherein
each $W_1$ and $W_2$ are independently null, O, or NH, or when $W_1$ and $W_2$ are both NH, then both $W_1$ and $W_2$ can be taken together to form a piperidine moiety;
- - - - - represents an optional bond that when present requires that Q is null;
each a and c are independently H, CH$_3$, —OCH$_3$, —OCH$_2$CH$_3$, or C(O)OH;
each b is H, CH$_3$, C(O)OH, or O—Z;
each d is H or C(O)OH;
each n, o, p, and q is independently 0 or 1;
each Z is H,

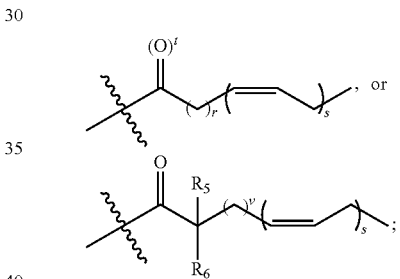

with the proviso that there is at least one

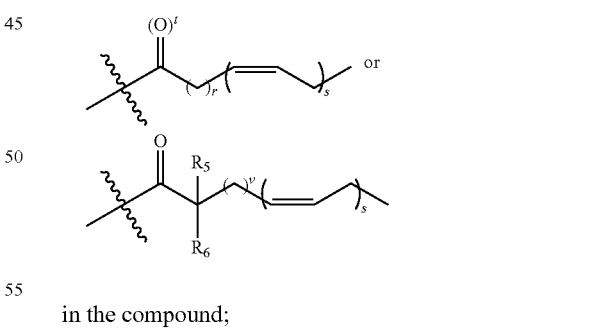

in the compound;
each r is independently 2, 3, or 7;
each s is independently 3, 5, or 6;
each t is independently 0 or 1;
each v is 1 or 2;
each $R_5$ and $R_6$ are independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl;

u is 0 or 1;

with the proviso that when r is 7, s is 3;

Q is null, C(O)CH$_3$, Z,

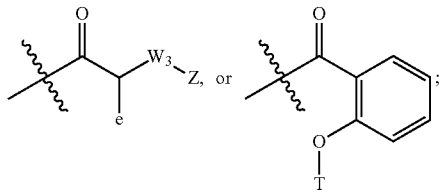

e is H or any one of the side chains of the naturally occurring amino acids;

W$_3$ is null, —O—, or —N(R)—;

R is H or C$_1$-C$_3$ alkyl; and

T is H, C(O)CH$_3$, or Z.

In some embodiments, W$_1$ is O. In some embodiments, W$_2$ is O. In some embodiments, - - - - - represents a bond. In some embodiments, a and c are each independently H, CH$_3$, —OCH$_3$, —OCH$_2$CH$_3$, or C(O)OH. In some embodiments, b is O—Z, Z is

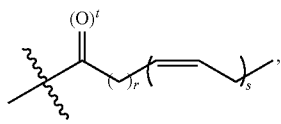

and t is 1. In some embodiments, d is C(O)OH. In some embodiments n, o, p, and q are each 1. In some embodiments, n is 0. In some embodiments, Z is

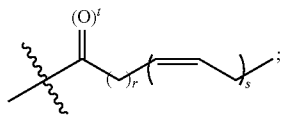

and r is 2. In some embodiments, Z is

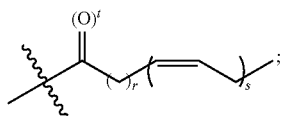

and r is 3. In some embodiments, Z is

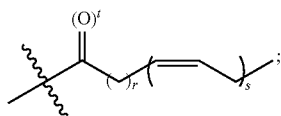

and s is 5. In some embodiments, Z is

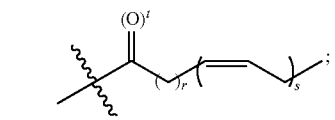

and s is 6. In some embodiments, Z is

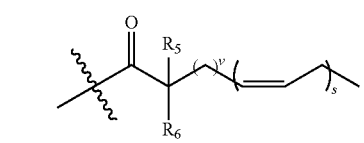

and r is 2. In other embodiments, Z is

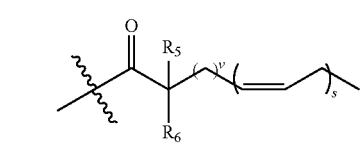

and r is 3. In some embodiments, Z is

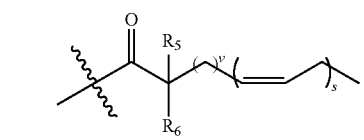

and s is 5. In other embodiments, Z is

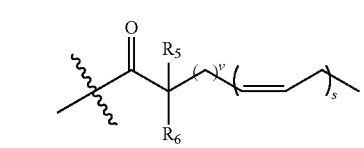

and s is 6. In some embodiments, t is 1. In some embodiments, Q is C(O)CH$_3$. In some embodiments, Q is Z. In some embodiments, Q is

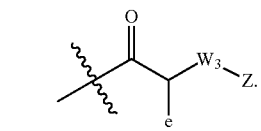

In some embodiments, W$_3$ is O. In other embodiments, W$_3$ is N(R). In further embodiments, W$_3$ is NH. In some embodiments, e is any one of the side chains of the naturally occurring amino acids. In some embodiments, e is H.

151

In some embodiments, Q is

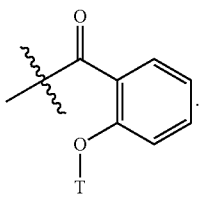

In some embodiments, T is H. In some embodiments, T is C(O)CH₃. In some embodiments, T is Z. In some embodiments, e is any one of the side chains of the naturally occurring amino acids. In some embodiments, e is H.

In another aspect, compounds of Formula IV' are described herein:

Formula IV'

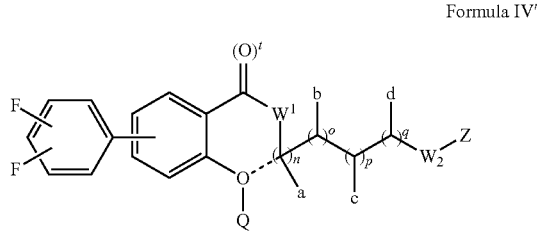

and pharmaceutically acceptable salts, hydrates, solvates, prodrugs, enantiomers, and stereoisomers thereof;

wherein $W_1$ and $W_2$ are each independently null, O, or NH;

- - - - - represents an optional bond that when present requires that Q is null;

a and c are each independently H, CH₃, —OCH₃, —OCH₂CH₃, or C(O)OH;

b is H, CH₃, C(O)OH, or O—Z;

d is H or C(O)OH;

each n, o, p, and q is independently 0 or 1;

each Z is H,

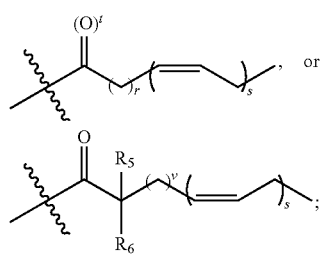

with the proviso that there is at least one

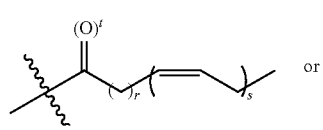

or

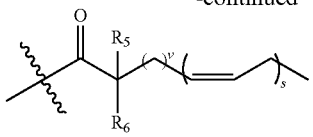

in the compound;

each r is independently 2 or 3;
each s is independently 5 or 6;
each t is independently 0 or 1;
each v is 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH₂, —NH($C_1$-$C_3$ alkyl), —N($C_1$-$C_3$ alkyl)₂, —NH(C(O)$C_1$-$C_3$ alkyl), —N(C(O)$C_1$-$C_3$ alkyl)₂, —SH, —S($C_1$-$C_3$ alkyl), —S(O)$C_1$-$C_3$ alkyl, —S(O)₂$C_1$-$C_3$ alkyl;

Q is null, C(O)CH₃, Z, or

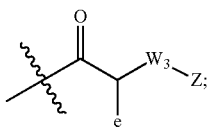

e is H, —C(O)OH, or any one of the side chains of the naturally occurring amino acids;

$W_3$ is null, —O—, —N(R)—; and

R is H or $C_1$-$C_3$ alkyl.

In some embodiments, $W_1$ is O. In other embodiments, $W_1$ is NH. In some embodiments, $W_2$ is O. In other embodiments, $W_2$ is NH.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, CH₃, —OCH₃, —OCH₂CH₃, or C(O)OH. In some embodiments, b is O—Z, Z is

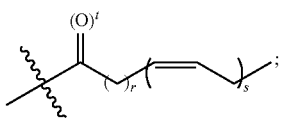

and t is 1. In some embodiments, d is C(O)OH. In some embodiments n, o, p, and q are each 1. In some embodiments, n is 0. In some embodiments, Z is

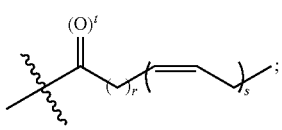

and r is 2. In some embodiments, Z is

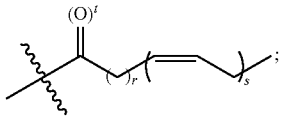

and r is 3. In some embodiments, Z is

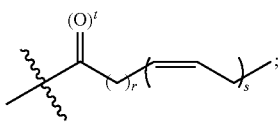

and s is 5. In some embodiments, Z is

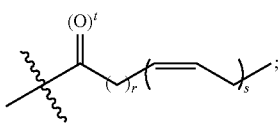

and s is 6. In some embodiments, Z is

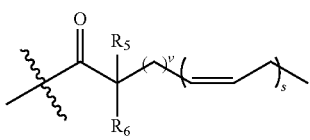

and r is 2. In other embodiments, Z is

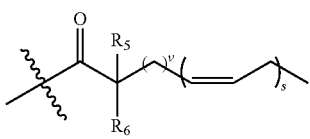

and r is 3. In some embodiments, Z is

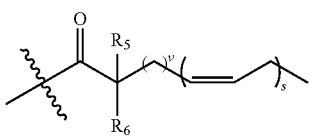

and s is 5. In other embodiments, Z is

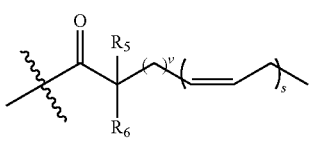

and s is 6. In some embodiments, t is 1. In some embodiments, Q is H. In other embodiments, Q is $C(O)CH_3$. In some embodiments, Q is Z. In some embodiments, Q is

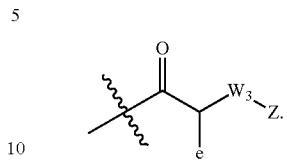

In some embodiments, e is any one of the side chains of the naturally occurring amino acids. In some embodiments, e is H. In other embodiments, e is —C(O)OH. In some embodiments, $W_3$—NH—. In some embodiments, $W_3$ is O.

In another aspect, compounds of the Formula IVa' are described:

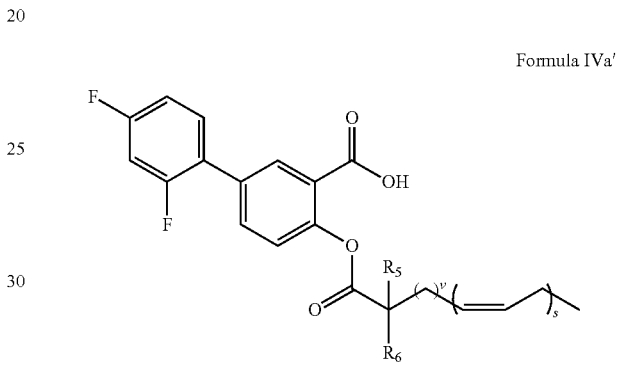

Formula IVa' and pharmaceutically acceptable salts, hydrates, solvates, prodrugs, enantiomers, and stereoisomers thereof;
wherein
v is 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and s is 5 or 6.

In some embodiments, r is 2. In some embodiments, r is 3. In some embodiments, s is 5. In some embodiments, s is 6.

In another aspect, compounds of the Formula IVb' are described:

Formula IVb'

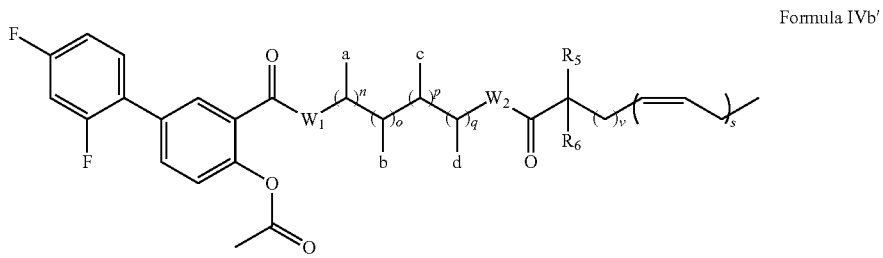

and pharmaceutically acceptable salts, hydrates, solvates, enantiomers, and stereoisomers thereof,
wherein
$W_1$ and $W_2$ are each independently null, O, or NH;
a and c are each independently H, $CH_3$, $-OCH_3$, $-OCH_2CH_3$, or C(O)OH;
b is H, $CH_3$, C(O)OH, or O—Z;
d is H or C(O)OH;
each n, o, p, and q is independently 0 or 1;
each Z is H,

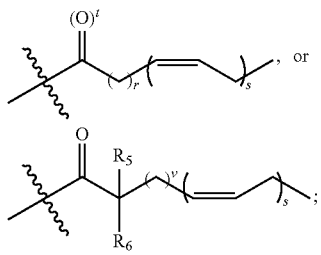, or

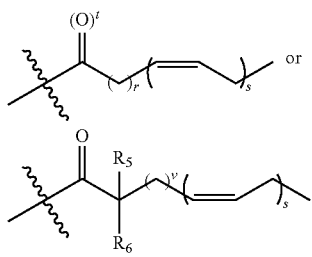;

with the proviso that there is at least one

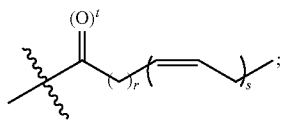 or

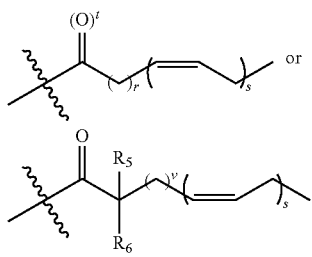

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is

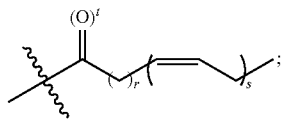;

and t is 1. In some embodiments, d is C(O)OH. In some embodiments n, o, p, and q are each 1. In some embodiments, n is 0.

In some embodiments, Z is

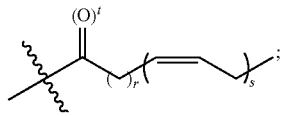;

and r is 2. In some embodiments, Z is

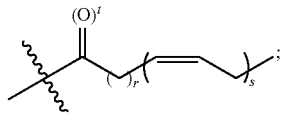;

and r is 3. In some embodiments, Z is

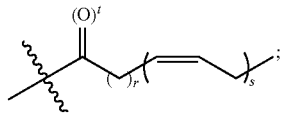;

and s is 5. In some embodiments, Z is

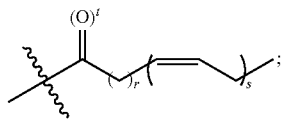;

and s is 6. In some embodiments, Z is

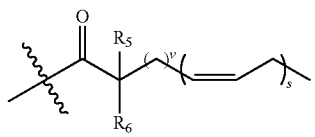

and r is 2. In other embodiments, Z is

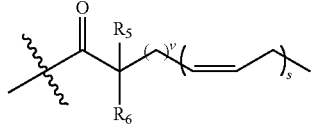

and r is 3. In some embodiments, Z is

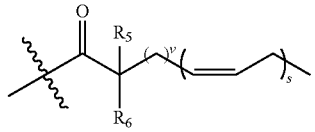

and s is 5. In other embodiments, Z is

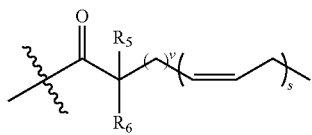

and s is 6. In some embodiments, Z is not H. In some embodiments, t is 1.

In another aspect, compounds of the Formula IVc' are described:

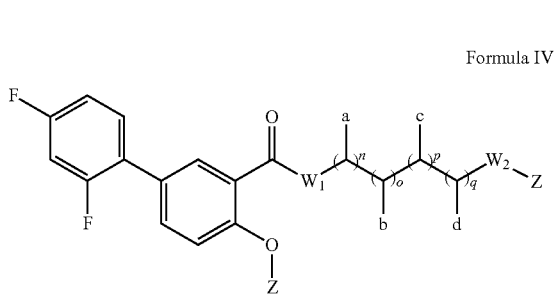

Formula IVc' and pharmaceutically acceptable salts, hydrates, solvates, prodrugs, enantiomers, and stereoisomers thereof;
wherein
$W_1$ and $W_2$ are each independently null, O, or NH;
a and c are each independently H, $CH_3$, —$OCH_3$, —$OCH_2CH_3$, or C(O)OH;
b is H, $CH_3$, C(O)OH, or O—Z;
d is H or C(O)OH;
each of n, o, p, and q is independently 0 or 1;
each Z is null, H,

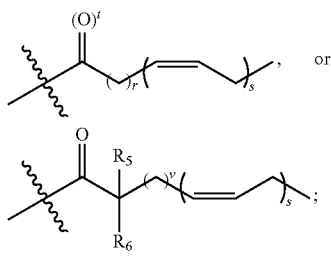

with the proviso that there is at least one

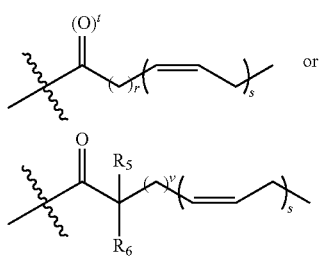

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is

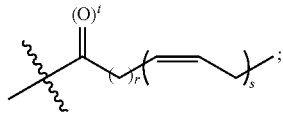

and t is 1. In some embodiments, d is C(O)OH. In some embodiments n, o, p, and q are each 1. In some embodiments, n is 0. In some embodiments, Z is

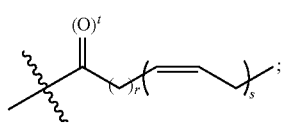

and r is 2. In some embodiments, Z is

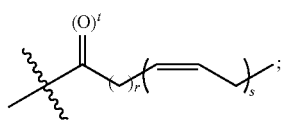

and r is 3. In some embodiments, Z is

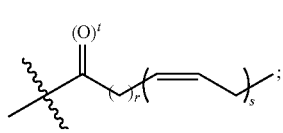

and s is 5. In some embodiments, Z is

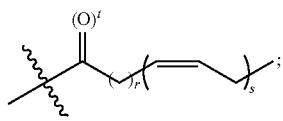

and s is 6. In some embodiments, Z is

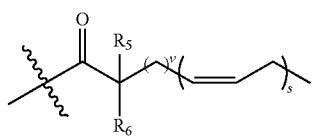

and r is 2. In other embodiments, Z is

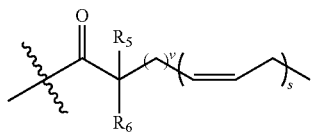

and r is 3. In some embodiments, Z is

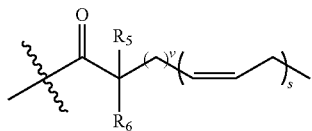

and s is 5. In other embodiments, Z is

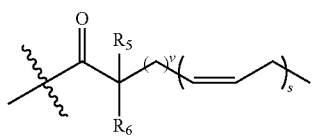

and s is 6. In some embodiments, at most one Z is H. In some embodiments, Z is not H. In other embodiments, Z is not —C(O)CH$_3$. In some embodiments, t is 1.

In another aspect, compounds of the Formula IVd' are described:

Formula IVd'

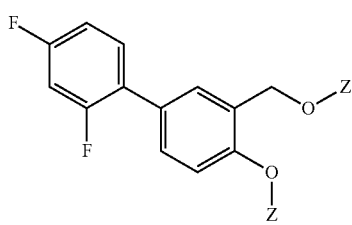

and pharmaceutically acceptable salts, hydrates, solvates, prodrugs, enantiomers, and stereoisomers thereof;
wherein
each Z is null, H,

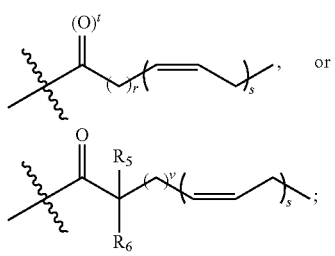

with the proviso that there is at least one

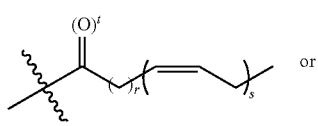

or

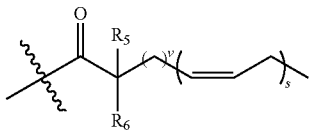

in the compound;

each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)C$_1$-C$_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl.

In some embodiments, Z is

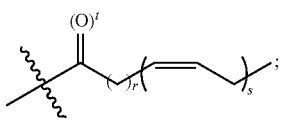

and r is 2. In some embodiments, Z is

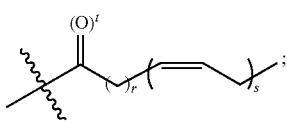

and r is 3. In some embodiments, Z is

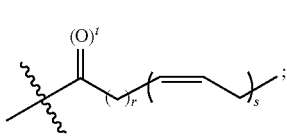

and s is 5. In some embodiments, Z is

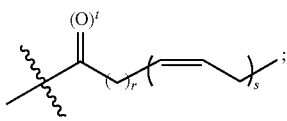

and s is 6. In some embodiments, Z is

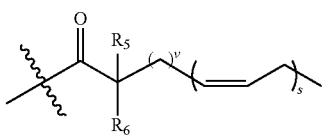

and r is 2. In other embodiments, Z is

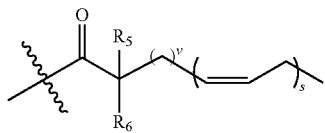

and r is 3. In some embodiments, Z is

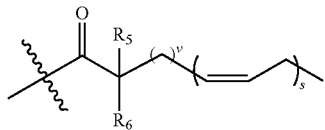

and s is 5. In other embodiments, Z is

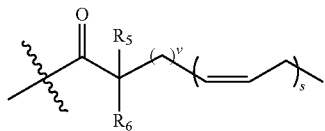

and s is 6. In some embodiments, t is 1.

In another aspect, compounds of the Formula IVe' are described:

Formula IVe'

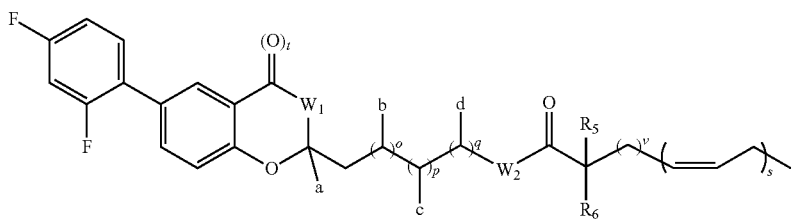

and pharmaceutically acceptable salts, hydrates, solvates, prodrugs, enantiomers, and stereoisomers thereof;
wherein
 $W_1$ is O, or NH;
 $W_2$ is null, O, or NH;
 a and c are each independently H, $CH_3$, —$OCH_3$, —$OCH_2CH_3$, or C(O)OH;
 b is H, $CH_3$, C(O)OH, or O—Z;
 d is H or C(O)OH;
 each o, p, and q is independently 0 or 1;
 each Z is H,

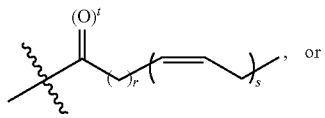

-continued

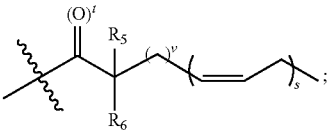

with the proviso that there is at least one

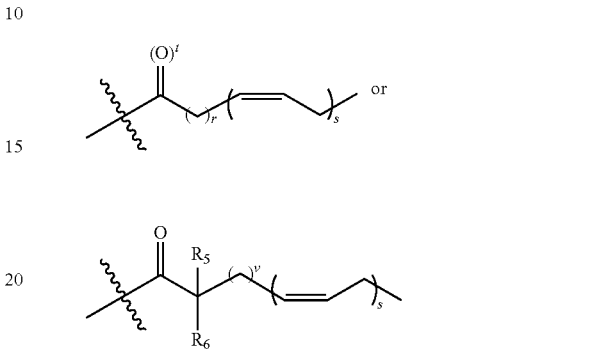

in the compound;
each r is independently 2 or 3;
each s is independently 5 or 6;
each t is independently 0 or 1;
each v is 1 or 2;
 $R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH. In some embodiments, b is O—Z, Z is

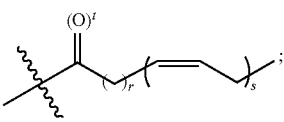

and t is 1. In some embodiments, d is C(O)OH. In some embodiments n, o, p, and q are each 1. In some embodiments, n is 0. In some embodiments, Z is

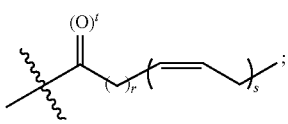

and r is 2. In some embodiments, Z is

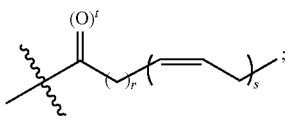

and r is 3. In some embodiments, Z is

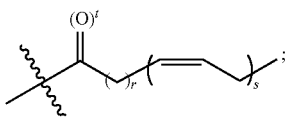

and s is 5. In some embodiments, Z is

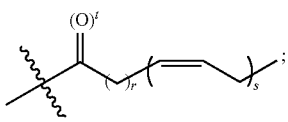

and s is 6. In some embodiments, Z is

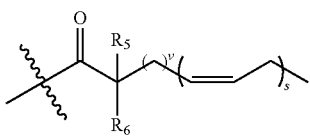

and r is 2. In other embodiments, Z is

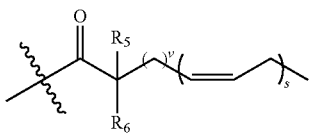

and r is 3. In some embodiments, Z is

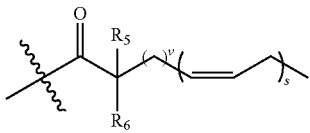

and s is 5. In other embodiments, Z is

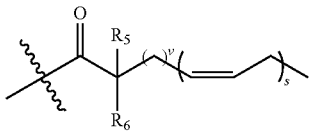

and s is 6. In some embodiments, t is 1.

In another aspect, compounds of the Formula IVf' are described:

Formula IVf'

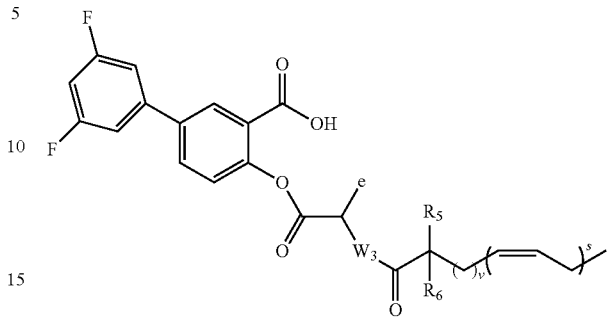

and pharmaceutically acceptable salts, hydrates, solvates, prodrugs, enantiomers, and stereoisomers thereof;
wherein
e is H, —C(O)OH or any one of the side chains of the naturally occurring amino acids;
$W_3$ is null, —O—, —N(R)—; and
R is H or $C_1$-$C_3$ alkyl,
v is 1 or 2;
s is 5 or 6; and
t is 0 or 1.

In some embodiments, $W_3$ is O. In some embodiments, e is sec-butyl. In other embodiments, e is —C(O)OH. In still other embodiments, e is H. In some embodiments, $W_3$ is —NR—. In some embodiments. In some embodiments, r is 2. In some embodiments, r is 3. In some embodiments, s is 5. In some embodiments, s is 6. In some embodiments, v is 1. In other embodiments, v is 2. In some embodiments, t is 1.

In another aspect, compounds of the Formula IVg' are described:

Formula IVg'

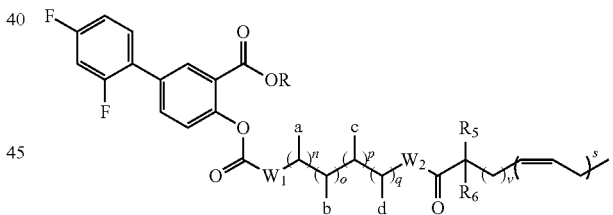

and pharmaceutically acceptable salts, hydrates, solvates, prodrugs, enantiomers, and stereoisomers thereof;
wherein
R is H or $C_1$-$C_3$ alkyl;
$W_1$ and $W_2$ are each independently null, O, or NH;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
each Z is H,

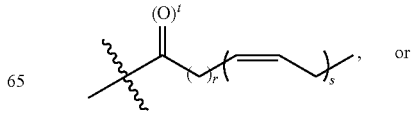

or

-continued

[structure: C(=O)-C(R5)(R6)-(CH2)v-CH=CH-(CH2)s]

with the proviso that there is at least one

[structure: C(=O)(O)t-(CH2)r-CH=CH-(CH2)s-] or

[structure: C(=O)-C(R5)(R6)-(CH2)v-CH=CH-(CH2)s-]

in the compound;

each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is

[structure: C(=O)(O)t-(CH2)r-CH=CH-(CH2)s-]

and t is 1. In some embodiments, d is C(O)OH. In some embodiments n, o, p, and q are each 1. In some embodiments, n is 0. In some embodiments, Z is

[structure: C(=O)(O)t-(CH2)r-CH=CH-(CH2)s-]

and r is 2. In some embodiments, Z is

[structure]

and r is 3. In some embodiments, Z is

[structure]

and s is 5. In some embodiments, Z is

[structure]

and s is 6. In some embodiments, Z is

[structure with R5, R6]

and r is 2. In other embodiments, Z is

[structure with R5, R6]

and r is 3. In some embodiments, Z is

[structure with R5, R6]

and s is 5. In other embodiments, Z is

[structure with R5, R6]

and s is 6. In some embodiments, at most one Z is H. In some embodiments, Z is not H. In other embodiments, Z is not —C(O)$CH_3$. In some embodiments, t is 1.

In still another aspect, compounds of the Formula V' are described:

Formula V'

[structure showing difluorobiphenyl attached to a ring system with W1, W2, substituents a, b, c, d, subscripts n, o, p, q, and group Q, Z]

and pharmaceutically acceptable salts, hydrates, solvates, prodrugs, enantiomers, and stereoisomers thereof;
wherein
$W_1$ and $W_2$ are each independently null, O, or NH;
- - - - - represents an optional bond that when present requires that Q is then null;
a and c are each independently H, $CH_3$, $—OCH_3$, $—OCH_2CH_3$, or C(O)OH;
b is H, $CH_3$, C(O)OH, or O—Z;
d is H or C(O)OH;
each n, o, p, and q is independently 0 or 1;
each Z is independently null, H,

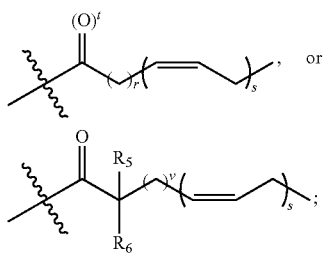, or

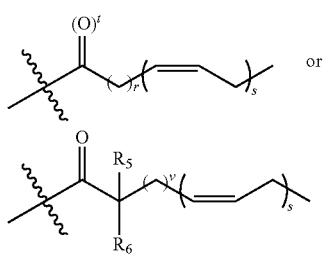;

with the proviso that there is at least one

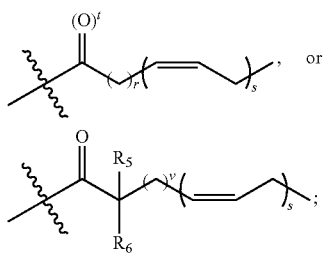 or

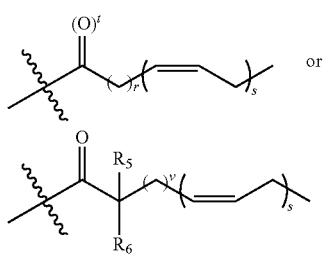

in the compound;
each r is independently 7;
each s is independently 3;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;
Q is null, C(O)$CH_3$, Z, or

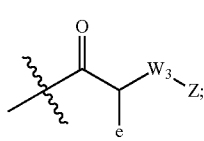

and
e is H, —C(O)OH or any one of the side chains of the naturally occurring amino acids.

In some embodiments, $W_1$ is O. In some embodiments, $W_1$ is NH. In some embodiments, $W_2$ is O. In some embodiments, $W_2$ is NH.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, $CH_3$, $—OCH_3$, $—OCH_2CH_3$, or C(O)OH. In some embodiments, b is O—Z, Z is

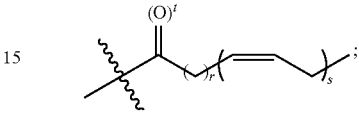

and t is 1. In some embodiments, d is C(O)OH. In some embodiments n, o, p, and q are each 1. In some embodiments, n is 0. In some embodiments, Z is

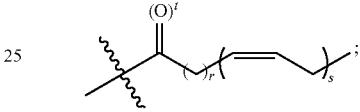

and r is 7. In some embodiments, Z is

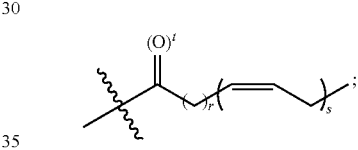

and s is 3. In some embodiments, Z is

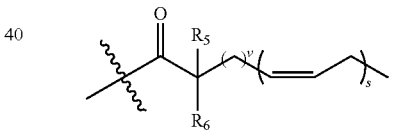

and r is 7. In other embodiments, Z is

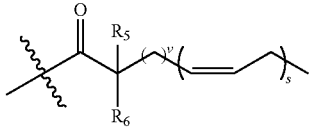

and s is 3. In some embodiments, t is 1. In some embodiments, Q is C(O)$CH_3$. In some embodiments, Q is Z. In some embodiments, Q is

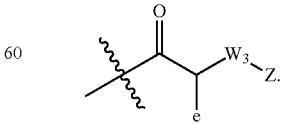

In some embodiments, e is any one of the side chains of the naturally occurring amino acids. In some embodiments, e is H. In other embodiments, e is —C(O)OH. In some embodiments, $W_3$—NR—. In some embodiments, $W_3$ is O.

In yet another aspect, compounds of the Formula VI' are described:

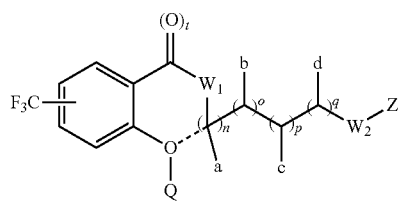

Formula VI' and pharmaceutically acceptable salts, hydrates, solvates, prodrugs, enantiomers, and stereoisomers thereof;
wherein
$W_1$ and $W_2$ are each independently null, O, or NH;
- - - - - represents an optional bond that when present requires that Q is null;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
each Z is H,

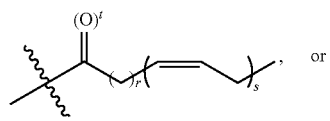, or

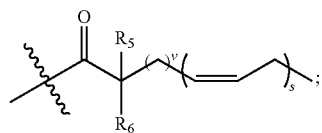

with the proviso that there is at least one

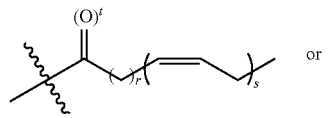 or

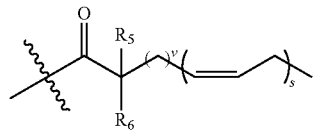

in the compound;
each r is independently 0, 1, 2, or 3;
each s is independently an integer from 1 to 10;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

Q is null, C(O)$CH_3$, Z, or

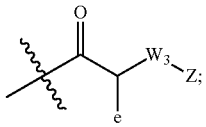

e is H, —C(O)OH, or any one of the side chains of the naturally occurring amino acids;
$W_3$ is null, —O—, —N(R)—; and
R is H or $C_1$-$C_3$ alkyl.

In some embodiments, $W_1$ is O. In other embodiments, $W_1$ is NH. In some embodiments, $W_2$ is O. In other embodiments, $W_2$ is NH.

In some embodiments, $W_1$ is N. In other embodiments $W_1$ is N substituted with a $C_1$-$C_6$ alkyl. In other embodiments, $W_1$ is an oxidized N.

In some embodiments, $W_2$ is N. In other embodiments $W_2$ is N substituted with a $C_1$-$C_6$ alkyl. In other embodiments, $W_2$ is an oxidized N.

In some embodiments, - - - - - represents a bond. In some embodiments, a and c are each independently H, $CH_3$, —$OCH_3$, —$OCH_2CH_3$, or C(O)OH. In some embodiments, b is O—Z, Z is

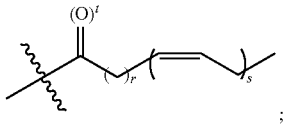

and t is 1. In some embodiments, d is C(O)OH. In some embodiments n, o, p, and q are each 1. In some embodiments, n is 0. In some embodiments, Z is

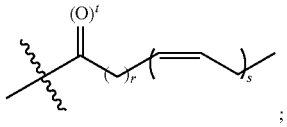

and r is 2. In some embodiments, Z is

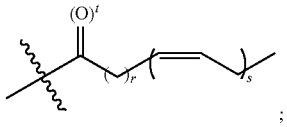

and r is 3. In some embodiments, Z is

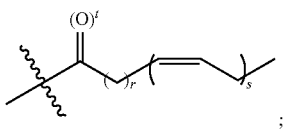

;

and s is 5. In some embodiments, Z is

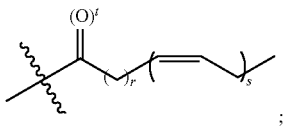

;

and s is 6. In some embodiments, Z is

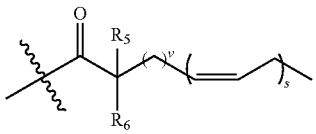

and r is 2. In other embodiments, Z is

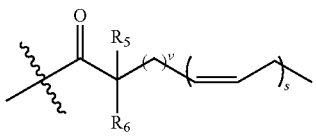

and r is 3. In some embodiments, Z is

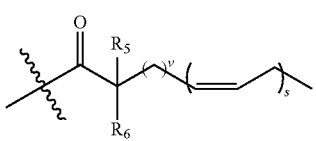

and s is 5. In other embodiments, Z is

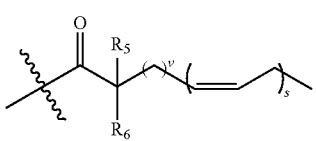

and s is 6. In some embodiments, t is 1. In some embodiments, Q is H. In other embodiments, Q is $C(O)CH_3$. In some embodiments, Q is Z. In some embodiments, Q is

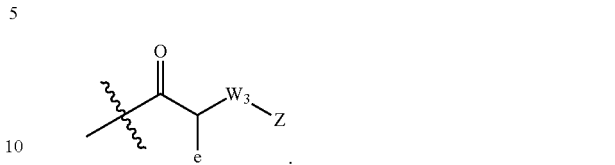

.

In some embodiments, e is any one of the side chains of the naturally occurring amino acids. In some embodiments, e is H. In other embodiments, e is —C(O)OH. In some embodiments, $W_3$ is —NR—. In some embodiments, $W_3$ is O.

In another aspect, compounds of the Formula VIa' are described:

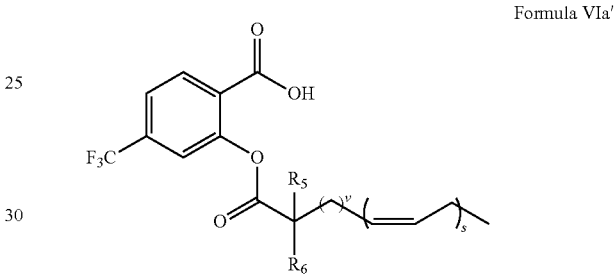

Formula VIa' and pharmaceutically acceptable salts, hydrates, solvates, prodrugs, enantiomers, and stereoisomers thereof;

wherein v is 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and s is independently 5 or 6.

In some embodiments, r is 2. In some embodiments, r is 3. In some embodiments, s is 5. In some embodiments, s is 6.

In another aspect, compounds of the Formula VIb' are described:

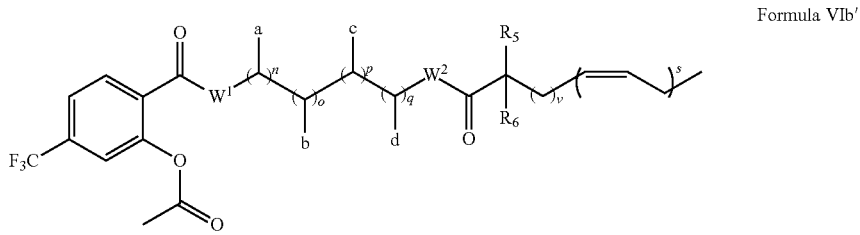

Formula VIb' and pharmaceutically acceptable salts, hydrates, solvates, enantiomers, and stereoisomers thereof,
wherein
$W_1$ and $W_2$ are each independently null, O, or NH;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
each Z is H,

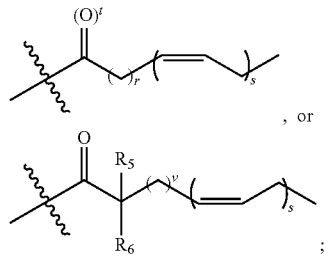

, or

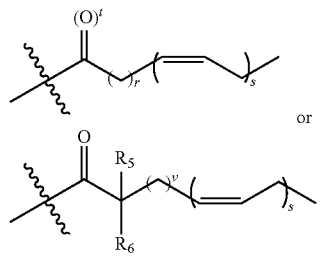

;

with the proviso that there is at least one

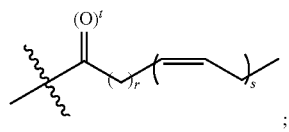

or

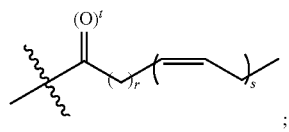

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is

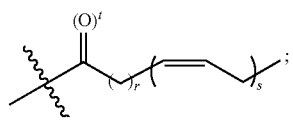

;

and t is 1. In some embodiments, d is C(O)OH. In some embodiments n, o, p, and q are each 1. In some embodiments, n is 0.

In some embodiments, Z is

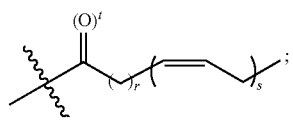

and r is 2. In some embodiments, Z is

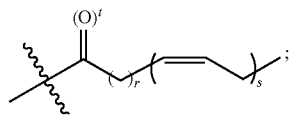

and r is 3. In some embodiments, Z is

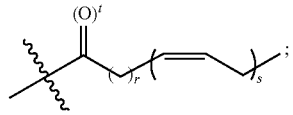

and s is 5. In some embodiments, Z is

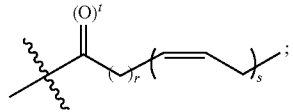

and s is 6. In some embodiments, Z is

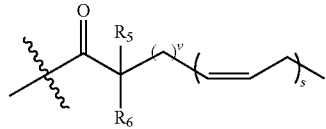

and r is 2. In other embodiments, Z is

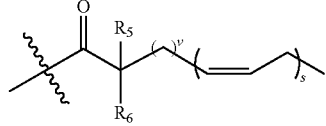

and r is 3. In some embodiments, Z is

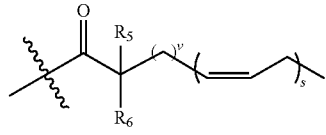

and s is 5. In other embodiments, Z is

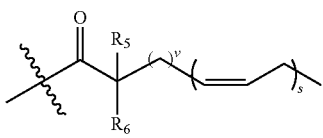

and s is 6. In some embodiments, Z is not H. In some embodiments, t is 1.

In another aspect, compounds of the Formula VIc' are described:

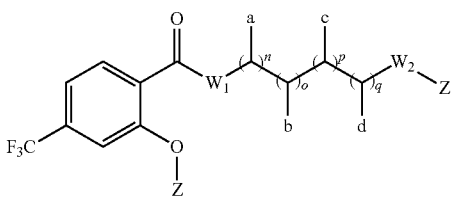

Formula VIc' and pharmaceutically acceptable salts, hydrates, solvates, prodrugs, enantiomers, and stereoisomers thereof;
wherein
$W_1$ and $W_2$ are each independently null, O, or NH;
a and c are each independently H, $CH_3$, —$OCH_3$, —$OCH_2CH_3$, or C(O)OH;
b is H, $CH_3$, C(O)OH, or O—Z;
d is H or C(O)OH;
each of n, o, p, and q is independently 0 or 1;
each Z is independently null, H,

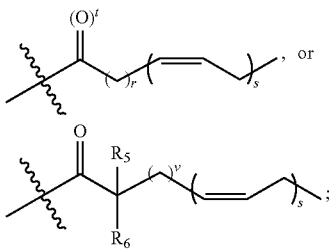

with the proviso that there is at least one

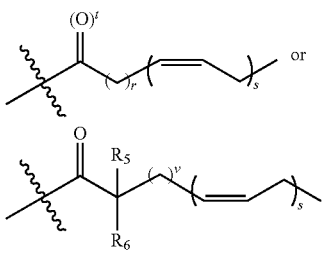

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is

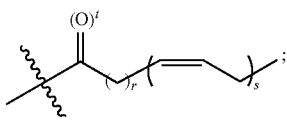

and t is 1. In some embodiments, d is C(O)OH. In some embodiments n, o, p, and q are each 1.

In some embodiments, n is 0. In some embodiments, Z is

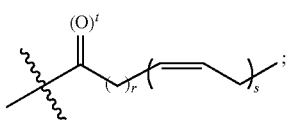

and r is 2. In some embodiments, Z is

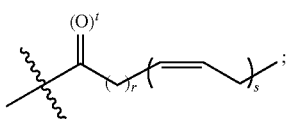

and r is 3. In some embodiments, Z is

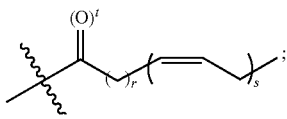

and s is 5. In some embodiments, Z is

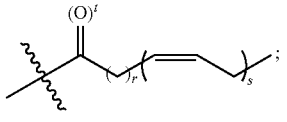

and s is 6. In some embodiments, Z is

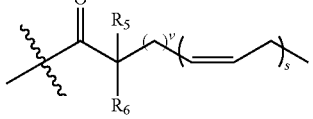

and r is 2. In other embodiments, Z is

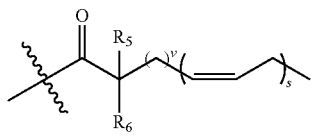

and r is 3. In some embodiments, Z is

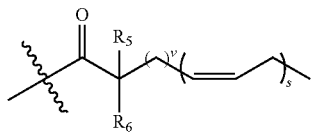

and s is 5. In other embodiments, Z is

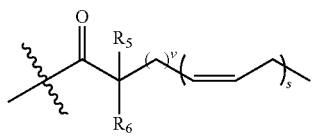

and s is 6. In some embodiments, at most one Z is H. In some embodiments, Z is not H.

In other embodiments, Z is not —C(O)CH$_3$. In some embodiments, t is 1.

In another aspect, compounds of the Formula VId' are described:

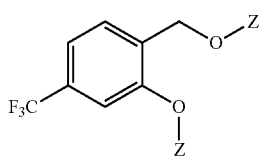

Formula VId' and pharmaceutically acceptable salts, hydrates, solvates, prodrugs, enantiomers, and stereoisomers thereof;
wherein
each Z is independently H,

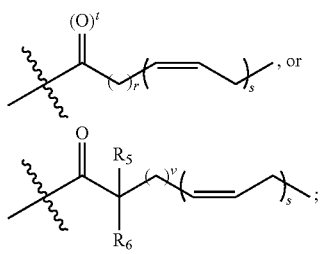

with the proviso that there is at least one

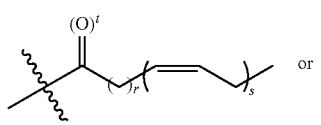

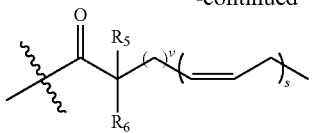

in the compound;
each r is independently 2 or 3;
each s is independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl.

In some embodiments, Z is

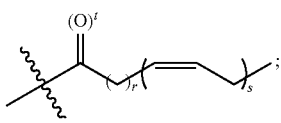

and r is 2. In some embodiments, Z is

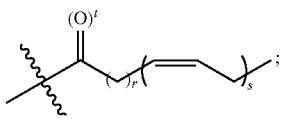

and r is 3. In some embodiments, Z is

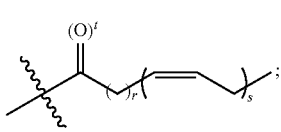

and s is 5. In some embodiments, Z is

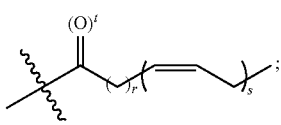

and s is 6. In some embodiments, Z is

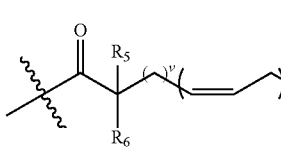

and r is 2. In other embodiments, Z is

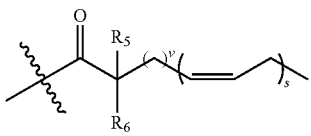

and r is 3. In some embodiments, Z is

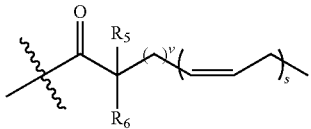

and s is 5. In other embodiments, Z is

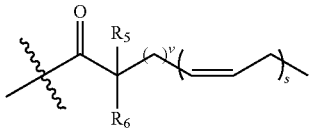

and s is 6. In some embodiments, t is 1.

In another aspect, compounds of the Formula VIe' are described:

Formula VIe'

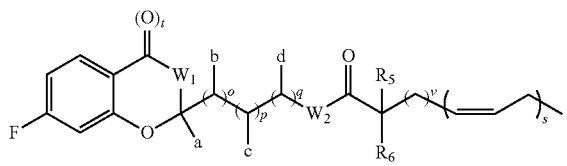

and pharmaceutically acceptable salts, hydrates, solvates, prodrugs, enantiomers, and stereoisomers thereof;
wherein
$W_1$ is O, or NH;
$W_2$ is null, O, or NH;
a and c are each independently H, $CH_3$, $-OCH_3$, $-OCH_2CH_3$, or C(O)OH;
b is H, $CH_3$, C(O)OH, or O—Z;
d is H or C(O)OH;
each o, p, and q is independently 0 or 1;
each Z is H,

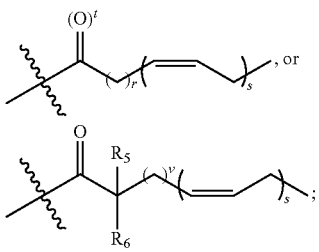

with the proviso that there is at least one

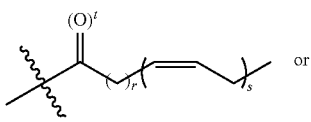

in the compound;
each r is independently 2 or 3;
each s is
independently 5 or 6;
each t is independently 0 or 1;
each v is 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH. In some embodiments, b is O—Z, Z is

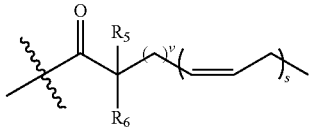

and t is 1. In some embodiments, d is C(O)OH. In some embodiments n, o, p, and q are each 1. In some embodiments, n is 0. In some embodiments, Z is

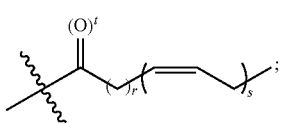

and r is 2. In some embodiments, Z is

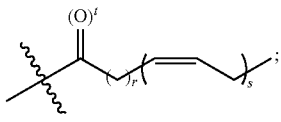

and r is 3. In some embodiments, Z is

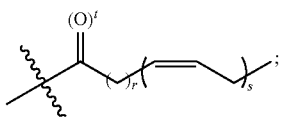

and s is 5. In some embodiments, Z is

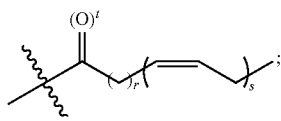

and s is 6. In some embodiments, Z is

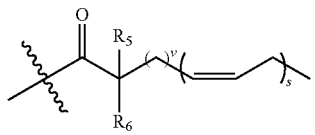

and r is 2. In other embodiments, Z is

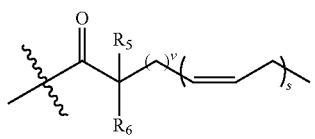

and r is 3. In some embodiments, Z is

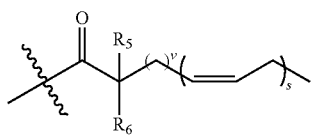

and s is 5. In other embodiments, Z is

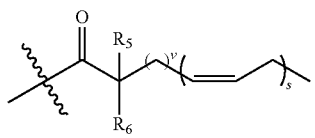

and s is 6. In some embodiments, t is 1.

In another aspect, compounds of the Formula VIf' are described:

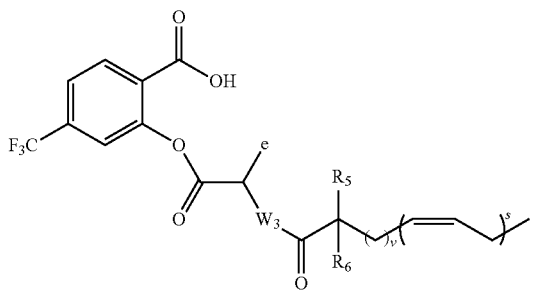

Formula VIf' and pharmaceutically acceptable salts, hydrates, solvates, prodrugs, enantiomers, and stereoisomers thereof;
wherein
e is H, —C(O)OH or any one of the side chains of the naturally occurring amino acids;

$W_3$ is null, —O—, —N(R) and
R is H or $C_1$-$C_3$ alkyl,
each v is 1 or 2;
each $R_5$ and $R_6$ are independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and
s is 5 or 6.

In some embodiments, $W_3$ is O. In some embodiments, e is sec-butyl. In other embodiments, e is —C(O)OH. In still other embodiments, e is H. In some embodiments, $W_3$ is —NR—. In some embodiments, $W_3$ is O. In some embodiments, r is 2. In some embodiments, r is 3. In some embodiments, s is 5. In some embodiments, s is 6. In some embodiments, t is 1.

In another aspect, compounds of the Formula VIg' are described:

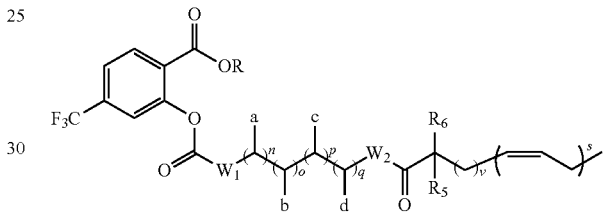

Formula VIg' and pharmaceutically acceptable salts, hydrates, solvates, prodrugs, enantiomers, and stereoisomers thereof;
wherein
R is H or $C_1$-$C_3$ alkyl;
$W_1$ and $W_2$ are each independently null, O, or NH;
a and c are each independently H, $CH_3$, —$OCH_3$, —$OCH_2CH_3$, or C(O)OH;
b is H, $CH_3$, C(O)OH, or O—Z;
d is H or C(O)OH;
each n, o, p, and q is independently 0 or 1;
each Z is H,

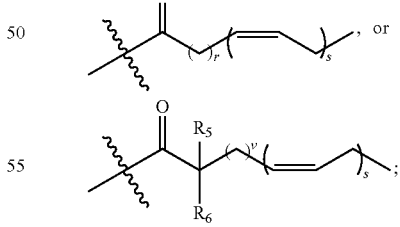

, or with the proviso that there is at least one

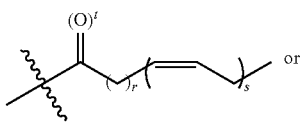

or

-continued

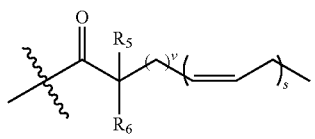

in the compound;

each r is independently 2 or 3;

each s is independently 5 or 6;

each t is independently 0 or 1;

each v is 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl.

In some embodiments, $W_1$ is O. In other embodiments, $W_1$ is NH. In some embodiments, $W_2$ is O. In other embodiments, $W_2$ is NH. In some embodiments, a and c are each independently H, $CH_3$, —$OCH_3$, —$OCH_2CH_3$, or C(O)OH; In some embodiments, b is O—Z, Z is

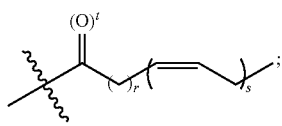

and t is 1. In some embodiments, d is C(O)OH. In some embodiments n, o, p, and q are each 1.

In some embodiments, n is 0. In some embodiments, Z is

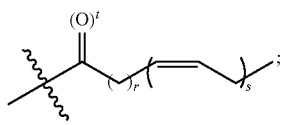

and r is 2. In some embodiments, Z is

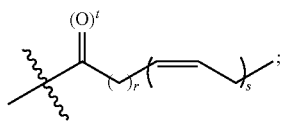

and r is 3. In some embodiments, Z is

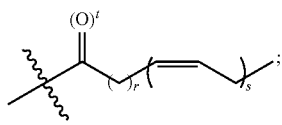

and s is 5. In some embodiments, Z is

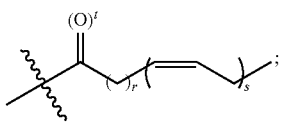

and s is 6. In some embodiments, Z is

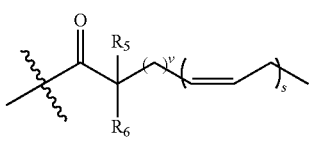

and r is 2. In other embodiments, Z is

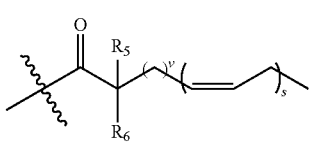

and r is 3. In some embodiments, Z is

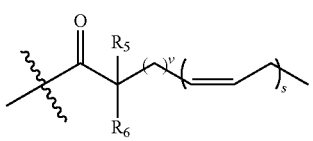

and s is 5. In other embodiments, Z is

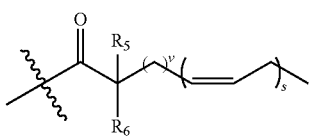

and s is 6. In some embodiments, at most one Z is H. In some embodiments, Z is not H. In other embodiments, Z is not —C(O)$CH_3$. In some embodiments, t is 1.

In another aspect, compounds of the Formula VII' are described:

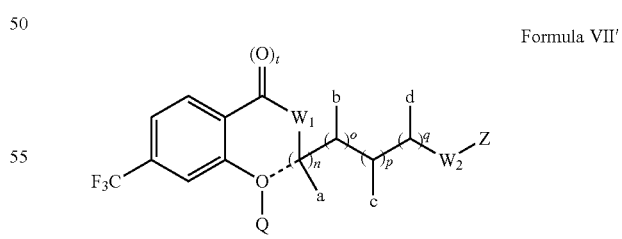

Formula VII' and pharmaceutically acceptable salts, hydrates, solvates, prodrugs, enantiomers, and stereoisomers thereof;
wherein
$W_1$ and $W_2$ are each independently null, O, or NH;
- - - - - represents an optional bond that when present requires that Q is then null;
a and c are each independently H, $CH_3$, —$OCH_3$, —$OCH_2CH_3$, or C(O)OH;

b is H, CH₃, C(O)OH, or O—Z;
d is H or C(O)OH;
each n, o, p, and q is independently 0 or 1;
each Z is H,

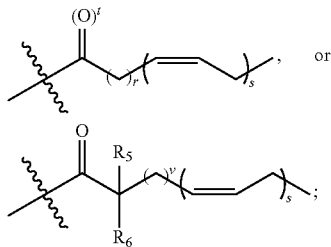, or

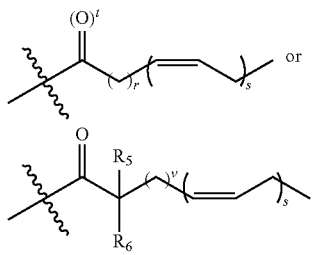;

with the proviso that there is at least one

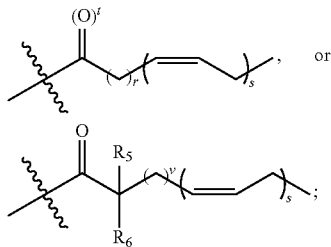 or

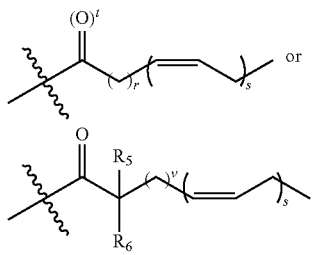

in the compound;
each r is independently 7;
each s is independently 3;
each t is independently 0 or 1;
each v is 1 or 2;
R₅ and R₆ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH₂, —NH($C_1$-$C_3$ alkyl), —N($C_1$-$C_3$ alkyl)₂, —NH(C(O)$C_1$-$C_3$ alkyl), —N(C(O)$C_1$-$C_3$ alkyl)₂, —SH, —S($C_1$-$C_3$ alkyl), —S(O)$C_1$-$C_3$ alkyl, —S(O)₂$C_1$-$C_3$ alkyl;
Q is null, C(O)CH₃, Z, or

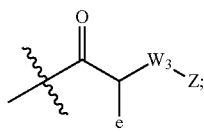;

W₃ is null, —O—, —N(R)—;
R is H or $C_1$-$C_3$ alkyl; and
e is H, —C(O)OH or any one of the side chains of the naturally occurring amino acids.

In some embodiments, W₁ is O. In some embodiments, W₁ is NH. In some embodiments, W₂ is O. In some embodiments, W₂ is NH.

In some embodiments, W₁ is N. In other embodiments W₁ is N substituted with a $C_1$-$C_6$ alkyl. In other embodiments, W₁ is an oxidized N.

In some embodiments, W₂ is N. In other embodiments W₂ is N substituted with a $C_1$-$C_6$ alkyl. In other embodiments, W₂ is an oxidized N.

In some embodiments, - - - - - represents a bond. In some embodiments, a and c are each independently H, CH₃, —OCH₃, —OCH₂CH₃, or C(O)OH. In some embodiments, b is O—Z, Z is

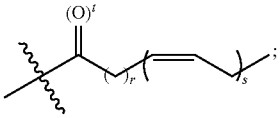

and t is 1. In some embodiments, d is C(O)OH. In some embodiments n, o, p, and q are each 1.

In some embodiments, n is 0. In some embodiments, Z is

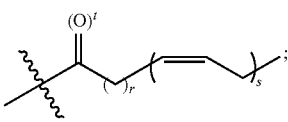

and r is 7. In some embodiments, Z is

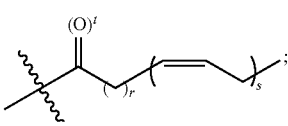

and s is 3. In some embodiments, Z is

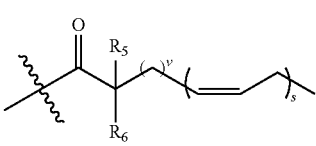

and r is 7. In other embodiments, Z is

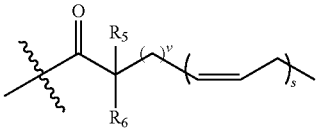

and s is 3. In some embodiments, t is 1. In some embodiments, Q is C(O)CH₃, In some embodiments, Q is Z. In some embodiments, Q is

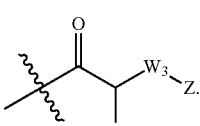

In some embodiments, e is any one of the side chains of the naturally occurring amino acids. In some embodiments, e is H. In other embodiments, e is —C(O)OH. In some embodiments, W₃ is —NR—. In some embodiments, W₃ is O.

In any of the above Formulae, any one or more of H may be substituted with a deuterium. It is also understood in any of the above Formulae that a methyl subtituent can be substituted with a $C_1$-$C_6$ alkyl.

Methods for Using Compounds of the Invention

The invention also includes methods for upregulating an anti-inflammatory pathway and downregulating a proinflammatory pathway in a cell.

In one embodiment, the method comprises contacting a cell with a Compound of the Invention in an amount sufficient to upregulate an anti-inflammatory pathway and down regulate a proinflammatory pathway in the cell. In general, any cell having, or capable of having, inflammatory activity or capable of expressing NFκB can be used. The cell can be provided in any form. For example, the cell can be provided in vitro, ex vivo, or in vivo. Inflammatory activity can be measured using any method known in the art, e.g., methods as described in Tran P. O., et al., *Diabetes*, 51; 1772-8, 2002. Illustrative examples of cells capable of inflammatory activity include, but are not limited to, immune cells including monocytes, macrophages, T-cell, Th-1, Th-2, Th-17, Treg, lymphocytes, spleen cells, muscle, adipose or fat, vascular cells such as endothelial or pericyte, bone, gum, nerve, brain, glial, astrocytes, nerve, liver, kidney, pancreas including islet cells such as beta cells, lung, heart, breast, bladder, stomach, colon, rectal, small intestine, skin, esophageal, eye, larynx, uterine, ovarian, prostate, tendon, bone marrow, blood, lymph, testicular, vaginal and neoplastic cells.

Also provided in the invention is a method for inhibiting, preventing, or treating inflammation or an inflammatory disease in a subject. The inflammation can be associated with an inflammatory disease or a disease where inflammation contributes to the disease. Inflammatory diseases can arise where there is an inflammation of the body tissue. These include local inflammatory responses and systemic inflammation. Examples of such diseases include, but are not limited to: organ transplant rejection; reoxygenation injury resulting from organ transplantation (see Grupp et al., J. Mol. Cell. Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, chronic obstructive airway disease, and cystic fibrosis; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis. Metabolic disease such as type II diabetes mellitus; the prevention of type I diabetes; dyslipedemia; hypertriglyceridemia; diabetic complications, including, but not limited to glaucoma, retinopathy, macula edema, nephropathy, such as microalbuminuria and progressive diabetic nephropathy, polyneuropathy, diabetic neuropathy, atherosclerotic coronary arterial disease, peripheral arterial disease, nonketotic hyperglycemichyperosmolar coma, mononeuropathies, autonomic neuropathy, joint problems, and a skin or mucous membrane complication, such as an infection, a shin spot, a candidal infection or necrobiosis lipoidica diabeticorum; immune-complex vasculitis, systemic lupus erythematosus; inflammatory diseases of the heart such as cardiomyopathy, ischemic heart disease hypercholesterolemia, and atherosclerosis; as well as various other diseases that can have significant inflammatory components, including preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines Such shock can be induced, e.g., by a chemotherapeutic agent that is administered as a treatment for cancer. Other disorders include depression, obesity, allergic diseases, acute cardiovascular events, arrhythmia, prevention of sudden death, muscle wasting diseases such as Duchenne's Muscular Dystrophy, inflammatory myopathies such as dermatomositis, inclusion body myositis, and polymyositis, and cancer cachexia. Also inflammation that results from surgery and trauma can be treated with Compound of the Invention.

In some embodiments, the subject is administered an effective amount of a Compound of the Invention.

The invention also includes pharmaceutical compositions useful for treating or preventing an inflammatory disease, or for inhibiting inflammation activity, or more than one of these activities. The compositions can be suitable for internal use and comprise an effective amount of a Compound of the Invention and a pharmaceutically acceptable carrier. The Compounds of the Invention are especially useful in that they demonstrate very low peripheral toxicity or no peripheral toxicity.

The Compounds of the Invention can each be administered in amounts that are sufficient to treat or prevent an inflammatory disease or a reperfusion disease and/or prevent the development thereof in subjects.

Administration of the Compounds of the Invention can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the Compound of the Invention is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the Compounds of the Invention.

The Compounds of the Invention can be also formulated as a suppository that can be prepared from fatty emulsions or suspensions; using polyalkylene glycols such as propylene glycol, as the carrier.

The Compounds of the Invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Compounds of the Invention can also be delivered by the use of monoclonal antibodies as individual carriers to which the Compounds of the Invention are coupled. The Compounds of the Invention can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Compounds of the Invention can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, Compounds of the Invention are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the Compound of the Invention by weight or volume.

The dosage regimen utilizing the Compound of the Invention is selected in accordance with a variety of factors including type, species, age, weight, sex and medical condition of the patient; the severity of the condition to be treated; the route of administration; the renal or hepatic function of the patient; and the particular Compound of the Invention employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 5000 mg of the Compound of the Invention per day. Compositions for in vivo or in vitro use can contain about 20, 50, 75, 100, 150, 250, 500, 750, 1000, 1250, 2500, 3500, or 5000 mg of the Compound of the Invention. In one embodiment, the compositions are in the form of a tablet that can be scored. Effective plasma levels of the Compound of the Invention can range from about 0.002 mg to about 100 mg per kg of body weight per day. Appropriate dosages of the Compounds of the Invention can be determined as set forth in L. S. Goodman, et al., *The Pharmacological Basis of Therapeutics*, 201-26 (5th ed. 1975).

Compounds of the Invention can be administered in a single daily dose, or the total daily dosage can be administered in divided doses of two, three or four times daily. Furthermore, Compounds of the Invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the Compound of the Invention ranges from about 0.1% to about 15%, w/w or w/v.

Methods for Making the Fatty Acid Acetylated Salicylate Derivatives

Examples of synthetic pathways useful for making Fatty Acid Acetylated Salicylate Derivatives of Formula I, Formula Ia, Formula Ib, Formula Ic, Formula Id, Formula Ie, Formula If, Formula Ig, and Formula II are set forth in the Examples below and generalized in Schemes 1-4.

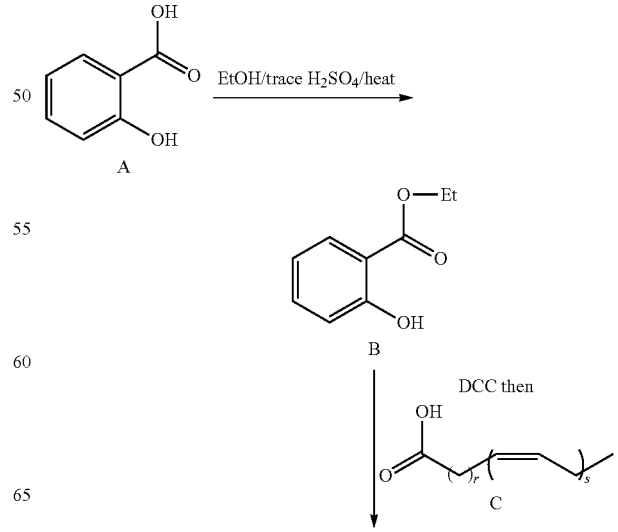

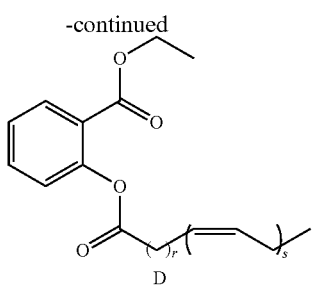

D wherein r and s are as defined above for Formula I, Formula Ia, Formula Ib, Formula Ic, Formula Id, Formula Ie, Formula If, Formula Ig, and Formula II.

Compound A can be esterified in the presence of acid catalyst and a suitable alcohol, e.g., ethanol to give ester B. Activation of compound B with a coupling reagent such as for example DCC, CDI, or EDC, optionally with a tertiary amine base and/or catalyst, e.g., DMAP, followed by addition of a fatty acid of Formula C affords compounds of Formula D. Alternatively, compound A can be esterified with benzyl bromide in the presence of base, e.g., $CsCO_3$, then subjected to the remaining steps of Scheme 1. Hydrogenolysis of the benzyl ester derived from A, for example using Pd/C and H2, can yield the free acid of compounds of Formula D.

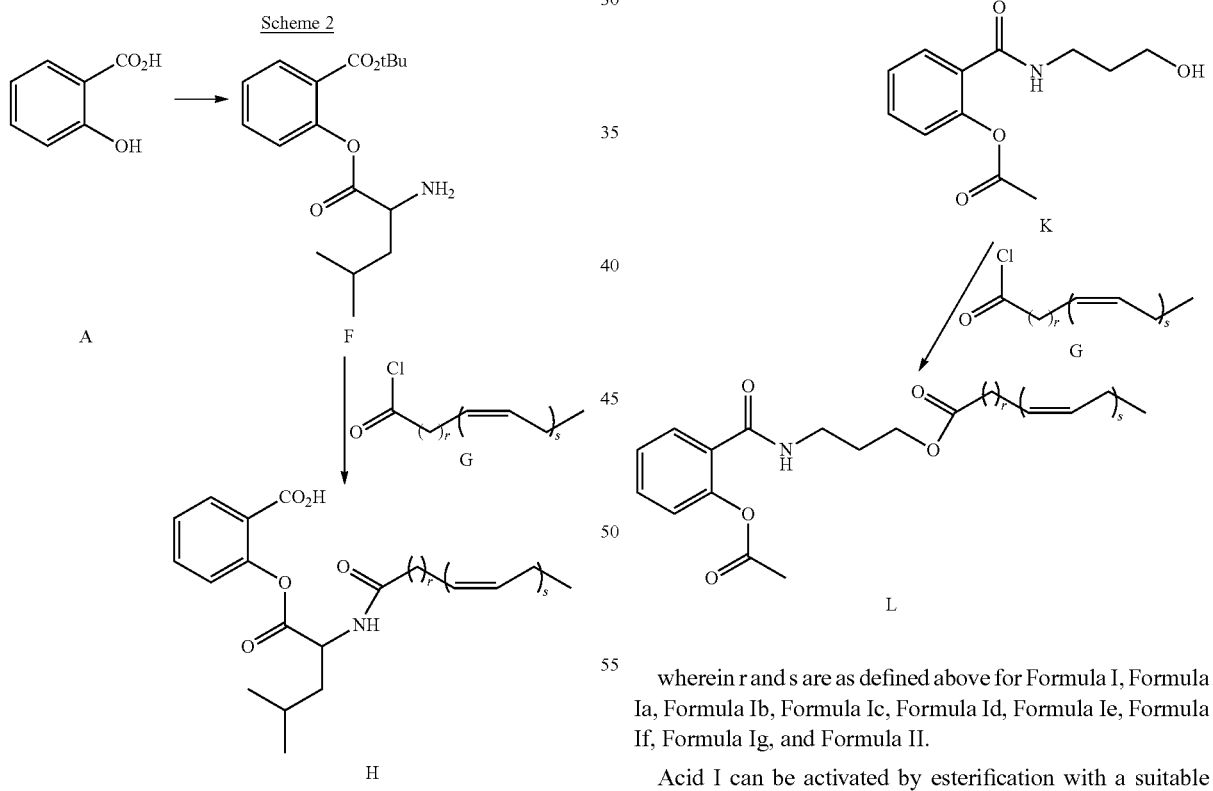

wherein r and s are as defined above for compounds of Formula I, Formula Ia, Formula Ib, Formula Ic, Formula Id, Formula Ie, Formula If, Formula Ig, Formula II, and Formula III.

Compound A can be esterified in the presence of acid catalyst and a suitable protecting alcohol such as, e.g., t-butanol, followed by coupling to an activated amino acid to give compound F. Condensation of the amino compound F with a fatty acid chloride of Formula G affords compounds of Formula H. The ester may be deprotected using methods disclosed in Greene, et al. *Protecting Groups in Organic Chemistry*. 4$^{th}$ ed. Wiley & Sons, Hoboken, N.J. (2007). See, e.g., Chapter 5, therein.

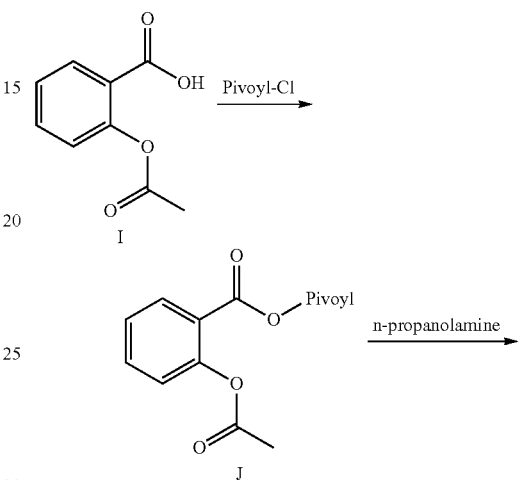

wherein r and s are as defined above for Formula I, Formula Ia, Formula Ib, Formula Ic, Formula Id, Formula Ie, Formula If, Formula Ig, and Formula II.

Acid I can be activated by esterification with a suitable activating agent such as, e.g., pivoyl chloride, followed by condensation with an amino alcohol such as for example n-propanolamine, to give compound K. Condensation of the alcohol compound K with a fatty acid chloride of Formula G affords compounds of Formula L. Diacylated compounds of the invention can be made by subjecting compound A to the above procedure.

Scheme 4

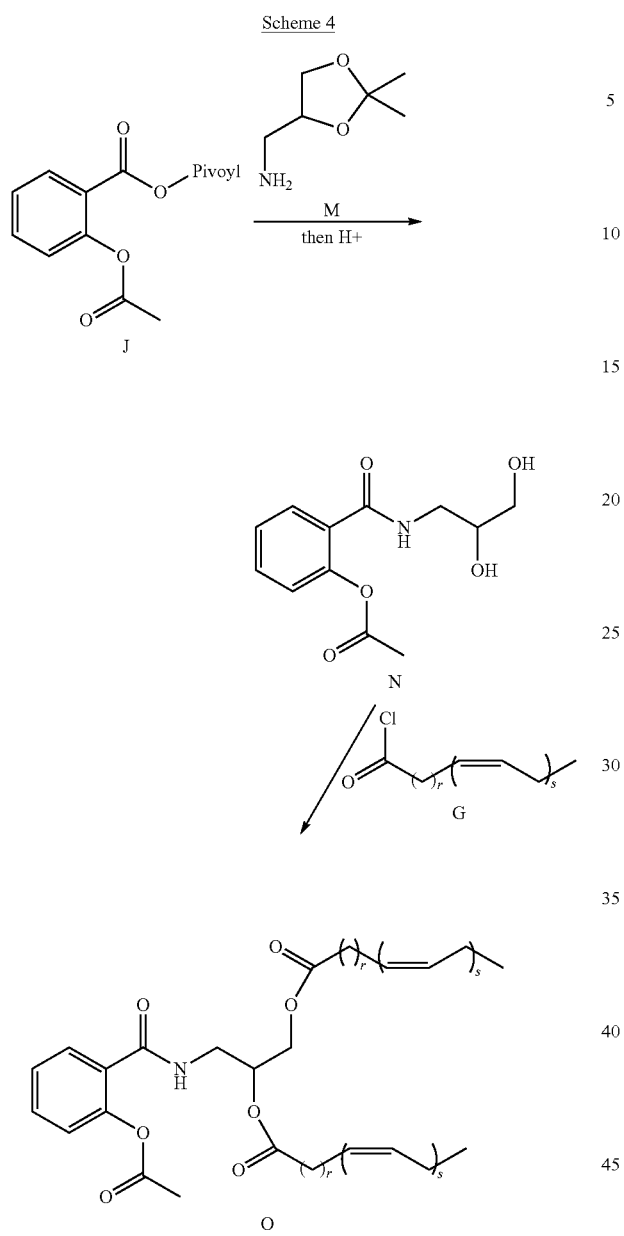

wherein r and s are as defined above for Formula I, Formula Ia, Formula Ib, Formula Ic, Formula Id, Formula Ie, Formula If, Formula Ig, and Formula II.

Activated ester J (see Scheme 3) can be condensed with an amino-masked diol M, which after acid workup gives the unmasked diol compound N. Condensation of the diol compound N with a fatty acid chloride of Formula G affords compounds of Formula O.

Methods for Making the Fatty Acid Acetylated Diflunisal Derivatives

Examples of synthetic pathways useful for making Fatty Acid Acetylated Diflunisal Derivatives of Formula IV, Formula IVa, Formula IVb, Formula IVc, Formula IVd, Formula IVe, Formula IVf, Formula IVg, and Formula V, are set forth herein and generalized in Schemes 5-9.

Scheme 5

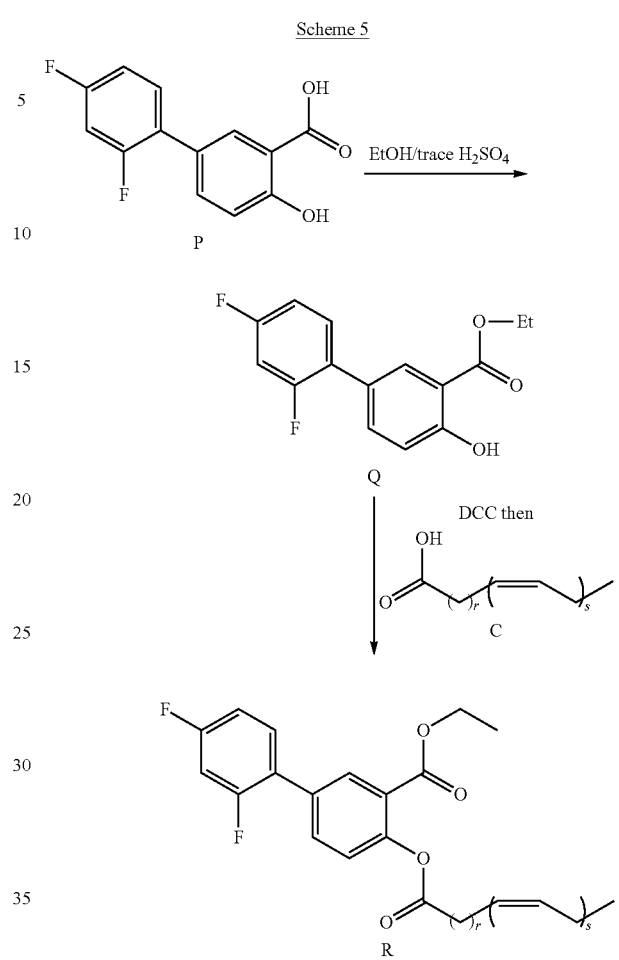

wherein r and s are as defined for Formula IV, Formula IVa, Formula IVb, Formula IVc, Formula IVd, Formula IVe, Formula IVf, Formula IVg, and Formula V.

Compound P can be esterified in the presence of acid catalyst and a suitable alcohol, e.g., ethanol to give ester Q. Activation of compound Q with a coupling reagent such as for example DCC, CDI, or EDC, optionally with a tertiary amine base and/or catalyst, e.g., DMAP, followed by addition of a fatty acid of Formula C affords compounds of Formula R. Alternatively, compound P can be esterified with benzyl bromide in the presence of base, e.g., $CsCO_3$, then subjected to the remaining steps of Scheme 5. Hydrogenolysis of the benzyl ester derived from P, for example using Pd/C and H2, can yield the free acid of compounds of Formula R.

Scheme 6

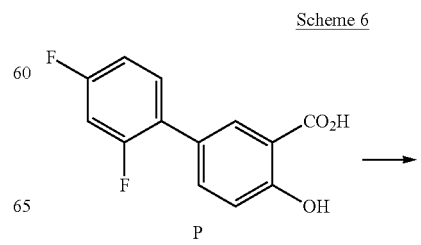

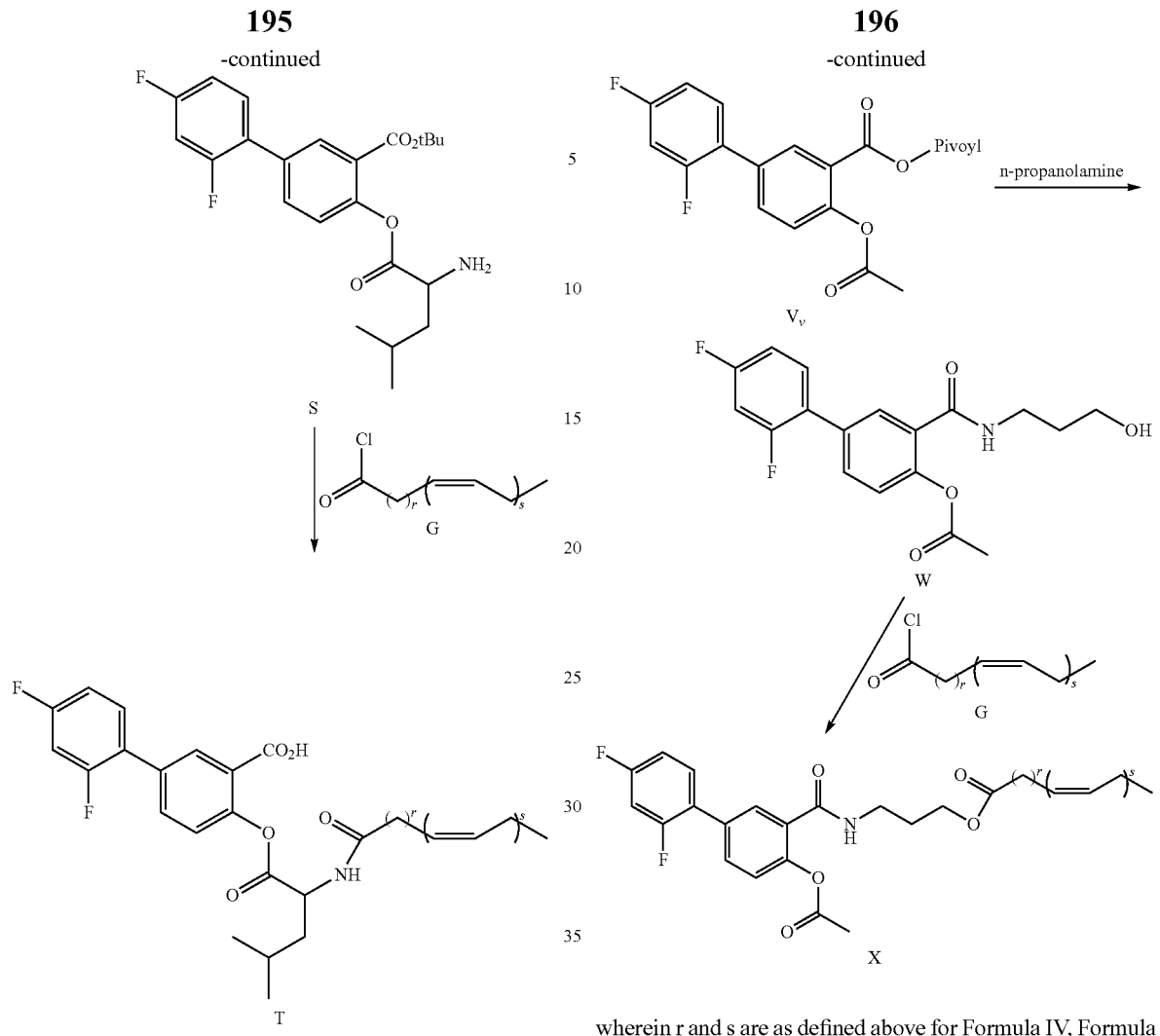

wherein r and s are as defined above for Formula IV, Formula IVa, Formula IVb, Formula IVc, Formula IVd, Formula IVe, Formula IVf, Formula IVg, and Formula V.

wherein r and s are as defined for Formula IV, Formula IVa, Formula IVb, Formula IVc, Formula IVd, Formula IVe, Formula IVf, Formula IVg, and Formula V.

Compound P can be esterified in the presence of acid catalyst and a suitable protecting alcohol such as, e.g., t-butanol, followed by coupling to an activated amino acid to give compound S. Condensation of the amino compound S with a fatty acid chloride of Formula G affords compounds of Formula T. The ester may be deprotected using methods disclosed in Greene, et al. *Protecting Groups in Organic Chemistry*. 4th ed. Wiley & Sons, Hoboken, N.J. (2007). See, e.g., Chapter 5, therein.

Acid U can be activated by esterification with a suitable activating agent such as, e.g., pivoyl chloride, followed by condensation with an amino alcohol such as for example n-propanolamine, to give compound W. Condensation of the alcohol compound W with a fatty acid chloride of Formula G affords compounds of Formula X. Diacylated compounds of the invention can be made by subjecting compound P to the above procedure.

Scheme 7

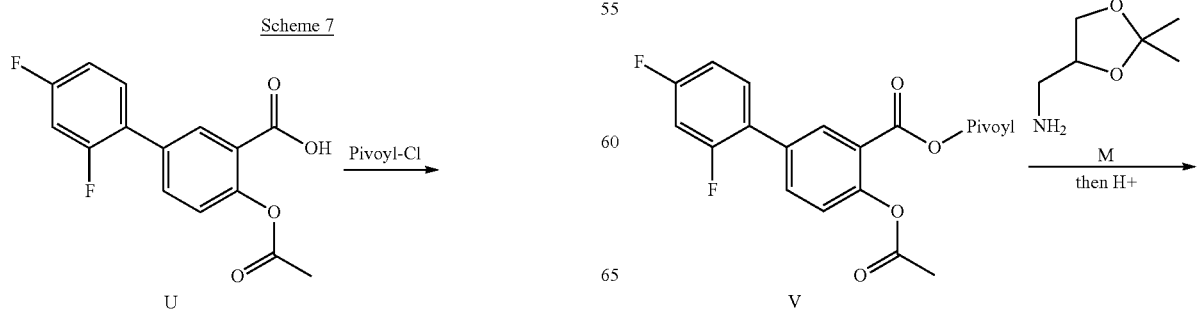

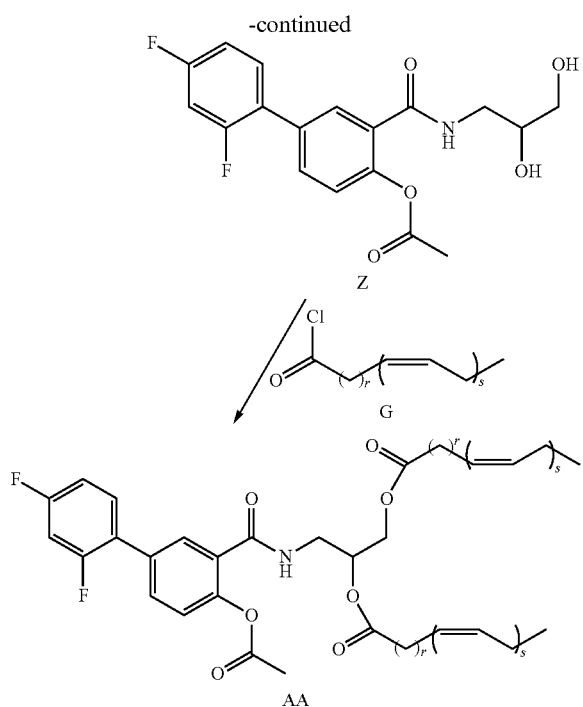

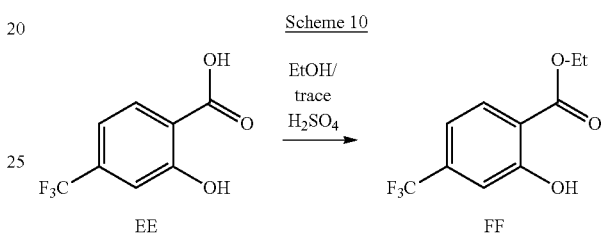

wherein r and s are as defined for Formula IV, Formula IVa, Formula IVb, Formula IVc, Formula IVd, Formula IVe, Formula IVf, Formula IVg, and Formula V.

Compound P can be esterified with benzyl bromide in the presence of a base, e.g. $CsCO_3$ yielding compound BB. Condensation of compound BB with a fatty acid chloride of Formula G affords compounds of Formula CC. Hydrogenolysis of the benzyl ester of compounds of Formula CC, e.g. using Pd/C and $H_2$, yields compounds of Formula DD.

Methods for Making the Fatty Acid Acetylated Triflusal Derivatives

Examples of synthetic pathways useful for making Fatty Acid Acetylated Triflusal Derivatives of Formula VI, Formula VIa, Formula VIb, Formula VIc, Formula VId, Formula VIe, Formula VIf, Formula VIg, and Formula VII, are set forth herein and generalized in Schemes 10-14.

Scheme 10 wherein r and s are as defined above for Formula IV, Formula IVa, Formula IVb, Formula IVc, Formula IVd, Formula IVe, Formula IVf, Formula IVg, and Formula V.

Activated ester V (see Scheme 7) can be condensed with a amino-masked diol M, which after acid workup gives the unmasked diol compound Z. Condensation of the diol compound Z with a fatty acid chloride of Formula G affords compounds of Formula AA.

Scheme 9

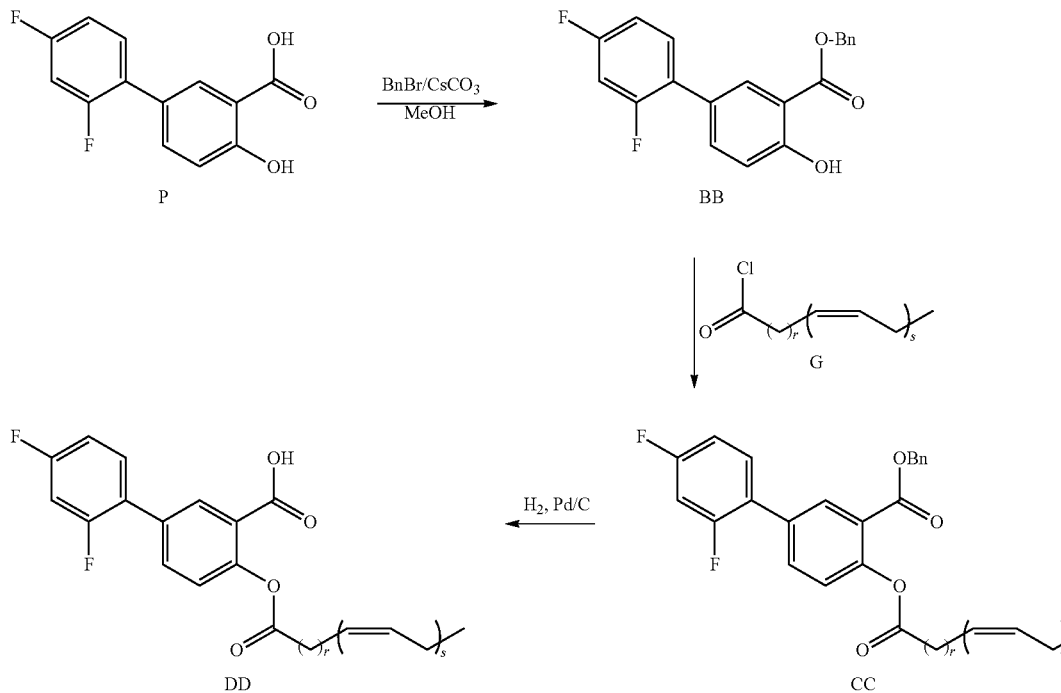

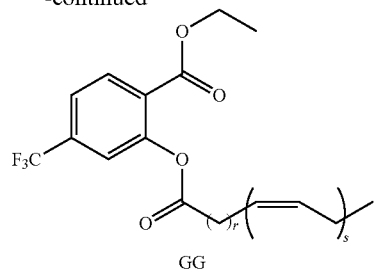

GG wherein r and s are as defined above for Formula VI, Formula VIa, Formula VIb, Formula VIc, Formula VId, Formula VIe, Formula VIf, Formula VIg, and Formula VII.

Compound EE can be esterified in the presence of acid catalyst and a suitable alcohol, e.g., ethanol to give ester FF. Activation of compound FF with a coupling reagent such as for example DCC, CDI, or EDC, optionally with a tertiary amine base and/or catalyst, e.g., DMAP, followed by addition of a fatty acid of Formula C affords compounds of Formula GG.

Alternatively, compound EE can be esterified with benzyl bromide in the presence of base, e.g., CsCO₃, then subjected to the remaining steps of Scheme 1. Hydrogenolysis of the benzyl ester derived from EE, for example using Pd/C and H₂, can yield the free acid of compounds of Formula GG.

Scheme 11

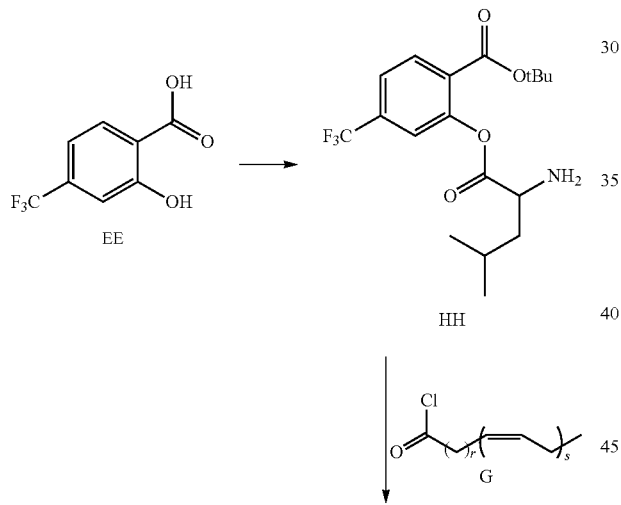

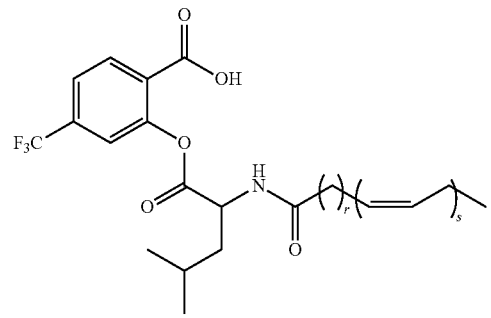

JJ wherein r, s and u can be as described for Formula VI, Formula VIa, Formula VIb, Formula VIc, Formula VId, Formula VIe, Formula VIf, Formula VIg, and Formula VII.

Compound EE can be esterified in the presence of acid catalyst and a suitable protecting alcohol such as, e.g., t-butanol, followed by coupling to an activated amino acid to give compound HH. Condensation of the amino compound HH with a fatty acid chloride of Formula G affords compounds of Formula JJ. The ester may be deprotected using methods disclosed in Greene, et al. *Protecting Groups in Organic Chemistry*. 4th ed. Wiley & Sons, Hoboken, N.J. (2007). See, e.g., Chapter 5, therein.

Scheme 12

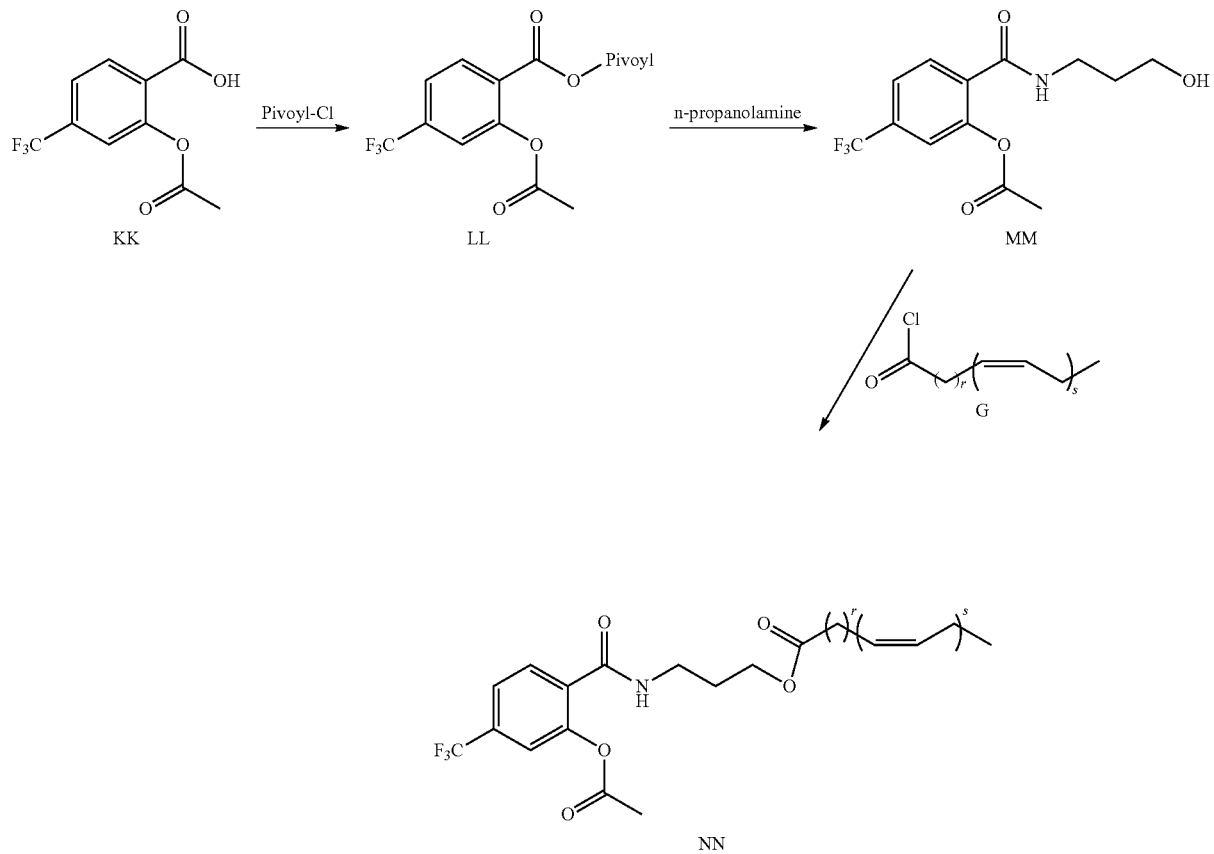

wherein r and s are as defined above for Formula VI, Formula VIa, Formula VIb, Formula VIc, Formula VId, Formula VIe, Formula VIf, Formula VIg, and Formula VII.

Acid KK can be activated by esterification with a suitable activating agent such as, e.g., pivoyl chloride, followed by condensation with an amino alcohol such as for example n-propanolamine, to give compound MM. Condensation of the alcohol compound MM with a fatty acid chloride of Formula G affords compounds of Formula NN. Diacylated compounds of the invention can be made by subjecting compound EE to the above procedure.

Scheme 13

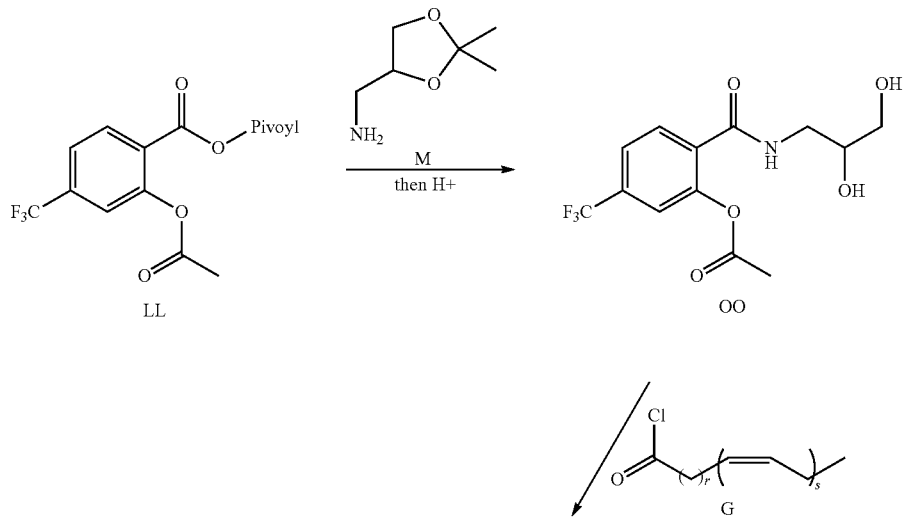

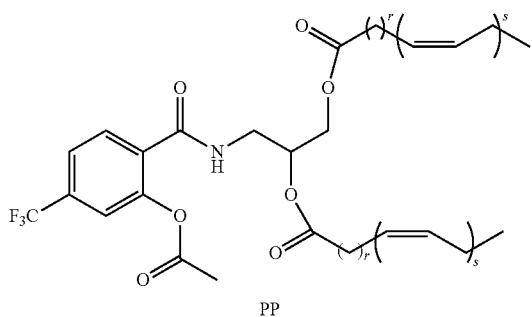

PP wherein r and s are as defined above for Formula VI, Formula VIa, Formula VIb, Formula VIc, Formula VId, Formula VIe, Formula VIf, Formula VIg, and Formula VII.

Activated ester LL (see Scheme 12) can be condensed with a amino-masked diol M, which after acid workup gives the unmasked diol compound OO. Condensation of the diol compound OO with a fatty acid chloride of Formula G affords compounds of Formula PP.

Scheme 14

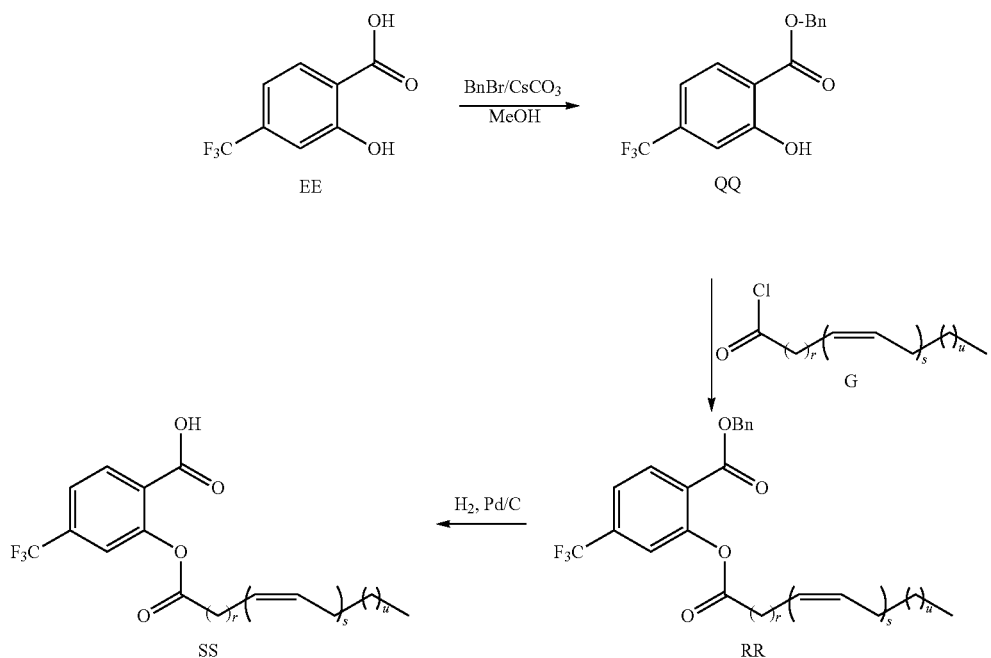

wherein r and s are as defined above for Formula VI, Formula VIa, Formula VIb, Formula VIc, Formula VId, Formula VIe, Formula VIf, Formula VIg, and Formula VII.

Compound EE can be esterified with benzyl bromide in the presence of a base, e.g. $CsCO_3$ yielding compound QQ. Condensation of compound QQ with a fatty acid chloride of Formula G affords compounds of Formula RR. Hydrogenolysis of the benzyl ester of compounds of Formula RR, e.g. using Pd/C and $H_2$, yields compounds of Formula SS.

Methods for Making the Fatty Acid Acetylated Amino Salicylate Derivatives

Examples of synthetic pathways useful for making Fatty Acid Acetylated Amino Salicylate Derivatives of Formula III are set forth in the Examples below and generalized in Schemes 15-18.

Scheme 15

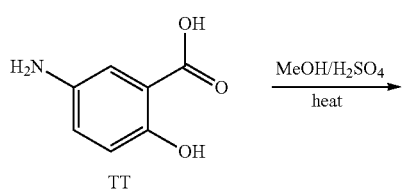

TT $\xrightarrow{MeOH/H_2SO_4}{heat}$

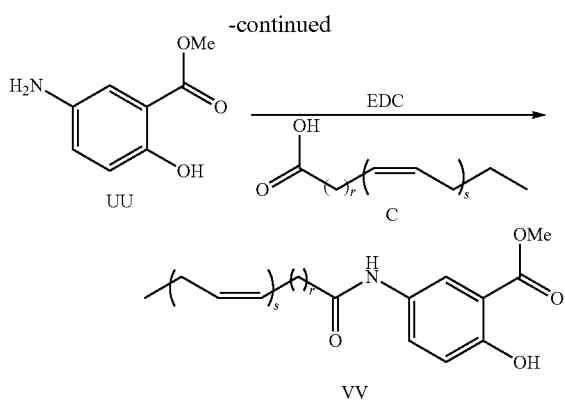

wherein r and s are as defined for Formula III.

Compound TT can be esterified in the presence of acid catalyst and a suitable alcohol, e.g., methanol to give ester UU. Activation of compound UU with a coupling reagent such as for example DCC, CDI, or EDC, optionally with a tertiary amine base and/or catalyst, e.g., DMAP, followed by addition of a fatty acid of Formula C affords compounds of Formula VV. Saponification of the esters of Formula VV with a suitable base, such as for example NaOH, can yield the free acid of compounds of Formula VV. Alternatively, compound TT can be esterified with benzyl bromide in the presence of base, e.g., $CsCO_3$, then subjected to the remaining steps of Scheme 1. Hydrogenolysis of the benzyl ester derived from TT, for example using Pd/C and $H_2$, can yield the free acid of compounds of Formula VV. Diacylated compounds of the invention can be made by subjecting compound TT to the above procedure.

Scheme 16

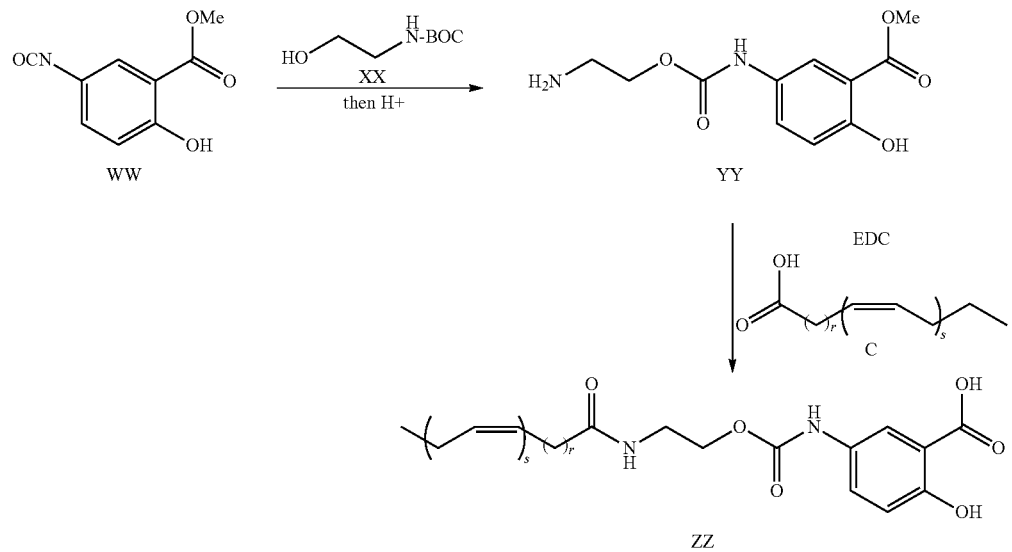

wherein r and s are as defined for Formula III.

Isocyanide WW can be condensed with an amino-masked ethanolamine XX, which after acid workup gives the unmasked aminocarbamate compound YY. Activation of compound YY with a coupling reagent such as for example DCC, CDI, or EDC, optionally with a tertiary amine base and/or catalyst, e.g., DMAP, followed by addition of a fatty acid of Formula C affords compounds of Formula ZZ. The ester may be deprotected using methods disclosed in Greene, et al. *Protecting Groups in Organic Chemistry.* 4th ed. Wiley & Sons, Hoboken, N.J. (2007). See, e.g., Chapter 5, therein.

Scheme 17

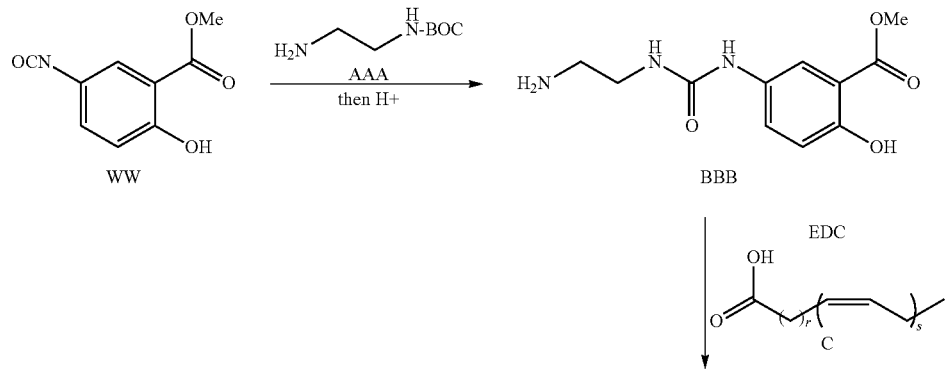

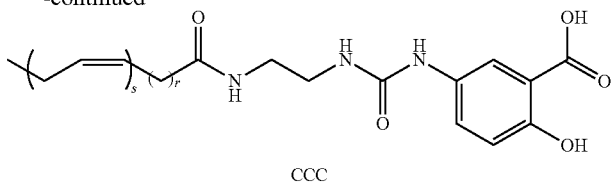

CCC wherein r and s are as defined for Formula III.

Isocyanide WW can be condensed with an mono amino-masked ethylenediamine AAA, which after acid workup gives the unmasked urea compound BBB. Activation of compound BBB with a coupling reagent such as for example DCC, CDI, or EDC, optionally with a tertiary amine base and/or catalyst, e.g., DMAP, followed by addition of a fatty acid of Formula C affords compounds of Formula CCC. The ester may be deprotected using methods disclosed in Greene, et al. *Protecting Groups in Organic Chemistry*. $4^{th}$ ed. Wiley & Sons, Hoboken, N.J. (2007). See, e.g., Chapter 5, therein.

Scheme 18

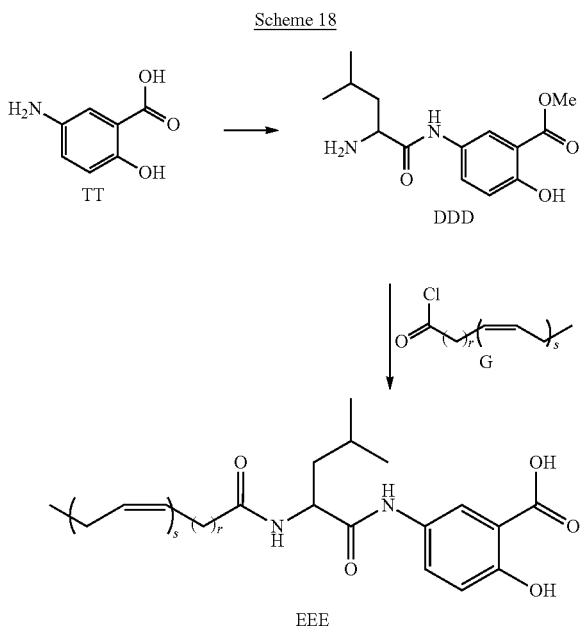

wherein r and s are as defined for Formula III.

Compound TT can be esterified in the presence of acid catalyst and a suitable protecting alcohol such as, e.g., methanol, followed by coupling to an activated amino acid to give compound DDD. Condensation of the amino compound DDD with a fatty acid chloride of Formula G affords compounds of Formula EEE. The ester may be deprotected using methods disclosed in Greene, et al. *Protecting Groups in Organic Chemistry*. $4^{th}$ ed. Wiley & Sons, Hoboken, N.J. (2007). See, e.g., Chapter 5, therein.

7. EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Effect of Illustrative Compounds of the Invention on Inflammatory Activity in Adipose Tissue in Mice Demonstration of the ability of illustrative Compounds of the Invention to mediate serum adiponectin concentrations in a rodent obesity model was shown using methods described in Itoh, M., et al., *Arterioscler. Thromb. Vasc. Biol.* 2007 27(9):1918-25. Male C57BL/6J ob/ob mice and their wild-type (WT) littermates are purchased from Charles River Laboratories (Wilmington, Mass.). The animals are housed in individual cages in a temperature-, humidity-, and light-controlled room (12-hour light and 12-hour dark cycle) and allowed free access to water and fish meal-free diet (fish meal-free F1 (Funabashi Farm, Chiba, Japan) supplemented with; 362 kcal/100 g, 4.4% energy as fat).

Six-week-old male ob/ob mice and WT littermates are allowed unrestricted access to the fish meal-free diet (control group) or fish meal-free diet supplemented with 5% EPA (wt/wt) (EPA-treated group) for 4 weeks (n=10 to 14). In the short-term administration protocol, 8-week-old male ob/ob mice are treated with the Compound of the Invention for 2 weeks (n=7 to 8). All diets are changed every day and served with nonmetallic feeder to prevent oxidization of fatty acids. At the end of the experiments, mice are euthanized after 5-hour starvation under intraperitoneal pentobarbital anesthesia (30 mg/kg). Blood glucose and serum concentrations of triglyceride (TG) and free fatty acid (FFA) are measured as described in Kouyama R, et al., *Endocrinology*, 146: 3481-3489, 2005. Serum fatty acid and salicylate concentrations are measured by gas chromatography.

Example 2

In Vivo Effects of Compounds of the Invention in Zucker Fatty Rats and ob/ob Mice Twelve-week-old male Zucker fa/fa rats and 8-week-old ob/ob (Lepob/ob) and ob/1 mice are given free access to food and water. A Compound of the Invention (120 mg/kg/day) is dosed orally by gavage once per day. For glucose tolerance tests, glucose (2.0 g/kg) is administered by oral gavage (rats) or intraperitoneal injection (mice) after an overnight fast. Blood glucose and serum insulin concentrations are determined during oral glucose tolerance tests in Zucker fa/fa rats or fa/1 rats. For insulin tolerance tests, insulin (2.0 U/kg) is injected intraperitoneally after an overnight fast. Cholesterol, triglyceride, long-chain FFA, and ALT concentrations are measured in sera from fasting Zucker fa/fa rats.

Example 3

Effects of Compounds of the Invention on Insulin Signaling in 3T3-L1 Adipocytes 3T3-L1 adipocytes are serum starved for 16 hours and treated or not treated with 5 mM aspirin for 2 hours and either 6.0 nM mTNFα (20 min) or the phosphatasen inhibitor calyculin A (Axxora, San Diego, USA) (at 2.0 nM for 30 min) as described in Yuan, M., et al., *Science*, 293, 1673-1677, 2001. After a 5-min stimulation with 10 nM insulin, the cells are chilled and solubilized and proteins are immunoprecipated with anti-IR or anti-IRS1. Proteins are separated by SDS-PAGE and identified by Western blotting with anti-pY, anti-IR, or anti-IRS1.

Example 4

Effects of Compounds of the Invention on IL-10 Levels in 3T3-L1 Adipocytes

IL-10 production in 3T3-L1 adipocytes is measured using a modification of the method described by Bradley et al, *Obesity* (2008) 16, 938-944. Fully differentiated 3T3-L1 adipocytes are serum starved for 18 hours in DMEM containing 0.2% fatty acid free bovine serum albumin (BSA) and 0.1 mM pyruvate. A stock of 5 mM test compound is prepared in 100% ethanol and then is diluted 1:100 in 2% fatty acid free BSA in DMEM (with 0.1 mM pyruvate), yielding a 50 µM solution of compound. Starvation media is removed from cells and is replaced by the 50 µM compound solution in DMEM or Vehicle (0.1% ethanol, 0.2% fatty acid free BSA in DMEM with 0.1 mM pyruvate). Test compound or Vehicle is incubated with cells for 48 hours. Subsequently, RNA is purified from cells and reverse transcribed to cDNA. IL-10 message levels are then measured by quantitative real-time PCR (Applied Biosystems Step-One) using gene-specific oligoneucleotide primers and fluorescently labeled probe. IL-10 levels are normalized to the house-keeping gene GAPDH, which was measured using the same method. IL-10 levels in Compound of the Invention treated samples are expressed as a fold increase over IL-10 levels in Vehicle treated samples. ($p<0.005$ by 2-tailed t-test). A sample graph showing the data obtained by using one of the Compounds of the Invention described above in Example 4 is shown in FIG. 1**.

Example 5

Effects of Compounds of the Invention in Fao Hepatoma Cells

Fao cells are serum starved for 16 hours followed by 2-hour incubations at 37° C. with 5 mM-25 mM a Compound of the Invention according to the method described in Yuan, M., et al., *Science*, 293, 1673-1677, 2001. Cells are then stimulated sequentially with 6.0 nM mTNFα for 20 min. and 10 nM insulin for 5 min. Cells are chilled and solubilized and proteins are then immunoprecipitated with anti-IR and detected by Western blotting using anti-pY. Phosphorylation is quantified by densitometry.

Example 6

TNFα Release Assay in RAW 264.7 Macrophages

The purpose of this assay is to measure the ability of small molecules to inhibit the secretion of TNFα in cultured macrophages stimulated with lipopolysaccharide (LPS). Treatment of macrophages with LPS activates inflammatory cytokine pathways primarily through the TLR4-NFκB signaling axis. Compounds of the Invention inhibit the transcriptional activation of NFκB and thus decrease the production and release of TNFα. Dexamethasone, a potent agonist of the glucocorticoid receptor is used a positive control for inhibition of TNFα release.

Day 1: Seed RAW 264.7 macrophages into 96 well culture plates. Remove culture media from RAW 264.7 cell growing in a 75 mm$^2$ tissue culture flask (cells should be at ~70% confluence) and add 10 ml of warmed complete growth media (DMEM+10% FBS+1× pen/step). The cells are scraped into suspension using a sterile plate scraper and homogenized by pipetting up and down with a 10 ml serological pipette. The cell concentration is determined using a clinical hematoctyometer. Cells are then diluted to 150,000 cells per ml into growth media. The diluted cells are then transferred to a sterile reagent reservoir and 100 µl of cell suspension is pipetted into each well of a 96 well culture plate using a multichannel pipette (15,000 cells/well). Plates are then incubated at 37° C. under normal tissue culture growth conditions (37° C., humidified $CO_2$ chamber).

Day 2: The test compound sample plate is prepared. Test compounds are prepared in growth media. Compounds are delivered to media from 1000× stocks in 100% DMSO (e.g. for a 10 µM final concentration of test compound, deliver 2 µl of 10 mM test compound to 2 ml of media). At least 150 µl of 1× compound in media is added to 96 well sample plate. Note: the perimeter wells of the 96 well plate are not used to avoid edge effects. Twelve sample wells are prepared with media plus 0.1% DMSO (these samples will serve as the vehicle controls; LPS-stimulated and non-stimulated. 10 µM dexamethasone is used as a positive control). Culture plates are then returned to the growth incubator for 2 hours. Cells are stimulated afterwards by adding 25 µl of 50 ng/ml LPS is added to every well (except the 6 unstimulated vehicle control wells: final concentration of 10 ng/ml LPS. Plates are returned to growth incubator for 3 hours. Afterwards, 100 µl of media supernatant is removed and transferred to a 96 well v-bottom sample plate. The media supernatant plate is centrifuged for 5 minutes at 1000 rpm in a swing-bucket centrifuge, pelleting any cellular debris that may remain in supernatant. 80 µl of supernatant is removed from sample plate and transferred to a fresh v-bottom 96 well plate. Cell viability is measured using Celltiter-glo kit. By measuring cell viability, a given compound's effects on TNFα secretion can determine whether effects are due to cytotoxicity or to true inhibition of inflammatory signaling. Add 100 µl of Celltiter-glo reagent to each well of the cell culture plate and afterwards measure the luminescence signal (CPS) of the plate using the Victor 5 plate reader (0.3 second read; 60 second plate shaking prior to read). Cell viability of a given compound at a given concentration is computed as follows:

Cell viability=CPS Sample/(Average CPS unstimulated controls)*100

Use 20 µl of media supernatant per well for TNFα ELISA. Follow Invitrogen/Biosource manufacture's protocol for the mouse TNFα ELISA. Chromogen development is typically conducted for 20-30 minutes as described in the manufacturer's protocol. After addition of stop solution, measure OD 450 nm using the Victor 5 plate reader (0.1 second/well scan). Determine the TNFα secretion percent of control. The following formula is used to determine the TNFα secretion percent of control:

$$\frac{100 \times (OD\ 45\ nm\ Sample\ X) - (\text{Average } OD\ 450\ nm\ \text{unstimulated vehicle controls})}{(\text{Average } OD\ 450\ nm\ LPS\ \text{stimulated vehicle controls}) - (\text{Average } OD\ 450\ nm\ \text{unstimulated vehicle controls})}$$

For each test compound, TNFα secretion percent of control can be plotted as a function of compound concentration using a four parameter dose-response curve fit equation (XLFIT Model #205):

$$\text{fit} = (A + ((B-A)/(1 + ((C/x)^D))))$$

$$\text{inv} = (C/((((B-A)/(y-A))-1)^{\wedge}(1/D)))$$

$$\text{res} = (y - \text{fit})$$

For compounds which cause greater than 50% inhibition of TNFα secretion, determine the $IC_{50}$ (concentration of compound which causes 50% inhibition of TNFα secretion). A sample graph showing the data obtained by using one of the Compounds of the Invention in the procedure described above in Example 6 is shown in FIG. 2.

Figure 2:
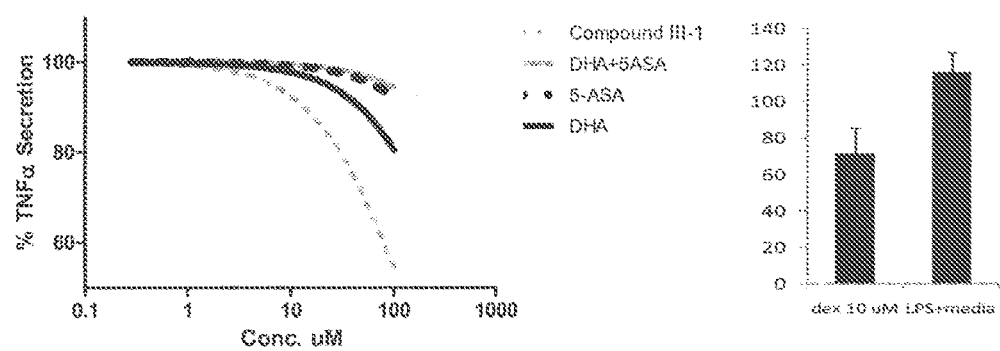
FIG. 2 is a graphic representation of the data showing the effects of a Compound of the Invention on TNFα release.

As seen in FIG. 2, salicylate alone, fatty acid alone, and the simple combination of salicylate and fatty acid administered together do not appreciably inhibit the production of TNFα. In contrast the fatty acid acetylated salicylate significantly inhibits the production of TNFα. This demonstrates that the fatty acid acetylated salicylate is the species responsible for the inhibition of TNFα production and not either of the individual components alone or in simple combination.

A sample table showing the data obtained by using additional Compounds of the Invention in the procedure described above in Example 6 is shown in Table 1, below:

TABLE 1

| Compound Number | TNFα Secretion, $IC_{50}$ μM |
|---|---|
| Ia-1 | 69.2 |
| III-1 | 145.6 |
| Ic-1 | NT |
| 31 | 15.0 |
| 5ASA | >100 |
| 32 | NT |
| DHA | >100 |
| III-6 | 65.3 |
| I-1 | 24.4% Inhibition at 6.2 uM |

Example 7

Figure 3:
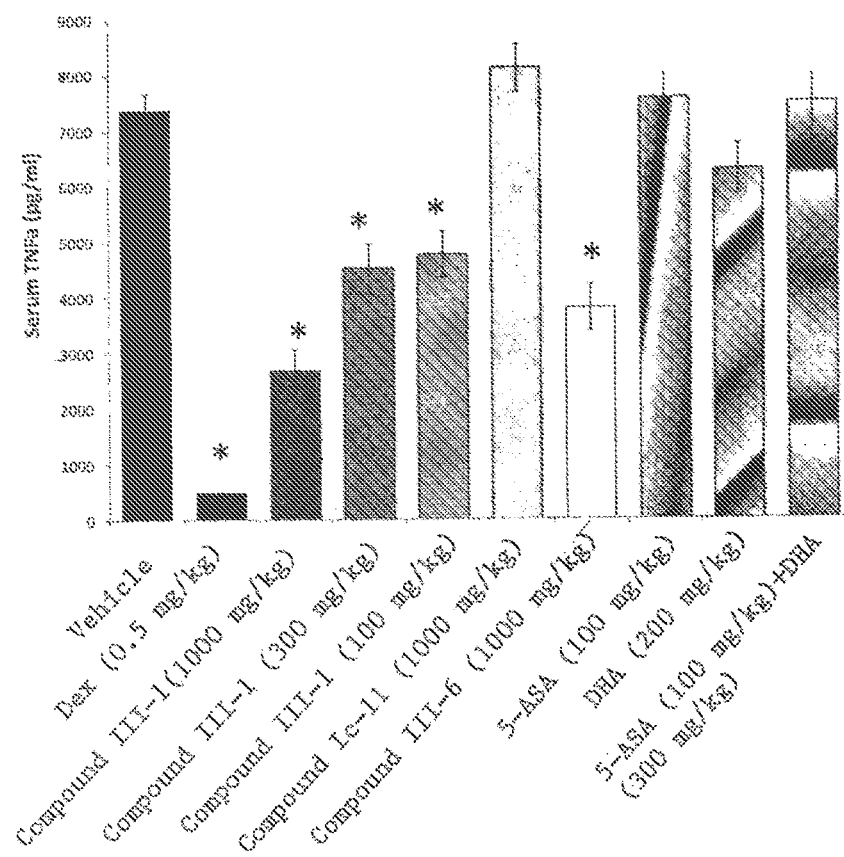
FIG. 3 is graphic representation of the data showing the in vivo effects of Compounds of the Invention in an LPS-challenge TNFα mouse model.

In Vivo Effects of Compounds of the Invention in an LPS-Challenge TNFα Mouse Model To measure the effects of compounds on TNFα secretion in vivo, Male Swiss Webster mice (n=10 animals per group) are dosed by oral gavage with each test compound. All compounds are formulated in an aqueous solution of 0.5% carboxymethylcellulose and 0.05% TWEEN-80 (Vehicle). One hour after compound dosing, animals are treated with 0.2 mg/kg LPS (lipopolysaccharide) by intraperitoneal (IP) injection. Ninety minutes after LPS challenge, mice are anesthetized and bled by cardiac puncture into serum separator tubes (with sodium heparin). Bleeds are allowed to clot at room temperature for 2 hours, and tubes are then spun for 20 minutes at 2000×g. Serum is harvested from tubes (100-150 μl per animal) and frozen at −70° C. TNFα serum levels are measured using commercially available TNFα ELISA kits. (*$p<0.05$ using a 2-tailed t-test). A sample graph showing the data obtained by using some of the Compounds of the Invention in the procedure described above in Example 7 is shown in FIG. 3.

Example 8

Effects of Compounds of the Invention on NFκB Levels in RAW 264.7 Macrophages

RAW 264.7 cells transfected with an NFκB-driven luciferase reporter are plated in 96 well plates. Cells are treated with Vehicle (0.1% ethanol) or test compounds for 2 hours. As a positive control for inhibition of NFκB signaling, 6 wells are treated with 10 μM dexamethasone. Cells are then challenged with 200 ng/ml LPS for 3 hours in the presence of test compounds. A subset of wells treated with vehicle should remain unstimulated with LPS to determine the floor signal of the assay. NFκB driven luciferase activity is developed by addition of BriteLite luciferase kit (Perkin-Elmer) and measured using a Victor V plate reader. NFκB activity (luciferase activity) for each treatment was normalized to Vehicle wells treated with LPS (% NFκB Response). AlamarBlue was used to monitor cell viability to ensure that inhibition of luciferase signal was not a result of compound cytotoxicity.

A sample table showing the data obtained by using additional Compounds of the Invention in the procedure described above in Example 8 is shown in Table 2, below:

TABLE 2

| Compound Number | NF-κB Inhibitory Activity, $IC_{50}$ μM |
|---|---|
| Ia-1 | − |
| III-1 | ++++ |
| 3 | +++ |
| Ic-1 | − |
| 31 | ++++ |
| 32 | − |
| III-6 | ++ |
| I-1 | ++++ |
| 9 | +++ |
| 10 | ++ |
| 11 | +++ |
| 12 | +++ |
| 13 | ++++ |
| 14 | ++++ |
| 15 | +++ |
| 16 | − |
| 17 | ++ |
| 18 | − |
| 19 | − |
| 20 | − |
| 21 | − |
| 22 | +++ |
| 23 | − |
| 24 | ++ |
| 5-ASA | − |
| DHA | − |
| DHA + SA | − |
| SA | − |

A − indicates that the compound showed no inhibitory activity. A + indicates that the compound showed inhibitory activity. A greater number of +'s indicates a higher level of inhibitory activity.

Compounds

The following non-limiting compound examples serve to illustrate further embodiments of the Compounds of the Invention. It is to be further understood that any embodiments listed in the Examples section are embodiments of the Compounds of the Invention and, as such, are suitable for use in the methods and compositions described above.

Example 9

Preparation of 2-((4Z,7Z,10Z,13Z,16Z,19Z)-docosa-4,7,10,13,16,19-hexaenoyloxy)benzoic acid (Ia-1)

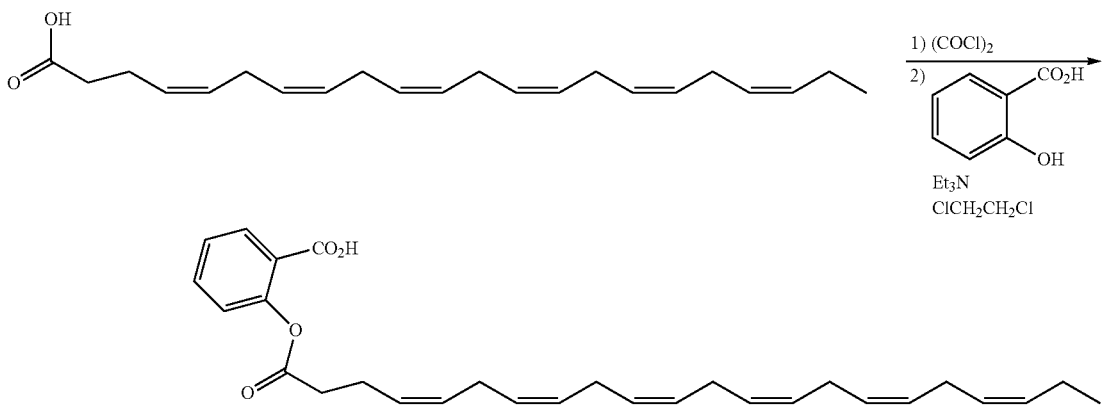

To a mixture of DHA (6.0 g, 18.3 mmol) in dichloroethane (30 mL) and DMF (0.05 mL) was slowly added oxalyl chloride (5.0 mL, 56.9 mmol). The reaction mixture was stirred (RT, 2 h) and concentrated under reduced pressure to obtain DHA-Cl as a yellow liquid. To a mixture of salicylic acid (3.78 g, 27.4 mmol) and $NEt_3$ (3.80 mL, 27.5 mmol) in dichloroethane (35 mL) at 0° C. was slowly added the DHA-Cl in dichloroethane (35 mL). The reaction mixture was stirred (RT, 16 h), washed with 1N HCl and brine, dried over $MgSO_4$, filtered and concentrated under reduced pressure. The crude material was purified by silica chromatography (PE-EtOAc, 19:1) to afford 2-(docosa-4,7,10,13,16,19-hexaenoyloxy)benzoic acid (5.83 g, 71%) as a light yellow oil. Mass calculated for $C_{29}H_{36}O_4$=448.59. found: $[M-H]^+$=447.7.

Example 10

Preparation of 5-(4Z,7Z,10Z,13Z,16Z,19Z)-docosa-4,7,10,13,16,19-hexaenamido-2-hydroxybenzoic acid (III-1)

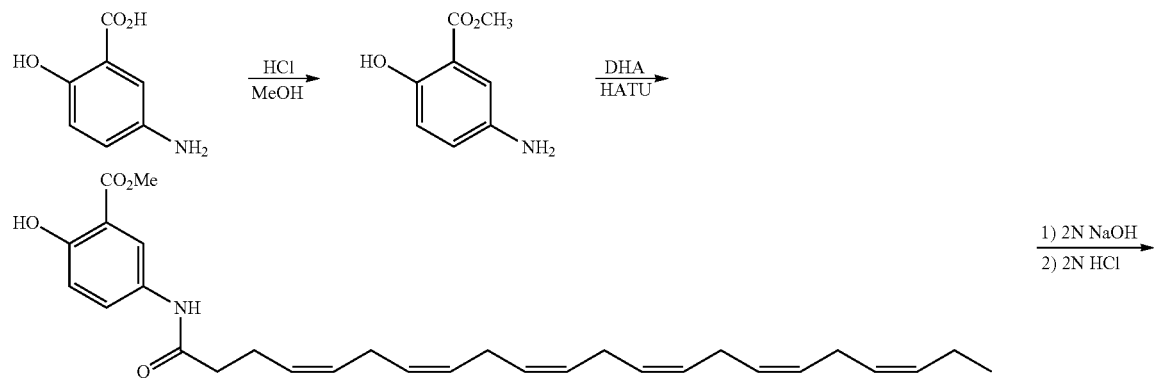

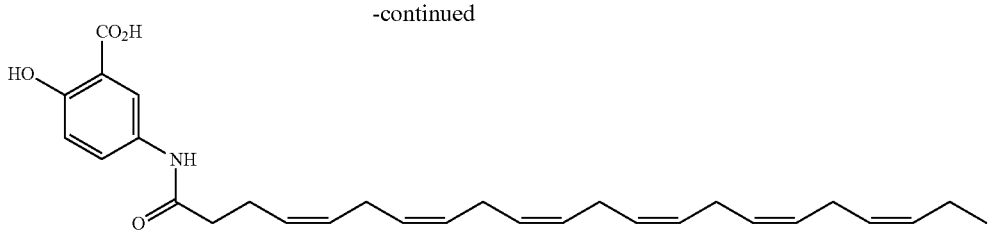

To a solution of saturated HCl in CH$_3$OH (20 mL) at RT was slowly added 5-amino-2-hydroxybenzoic acid (2 g, 13.06 mmol). The resulting mixture was stirred at (RT, 16 h) and then heated (reflux, 24 h). The mixture was cooled and the solvent was removed under reduced pressure. The residue was diluted with EtOAc (50 mL) and washed with saturated aqueous NaHCO$_3$. The organic solution was dried over MgSO$_4$, filtered, concentrated under reduced pressure to afford methyl 5-amino-2-hydroxybenzoate as a pale yellow solid (1.72 g, 78.5%). Mass calculated for C$_8$H$_9$NO$_3$=167.16. found: [M+H]$^+$=168.2.

To a mixture of methyl 5-amino-2-hydroxybenzoate (52.9 mg, 0.317 mmol), DHA (100 mg, 0.305 mmol) and Et$_3$N (61.7 mg, 0.61 mmol) in CH$_3$CN (2 mL) was added HATU (120 mg, 0.260 mmol). The mixture was stirred (RT, 4.5 h). The solvent was removed under reduced pressure and the residue was extracted with EtOAc (4×20 mL). The combined organic layer was washed with 1N aq. HCl, water, 5% NaHCO$_3$, water, and dried over MgSO$_4$. The solvent was removed under reduced pressure. The crude product was purified by silica chromatography (EtOAc:PE, 1:10 to 2:3) to afford methyl 5-docosa-4,7,10,13,16,19-hexaenamido-2-hydroxybenzoate (3) as a light yellow oil (104.5 mg, 72.1%). Mass calculated for C$_{30}$H$_{39}$NO$_4$=477.63. found: [M+H]$^+$=478.5.

A mixture of methyl 5-docosa-4,7,10,13,16,19-hexaenamido-2-hydroxybenzoate (0.1 g, 0.2 mmol) in 2N NaOH (5 mL) and CH$_3$OH (2.5 mL) was stirred (50° C., 24 h). The mixture was cooled and acidified to pH 1 with 2N aq. HCl, then extracted with EtOAc (3×10 mL). The organic layer was washed with brine, dried over MgSO$_4$, filtered and concentrated under reduced pressure. The residue was purified by silica chromatography (CH$_2$Cl$_2$-EtOAc, 20:1 to 1:1) to afford 5-docosa-4,7,10,13,16,19-hexaenamido-2-hydroxybenzoic acid as a white solid (90.4 mg, yield: 90%). Mass calculated for C$_{29}$H$_{37}$NO$_4$=463.61. found: [M+H]$^+$=464.3.

Example 11

Preparation of 3-(4Z,7Z,10Z,13Z,16Z,19Z)-docosa-4,7,10,13,16,19-hexaenamidopropyl 2-acetoxybenzoate (Ic-1)

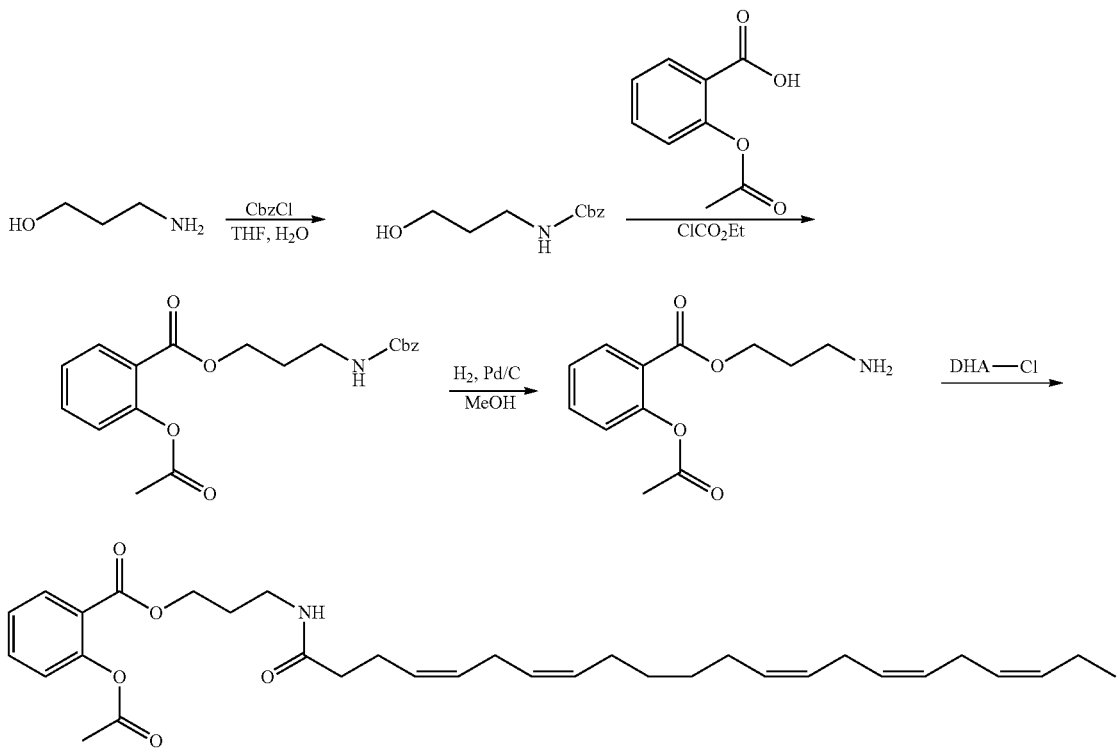

To a mixture of 3-aminopropan-1-ol (5.0 g, 67 mmol), Na$_2$CO$_3$ (8.8 g, 83 mmol) in THF (40 mL) and H$_2$O (130 mL) at 0° C. was added Cbz-Cl (14.8 g, 87 mmol). The reaction mixture was stirred (RT, 1 h). Water (500 mL) and CH$_2$Cl$_2$ (500 mL) were added, and the layers were separated. The organic layer was dried over MgSO$_4$ and concentrated under reduced pressure. The residue was purified by silica chromatography (PE:EA, 5:1) to afford benzyl 3-hydroxypropylcarbamate as a white solid (12.6 g, 90.5%).

To a solution of 2-acetoxybenzoic acid (2.0 g, 11.1 mmol) and triethylamine (1.8 mL, 11.1 mmol) in CH$_2$Cl$_2$ (40 mL) at 0° C. was slowly added ClCO$_2$Et (1.1 mL, 167 mmol). The reaction mixture was stirred (0° C., 2 h) and filtered. The filtrate was added to a solution of benzyl 3-hydroxypropylcarbamate (2.1 g, 10.0 mmol) and triethylamine (15 mL) in CH$_2$Cl$_2$ (40 mL). The reaction mixture was stirred (RT, 4 h) and quenched with H$_2$O (50 mL). The organic layer was washed with 1 M HCl, saturated Na$_2$CO$_3$ (30 mL) and H$_2$O (50 mL). The organic solution was dried over MgSO$_4$ and concentrated under reduced pressure. The residue was purified by silica chromatography, (PE-EtOAc, 5:1) to afford 3-(benzyloxycarbonylamino)propyl 2-acetoxybenzoate (2.0 g, 54%) as a colorless oil. Mass calculated for C$_{20}$H$_{21}$NO$_6{_4}$=371.38. found: [M+H]$^+$=372.3.

A mixture of 3-(benzyloxycarbonylamino)propyl 2-acetoxybenzoate (2.0 g, 5.4 mmol), 10% Pd/C (0.2 g) and CH$_3$OH (50 mL) was stirred under a H$_2$ atmosphere (RT, 16 h). The mixture was filtered and concentrated under reduced pressure to afford a colorless oil. Purification by silica chromatography afforded 3-aminopropyl 2-acetoxybenzoate as a colorless oil. Mass calculated for C$_{12}$H$_{15}$NO$_4$=237.25. found: [M+H]$^+$=238.3.

To a solution of DHA (500 mg, 1.52 mmol) in ClCH$_2$CH$_2$Cl (10 mL) and one drop of DMF at 0° C. was slowly added oxalyl chloride (0.3 mL, 3.42 mmol). The reaction mixture was stirred (RT, 2 h) and concentrated under reduced pressure. The residue was treated with toluene (5 mL) and the solvent was removed under reduced pressure to obtain the DHA acid chloride as a yellow liquid. To a solution of 3-aminopropyl 2-acetoxybenzoate (360 mg, 1.52 mmol) and NEt$_3$ (0.36 g, 3.56 mmol) in ClCH$_2$CH$_2$Cl (10 mL) at 0° C. was added a solution of DHA-acid chloride in ClCH$_2$CH$_2$Cl. The reaction mixture was stirred (0° C., 2 h, then warmed to RT, 12 h). Purification by silica chromatography afforded 3-docosa-4,7,10,13,16,19-hexaenamidopropyl 2-acetoxybenzoate. Mass calculated for C$_{34}$H$_{45}$NO$_5$=547.72. found: [M+H]$^+$=548.3.

Example 12

Preparation of N-(2-(4Z,7Z,10Z,13Z,16Z,19Z)-docosa-4,7,10,13,16,19-hexaenamidoethyl)-2-hydroxybenzamide (31)

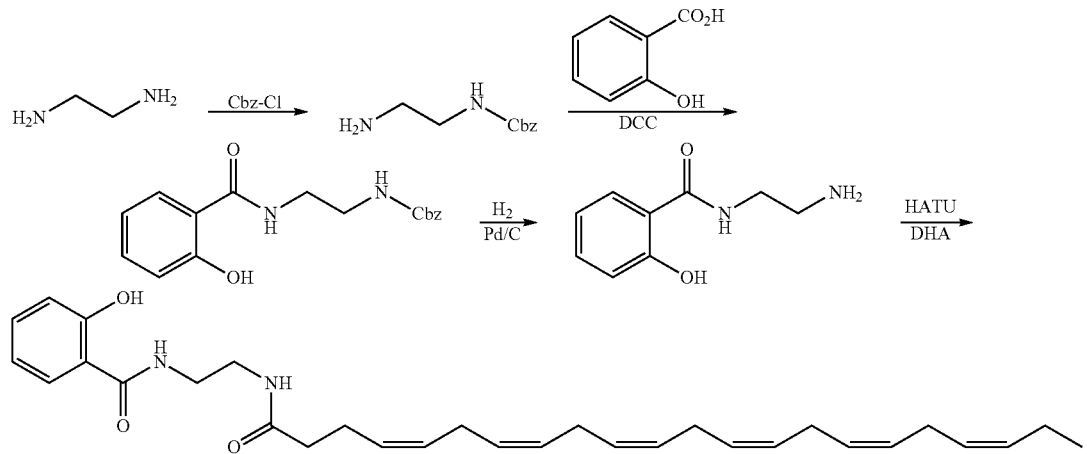

Ethylenediamine (1.0 g, 16.7 mmol) is dissolved in water (3.0 mL) containing bromoaresal green as an indicator. Methane sulfonic acid (2.8 g, 31 mmol) in water (3.0 ml) was added until a blue to pale yellow color transition is just achieved. The solution was diluted with ethanol (8.0 mL) and vigorously stirred. To the mixture was added the solution of Cbz-Cl (2.8 g, 16.7 mmol) in dimethoxyethane (4 mL) and 50% w/v aqueous AcOK (10 mL) at 20° C. simultaneously to maintain the pale yellow-green color of the indicator. After the additions are complete the mixture was stirred (RT, 1 h) and concentrated at low temperature under vacuum to removed the volatiles. The residue was shaken with water (20 mL) and filtered. The filtrate was then washed with toluene (3×50 mL), basified with excess 40% aqueous NaOH and extracted with toluene (3×50 mL). The organic layer was washed with brine (50 mL), dried over Na$_2$SO$_4$ and evaporated to give benzyl 2-aminoethylcarbamate as an oil (1.65 g, 51%). Mass calculated for C$_{10}$H$_{14}$N$_2$O$_2$=194.23. found: [M–H]$^+$=193.3.

To a mixture of benzyl 2-aminoethylcarbamate (1.65 g, 8.5 mmol), imidazole (0.58 g, 8.5 mmol), salicylic acid (1.73 g, 8.5 mmol) in ethyl acetate (30 mL) was added a solution of DCC (1.75 g, 8.5 mmol) in ethyl acetate (50 mL). The mixture was stirred (RT, 16 h) and filtered. The solution was concentrated under reduced pressure and the crude product was purified by silica chromatography (EtOAc:PE, 0-50%) to afford benzyl 2-(2-hydroxybenzamido)ethylcarbamate as a white solid (1.84 g, 66%). Mass calculated for $C_{17}H_{18}N_2O_4$=314.34. found: $[M+H]^+$=315.2.

A mixture of benzyl 2-(2-hydroxybenzamido)ethylcarbamate (1.84 g, 5.86 mmol) and Pd/C (0.18 g) in MeOH (30 mL) was stirred under a $H_2$ atmosphere (16 h). The mixture was filtered and concentrated under reduced pressure. The crude product was purified by silica chromatography (EtOAc-MeOH—$NH_3OH$ (5:1:0.01) to afford N-2-(aminoethyl)-2-hydroxybenzamide as a white powder (0.68 g, 65%). Mass calculated for $C_9H_{12}N_2O_2$=180.20; found: $[M+H]^+$=181.2.

To a mixture of N-2-(aminoethyl)-2-hydroxybenzamide (58 mg, 0.32 mmol), DHA (100 mg, 0.3 mmol) and $Et_3N$ (0.1 ml, 0.7 mmol) in $CH_3CN$ (2 mL) was added HATU (115 mg, 0.3 mmol). The mixture was stirred (RT, 24 h) and concentrated under reduced pressure. The residue was treated with brine (15 mL) and extracted with EtOAc (3×30 mL). The combined organic layers were washed with 1M HCl, brine, 5% $NaHCO_3$ and brine. The organic solution was dried over $MgSO_4$ and concentrated under reduced pressure. The crude product was purified by silica chromatography (EtOAc:PE, 1:1) to afford N-(2-docosa-4,7,10,13,16,19-hexaenamidoethyl)-2-hydroxybenzamide (94 mg, 64%) as light yellow oil. Mass calculated for $C_{31}H_{42}N_2O_3$=490.68. found: $[M+H]^+$=491.4.

Example 13

Preparation of (4Z,7Z,10Z,13Z,16Z,19Z)-1-(4-(2-hydroxybenzoyl)piperazin-1-yl)docosa-4,7,10,13,16,19-hexaen-1-one (32)

To a mixture of tert-butylpiperazine-1-carboxylate (0.57 g, 3.05 mmol), DHA (1 g, 3.05 mmol) and $Et_3N$ (0.61 g, 6.1 mmol) in $CH_3CN$ (20 mL) was added HATU (1.16 g, 3.05 mmol). The mixture was stirred (RT, 16 h). The solvent was removed under reduced pressure and the residue was extracted with EtOAc (4×30 mL). The combined organic layers were washed successively with 1N aqueous HCl, water, 5% $NaHCO_3$ and water, and dried over $MgSO_4$. The solvent was removed under reduced pressure and the crude product was purified by silica chromatography (EA-PE, 1:10 to 1:1) to afford tert-butyl 4-docosa-4,7,10,13,16,19-hexaenoylpiperazine-1-carboxylate (1.5 g, 99%) as a colorless oil. Mass calculated for $C_{31}H_{48}N_2O_3$=496.72. found: $[M+H]^+$=497.6.

To a mixture of tert-butyl 4-docosa-4,7,10,13,16,19-hexaenoylpiperazine-1-carboxylate (1.5 g, 3 mmol) in $CH_2Cl_2$ (20 mL) at 0° C. was added $CF_3CO_2H$ (7 mL, 91 mmol). The mixture solution was stirred (0° C., 2 h) and then 10% $Na_2CO_3$ was added to adjust pH=10. The mixture was extracted with $CH_2Cl_2$ (3×30 mL). The combined organic layers were dried over $MgSO_4$, filtered and concentrated under reduced pressure. The crude product was purified by silica chromatography ($CH_2Cl_2$:$CH_3OH$, 20:1) to afford 1-(piperazin-1-yl)docosa-4,7,10,13,16,19-hexaen-1-one (1.17 g, 97.5%) as a colorless oil. Mass calculated for $C_{26}H_{40}N_2O$=396.61. found: $[M+H]^+$=396.7, 398.2.

To a mixture of 1-(piperazin-1-yl)docosa-4,7,10,13,16,19-hexaen-1-one (1.17 g, 2.95 mmol), salicylic acid (0.61 g, 4.43 mmol) and $Et_3N$ (0.89 g, 8.85 mmol) in $CH_3CN$ (10 mL) was added HATU (1.68 g, 4.43 mmol). The mixture was stirred (RT, 16 h). The solvent was removed under reduced pressure and the residue was extracted with EtOAc (4×50 mL). The combined organic layers were washed successively with 1N aqueous HCl, water, 5% $NaHCO_3$ and water, and dried over $MgSO_4$. The solvent was removed under reduced pressure. Purification of the crude product by prep-HPLC afforded 1-(4-(2-hydroxybenzoyl)piperazin-1-yl)docosa-4,7,10,13,16,19-hexaen-1-one (300 mg, 19.6%) as a light yellow oil. Mass calculated for $C_{33}H_{44}N_2O_3$=516.71. found: $[M+H]^+$ 517.6.

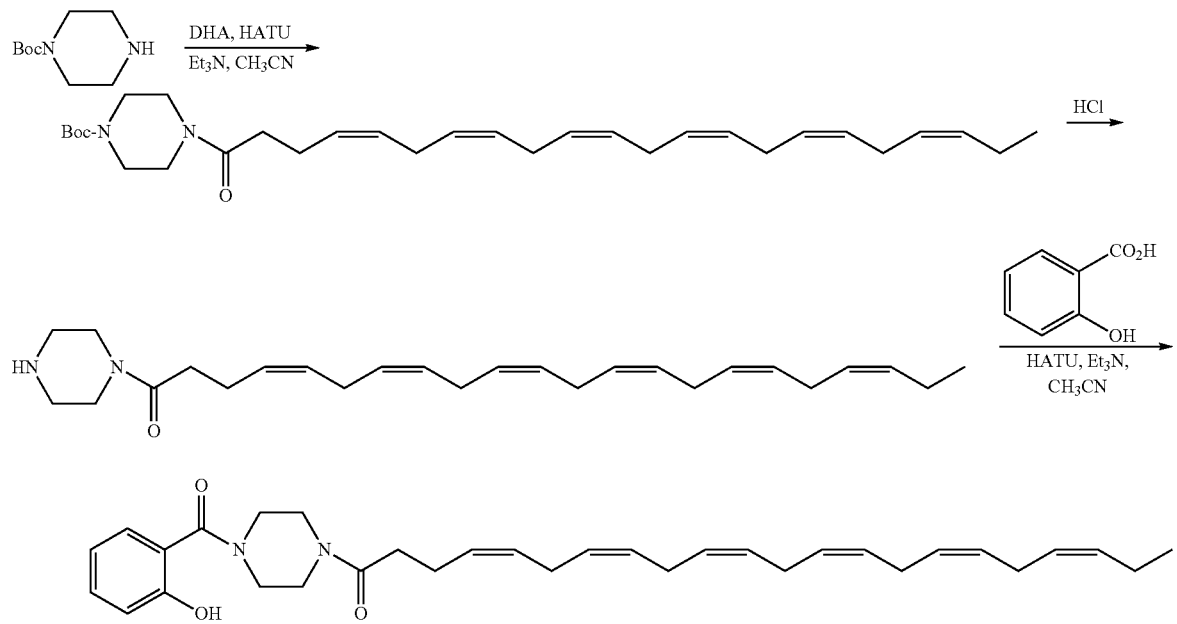

Example 14

Preparation of 5-(2-(4Z,7Z,10Z,13Z,16Z,19Z)-docosa-4,7,10,13,16,19-hexaenamido-4-methylpentanamido)-2-hydroxybenzoic acid (III-6)

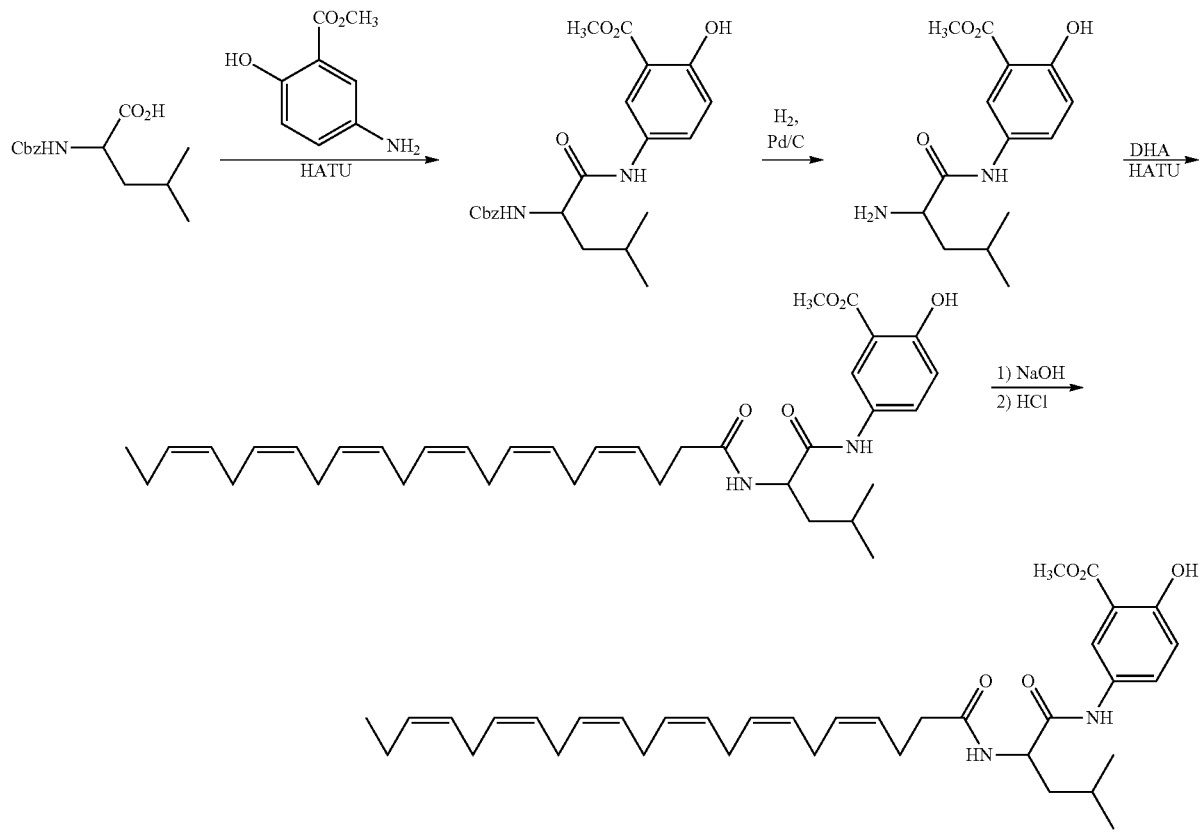

A mixture of 2-(benzyloxycarbonylamino)-4-methylpentanoic acid (1 g, 3.8 mmol), methyl 5-amino-2-hydroxybenzoate (0.66 g, 3.95 mmol) and Et$_3$N (0.76 g, 7.6 mmol) were dissolved in CH$_3$CN (10 mL) and HATU (1.503 g, 3.95 mmol) was added. The mixture was stirred (RT, 16 h). The solvent was removed under reduced pressure. Brine (50 mL) was added to the resulting residue, and the mixture was extracted with EtOAc (3×50 mL). The combined organic layers were washed successively with 2N aq. HCl (3×50 mL), brine (50 mL), 5% NaHCO$_3$ (50 mL×3), brine (50 mL), dried over MgSO$_4$, filtered, and concentrated under reduced pressure. The crude material was purified by silica chromatography on (CH$_2$Cl$_2$) to give methyl 5-(2-(benzyloxycarbonylamino)-4-methylpentanamido)-2-hydroxybenzoate as a white solid (0.81 g, 51.8%).

The mixture of 5-(2-(benzyloxycarbonylamino)-4-methylpentanamido)-2-hydroxybenzoate (0.81 g, 1.9 mmol) and 0.1 g Pd/C in MeOH (15 mL) was stirred under H$_2$ (RT, 16 h). The mixture was filtered and the filtrate was concentrated under reduced pressure. The crude product was purified by silica chromatography (MeOH/DCM, 0 to 5%)) to afford methyl 5-(2-amino-4-methylpentanamido)-2-hydrozybenzoate as a white solid (0.53 g, 90%). Mass calculated for C$_{14}$H$_{20}$N$_2$O$_4$=280.32. found: [M+H]$^+$=281.2.

To a solution of methyl 5-(2-amino-4-methylpentanamido)-2-hydrozybenzoate (85 mg, 0.30 mmol), DHA (100 mg, 0.30 mmol), Et$_3$N (0.1 ml 0.71 mmol) in CH$_3$CN (2 mL) was added HATU (114 mg, 0.30 mmol). The mixture was stirred (RT, 16 h) and the solvent was removed under reduced pressure. The residue was diluted with brine (20 mL) and extracted with ethyl acetate (50 mL). The combined organic layer was washed with 1M HCl (20 mL), brine (20 mL), 5% aq. NaHCO$_3$ (20 mL) and brine (20 mL), dried over MgSO$_4$, and concentrated under reduced pressure. The crude product was purified by silica chromatography (EtOAc/DCM, 0 to 10%) to afford methyl 5-(2-docosa-4,7,10,13,16,19-hexaenamido-4-methylpentanamido)-2-hydroxybenzoate as light yellow oil. (155 mg, 87%). Mass calculated for C$_{36}$H$_{50}$N$_2$O$_5$=590.79; found: [M+H]$^+$=591.6.

To a solution of methyl 5-(2-docosa-4,7,10,13,16,19-hexaenamido-4-methylpentanamido)-2-hydroxybenzoate (155 mg, 0.26 mmol) in MeOH (3 mL) was added 2M NaOH (5 mL). The mixture was heated (45-50° C., 16 h), and then cooled to RT. 2M HCl was added dropwise to adjust pH=1. The mixture was then extracted by EA (3×20 mL). The combined organic layers were washed with brine, dried over MgSO$_4$ and concentrated under reduced pressure. The crude product was purified by silica chromatography (MeOH/DCM, 0-10%) to afford of 5-(2-docosa-4,7,10,13,16,19-hexaenamido-4-methylpentanamido)-2-hydroxybenzoic acid as light yellow oil (92 mg, 61%). Mass calculated for C$_{35}$H$_{48}$N$_2$O$_5$=576.77. found: [M+H]$^+$=577.3.

Example 15

Preparation of ethyl 2-(2-(4Z,7Z,10Z,13Z,16Z,19Z)-docosa-4,7,10,13,16,19-hexaenamido-4-methylpentanoyloxy)benzoate (I-1)

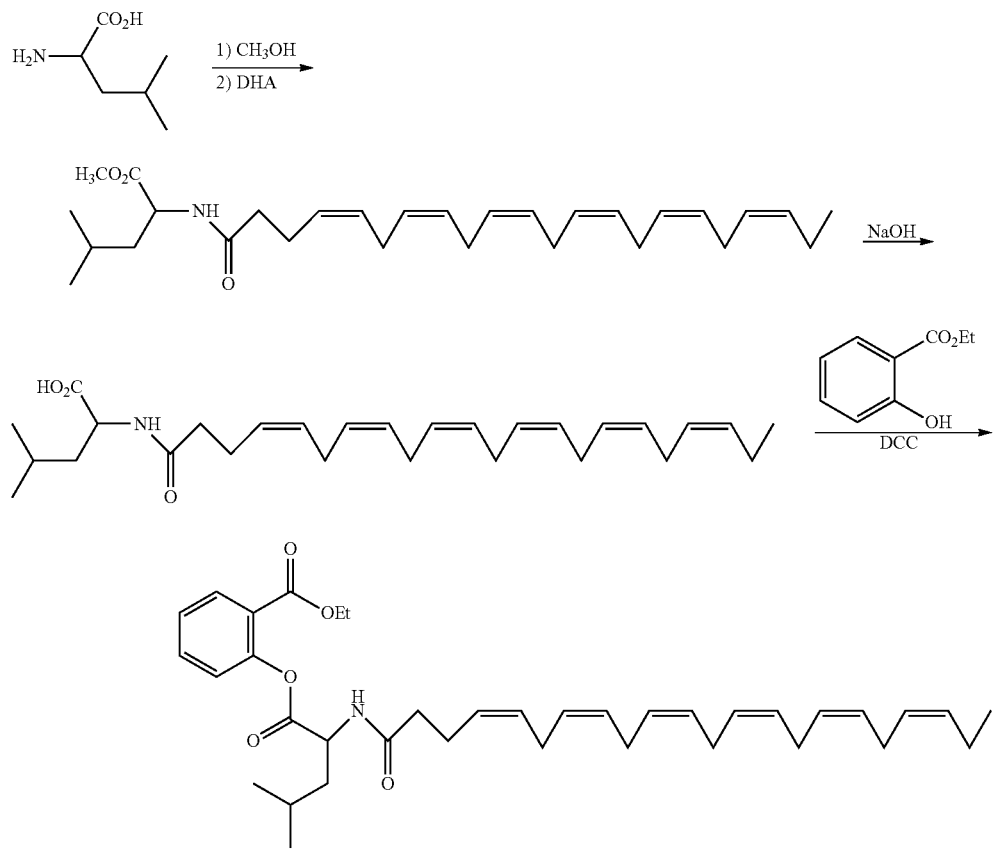

2-Amino-4-methylpentanoic acid (5.0 g 38.2 mmol) was slowly added to sat. HCl/MeOH (50 mL). The mixture was stirred (RT, 5 h) then heated to reflux (16 h). After the reaction, the solvent was removed under reduced pressure. The residue was diluted with water (50 mL), then NaHCO$_3$ was added to adjust pH=7. The mixture was then extracted with DCM (3×50 mL), the combined organic layers were dried over MgSO$_4$, concentrated under reduced pressure to afford methyl 2-amino-4-methylpentanoate as a colorless liquid (5.3 g, 96%). Mass calculated for C$_7$H$_{15}$NO$_2$=145.20. found: [M+H]$^+$=145.9. The product was used in next step without further purification.

To a solution of methyl 2-amino-4-methylpentanoate (250 mg, 1.6 mmol), DHA (510 mg, 1.5 mmol), Et$_3$N (0.42 mL, 3 mmol) in CH$_3$CN (20 mL) at RT was added HATU (570 mg, 1.5 mmol). The mixture was stirred (RT, 16 h) and the solvent was removed under reduced pressure. The residue was diluted with brine and extracted with EtOAc. The organic layer was washed with 1M HCl (50 mL), brine (50 mL), 5% NaHCO$_3$ (50 mL) and brine (50 mL). The organic solution was dried over MgSO$_4$ and concentrated under reduced pressure. The crude product was purified by silica chromatography (EtOAc:PE, 0-25%) to afford methyl 2-docosa-4,7,10,13,16,19-hexaenamido-4-methylpentanoate (0.61 g, 85%) as a light yellow oil. Mass calculated for C$_{29}$H$_{45}$NO$_3$=455.67. found: [M+H]$^+$=456.2.

To a solution of methyl 2-docosa-4,7,10,13,16,19-hexaenamido-4-methylpentanoate (610 mg, 1.34 mmol) in MeOH (15 mL) was added 2 M NaOH (30 mL). The reaction mixture was heated (50° C., 16 h), cooled (RT), and acidified with 2 M HCl to pH=1. The mixture was extracted with EtOAc (3×50 mL). The combined organic layers were washed with brine, dried over MgSO$_4$, and concentrated under reduced pressure. The crude product was purified by silica chromatography, (MeOH:DCM, 0-10%) to afford 2-docosa-4,7,10,13,16,19-hexaenamido-4-methylpentanoic acid (0.51 g, 89%) as a light yellow solid. Mass calculated for C$_{28}$H$_{43}$NO$_3$=441.65. found: [M+H]$^+$=442.1.

To a solution of 2-docosa-4,7,10,13,16,19-hexaenamido-4-methylpentanoic acid (50 mg, 0.11 mmol) and ethyl 2-hydroxybenzoate (19 mg, 0.11 mmol) in CH$_3$CN/THF (1:1, 0.5 mL) at −10° C. was added DCC (12 mg, 0.11 mmol) and DMAP (1 mg). The mixture was stirred (RT, 16 h), filtered and concentrated under reduced pressure. The crude product was purified by silica chromatography (EtOAc-PE, 0-20%) to afford ethyl 2-(2-docosa-4,7,10,13,16,19-hexaenamido-4-methylpentanoyloxy)benzoate (40 mg, 67%) as colorless oil. Mass calculated for C$_{37}$H$_{51}$NO$_5$=589.80. found: [M+H]$^+$=590.4.

Example 16

Preparation of 1-((4Z,7Z,10Z,13Z,16Z,19Z)-docosa-4,7,10,13,16,19-hexaenoyloxy)ethyl 2-acetoxybenzoate (9)

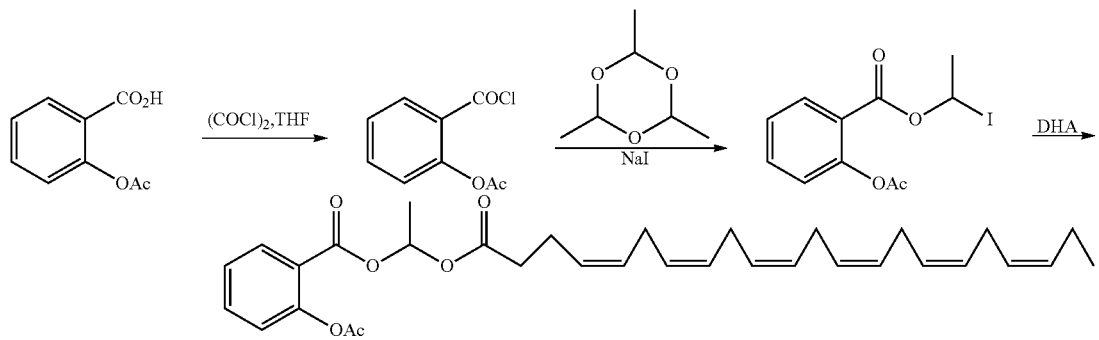

To a solution of compound 2-acetoxybenzoic acid (1.0 g, 5.5 mmol) in THF (30 mL) was added (COCl)$_2$ (0.8 ml, 9.1 mmol) at 0° C. The mixture was heated (reflux, 1.5 h) and concentrated under reduced pressure to afford 2-(chlorocarbonyl)phenyl acetate.

To a mixture of 2,4,6-trimethyl-1,3,5-trioxane (245 mg, 1.85 mmol) and NaI (0.972 g, 6.48 mmol) in DCM (15 mL) was added a solution of 2-(chlorocarbonyl)phenyl acetate in DCM (5 mL, 0° C.). The resulting mixture was allowed to stir (RT, 16 h). The mixture was filtrated and concentrated under reduced pressure. The crude was purified by silica chromatography (EtOAc-PE, 0-10%) to afford 1-iodoethyl 2-acetoxybenzoate (0.75 g, 40%) as a light yellow oil.

To a solution of DHA (0.1 g, 0.3 mmol) in CH$_3$CN (1 mL) was added K$_2$CO$_3$ (41.4 mg, 0.3 mmol) followed by Bu$_4$NBr (96.6 mg, 0.3 mmol). The mixture was stirred (RT, 0.5 h) and cooled to 0° C. To it was added 1-iodoethyl 2-acetoxybenzoate (0.1 g, 0.3 mmol) and the mixture was stirred (RT, 16 h). The mixture was filtered, washed with brine and concentrated under reduced pressure. The crude was purified by silica chromatography (PE:EtOAc, 20:1-15:1) to afford 1-(docosa-4,7,10,13,16,19-hexaenoyloxy)ethyl 2-acetoxybenzoate (85.3 mg, 53.3%) as a light yellow oil. Mass calculated for C$_{33}$H$_{42}$O$_6$=534.68. found: [M+Na]$^+$=557.2.

Example 17

Preparation of 2-hydroxy-5-(9Z,12Z,15Z)-octadeca-9,12,15-trienamidobenzoic acid (III-7)

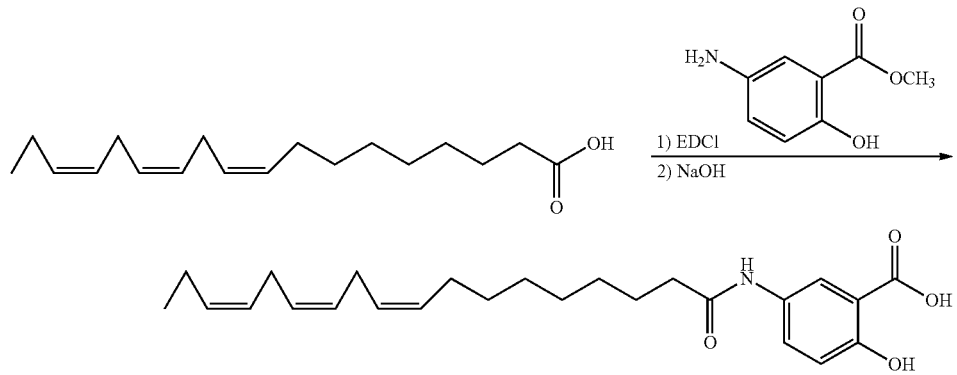

To a solution of (9Z,12Z,15Z)-octadeca-9,12,15-trienoic acid (1.66 g, 5.98 mmol) and methyl 5-amino-2-hydroxybenzoate (1 g, 5.98 mmol) in methylene chloride (100 mL) was added 1-ethyl-3-(3-dimethylaminopropyl)carbodiimide hydrochloride (1.16 g, 6.0 mmol) and dimethylaminopyridine (100 mg). The mixture was stirred under $N_2$ (14 h) and then diluted with methylene chloride (100 mL) and washed successively with 3N HCl, sat sodium bicarbonate solution and sat sodium chloride solution. The organic layer was dried over anhydrous magnesium sulfate, filtered and concentrated to give the corresponding amide, 2.0 grams.

To the amide was added 2N NaOH (100 mL) and methanol (100 mL) and the resulting slurry was heated to 40° C. and after 12 hours an additional 500 mg NaOH was added and the reaction stirred at 40° C. (12 hours). The reaction mixture was cooled to room temperature, acidified with 3 N HCl and extracted with ethyl acetate (300 mL). The organic phase was washed successively with water and sat sodium chloride, dried over anhydrous magnesium sulfate, filtered and was concentrated to give the product 2-hydroxy-5-(9Z,12Z,15Z)-octadeca-9,12,15-trienamidobenzoic acid (1.5 grams, 61%). Mass calculated for $C_{25}H_{35}NO_4$=413.55. found: $[M-H]^+$=412.3.

Example 18

Preparation of N-(2-(4Z,7Z,10Z,13Z,16Z,19Z)-docosa-4,7,10,13,16,19-hexaenamidoethyl)-2-hydroxy-N-methylbenzamide (11)

To a solution of tert-butyl 2-aminoethylcarbamate (3.7 g, 22.3 mmol), benzaldehyde (2.36 g, 22.3 mmol) and $MgSO_4$ (1.33 g) in 1,2-dichoroethane (300 mL) and $Et_3N$ (30.1 mL, 22.3 mmol) at RT was added $NaHB(AcO)_3$. The mixture was stirred (RT, 16 h) and filtered. The solution was washed with saturated $NaHCO_3$ (200 ml), dried over $MgSO_4$ and concentrated under reduced pressure. The crude product was purified by chromatography on silica gel, eluting with MeOH-DCM (0-10%) to afford tert-butyl 2-(benzylamino)ethylcarbamate (1.4 g, 23%). Mass calculated for $C_{14}H_{22}N_2O_2$=250.34. found: $[M+H]^+$=251.3.

To a mixture of tert-butyl 2-(benzylamino)ethylcarbamate (2.8 g, 11.2 mmol) and 37% aqueous $CH_2O$ (1.0 mL, 11.2 mmol) in 1,2-dichloroethane (35 mL) at RT was added $NaHB(AcO)_3$ (3.7 g, 11.2 mmol). The mixture was stirred (RT, 16 h), diluted with saturated aqueous $NaHCO_3$ (400 ml) and extracted with EA (3×300 ml). The organic layer was dried over $MgSO_4$ and concentrated under reduced pressure to afford tert-butyl 2-(benzyl(methyl)amino)ethylcarbamate (1.38 g, 46.8%). $^1$HNMR ($CDCl_3$): δ7.25 (m, 5H, CH), 3.5 (s, 2H, $CH_2$), 3.3 (m, 2H, $CH_2$), 2.48 (m, 2H, $CH_2$), 2.2 (s, 3H, $CH_3$), 1.4 (s, 9H, $CH_3$).

A mixture of tert-butyl 2-(benzyl(methyl)amino)ethylcarbamate (1.20 g, 4.54 mmol), 10% Pd/C (0.90 g) and MeOH (60 ml) was stirred under a $H_2$ atmosphere (0.8 MPa, RT, 16 h). The mixture was filtered and concentrated under reduced pressure. The crude material was purified by column chromatography on silica gel, eluting with saturated $NH_3$ in MeOH-DCM (0-10%) to afford tert-butyl 2-(methylamino)ethylcarbamate as a colorless oil (0.54 g, 68.3%). $^1$HNMR ($CDCl_3$): δ3.25 (m, 2H, $CH_2$), 2.7 (m, 2H, $CH_2$), 2.49 (s, 3H, $CH_3$), 1.49 (s, 9H, $CH_3$).

To a mixture of tert-butyl 2-(methylamino)ethylcarbamate (0.348 g, 2 mmol), 2-hydroxybenzoyl chloride (0.276 g, 2

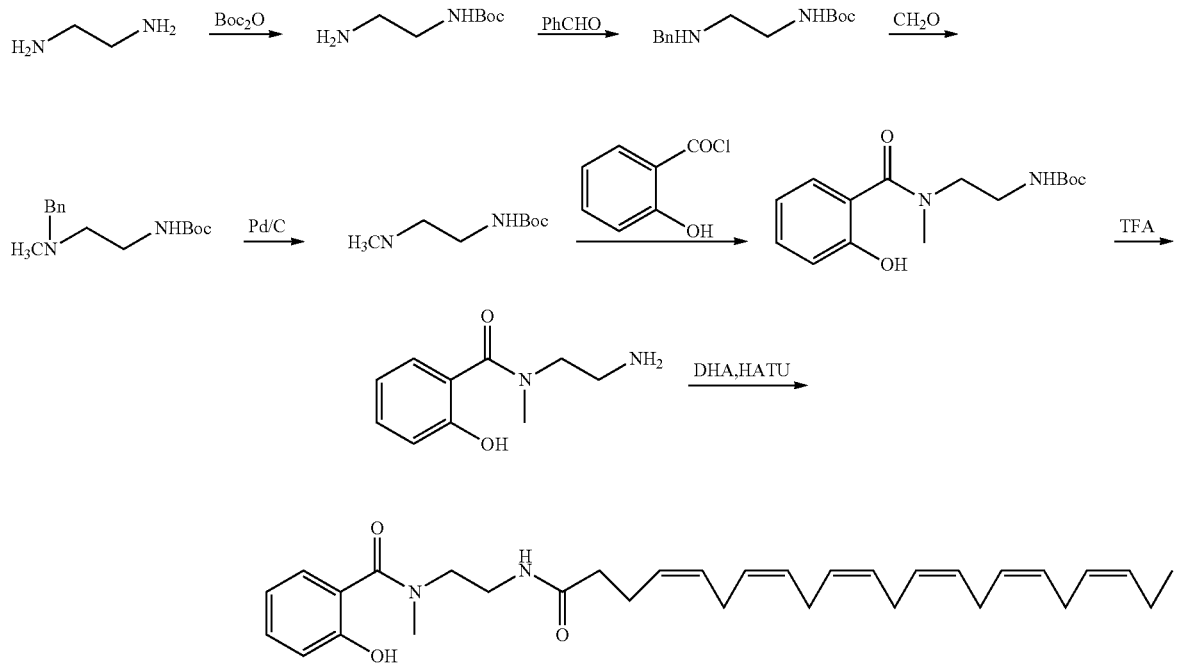

To a solution of ethylenediamine (20 mL, 0.28 mol) in $CHCl_3$ (300 mL) at 0° C. was slowly added a solution of $Boc_2O$ (6.2 g, 0.028 mol) in $CHCl_3$ (150 mL). The mixture was allowed to warm to room temperature. After 16 h, the solution was filtered and washed with brine (6×100 ml) and water (100 ml). The organic solution was dried over $MgSO_4$, filtered and concentrated under reduced pressure to afford tert-butyl 2-aminoethylcarbamate (3.7 g, 78%) as a colorless oil.

mmol) and imidazole (0.136 g, 2 mmol) in ethyl acetate (8 mL) at 0° C. was slowly added a solution of DCC (0.412 g, 2 mmol) in ethyl acetate (2 mL). The mixture was stirred (RT, 16 h), filtered and concentrated under reduced pressure. The crude material was purified by chromatography on silica gel, eluting with ethyl acetate/petroleum ether (20-50%) to afford tert-butyl 2-(2-hydroxy-N-methylbenzamido)ethylcarbamate (0.2 g, 34%) as a colorless oil. $^1$HNMR (CDCl$_3$): δ7.5 (m, 2H, CH), 7.0 (d, 1H, CH), 6.8 (d, 1H, CH), 3.7 (m, 2H, CH$_2$), 3.48 (m, 2H, CH$_2$), 3.2 (m, 3H, CH$_3$), 1.5 (s, 9H, CH$_3$).

To a solution of tert-butyl 2-(2-hydroxy-N-methylbenzamido)ethylcarbamate (0.2 g, 0.68 mmol) in CH$_2$Cl$_2$ (5 mL) at 0° C. was added trifluoroacetic acid (1.8 mL, 23.4 mmol). The mixture was stirred (0° C., 16 h), concentrated under reduced pressure and neutralized with saturated NH$_3$ in CH$_3$OH. The mixture was concentrated under reduced pressure to afford N-(2-aminoethyl)-2-hydroxy-N-methylbenzamide as a colorless oil (0.5 g). This compound was used in the next step without further purification. Mass calculated for C$_{10}$H$_{14}$N$_2$O$_2$=194.23. found: [M+H]$^+$=195.1.

To a mixture of the crude N-(2-aminoethyl)-2-hydroxy-N-methylbenzamide, DHA (100 mg, 0.3 mmol) and Et$_3$N (92.3 mg, 0.9 mmol) in CH$_3$CN (2 mL) at RT was added HATU (115.8 mg, 0.3 mmol). The mixture was stirred (RT, 16 h) and concentrated under reduced pressure. The residue was diluted with 50 mL ethyl acetate, washed with brine, 1N HCl, saturated NaHCO$_3$ and brine. The organic layer was dried over MgSO$_4$, filtered and concentrated under reduced pressure. The residue was purified by chromatography on silica gel, eluting with CH$_2$Cl$_2$-EA (1:1) to afford N-(2-(4Z,7Z,10Z, 13Z,16Z,19Z)-docosa-4,7,10,13,16,19-hexaenamidoethyl)-2-hydroxy-N-methylbenzamide (40 mg, 26%) as a light yellow oil. Mass calculated for C$_{32}$H$_{44}$N$_2$O$_3$=504.70. found: [M+H]$^+$=505.5.

Example 19

Preparation of 2-hydroxy-N-(2-((4Z,7Z,10Z,13Z, 16Z,19Z)—N-methyldocosa-4,7,10,13,16,19-hexaenamido)ethyl)benzamide (12)

To a solution of tert-butyl 2-(methylamino)ethylcarbamate (0.82 g, 4.7 mmol), prepared as previously described, DHA (1.55 g, 4.7 mmol) and Et$_3$N (1.32 mL, 9.4 mmol) in CH$_3$CN (40 mL) was added HATU (1.79 g, 4.7 mmol). The mixture was stirred (RT, 16 h) and concentrated under reduced pressure. The residue was diluted with brine (150 mL) and extracted with ethyl acetate (2×150 mL). The combined organic layers were washed with saturated NaHCO$_3$ (150 mL) and brine (150 mL), dried over MgSO$_4$, and concentrated under reduced pressure. The crude product was purified by chromatography on silica gel, eluting with EA-PE (0-50%) to afford tert-butyl 2-((4Z,7Z,10Z,13Z,16Z,19Z)—N-methyldocosa-4,7,10,13,16,19-hexaenamido)ethylcarbamate (1.71 g, 77%) as a light yellow oil. Mass calculated for C$_{30}$H$_{48}$N$_2$O$_3$=484.71. found: [M+H]$^+$=485.6.

To a solution of tert-butyl 2-((4Z,7Z,10Z,13Z,16Z,19Z)—N-methyldocosa-4,7,10,13,16,19-hexaenamido)ethylcarbamate (1.71 g, 3.5 mmol)) in dichloromethane (50 mL) at 0° C. was slowly added TFA (17 mL). The mixture was stirred (0° C., 2 h) basified to pH 10 with saturated aqueous Na$_2$CO$_3$ and extracted with EA (3×150 mL). The combined organic layers were dried over MgSO$_4$ and concentrated under reduced pressure to afford (4Z,7Z,10Z,13Z,16Z,19Z)—N-(2-aminoethyl)-N-methyldocosa-4,7,10,13,16,19-hexaenamide (1.31 g, 97%) as a light yellow oil.

To a solution of (4Z,7Z,10Z,13Z,16Z,19Z)—N-(2-aminoethyl)-N-methyldocosa-4,7,10,13,16,19-hexaenamide (104 mg, 0.27 mmol), 2-hydroxybenzoyl chloride (37 mg, 0.27 mmol) and imidazole (19 mg, 0.27 mmol) in EA (4 mL) at 0° C. was added dropwise a solution of DCC (0.57 g, 0.27 mmol) in EA (4 mL). The mixture was stirred (RT, 16 h), filtered and concentrated under reduced pressure. The crude material was purified by chromatography on silica gel, eluting with EA-PE (1:3) to afford 2-hydroxy-N-(2-((4Z,7Z,10Z,13Z,16Z, 19Z)—N-methyldocosa-4,7,10,13,16,19-hexaenamido) ethyl)benzamide (100 mg, 73%) as a colorless oil. Mass calculated for C$_{32}$H$_{44}$N$_2$O$_3$=504.70. found: [M+H]$^+$=505.5.

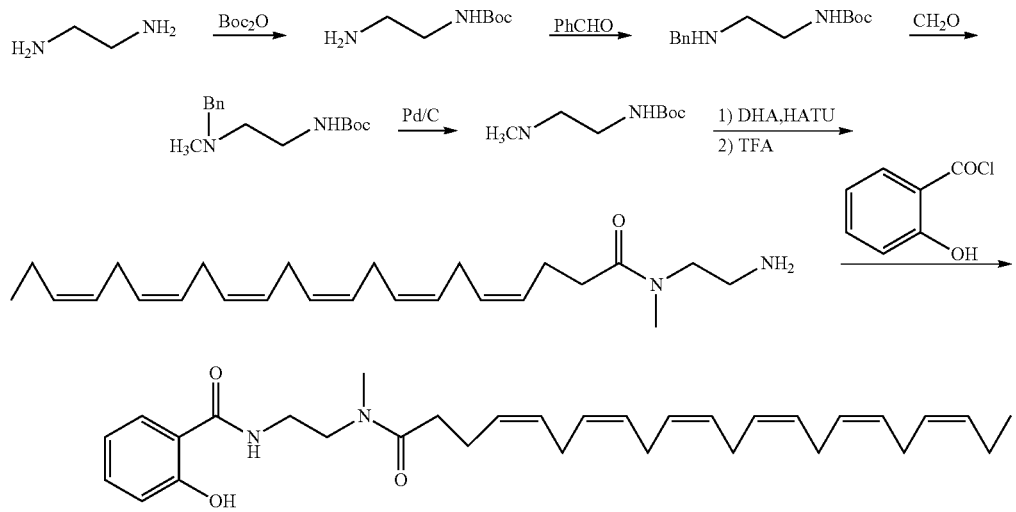

Example 20

Preparation of N-(1-(4Z,7Z,10Z,13Z,16Z,19Z)-docosa-4,7,10,13,16,19-hexaenamidopropan-2-yl)-2-hydroxybenzamide (13)

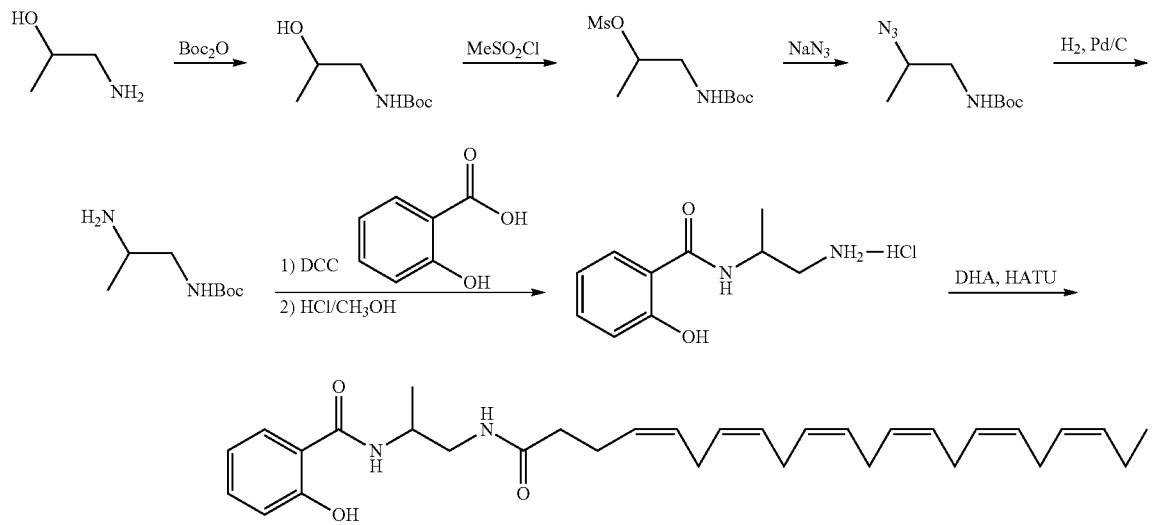

To a solution of 1-aminopropan-2-ol (7.5 g, 0.1 mol) in THF-H$_2$O (1:1, 150 mL) at RT was slowly added a solution of Boc$_2$O (21.8 g, 0.1 mol) in THF (50 mL). The mixture was stirred (RT, 2 h) and concentrated under reduced pressure. The residue was extracted with EA (2×100 mL) and the combined organic layers were washed with citric acid (0.5 M, 2×50 mL) and brine (100 mL). The organic solution was dried over MgSO$_4$, filtered and concentrated under reduced pressure to afford tert-butyl 2-hydroxypropylcarbamate (15.3 g, 87.4%) as a colorless oil. Mass calculated for C$_8$H$_{17}$NO$_3$=175.23. found: [M+H]$^+$=176.3.

To a solution of tert-butyl 2-hydroxypropylcarbamate (14.3 g, 81.7 mmol) and Et$_3$N (35.6 ml, 245.1 mmol) in CH$_2$Cl$_2$ (250 mL) at 0° C. was slowly added a solution of methanesulfonyl chloride (9.5 mL, 122.6 mmol) in CH$_2$Cl$_2$ (250 mL). The mixture was stirred at 0° C. for 2 h, diluted with CH$_2$Cl$_2$ (300 mL) and washed with water, 1 N HCl, 5% NaHCO$_3$ and brine. The organic layer was dried over MgSO$_4$ and concentrated under reduced pressure to afford 1-(tert-butoxycarbonylamino)propan-2-ylmethanesulfonate (19.5 g, 94%) as a light yellow oil. Mass calculated for C$_9$H$_{19}$NO$_5$S=253.32. found: [M+H]$^+$=254.2.

To a solution of 1-(tert-butoxycarbonylamino)propan-2-ylmethanesulfonate (10.0 g, 39.5 mmol) in DMF (100 mL) at RT was added NaN$_3$ (7.7 g, 118.5 mmol). The reaction mixture was stirred at 85° C. for 24 h, cooled to RT, diluted with cold water (300 mL) and extracted with diethyl ether (3×300 mL). The combined organic layers were washed with saturated NaHCO$_3$ (2×200 mL) and brine (200 mL), dried over MgSO$_4$, filtered and concentrated under reduced pressure to afford tert-butyl 2-azidopropylcarbamate (7.0 g, 88.6%) as a light yellow oil. $^1$HNMR (CDCl$_3$): δ3.6 (m, 1H, CH), 3.25 (m, 1H, CH$_2$), 2.9 (m, 1H, CH$_2$), 1.49 (s, 9H, CH$_3$), 1.2 (d, 3H, CH$_3$).

A mixture of afford tert-butyl 2-azidopropylcarbamate (7.0 g, 3.6 mmol) and Pd/C (0.7 g) in MeOH (250 mL) was stirred under an H$_2$ (1 atm) atmosphere (RT, 16 h). The mixture was filtered and concentrated under reduced pressure. The crude product was purified by chromatography on silica gel, eluting with saturated NH$_3$ in MeOH-DCM (0-10%) to afford tert-butyl 2-aminopropylcarbamate (5.1 g, 83.7%) as a light yellow oil. $^1$HNMR (CDCl$_3$): δ4.9 (bs, 1H, NH), 3.15 (m, 1H, CH), 3.0 (m, 1H, CH$_2$), 2.8 (m, 1H, CH$_2$), 1.7 (bs, 2H, NH$_2$), 1.5 (s, 9H, CH$_3$), 1.0 (d, 3H, CH$_3$).

To a solution of tert-butyl 2-aminopropylcarbamate (3.6 g, 20.6 mmol), 2-hydroxybenzoic acid (2.79 g, 20.6 mmol) and imidazole (1.41 g, 20.6 mmol) in EtOAc (100 mL) at 0° C. was slowly added a solution of DCC (4.26 g, 20.6 mmol) in EtOAc (50 mL). The reaction mixture was stirred (RT, 16 h), filtered and concentrated under reduced pressure. The crude product was purified by silica chromatography, EtOAc/Petroleum ether (0-20%) to afford tert-butyl 2-(2-hydroxybenzamido)propylcarbamate (2.4 g, 40%) as a white solid.

A mixture of tert-butyl 2-(2-hydroxybenzamido)propylcarbamate (2.4 g, 8.16 mmol) in saturated HCl-MeOH (50 mL) was stirred (RT, 2 h) and concentrated under reduced pressure to afford N-(1-aminopropan-2-yl)-2-hydroxybenzamide (1.8 g, 96%) as a white solid. Mass calculated for C$_{10}$H$_{14}$N$_2$O$_2$=194.23. found: [M+H]$^+$=195.2.

To a solution of N-(1-aminopropan-2-yl)-2-hydroxybenzamide (1.7 g, 7.3 mmol), DHA (2.0 g, 6.1 mmol) and Et$_3$N (3.1 mL, 21.9 mmol) in CH$_3$CN (50 mL) at 0° C. was added HATU (2.77 g, 7.3 mmol). The mixture was allowed to warm to RT, stirred for 16 h and concentrated under reduced pressure. The residue was diluted with brine (150 mL) and extracted with EA (2×200 mL). The combined organic layers were washed with 1 N HCl (2×150 mL), saturated NaHCO$_3$ (2×150 mL) and brine (150 mL), dried over MgSO$_4$, filtered and concentrated under reduced pressure. The residue was purified by chromatography on silica gel, eluting with EA-PE (0-25%) to afford the crude product, which was further purified by Prep-HPLC to afford N-(1-(4Z,7Z,10Z,13Z,16Z,19Z)-docosa-4,7,10,13,16,19-hexaenamidopropan-2-yl)-2-hydroxybenzamide (1.31 g, 42.6%) as a light yellow oil. Mass calculated for C$_{32}$H$_{44}$N$_2$O$_3$=504.70. found: [M+H]$^+$=505.5.

Example 21

Preparation of N-(2-(4Z,7Z,10Z,13Z,16Z,19Z)-docosa-4,7,10,13,16,19-hexaenamidopropyl)-2-hydroxybenzamide (14)

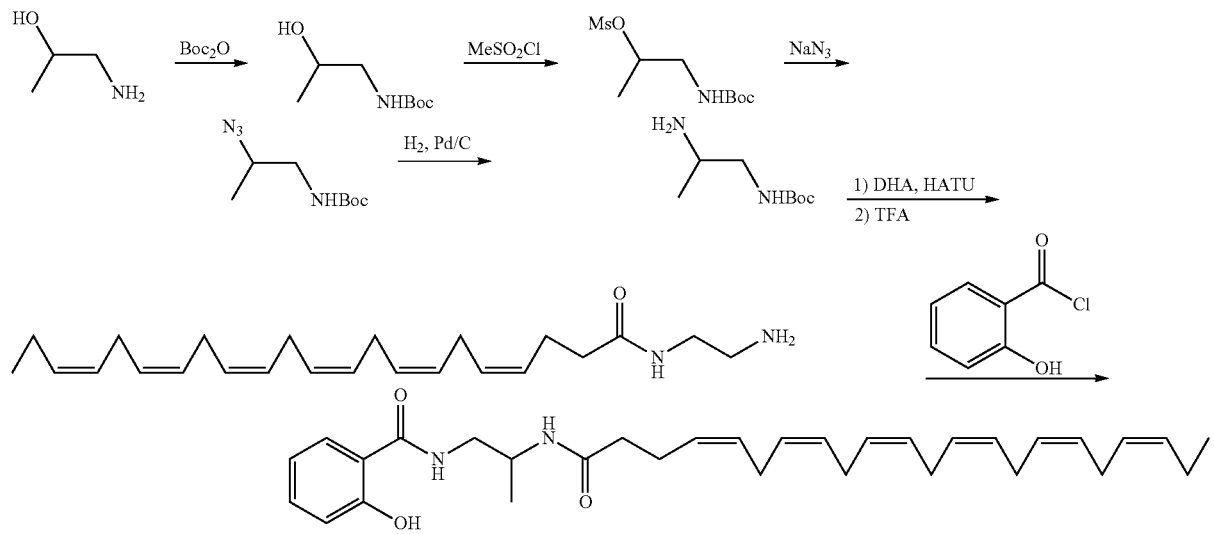

To a solution of tert-butyl 2-aminopropylcarbamate (1.06 g, 6.09 mmol, prepared as previously described), DHA (2.0 g, 6.09 mmol) and Et$_3$N (1.7 mL, 12.8 mmol) in CH$_3$CN (40 mL) at 0° C. was added HATU (2.31 g, 6.09 mmol). The mixture was stirred (RT, 16 h) and concentrated under reduced pressure. The residue was diluted with brine (100 mL) and extracted with EA (2×100 mL). The combined organic layers were washed with saturated NaHCO$_3$ (100 mL) and brine (100 mL), dried over MgSO$_4$, filtered and concentrated under reduced pressure. The crude product was purified by chromatography on silica gel, eluting with EA-PE (0-25%) to afford tert-butyl 2-(4Z,7Z,10Z,13Z,16Z,19Z)-docosa-4,7,10,13,16,19-hexaenamidopropylcarbamate (2.1 g, 70%) as a light yellow oil. Mass calculated for C$_{30}$H$_{48}$N$_2$O$_3$=484.71. found: [M+H]$^+$=485.6.

To a solution of tert-butyl 2-(4Z,7Z,10Z,13Z,16Z,19Z)-docosa-4,7,10,13,16,19-hexaenamidopropylcarbamate (2.10 g, 4.34 mmol) in DCM (100 mL) at 0° C. was slowly added TFA (30 mL). The mixture was stirred (0° C., 2 h), warmed to RT and stirred (16 h). The mixture was basified to pH=10 with saturated aqueous Na$_2$CO$_3$ and extracted with EA (2×200 mL). The combined organic layers were dried over MgSO$_4$, filtered and concentrated under reduced pressure to afford (4Z,7Z,10Z,13Z,16Z,19Z)—N-(1-aminopropan-2-yl) docosa-4,7,10,13,16,19-hexaenamide (1.60 g, 98%) as a light yellow oil. Mass calculated for C$_{25}$H$_{40}$N$_2$O=384.6. found: [M+H]$^+$=385.2.

To a solution of (4Z,7Z,10Z,13Z,16Z,19Z)—N-(1-aminopropan-2-yl)docosa-4,7,10,13,16,19-hexaenamide (1.60 g, 4.2 mmol), 2-hydroxybenzoic acid (0.57 g, 4.2 mmol) and imidazole (0.29 g, 4.2 mmol) in EA (40 mL) at 0° C. was added a solution of DCC (0.87 g, 4.2 mmol) in EA (40 mL). The mixture was allowed to warm to RT, stirred (16 h) and filtered. The solvent was removed under reduced pressure and the crude product was purified by chromatography on silica gel, eluting with EA-PE (0-50%) to afford N-(2-(4Z,7Z,10Z,13Z,16Z,19Z)-docosa-4,7,10,13,16,19-hexaenamidopropyl)-2-hydroxybenzamide (1.07 g, 50.5%) as a light yellow oil. Mass calculated for C$_{32}$H$_{44}$N$_2$O$_3$=504.70. found: [M+H]$^+$=505.5.

Example 22

Preparation of N-(3-(4Z,7Z,10Z,13Z,16Z,19Z)-docosa-4,7,10,13,16,19-hexaenamidobutan-2-yl)-2-hydroxybenzamide (15)

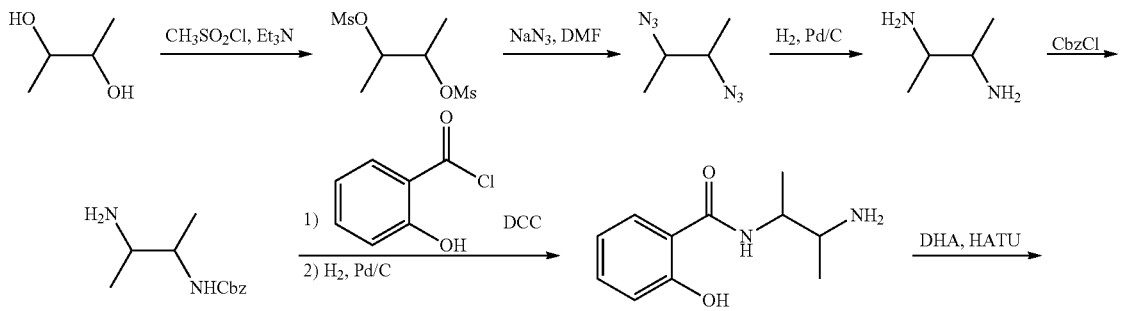

-continued

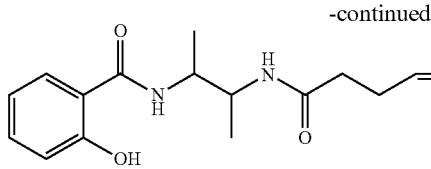

To a solution of butane 2,3-diol (15 g, 0.166 mol) and Et₃N (57.7 mL, 0.415 mol) in CH₂Cl₂ (150 mL) at 0° C. was slowly added a solution of CH₃SO₂Cl (32.1 mL, 0.415 mol) in CH₂Cl₂ (75 mL). The mixture was stirred at 0° C. for 2 h and diluted with CH₂Cl₂. The mixture was washed with water, 1 N HCl, 5% aqueous NaHCO₃ and brine. The organic layer was dried over MgSO₄, filtered and concentrated under reduced pressure to afford butane-2,3-diyl dimethanesulfonate (40 g, 98%) as a light yellow oil. ¹HNMR (CDCl₃): δ4.9 (m, 2H, CH), 3.05 (s, 6H, CH₃), 1.4 (m, 6H, CH₃).

To a solution of butane-2,3-diyl dimethanesulfonate (15.0 g, 63.7 mmol) in DMF (150 mL) at RT was added NaN₃ (19.6 g, 301.5 mmol). The reaction mixture was stirred at 85° C. for 24 h, cooled to RT, diluted with cold water (100 mL) and extracted with diethyl ether (4×100 mL). The combined organic layers were washed with saturated NaHCO₃ (2×100 mL) and brine (100 mL), dried over MgSO₄, filtered and concentrated under reduced pressure. The crude product was purified by flash chromatography on silica gel, eluting with PE:EA (5:1) to afford 2,3-diazidobutane (6.10 g, 68%) as a colorless oil.

A mixture of 2,3-diazidobutane (9.0 g, 64.3 mmol) and 10% Pd/C (0.90 g) in MeOH (300 mL) was stirred under a H₂ atmosphere (RT, 16 h). The mixture was filtered and concentrated under reduced pressure. The crude product was purified by column chromatography on silica gel, eluting with saturated NH₃ in MeOH-DCM (0-20%) to afford butane-2,3-diamine (4.8 g, 85%) as a yellow oil. ¹HNMR (CDCl₃): δ2.8 (m, 1H, CH), 2.6 (m, 1H, CH), 1.65 (s, 4H, NH₂), 1.0 (d, 6H, CH₃).

To a mixture of butane-2,3-diamine (4.8 g, 54.5 mmol) in water (50 mL) containing bromocresol green as indicator was slowly added a solution of methane sulfonic acid (10.46 g) in water (50 mL) until a blue to yellow color transition was observed. The mixture was diluted with ethanol (100 mL) and to it was added a solution of Cbz-Cl (7.61 g, 45.5 mmol) in DME (50 mL) and aqueous AcOK (w/v=50%) to maintain the pale-green color. The reaction mixture was stirred (RT, 1 h), concentrated under reduced pressure, treated with water and filtered. The solution was washed with toluene, basified with 40% aqueous NaOH and extracted with toluene (4×100 mL). The combined organic layers were washed with brine, dried over MgSO₄, filtered and concentrated under reduced pressure to afford benzyl 3-aminobutan-2-ylcarbamate (4.2 g, 35%) as a colorless oil. Mass calculated for C₁₂H₁₈N₂O₂=222.28. found: [M−H]⁺=221.2.

To a mixture of benzyl 3-aminobutan-2-ylcarbamate (5.3 g, 23.8 mmol), 2-hydroxybenzoic acid (3.28 g, 23.8 mmol) and imidazole (1.62 g, 23.8 mmol) in EtOAc (180 mL) at 0° C. was slowly added a solution of DCC (4.90 g, 23.8 mmol) in EtOAc (20 mL). The reaction mixture was stirred (RT, 16 h), filtered and concentrated under reduced pressure. The crude product was purified by column chromatography on silica gel, eluting with PE-EA (5:1) to afford benzyl 3-(2-hydroxybenzamido)butan-2-ylcarbamate (3.2 g, 40%) as a colorless oil. Mass calculated for C₁₉H₂₂N₂O₄=342.39. found: [M+H]⁺=343.2.

A mixture of benzyl 3-(2-hydroxybenzamido)butan-2-ylcarbamate (3.2 g, 9.36 mmol) and 10% Pd/C (0.32 g) in MeOH (120 mL) was stirred under a H₂ (1 atm) atmosphere (RT, 16 h). The mixture was filtered and concentrated under reduced pressure. The crude product was purified by column chromatography on silica gel, eluting with MeOH-DCM (0-20%) to afford N-(3-aminobutan-2-yl)-2-hydroxybenzamide (1.67 g, 86%) as a yellow oil.

To a solution of N-(3-aminobutan-2-yl)-2-hydroxybenzamide (1.52 g, 7.3 mmol), DHA (2 g, 6.0 mmol) and Et₃N (1.21 g, 12.0 mmol) in CH₃CN (50 mL) at 0° C. was added HATU (2.37 g, 6.24 mmol). The mixture was stirred (RT, 16 h) and concentrated under reduced pressure. The residue was diluted with brine (50 mL) and extracted with EA (3×50 mL). The combined organic layers were washed with 1 N HCl (2×50 mL), saturated NaHCO₃ (2×50 mL) and brine (50 mL), dried over MgSO₄, and concentrated under reduced pressure. The crude product was purified by chromatography on silica gel, eluting with EA-PE (0-25%) to afford N-(3-(4Z,7Z,10Z,13Z,16Z,19Z)-docosa-4,7,10,13,16,19-hexaenamidobutan-2-yl)-2-hydroxybenzamide (1.08 g, 34.3%) as a light yellow oil. Mass calculated for C₃₃H₄₆N₂O₃=518.73. found: [M+H]⁺=519.6.

Example 23

Preparation of 3-(4Z,7Z,10Z,13Z,16Z,19Z)-docosa-4,7,10,13,16,19-hexaenamidobenzoic acid (17)

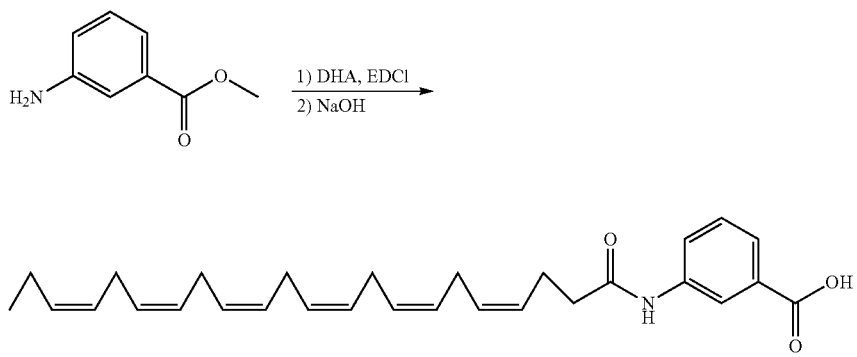

To a solution of DHA (0.10 g, 0.3 mmol) in dichloromethane (3 mL) was added methyl 3-aminobenzoate (0.046 g, 0.3 mmol), EDCI (0.064 g, 0.3 mmol) and dimethylaminopyridine (4 mg, 0.03 mmol). The reaction mixture was stirred (RT, 2 h) and then partitioned between $CH_2Cl_2$ and water. The aqueous layer was extracted with $CH_2Cl_2$, and the combined organic extracts were washed with 10% HCl, brine and dried over $MgSO_4$. The crude material was purified by silica chromatography (0-30% ethyl acetate/pentane) to afford methyl 3-(4Z,7Z,10Z,13Z,16Z,19Z)-docosa-4,7,10,13,16,19-hexaenamidobenzoate. Mass calculated for $C_{30}2H_{39}NO_3$=461.64. found: $[M+H]^+$=462.3. This was then dissolved in MeOH (10 mL) and 5 N NaOH (2 mL). The mixture was stirred at reflux (4 h), and then concentrated. The aqueous solution was acidified to pH 3 with HCl, and the product was extracted with ethyl acetate. The organic layer was washed with water, brine and dried over $MgSO_4$. The crude product was purified by silica chromatography (0-30% ethyl acetate/pentane) to afford 0.066 g of 3-(4Z,7Z,10Z,13Z,16Z,19Z)-docosa-4,7,10,13,16,19-hexaenamidobenzoic acid as an off-white solid. Mass calculated for $C_{29}H_{37}NO_3$=447.61. found: $[M-H]^+$=446.2.

Example 24

Preparation of 2-hydroxy-5-(5Z,8Z,11Z,14Z)-icosa-5,8,11,14-tetraenamidobenzoic acid (18)

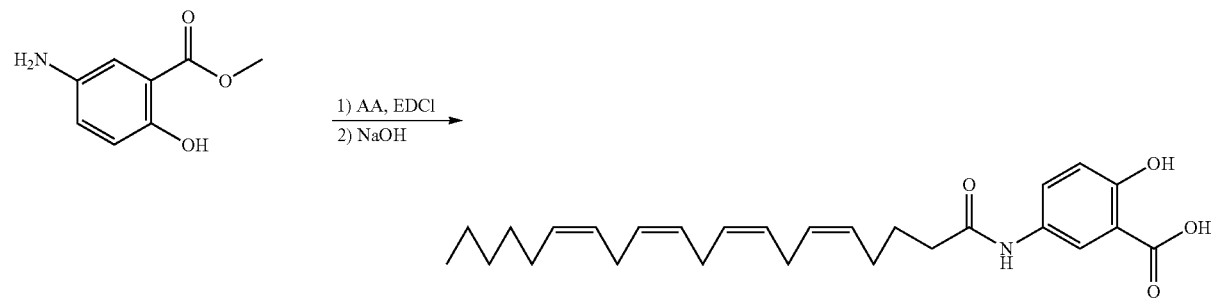

To a solution of methyl 5-amino-2-hydroxybenzoate (0.27 g, 1.6 mmol) in dichloromethane (10 mL) was added arachidonic acid (0.5 g, 1.6 mmol), EDCI (0.32 g, 1.7 mmol) and dimethylaminopyridine (0.020 g, 0.2 mmol). The reaction was stirred (RT, 2 h), and then partitioned between $CH_2Cl_2$ and brine. The aqueous layer was extracted with $CH_2Cl_2$, and the combined organic layers were washed with 1 N HCl, water, saturated aqueous $NaHCO_3$ and water, and then dried over $MgSO_4$. The crude product was purified by silica chromatography (0-5% MeOH/$CH_2Cl_2$) to afford 0.6 g of methyl 2-hydroxy-5-(5Z,8Z,11Z,14Z)-icosa-5,8,11,14-tetraenamidobenzoate as a brown oil. Mass calculated for $C_{28}H_{39}NO_4$=453.61. found: $[M+H]^+$=454.3.

The methyl 2-hydroxy-5-(5Z,8Z,11Z,14Z)-icosa-5,8,11,14-tetraenamidobenzoate was then dissolved in THF (15 mL) and 3 N NaOH (5 mL). The mixture was heated (60° C., 2 h) and then concentrated and acified to pH 3 with 2 N HCl. The product was extracted with ethyl acetate, and the combined organic extracts were washed with brine and dried over $MgSO_4$. The crude product was purified by silica chromatography (0-15% MeOH/$CH_2Cl_2$) to afford 0.3 g of as 2-hydroxy-5-(5Z,8Z,11Z,14Z)-icosa-5,8,11,14-tetraenamidobenzoic acid an orange solid. Mass calculated for $C_{27}H_{37}NO_4$=439.59. found: $[M-H]^+$=438.3.

Example 25

Preparation of 5-(2-(4Z,7Z,10Z,13Z,16Z,19Z)-docosa-4,7,10,13,16,19-hexaenamidoacetamido)-2-hydroxybenzoic acid (19)

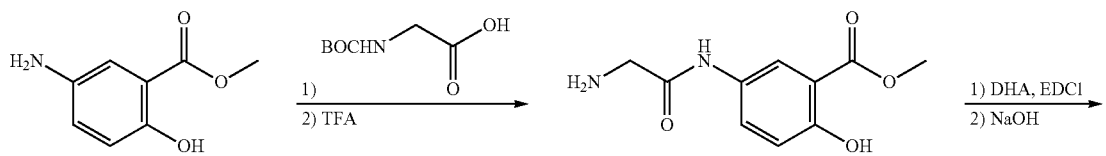

To a solution of methyl 5-amino-2-hydroxybenzoate (1.5 g, 9.0 mmol) in dichloromethane (50 mL) was added BOC-glysine (1.57 g, 9.0 mmol), EDCI (1.89 g, 9.9 mmol) and dimethylaminopyridine (0.11 g, 0.9 mmol). The reaction was stirred (RT, 2.5 h), and then partitioned between $CH_2Cl_2$ and brine. The aqueous layer was extracted with $CH_2Cl_2$ and the combined organic layers were washed with brine and dried over $MgSO_4$. The crude product was purified by silica chromatography (0-5% $MeOH/CH_2Cl_2$) to afford 1.37 g of methyl 5-(2-(tert-butoxycarbonylamino)acetamido)-2-hydroxybenzoate. Mass calculated for $C_{15}H_{20}N_2O_6$=324.33. found: $[M+Na]^+$=347.2.

The methyl 5-(2-(tert-butoxycarbonylamino)acetamido)-2-hydroxybenzoate (1.3 g, 4.0 mmol) was dissolved in $CH_2Cl_2$ (15 mL) and TFA (8 mL). The reaction was stirred (RT, 2.5 h) and then concentrated to afford methyl 5-(2-aminoacetamido)-2-hydroxybenzoate as a clear oil. $[M+H]^+$=225.1. The oil was dissolved in $CH_2Cl_2$ (20 mL) and to this was added DHA (1.3 g, 4.0 mmol), EDCI (0.84 g, 4.4 mmol) and triethylamine (2.0 g, 20.0 mmol). The reaction was stirred (RT, 4 h) and then partitioned between $CH_2Cl_2$ and brine. The aqueous layer was extracted with $CH_2Cl_2$, and the combined organic layers were dried over $MgSO_4$. The crude material was purified by silica chromatography (0-5% $MeOH/CH_2Cl_2$) to afford 0.9 g of methyl 5-(2-(4Z,7Z,10Z,13Z,16Z,19Z)-docosa-4,7,10,13,16,19-hexaenamidoacetamido)-2-hydroxybenzoate as a tan solid. Mass calculated for $C_{10}H_{12}N_2O_4$=534.69. found: $[M+H]^+$=535.4.

The methyl 5-(2-(4Z,7Z,10Z,13Z,16Z,19Z)-docosa-4,7,10,13,16,19-hexaenamidoacetamido)-2-hydroxybenzoate (0.9 g, 1.7 mmol) was dissolved in THF (15 mL) and 1 N NaOH (8 mL). The reaction was stirred (50° C., 5 h), and then acidified to pH 3 with 2 N HCl. The product was extracted with ethyl acetate, and the combined organic extracts were washed with water, brine and dried over $MgSO_4$. The crude material was purified by silica chromatography (0-5% $MeOH/CH_2Cl_2$) to afford 0.4 0 g of 5-(2-(4Z,7Z,10Z,13Z,16Z,19Z)-docosa-4,7,10,13,16,19-hexaenamidoacetamido)-2-hydroxybenzoic acid as a yellow solid. $[M+H]+$=521.3. Mass calculated for $C_{31}H_{40}N_2O_5$=520.66. found: $[M-H]^+$=519.2.

Example 26

Preparation of N-(2-(4Z,7Z,10Z,13Z,16Z,19Z)-docosa-4,7,10,13,16,19-hexaenamidoethyl)-2-hydroxy-4-(trifluoromethyl)benzamide (21)

To a solution of 2-hydroxy-4-(trifluoromethyl)benzoic acid (0.5 g, 2.4 mmol) in $CH_2Cl_2$ (8 mL0 was added oxalyl chloride (0.46 g, 3.6 mmol) and 2 drops of DMF. The reaction was stirred (RT, 2 h) and then concentrated. The resulting residue was dissolved in $CH_2Cl_2$ (8 mL) and tert-butyl 2-aminoethylcarbamate (0.39 g, 2.4 mmol) and diisopropylethylamine (0.41 g, 3.2 mmol) were added. The reaction was stirred (RT, 16 h) and then partitioned between $CH_2Cl_2$ and brine. The aqueous layer was extracted with $CH_2Cl_2$ and the combined organic extracts were dried over $MgSO_4$. The crude material was purified by silica chromatography (0-10% $MeOH/CH_2Cl_2$) to afford 0.55 g of tert-butyl 2-(2-hydroxy-4-(trifluoromethyl)benzamido)ethylcarbamate. Mass calculated for $C_{15}H_{19}F_3N_2O_4$=348.32; found: $[M+Na]^+$=371.1. This was then dissolved in $CH_2Cl_2$ (10 mL) and TFA (4 mL). The reaction was stirred (RT, 3 h) and concentrated and dried to afford 0.7 g of N-(2-aminoethyl)-2-hydroxy-4-(trifluoromethyl)benzamide as a clear oil. Mass calculated for $C_{10}H_{11}F_3N_2O_2$=248.20. found: $[M+H]^+$=249.1.

The N-(2-aminoethyl)-2-hydroxy-4-(trifluoromethyl)benzamide (0.7 g, 1.5 mmol) was dissolved in $CH_2Cl_2$ (10 mL) and to this was added DHA (0.48 g, 1.5 mmol), HATU (0.67 g, 1.8 mmol) and triethylamine (0.59 g, 5.9 mmol). The reaction was stirred (RT, 16 h) and then partitioned between $CH_2Cl_2$ and brine. The aqueous layer was extracted with $CH_2Cl_2$ and the combined organic extracts were dried over $MgSO_4$. The crude material was purified by silica chromatography (0-10% $MeOH/CH_2Cl_2$) to afford 0.28 g of N-(2-(4Z,7Z,10Z,13Z,16Z,19Z)-docosa-4,7,10,13,16,19-hexaenamidoethyl)-2-hydroxy-4-(trifluoromethyl)benzamide as a yellow oil. Mass calculated for $C_{32}H_{41}F_3N_2O_3$=558.67. found: $[M+H]^+$=559.3.

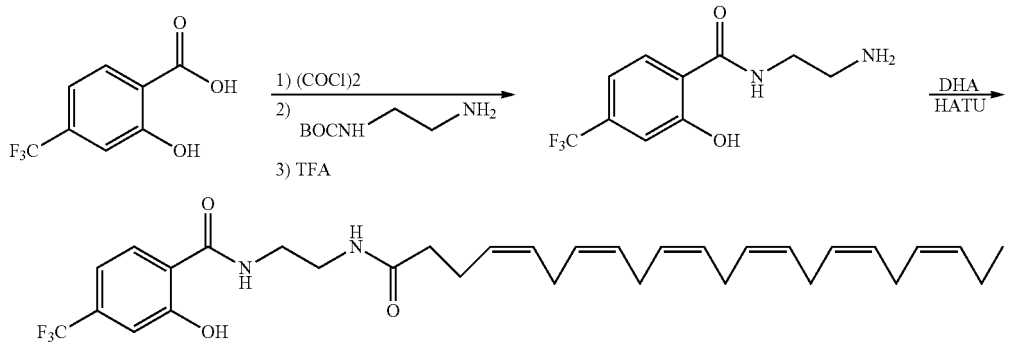

Example 27

Preparation of ethyl 2-(2-(4Z,7Z,10Z,13Z,16Z,19Z)-docosa-4,7,10,13,16,19-hexaenamido-3-phenylpropanoyloxy)benzoate (22)

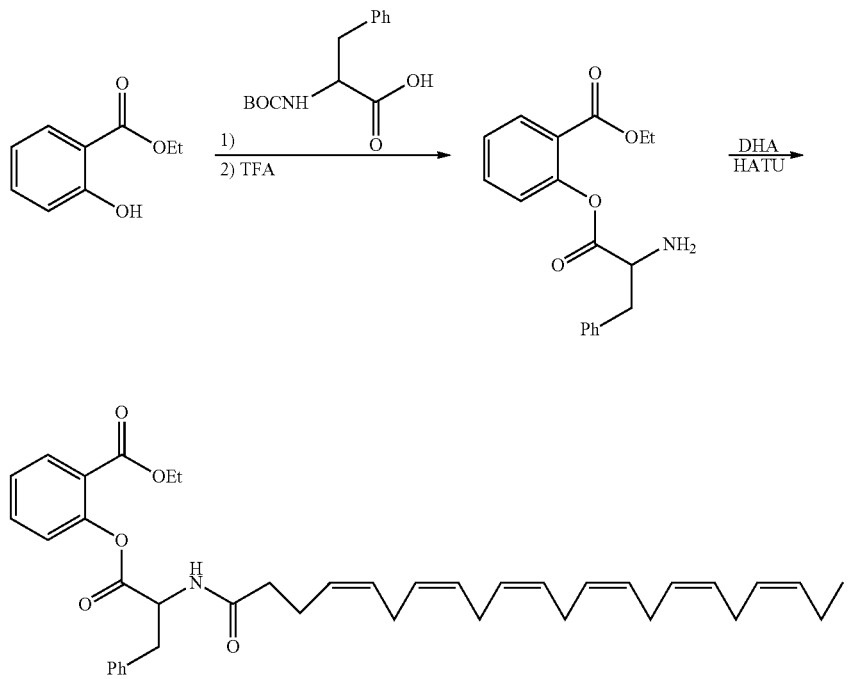

To a solution of ethyl 2-hydroxybenzoate (0.5 g, 3.0 mmol) in $CH_2Cl_2$ (8 mL) was added 2-(tert-butoxycarbonylamino)-3-phenylpropanoic acid (0.8 g, 3.0 mmol), EDCI (0.63 g, 3.3 mmol) and dimethylaminopyridine (0.037 g, 0.3 mmol). The reaction was stirred (RT, 3 h) and then partitioned between $CH_2Cl_2$ and brine. The aqueous layer was extracted with $CH_2Cl_2$ and the combined organic extracts were dried over $MgSO_4$. The crude material was purified by silica chromatography (0-10% MeOH/$CH_2Cl_2$) to afford 1.2 g of ethyl 2-(2-(tert-butoxycarbonylamino)-3-phenylpropanoyloxy)benzoate. Mass calculated for $C_{235}H_{27}NO_6$=413.46. found: $[M+Na]^+$=437.1.

The ethyl 2-(2-(tert-butoxycarbonylamino)-3-phenylpropanoyloxy)benzoate (1.2 g, 2.9 mmol) was dissolved in $CH_2Cl_2$ (10 mL) and TFA (4 mL). The reaction was stirred (RT, 3 h) and then concentrated. The crude material was purified by silica chromatography (0-10% MeOH/$CH_2Cl_2$) to afford 0.63 g of ethyl 2-(2-amino-3-phenylpropanoyloxy)benzoate. Mass calculated for $C_{18}H_{19}NO_4$=313.35. found: $[M+H]^+$=314.1.

Ethyl 2-(2-amino-3-phenylpropanoyloxy)benzoate (0.24 g, 0.8 mmol) and DHA (0.25 g, 0.8 mmol) were combined in $CH_2Cl_2$ (10 mL) and to this was added HATU (0.35 g, 0.9 mmol) and diisopropylethylamine (0.30 g, 2.3 mmol). The reaction was stirred (RT, 3 h) and then partitioned between $CH_2Cl_2$ and brine. The aqueous layer was extracted with $CH_2Cl_2$ and the combined organic extracts were dried over $MgSO_4$. The crude material was purified by silica chromatography (0-10% MeOH/$CH_2Cl_2$) to afford ethyl 2-(2-(4Z,7Z,10Z,13Z,16Z,19Z)-docosa-4,7,10,13,16,19-hexaenamido-3-phenylpropanoyloxy)benzoate as a tan solid. Mass calculated for $C_{40}H_{49}NO_5$=623.82. found: $[M+H]^+$=624.2.

Example 28

Preparation of 5-(2-(4Z,7Z,10Z,13Z,16Z,19Z)-docosa-4,7,10,13,16,19-hexaenamido-3-phenylpropanamido)-2-hydroxybenzoic acid (23)

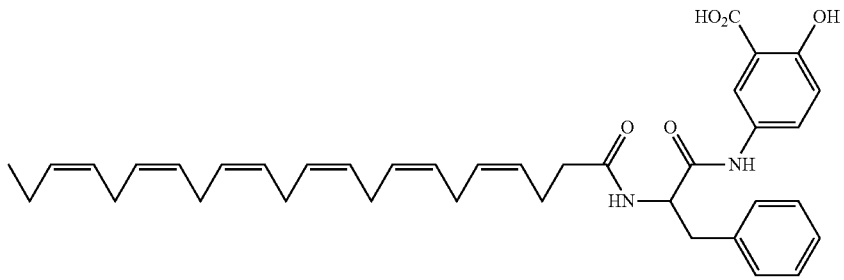 [SMILES: CC/C=C\C/C=C\C/C=C\C/C=C\C/C=C\C/C=C\CCC(=O)NC(Cc1ccccc1)C(=O)Nc1ccc(O)c(C(=O)O)c1]

5-(2-(4Z,7Z,10Z,13Z,16Z,19Z)-Docosa-4,7,10,13,16,19-hexaenamido-3-phenylpropanamido)-2-hydroxybenzoic acid was prepared in a similar fashion as 5-(2-(4Z,7Z,10Z,13Z,16Z,19Z)-docosa-4,7,10,13,16,19-hexaenamido-4-methylpentanamido)-2-hydroxybenzoic acid, using the appropriate phenylalanine starting material. Mass calculated for $C_{38}H_{46}N_2O_5$=610.78. found: $[M-H]^+$=609.3.

Example 29

Preparation of 2-hydroxy-5-(5Z,8Z,11Z,14Z,17Z)-icosa-5,8,11,14,17-pentaenamidobenzoic acid (24)

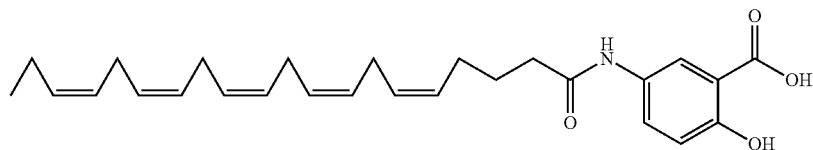 [SMILES: CC/C=C\C/C=C\C/C=C\C/C=C\C/C=C\CCCC(=O)Nc1ccc(O)c(C(=O)O)c1]

2-Hydroxy-5-(5Z,8Z,11Z,14Z,17Z)-icosa-5,8,11,14,17-pentaenamidobenzoic acid was prepared in a similar fashion as 5-(4Z,7Z,10Z,13Z,16Z,19Z)-docosa-4,7,10,13,16,19-hexaenamido-2-hydroxybenzoic acid, using the appropriate EPA starting material. Mass calculated for $C_{27}H_{35}NO_4$=437.57. found: $[M-H]^+$=436.2.

Example 30

Preparation of N-(2-(4Z,7Z,10Z,13Z,16Z,19Z)-docosa-4,7,10,13,16,19-hexaenamidoethyl)-2',4'-difluoro-4-hydroxybiphenyl-3-carboxamide (25)

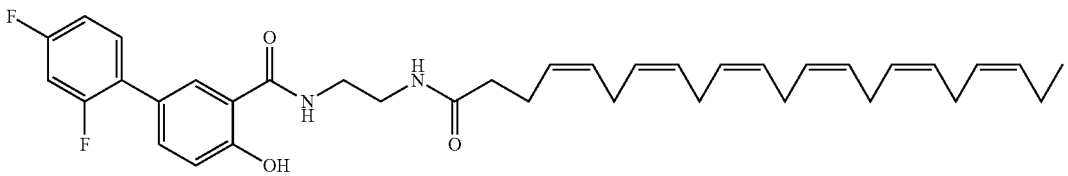 [SMILES: CC/C=C\C/C=C\C/C=C\C/C=C\C/C=C\C/C=C\CCC(=O)NCCNC(=O)c1cc(-c2ccc(F)cc2F)ccc1O]

N-(2-(4Z,7Z,10Z,13Z,16Z,19Z)-docosa-4,7,10,13,16,19-hexaenamidoethyl)-2',4'-difluoro-4-hydroxybiphenyl-3-carboxamide was prepared in a similar fashion as N-(2-(4Z,7Z,10Z,13Z,16Z,19Z)-docosa-4,7,10,13,16,19-hexaenamidoethyl)-2-hydroxybenzamide, using the appropriate 2',4'-difluoro-4-hydroxybiphenyl-3-carboxylic acid starting material. Mass calculated for $C_{37}H_{44}F_2N_2O_3$=602.75. found: $[M+H]^+$=603.3.

Example 31

Preparation of 2',4'-difluoro-4-hydroxy-N-(2-(5Z,8Z,11Z,14Z,17Z)-icosa-5,8,11,14,17-pentaenamidoethyl)biphenyl-3-carboxamide (26)

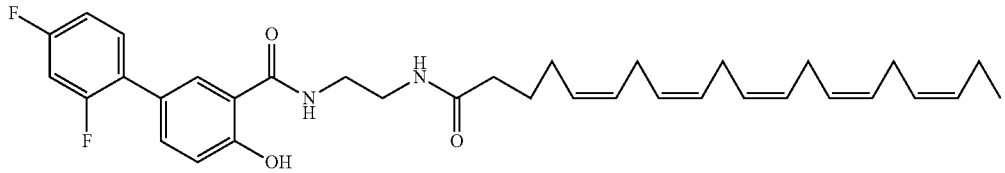 [SMILES: CC/C=C\C/C=C\C/C=C\C/C=C\C/C=C\CCCC(=O)NCCNC(=O)c1cc(-c2ccc(F)cc2F)ccc1O]

2',4'-Difluoro-4-hydroxy-N-(2-(5Z,8Z,11Z,14Z,17Z)-icosa-5,8,11,14,17-pentaenamidoethyl)biphenyl-3-carboxamide was prepared in a similar fashion as N-(2-(4Z,7Z,10Z,13Z,16Z,19Z)-docosa-4,7,10,13,16,19-hexaenamidoethyl)-2-hydroxybenzamide, using the appropriate 2',4'-difluoro-4-hydroxybiphenyl-3-carboxylic acid and EPA starting materials. Mass calculated for $C_{35}H_{42}F_2N_2O_3$=576.72. found: $[M+H]^+$=577.3.

Example 32

Preparation of ethyl 4-((4Z,7Z,10Z,13Z,16Z,19Z)-docosa-4,7,10,13,16,19-hexaenoyloxy)-2',4'-difluorobiphenyl-3-carboxylate (27)

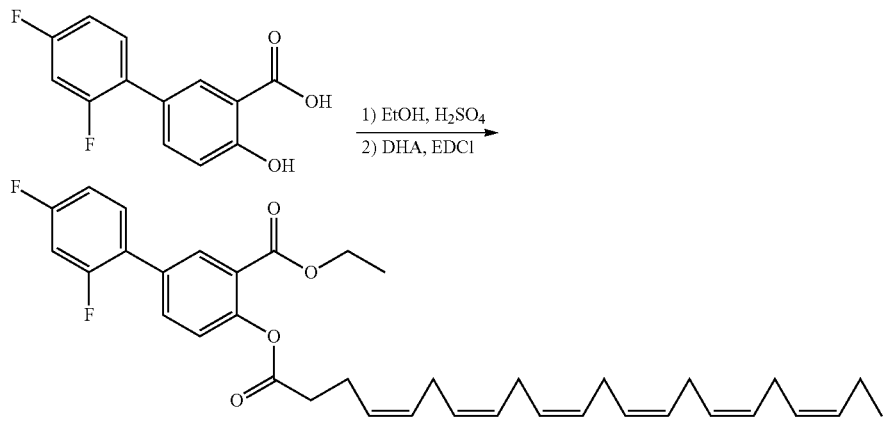

The 2',4'-difluoro-4-hydroxybiphenyl-3-carboxylic acid (1.0 g, 4.0 mmol) was dissolved in ethanol (30 mL) and sulfuric acid (8 mL). The solution was stirred (80° C., 18 h) and then concentrated. The residue was dissolved in ethyl acetate and washed with water, brine and dried over MgSO$_4$. Solvent evaporation afforded 1.0 g of ethyl 2',4'-difluoro-4-hydroxybiphenyl-3-carboxylate. Mass calculated for $C_{15}H_{12}F_2O_3$=278.25. found: $[M+H]^+$=279.1.

The ethyl 2',4'-difluoro-4-hydroxybiphenyl-3-carboxylate (0.3 g, 1.1 mmol) was dissolved in CH$_2$Cl$_2$ (10 mL) and to this was added DHA (0.35 g, 1.1 mmol), EDCI (0.23 g, 1.2 mmol) and dimethylaminopyridine (0.13 g, 0.1 mmol). The reaction was stirred (RT, 3 h) and then partitioned between CH$_2$Cl$_2$ and brine. The aqueous layer was extracted with CH$_2$Cl$_2$ and the combined organic extracts were dried over MgSO MgSO$_4$. The crude material was purified by silica chromatography (0-40% ethyl acetate/pentane) to afford 0.1 g of ethyl 4-((4Z,7Z,10Z,13Z,16Z,19Z)-docosa-4,7,10,13,16,19-hexaenoyloxy)-2',4'-difluorobiphenyl-3-carboxylate. Mass calculated for $C_{37}H_{42}F_2O_4$=588.72. found: $[M+H]^+$=589.3.

Example 33

Preparation of ethyl 2-((4Z,7Z,10Z,13Z,16Z,19Z)-docosa-4,7,10,13,16,19-hexaenoyloxy)-4-(trifluoromethyl)benzoate (28)

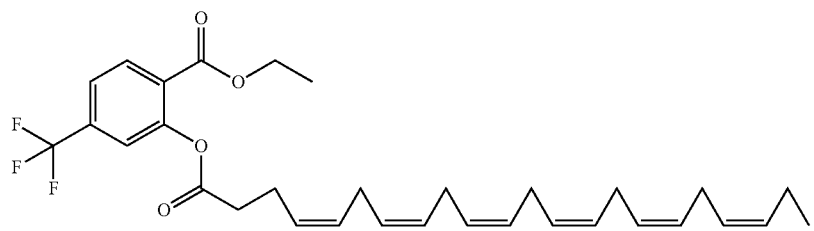 [SMILES: CC/C=C\C/C=C\C/C=C\C/C=C\C/C=C\C/C=C\CCC(=O)Oc1cc(C(F)(F)F)ccc1C(=O)OCC]

Ethyl 2-((4Z,7Z,10Z,13Z,16Z,19Z)-docosa-4,7,10,13,16,19-hexaenoyloxy)-4-(trifluoromethyl)benzoate was prepared in a similar fashion as ethyl 4-((4Z,7Z,10Z,13Z,16Z,19Z)-docosa-4,7,10,13,16,19-hexaenoyloxy)-2',4'-difluorobiphenyl-3-carboxylate, using the appropriate 2-hydroxy-4-(trifluoromethyl)benzoic acid starting material. Mass calculated for $C_{32}H_{39}F_3O_4$=544.64. found: [M+Na]$^+$=567.3.

Example 34

Preparation of ethyl 4-(2-(4Z,7Z,10Z,13Z,16Z,19Z)-docosa-4,7,10,13,16,19-hexaenamido-4-methylpentanoyloxy)-2',4'-difluorobiphenyl-3-carboxylate (29)

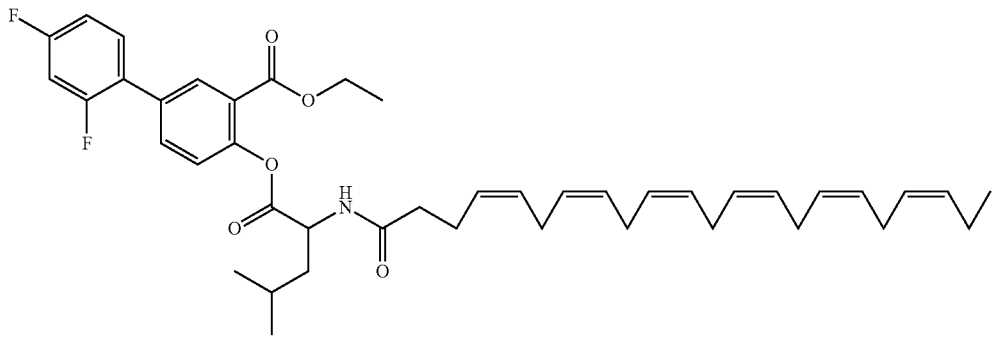 [SMILES: CC/C=C\C/C=C\C/C=C\C/C=C\C/C=C\C/C=C\CCC(=O)NC(CC(C)C)C(=O)Oc1ccc(-c2ccc(F)cc2F)cc1C(=O)OCC]

Ethyl 4-(2-(4Z,7Z,10Z,13Z,16Z,19Z)-docosa-4,7,10,13,16,19-hexaenamido-4-methylpentanoyloxy)-2',4'-difluorobiphenyl-3-carboxylate was prepared as described for ethyl 2-(2-(4Z,7Z,10Z,13Z,16Z,19Z)-docosa-4,7,10,13,16,19-hexaenamido-4-methylpentanoyloxy)benzoate, using the appropriate 2',4'-difluoro-4-hydroxybiphenyl-3-carboxylic acid starting material. Mass calculated for $C_{43}H_{53}F_2NO_5$=701.88. found: [M+H]$^+$=702.4.

Example 35

Preparation of ethyl 2-(2-(4Z,7Z,10Z,13Z,16Z,19Z)-docosa-4,7,10,13,16,19-hexaenamido-4-methylpentanoyloxy)-4-(trifluoromethyl)benzoate (30)

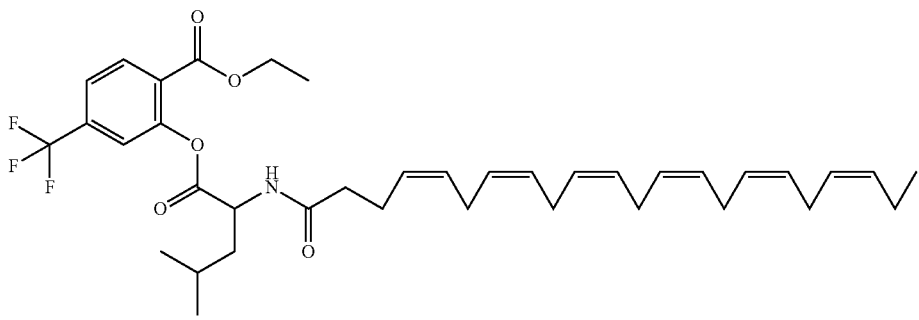 [SMILES: CC/C=C\C/C=C\C/C=C\C/C=C\C/C=C\C/C=C\CCC(=O)NC(CC(C)C)C(=O)Oc1cc(C(F)(F)F)ccc1C(=O)OCC]

Ethyl 2-(2-(4Z,7Z,10Z,13Z,16Z,19Z)-docosa-4,7,10,13,16,19-hexaenamido-4-methylpentanoyloxy)-4-(trifluoromethyl)benzoate was prepared as described for ethyl 2-(2 (4Z,7Z,10Z,13Z,16Z,19Z)-docosa-4,7,10,13,16,19-hexaenamido-4-methylpentanoyloxy)benzoate, using the appropriate 2-hydroxy-4-(trifluoromethyl)benzoic acid starting material. Mass calculated for $C_{38}H_{50}F_3NO_5$=657.80. found: [M+H]$^+$=658.4.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A method of treating inflammation that is associated with a metabolic disorder, wherein the metabolic disorder is selected from the group consisting of cardiovascular disease, and hypertriglyceridemia, comprising administering to a patient in need thereof an effective amount of a compound of Formula III:

Formula III

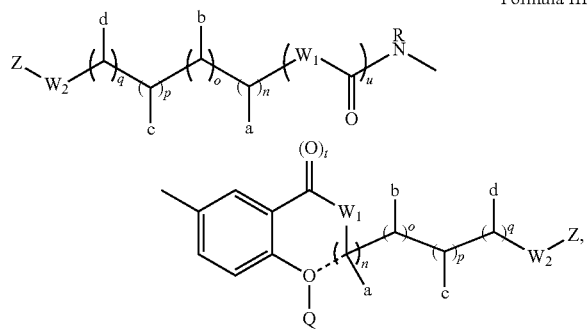

or a pharmaceutically acceptable salt, enantiomer, or stereoisomer thereof,
wherein
  $W_1$ is null and $W_2$ is independently null, O, or NH;
  - - - - - represents an optional bond that when present requires that Q is null;
  each a and c are independently H, $CH_3$, $-OCH_3$, $-OCH_2CH_3$, or C(O)OH;
  each b is H, $CH_3$, C(O)OH, or O—Z;
  each d is H or C(O)OH;
  each n, o, p, and q is independently 0 or 1;
  each Z is H or

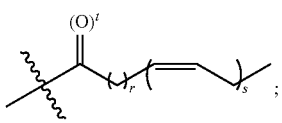

with the proviso that there is at least one

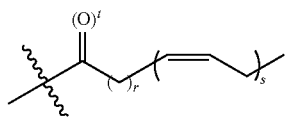

in the compound;
  each r is independently 2, 3, or 7;
  each s is independently 3, 5, or 6;
  each t is independently 0 or 1;
  u is 0 or 1;
  with the proviso that when r is 7, s is 3;
  Q is null, C(O)$CH_3$, Z,

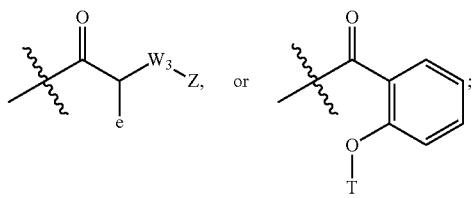

e is H or any one of the side chains of the naturally occurring amino acids;
  $W_3$ is null, O, or —N(R)—;
  R is H or $C_1$-$C_3$ alkyl; and
  T is H, C(O)$CH_3$, or Z.

2. The method of claim 1, wherein Q is H.

3. The method of claim 2, wherein the compound of Formula III is

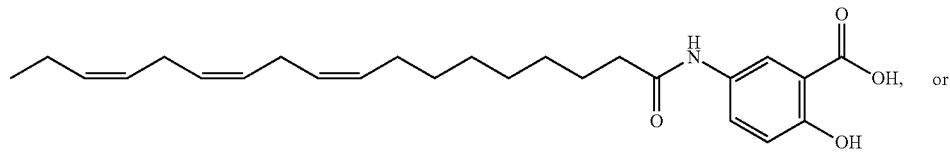

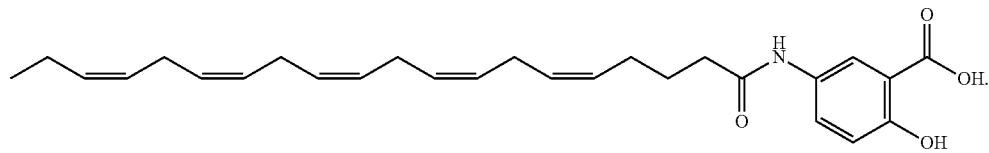

4. The method of claim 3, wherein the compound of Formula III is

5. A method of treating inflammation that is associated with a neurodegenerative disorder selected from the group consisting of Huntington's Disease, infectious meningitis, encephalomyelitis, Parkinson's disease, amyotrophic lateral sclerosis, and encephalitis, comprising administering to a patient in need thereof an effective amount of a compound of Formula III:

Formula III

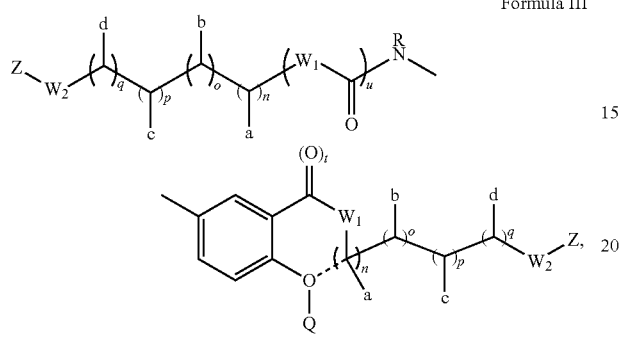

or a pharmaceutically acceptable salt, enantiomer, or stereoisomer thereof,
wherein
$W_1$ is null and $W_2$ is independently null, O, or NH;
- - - - - represents an optional bond that when present requires that Q is null;
each a and c are independently H, $CH_3$, $—OCH_3$, $—OCH_2CH_3$, or C(O)OH;
each b is H, $CH_3$, C(O)OH, or O—Z;
each d is H or C(O)OH;
each n, o, p, and q is independently 0 or 1;
each Z is H or

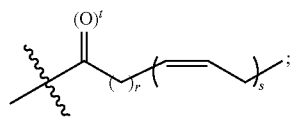

with the proviso that there is at least one

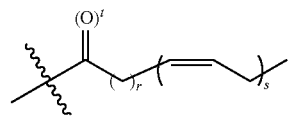

in the compound;
each r is independently 2, 3, or 7;
each s is independently 3, 5, or 6;
each t is independently 0 or 1;
u is 0 or 1;
with the proviso that when r is 7, s is 3;
Q is null, $C(O)CH_3$, Z,

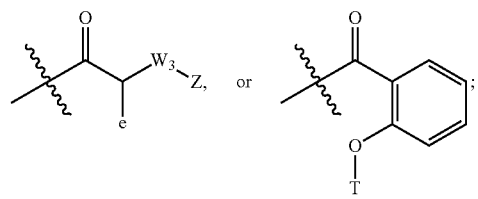

e is H or any one of the side chains of the naturally occurring amino acids;
$W_3$ is null, O, or —N(R)—;
R is H or $C_1$-$C_3$ alkyl; and
T is H, $C(O)CH_3$, or Z.

6. The method of claim 5, wherein Q is H.

7. The method of claim 5, wherein the compound of Formula III is

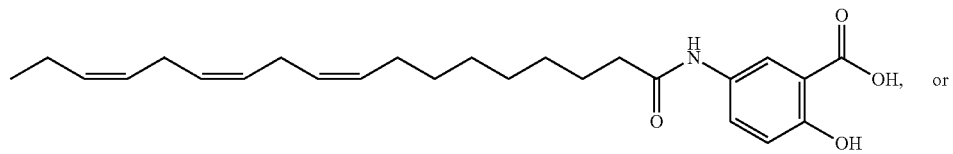

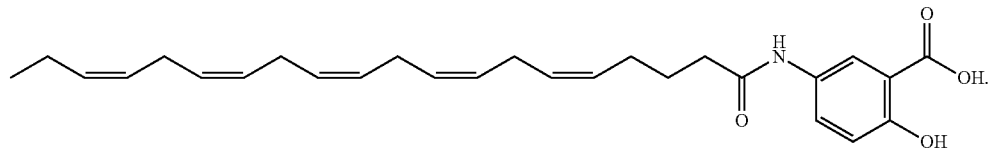

8. The method of claim 5, wherein the compound of Formula III is

9. A method of treating inflammation that is associated with a muscle wasting disorder selected from the group consisting of dermatomyositis, inclusion body myositis, polymyositis, and cachexia, comprising administering to a patient in need thereof an effective amount of a compound of Formula III:

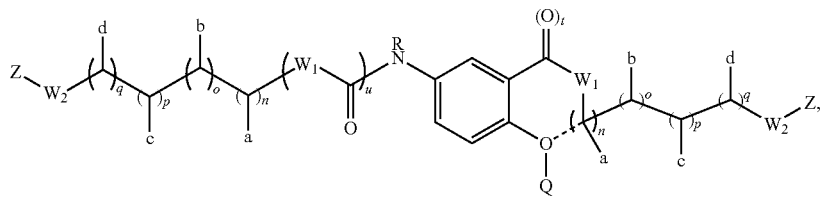

Formula III or a pharmaceutically acceptable salt, enantiomer, or stereoisomer thereof,
wherein
$W_1$ is null and $W_2$ is independently null, O, or NH;
- - - - - represents an optional bond that when present requires that Q is null;
each a and c are independently H, $CH_3$, $-OCH_3$, $-OCH_2CH_3$, or C(O)OH;
each b is H, $CH_3$, C(O)OH, or O—Z;
each d is H or C(O)OH;
each n, o, p, and q is independently 0 or 1;
each Z is H or

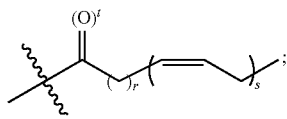

with the proviso that there is at least one

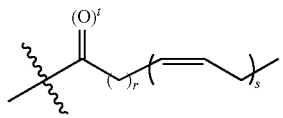

in the compound;

each r is independently 2, 3, or 7;
each s is independently 3, 5, or 6;
each t is independently 0 or 1;
u is 0 or 1;
with the proviso that when r is 7, s is 3;
Q is null, $C(O)CH_3$, Z,

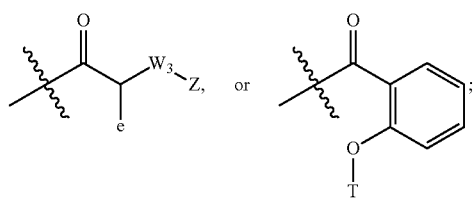

e is H or any one of the side chains of the naturally occurring amino acids;
$W_3$ is null, O, or —N(R)—;
R is H or $C_1$-$C_3$ alkyl; and
T is H, $C(O)CH_3$, or Z.

10. The method of claim 9, wherein Q is H.

11. The method of claim 10, wherein the compound of Formula III is

-continued
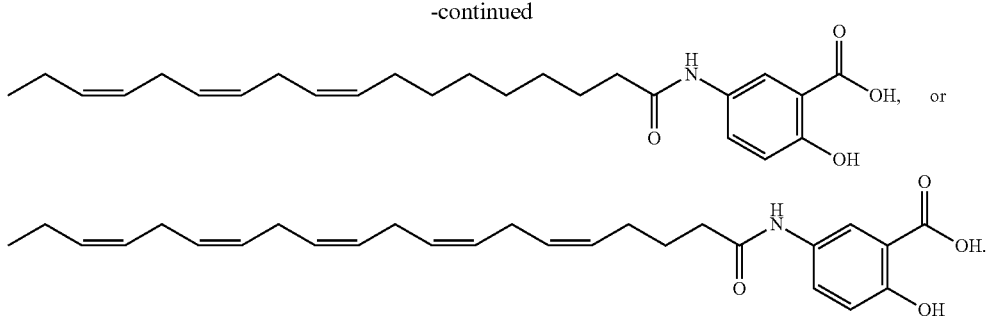
12. The method of claim 11, wherein the compound of Formula III is
13. The method of claim 1, wherein the cardiovascular disease is selected from the group consisting of arrhythmia and coronary artery disease.
14. The method of claim 13, wherein Q is H.
15. The method of claim 13, wherein the compound of Formula III is
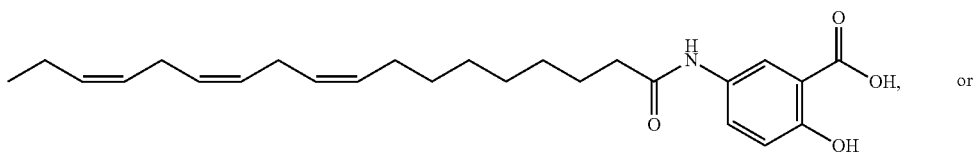
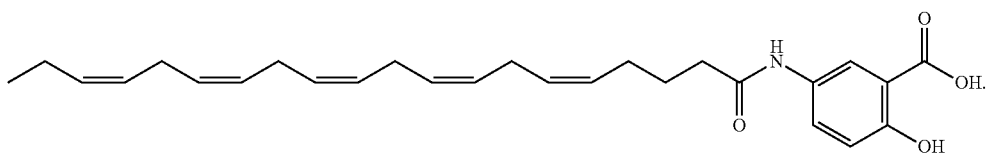
16. The method of claim 13, wherein the compound of Formula III is
* * * * *